US010329537B2

(12) United States Patent
Mason et al.

(10) Patent No.: US 10,329,537 B2
(45) Date of Patent: Jun. 25, 2019

(54) INFLUENZA VIRUS REASSORTMENT

(71) Applicants: Seqirus UK Limited, Berkshire (GB); Synthetic Genomics, Inc., La Jolla, CA (US)

(72) Inventors: Peter Mason, Cambridge, MA (US); Pirada Suphaphiphat, Cambridge, MA (US); Raul Gomila, Cambridge, MA (US); Philip Dormitzer, Cambridge, MA (US)

(73) Assignees: Seqirus UK Limited, Berkshire (GB); Synthetic Genomics, Inc., La Jolla, CA (US)

(*) Notice: Subject to any disclaimer, the term of this patent is extended or adjusted under 35 U.S.C. 154(b) by 0 days.

(21) Appl. No.: 14/896,348

(22) PCT Filed: Jun. 6, 2014

(86) PCT No.: PCT/IB2014/062030
§ 371 (c)(1),
(2) Date: Dec. 4, 2015

(87) PCT Pub. No.: WO2014/195920
PCT Pub. Date: Dec. 11, 2014

(65) Prior Publication Data

US 2016/0122726 A1 May 5, 2016

Related U.S. Application Data

(60) Provisional application No. 61/832,091, filed on Jun. 6, 2013.

(30) Foreign Application Priority Data

Sep. 26, 2013 (EP) .................................... 13179013

(51) Int. Cl.

| | |
|---|---|
| *C12N 7/00* | (2006.01) |
| *C12N 15/00* | (2006.01) |
| *A61K 38/00* | (2006.01) |
| *C07K 1/00* | (2006.01) |
| *C07H 21/04* | (2006.01) |
| *C07K 19/00* | (2006.01) |
| *A61K 39/12* | (2006.01) |
| *C07K 14/005* | (2006.01) |
| *C12N 9/24* | (2006.01) |

(52) U.S. Cl.
CPC ................ *C12N 7/00* (2013.01); *A61K 39/12* (2013.01); *C07K 14/005* (2013.01); *C07K 19/00* (2013.01); *C12N 9/2402* (2013.01); *C12N 2760/16121* (2013.01); *C12N 2760/16134* (2013.01); *C12N 2760/16143* (2013.01); *C12N 2760/16151* (2013.01); *C12N 2760/16161* (2013.01); *C12N 2760/16234* (2013.01); *C12Y 302/01018* (2013.01)

(58) Field of Classification Search
None
See application file for complete search history.

(56) References Cited

U.S. PATENT DOCUMENTS

| | | | | |
|---|---|---|---|---|
| 7,459,162 B2 * | 12/2008 | Yang | A61K 39/145 | |
| | | | 424/186.1 | |
| 9,422,528 B2 * | 8/2016 | Suphaphiphat | C12N 7/00 | |
| 2015/0191703 A1 * | 7/2015 | Legastelois | C12N 7/00 | |
| | | | 435/237 | |

FOREIGN PATENT DOCUMENTS

WO 2010/148511 A1 12/2010

OTHER PUBLICATIONS

Harvey. Improved Antigen Yield in Pandemic H1N1 (2009) Candidate Vaccine Viruses with Chimeric Hemagglutinin MoleculesJournal of Virology, Jun. 2011, p. 6086-6090.*
International Preliminary Report on Patentability received for PCT Patent Application No. PCT/IB2014/062030 dated Dec. 17, 2015, 18 pages.
International Search Report and Written Opinion received for PCT Patent Application No. PCT/IB2014/062030 dated Feb. 6, 2015, 24 pages.
Gomila et al., "Improving Influenza Virus Backbones by Including Terminal Regions of MDCK-Adapted Strains on Hemagglutinin and Neuraminidase Gene Segments", Vaccine; vol. 31, No. 42, Oct. 2013, pp. 4736-4743.
Hai et al., "A Reassortment-Incompetent Live Attenuated Influenza Virus Vaccine for Protection against Pandemic Virus Strains", Journal of Virology, vol. 85, No. 14, Jul. 2011, pp. 6832-6843.

* cited by examiner

*Primary Examiner* — Yong D Pak
(74) *Attorney, Agent, or Firm* — Finnegan, Henderson, Farabow, Garrett & Dunner, L.L.P.

(57) ABSTRACT

The invention provides reassortant influenza strains.

7 Claims, 10 Drawing Sheets

Specification includes a Sequence Listing.

*FIG. 4B*

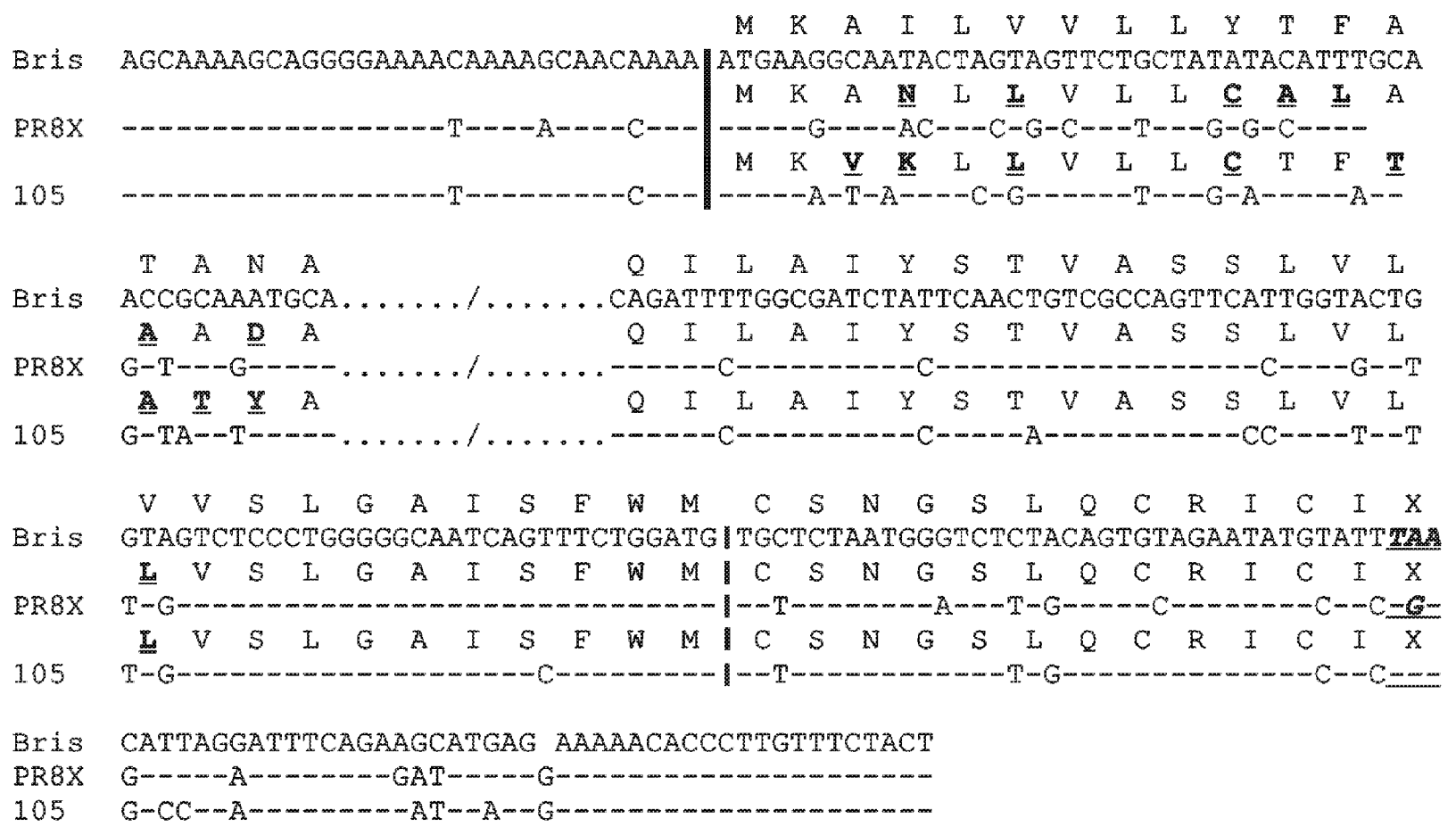

```
                                            M  K  A  I  L  V  V  L  L  Y  T  F  A
Bris  AGCAAAAGCAGGGGAAAACAAAAGCAACAAAA|ATGAAGGCAATACTAGTAGTTCTGCTATATACATTTGCA
                                            M  K  A  N  L  L  V  L  L  C  A  L  A
PR8X  ------------------T----A----C---|-----G----AC---C-G-C---T---G-G-C----
                                            M  K  V  K  L  L  V  L  L  C  T  F  T
105   ------------------T---------C---|-----A-T-A----C-G------T---G-A-----A--

       T  A  N  A                   Q  I  L  A  I  Y  S  T  V  A  S  S  L  V  L
Bris  ACCGCAAATGCA......./.......CAGATTTTGGCGATCTATTCAACTGTCGCCAGTTCATTGGTACTG
       A  A  D  A                   Q  I  L  A  I  Y  S  T  V  A  S  S  L  V  L
PR8X  G-T---G-----......./.......------C----------C-----------------C----G--T
       A  T  Y  A                   Q  I  L  A  I  Y  S  T  V  A  S  S  L  V  L
105   G-TA--T-----......./.......------C----------C-----A-----------CC----T--T

       V  V  S  L  G  A  I  S  F  W  M  C  S  N  G  S  L  Q  C  R  I  C  I  X
Bris  GTAGTCTCCCTGGGGGCAATCAGTTTCTGGATG|TGCTCTAATGGGTCTCTACAGTGTAGAATATGTATTTAA
       L  V  S  L  G  A  I  S  F  W  M| C  S  N  G  S  L  Q  C  R  I  C  I  X
PR8X  T-G------------------------------|--T--------A---T-G-----C---------C--C-G-
       L  V  S  L  G  A  I  S  F  W  M| C  S  N  G  S  L  Q  C  R  I  C  I  X
105   T-G-------------------C----------|--T------------T-G--------------C--C---

Bris  CATTAGGATTTCAGAAGCATGAG AAAAACACCCTTGTTTCTACT
PR8X  G-----A---------GAT-----G---------------------
105   G-CC--A----------AT--A--G---------------------
```

INFLUENZA VIRUS REASSORTMENT

CROSS REFERENCE TO RELATED APPLICATIONS

This application is a U.S. national phase of PCT/M2014/062030, filed Jun. 6, 2014, which claims priority to U.S. Provisional Patent Application No. 61/832,091, filed Jun. 6, 2013, and European Patent Application No. 13179013.1, filed Sep. 26, 2013, all of which are herein incorporated by reference in the present disclosure in their entirety.

STATEMENT REGARDING FEDERALLY-SPONSORED RESEARCH

This invention was made in part with Government support under grant no. HHS010020100061C awarded by the Biomedical Advanced Research and Development Authority (BARDA). The Government has certain rights in the invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 529552005700SeqList.txt, date recorded: Dec. 3, 2015, size: 349 KB).

TECHNICAL FIELD

This invention is in the field of influenza virus reassortment. Furthermore, it relates to manufacturing vaccines for protecting against influenza viruses.

BACKGROUND ART

The most efficient protection against influenza infection is vaccination against circulating strains and it is important to produce influenza viruses for vaccine production as quickly as possible.

Wild-type influenza viruses often grow to low titres in eggs and cell culture. In order to obtain a better-growing virus strain for vaccine production it is currently common practice to reassort the circulating vaccine strain with a faster-growing high-yield donor strain. This can be achieved by co-infecting a culture host with the circulating influenza strain (the vaccine strain) and the high-yield donor strain and selecting for reassortant viruses which contain the hemagglutinin (HA) and neuraminidase (NA) segments from the vaccine strain and the other viral segments (i.e. those encoding PB1, PB2, PA, NP, $M_1$, $M_2$, $NS_1$ and $NS_2$) from the donor strain. Another approach is to reassort the influenza viruses by reverse genetics (see, for example references 1 and 2).

References 3 and 4 report that influenza viruses with a chimeric HA segment which comprises the ectodomain from a vaccine strain and the other domains from A/Puerto Rico/8/34 grew faster in eggs compared to the wild-type vaccine strain. Reference 5 teaches influenza viruses with chimeric NA proteins which contain the transmembrane and stalk domains from A/PR/8/34. References 6 and 7 teach reassortant influenza viruses which comprise chimeric HA segments that have domains from both influenza A and B viruses.

Most of the studies with chimeric HA proteins were done in eggs and reference 3 teaches that "it is likely that the improvement seen with [the described] chimeric viruses is very specific to the egg substrate". The studies which tested growth in cell culture found that the tested viruses showed poor growth in cell culture. There is therefore still a need in the art to provide high-yielding reassortant influenza viruses, especially in cell culture.

SUMMARY OF PREFERRED EMBODIMENTS

The invention provides a chimeric influenza hemagglutinin segment having an ectodomain, a 5'-non-coding region, a 3'-non-coding region, a signal peptide, a transmembrane domain and a cytoplasmic domain wherein the ectodomain is from a first influenza strain and one or more of the 5'-non-coding region, the 3'-non-coding region, the signal peptide, the transmembrane domain and the cytoplasmic domain are from a second influenza strain which is not A/Puerto Rico/8/34, A/WSN/33 or B/Lee/40.

Also provided is a chimeric influenza hemagglutinin segment having an ectodomain, a 5'-non-coding region, a 3'-non-coding region, a signal peptide, a transmembrane domain and a cytoplasmic domain, wherein the ectodomain is from a first influenza A strain which is not a H1 or H5 influenza strain, and one or more of the 5'-non-coding region, the 3'-non-coding region, the signal peptide, the transmembrane domain and the cytoplasmic domain are from a second influenza strain.

The invention also provides a chimeric influenza hemagglutinin segment having an ectodomain, a 5'-non-coding region, a 3'-non-coding region, a signal peptide, a transmembrane domain and a cytoplasmic domain, wherein the ectodomain is from a first influenza B strain, and one or more of the 5'-non-coding region, the 3'-non-coding region, the signal peptide, the transmembrane domain and the cytoplasmic domain are from a second influenza strain which is an influenza B strain or an influenza A strain which is not a H1 strain or a H3 strain. The chimeric hemagglutinin segment preferably comprises all of the 5'-non-coding region, the 3'-non-coding region, the signal peptide, the transmembrane domain and the cytoplasmic domain from the second influenza virus as the inventors have found that reassortant influenza viruses comprising such a chimeric hemagglutinin segment give particularly good HA yields in cell culture.

Also provided is a chimeric influenza hemagglutinin segment having an ectodomain, a 5'-non-coding region, a 3'-non-coding region, a signal peptide, a transmembrane domain and a cytoplasmic domain wherein the ectodomain is from a first influenza strain and one or more of the 5'-non-coding region, the 3'-non-coding region, the signal peptide, the transmembrane domain and the cytoplasmic domain are from a second influenza strain, wherein the segment comprises one or more of: (a) guanine in the position corresponding to nucleotide 24, and/or (b) adenine in the position corresponding to nucleotide 38; and/or (c) thymine in the position corresponding to nucleotide 40; and/or (d) adenine in the position corresponding to nucleotide 44; (e) and/or thymine in the position corresponding to nucleotide 53; and/or (f) adenine in the position corresponding to nucleotide 63; and/or (g) thymine in the position corresponding to nucleotide 66; and/or (h) adenine in the position corresponding to nucleotide 69; and/or (i) adenine in the position corresponding to nucleotide 75; and/or (j) thymine in the position corresponding to nucleotide 78; and/or (k) adenine in the position corresponding to nucleotide 1637; and/or (l) cytosine in the position corresponding to nucleotide 1649, and/or (m) thymine in the position corresponding to nucleotide 1655, and/or (n) cytosine in the position corresponding to nucleotide 1682, and/or (o) cytosine in the position corresponding to nucleotide 1697; and/or (p) guanine in the position corresponding to nucleotide 1703, and/or (q) thymine in the position corresponding to nucleotide 1715, and/or (r) adenine in the position corresponding to nucleotide 1729, and/or (s) cytosine in the position corresponding to nucleotide 1733, and/or (t) cytosine in the position corresponding to nucleotide 1734, and/or (u) adenine in the position corresponding to nucleotide 1746, and/or (v) adenine in the position corresponding to nucleotide 1751; when aligned to SEQ ID NO: 15 using a pairwise alignment algorithm. Preferably, the chimeric hemagglutinin comprises all of the nucleotides of (a) to (v).

The invention also provides a chimeric hemagglutinin segment, having an ectodomain, a 5'-non-coding region, a 3'-non-coding region, a signal peptide, a transmembrane domain and a cytoplasmic domain wherein the ectodomain is from a first influenza strain and one or more of the 5'-non-coding region, the 3'-non-coding region, the signal peptide, the transmembrane domain and the cytoplasmic domain are from a second influenza strain, wherein the segment encodes a protein which does not have alanine in the position corresponding to amino acid 3 of SEQ ID NO: 63 when aligned to SEQ ID NO: 63 using a pairwise alignment algorithm; and/or which does not have asparagine in the position corresponding to amino acid 4 of SEQ ID NO: 63 when aligned to SEQ ID NO: 63 using a pairwise alignment algorithm; and/or which does not have alanine in the position corresponding to amino acid 11 of SEQ ID NO: 63 when aligned to SEQ ID NO: 63 using a pairwise alignment algorithm; and/or which does not have leucine in the position corresponding to amino acid 12 of SEQ ID NO: 63 when aligned to SEQ ID NO: 63 using a pairwise alignment algorithm; and/or which does not have alanine in the position corresponding to amino acid 13 of SEQ ID NO: 63 when aligned to SEQ ID NO: 63 using a pairwise alignment algorithm; and/or which does not have alanine in the position corresponding to amino acid 15 of SEQ ID NO: 63 when aligned to SEQ ID NO: 63 using a pairwise alignment algorithm; and/or which does not have aspartic acid in the position corresponding to amino acid 16 of SEQ ID NO: 63 when aligned to SEQ ID NO: 63 using a pairwise alignment algorithm.

In some aspects, the chimeric hemagglutinin segment may encode a protein which has one or more of valine in the position corresponding to amino acid 3 of SEQ ID NO: 63 when aligned to SEQ ID NO: 63 using a pairwise alignment algorithm; and/or lysine in the position corresponding to amino acid 4 of SEQ ID NO: 63 when aligned to SEQ ID NO: 63 using a pairwise alignment algorithm; and/or threonine in the position corresponding to amino acid 11 of SEQ ID NO: 63 when aligned to SEQ ID NO: 63 using a pairwise alignment algorithm; and/or phenylalanine in the position corresponding to amino acid 12 of SEQ ID NO: 63 when aligned to SEQ ID NO: 63 using a pairwise alignment algorithm; and/or threonine in the position corresponding to amino acid 13 of SEQ ID NO: 63 when aligned to SEQ ID NO: 63 using a pairwise alignment algorithm; and/or threonine in the position corresponding to amino acid 15 of SEQ ID NO: 63 when aligned to SEQ ID NO: 63 using a pairwise alignment algorithm; and/or tyrosine in the position corresponding to amino acid 16 of SEQ ID NO: 63 when aligned to SEQ ID NO: 63 using a pairwise alignment algorithm. The chimeric HA segment may comprise all of these amino acids which is preferred as reassortant influenza viruses comprising such a chimeric hemagglutinin segment give particularly good HA yields in cell culture.

The chimeric hemagglutinin segment may comprise one or more of the 5'-NCR domain of SEQ ID NO: 110; and/or the CT domain of SEQ ID NO: 111; and/or the TM domain of SEQ ID NO: 112; and/or the 3'-NCR of SEQ ID NO: 113.

The invention also provides a chimeric hemagglutinin segment, having an ectodomain, a 5'-non-coding region, a 3'-non-coding region, a signal peptide, a transmembrane domain and a cytoplasmic domain wherein the ectodomain is from a first influenza strain and one or more of the 5'-non-coding region, the 3'-non-coding region, the signal peptide, the transmembrane domain and the cytoplasmic domain are from a second influenza strain, wherein the segment comprises one or more (preferably all) of: guanine at position 24, adenine at position 38, thymine at position 40, thymine at position 53, adenine at position 63, thymine at position 66, adenine at position 69, adenine at position 75, thymine at position 78, guanine at position 1703, thymine at position 1715, adenine at position 1729, cytosine at position 1733, cytosine at position 1734, adenine at position 1746, and/or adenine at position 1751. All of these positions are relative to the corresponding position in SEQ ID NO: 15 when aligned to SEQ ID NO: 15 using a pairwise alignment algorithm.

The chimeric hemagglutinin segment may comprise one or more of the 5'-non-coding region, the 3'-non-coding region, the signal peptide, the transmembrane domain and the cytoplasmic domain from the 105p30 influenza strain, which is discussed below. Preferably, the chimeric hemagglutinin segment comprises all of the 5'-non-coding region, the 3'-non-coding region, the signal peptide, the transmembrane domain and the cytoplasmic domain from the 105p30 influenza strain as reassortant influenza viruses comprising such a chimeric hemagglutinin segment give particularly good HA yields in cell culture.

Also provided is a chimeric HA protein which is encoded by a chimeric HA segment of the invention.

The inventors have discovered that reassortant influenza viruses which comprise a chimeric HA segment of the invention can provide HA yields which are up to 5-fold higher in the same time frame and under the same conditions compared to a reassortant influenza virus which does not comprise a chimeric HA segment.

Further provided is a chimeric influenza neuraminidase segment having an ectodomain, a 5'-non-coding region, a 3'-non-coding region, a transmembrane domain and a cytoplasmic domain wherein the ectodomain is from a first influenza strain and one or more of the 5'-non-coding region, the 3'-non-coding region, the transmembrane domain and the cytoplasmic domain are from a second influenza strain which is not A/Puerto Rico/8/34 or A/WSN/33.

Also provided is a chimeric influenza neuraminidase segment having an ectodomain, a 5'-non-coding region, a 3'-non-coding region, a transmembrane domain and a cytoplasmic domain wherein the ectodomain is a first influenza strain and the 5'-non-coding region, the 3'-non-coding region, the transmembrane domain and the cytoplasmic domain are from a second influenza strain wherein the first and the second influenza strain are both influenza A strains or both influenza B strains.

The invention also provides a chimeric neuraminidase segment having an ectodomain, a 5'-non-coding region, a 3'-non-coding region, a transmembrane domain and a cytoplasmic domain, wherein the ectodomain is from a first influenza strain and one or more of the 5'-non-coding region, the 3'-non-coding region, the transmembrane domain and the cytoplasmic domain are from a second influenza strain, wherein the segment comprises one or more (preferably all) of: adenine in the position corresponding to nucleotide 13; and/or adenine in the position corresponding to nucleotide 35; and/or adenine in the position corresponding to nucleotide 60; and/or adenine in the position corresponding to nucleotide 63; and/or adenine in the position corresponding to nucleotide 65; and/or cytosine in the position corresponding to nucleotide 67; and/or adenine in the position corresponding to nucleotide 69; and/or adenine in the position corresponding to nucleotide 75; and/or thymine in the position corresponding to nucleotide 83; and/or guanine in the position corresponding to nucleotide 89; and/or adenine in the position corresponding to nucleotide 101; and/or thymine in the position corresponding to nucleotide 107; and/or thymine in the position corresponding to nucleotide 110; and/or guanine in the position corresponding to nucleotide 120; and/or cytosine in the position corresponding to nucleotide 121; and/or thymine in the position corresponding to nucleotide 125; and/or thymine in the position corresponding to nucleotide 127. All of these positions are relative to the corresponding position in SEQ ID NO: 16 when aligned to SEQ ID NO: 16 using a pairwise alignment algorithm.

The invention also provides a chimeric neuraminidase segment having an ectodomain, a 5'-non-coding region, a 3'-non-coding region, a transmembrane domain and a cytoplasmic domain, wherein the ectodomain is from a first influenza strain and one or more of the 5'-non-coding region, the 3'-non-coding region, the transmembrane domain and the cytoplasmic domain are from a second influenza strain, wherein the segment encodes a protein which does not have cysteine in the position corresponding to amino acid 14 of SEQ ID NO: 64 when aligned to SEQ ID NO: 64 using a pairwise alignment algorithm, and/or which does not have leucine in the position corresponding to amino acid 15 of SEQ ID NO: 64 when aligned to SEQ ID NO: 64 using a pairwise alignment algorithm; and/or which does not have valine in the position corresponding to amino acid 16 of SEQ ID NO: 64 when aligned to SEQ ID NO: 64 using a pairwise alignment algorithm; and/or which does not have valine in the position corresponding to amino acid 17 of SEQ ID NO: 64 when aligned to SEQ ID NO: 64 using a pairwise alignment algorithm; and/or which does not have leucine in the position corresponding to amino acid 19 of SEQ ID NO: 64 when aligned to SEQ ID NO: 64 using a pairwise alignment algorithm; and/or which does not have isoleucine in the position corresponding to amino acid 23 of SEQ ID NO: 64 when aligned to SEQ ID NO: 64 using a pairwise alignment algorithm; and/or which does not have isoleucine in the position corresponding to amino acid 34 of SEQ ID NO: 64 when aligned to SEQ ID NO: 64 using a pairwise alignment algorithm.

In some aspects, the chimeric neuraminidase segment may encode a protein which comprises one or more of: serine in the position corresponding to amino acid 14 of SEQ ID NO: 64 when aligned to SEQ ID NO: 64 using a pairwise alignment algorithm, and/or isoleucine in the position corresponding to amino acid 15 of SEQ ID NO: 64 when aligned to SEQ ID NO: 64 using a pairwise alignment algorithm; and/or alanine in the position corresponding to amino acid 16 of SEQ ID NO: 64 when aligned to SEQ ID NO: 64 using a pairwise alignment algorithm; and/or isoleucine in the position corresponding to amino acid 17 of SEQ ID NO: 64 when aligned to SEQ ID NO: 64 using a pairwise alignment algorithm; and/or isoleucine in the position corresponding to amino acid 19 of SEQ ID NO: 64 when aligned to SEQ ID NO: 64 using a pairwise alignment algorithm; and/or methionine in the position corresponding to amino acid 23 of SEQ ID NO: 64 when aligned to SEQ ID NO: 64 using a pairwise alignment algorithm; and/or alanine in the position corresponding to amino acid 34 of SEQ ID NO: 64 when aligned to SEQ ID NO: 64 using a pairwise alignment algorithm. The chimeric NA segment may comprise all of these amino acids which is preferred as reassortant influenza viruses comprising such a chimeric hemagglutinin segment give particularly good HA yields in cell culture.

The chimeric neuraminidase segment may comprise one or more of the 5'-NCR domain of SEQ ID NO: 110; and/or the CT domain of SEQ ID NO: 111; and/or the TM domain of SEQ ID NO: 112; and/or the 3'-NCR of SEQ ID NO: 113.

The invention also provides a chimeric neuraminidase segment having an ectodomain, a 5'-non-coding region, a 3'-non-coding region, a transmembrane domain and a cytoplasmic domain, wherein the ectodomain is from a first influenza strain and one or more of the 5'-non-coding region, the 3'-non-coding region, the transmembrane domain and the cytoplasmic domain are from a second influenza strain, wherein the segment comprises one or more (preferably all) of: adenine at position 13, adenine at position 35, adenine at position 63, adenine at position 65, cytosine at position 67, adenine at position 69, adenine at position 75, thymine at position 83, guanine at position 89, adenine at position 101, thymine at position 107, thymine at position 110, guanine at position 120, cytosine at position 121, thymine at position 125, cytosine at position 1385, thymine at position 1386, cytosine at position 1387, and/or guanine at position 1392. All of these positions are relative to the corresponding position in SEQ ID NO: 16 when aligned to SEQ ID NO: 16 using a pairwise alignment algorithm.

A chimeric neuraminidase segment may comprise one or more of the 5'-non-coding region, the 3'-non-coding region, the transmembrane domain and the cytoplasmic domain from the 105p30 influenza strain, which is discussed below. Preferably, the chimeric hemagglutinin segment comprises all of the 5'-non-coding region, the 3'-non-coding region, the transmembrane domain and the cytoplasmic domain from the 105p30 influenza strain as reassortant influenza viruses comprising such a chimeric neuraminidase segment give particularly good HA yields in cell culture.

Also provided is a chimeric NA protein which is encoded by a chimeric NA segment of the invention.

The inventors have discovered that reassortant influenza viruses which comprise a chimeric NA segment of the invention can provide HA yields which are up to 2-fold higher in the same time frame and under the same conditions compared to a reassortant influenza virus which does not comprise a chimeric NA segment.

The invention provides reassortant influenza viruses which comprise a chimeric HA and/or NA segment of the invention. Preferably, the reassortant influenza virus comprises both a chimeric HA and a chimeric NA segment of the invention as the inventors have discovered that such reassortant influenza viruses grow faster and give better HA yields than reassortant influenza viruses which comprise only a chimeric HA or a chimeric NA segment.

The invention also provides a reassortant influenza virus comprising:

a) a chimeric hemagglutinin protein having an ectodomain, a 5'-non-coding region, a 3'-non-coding region, a signal peptide, a transmembrane domain and a cytoplasmic domain wherein the ectodomain is from a first influenza strain and one or more of the 5'-non-coding region, the 3'-non-coding region, the signal peptide, the transmembrane domain and the cytoplasmic domain are from a second influenza strain; and/or a chimeric neuraminidase protein having an ectodomain, a 5'-non-coding region, a 3'-non-coding region, a transmembrane domain and a cytoplasmic domain wherein the ectodomain is from a first influenza strain and one or more of the non-coding regions, the cytoplasmic domain, and the transmembrane domain are from a second influenza strain; and (b) one or more of:

i. backbone segments from two or more different donor strains ii. backbone segments from two or more donor strains, wherein the PB1 and the PB2 segments are from the same donor strain;

iii. backbone segments from two or three donor strains, wherein each donor strain provides more than one backbone segment;

iv. backbone segments from two or more donor strains, wherein the PB1 segment is not from the A/Texas/1/77 influenza strain;

v. backbone segments from two or more donor strains, wherein at least the PA, NP, or M segment are not from A/Puerto Rico/8/34;

vi. backbone segments from two or more donor strains, wherein the HA segment and the PB1 segment are from different influenza A strains with the same influenza virus HA subtype.

These reassortant influenza viruses are particularly useful because the inventors have discovered that influenza viruses which comprise backbone segments from two or more influenza donor strains can grow faster in a culture host compared with reassortant influenza viruses which contain all backbone segments from the same donor strain. In particular, the inventors have found that influenza viruses which comprise backbone segments from two high-yield donor strains can produce higher yield reassortants with target vaccine-relevant HA/NA genes than reassortants made with either of the two original donor strains. The first and the second influenza strains are preferably both influenza A or influenza B strains The invention also provides a method of preparing a reassortant influenza virus comprising steps of (a) infecting a culture host with a reassortant influenza virus of the invention or a reassortant influenza virus produced by a method of the invention; (b) culturing the host from step (a) to produce the virus; and optionally (c) purifying the virus obtained in step (b).

The reassortant influenza virus may be formulated into a vaccine. The invention thus provides a method of preparing a vaccine, comprising steps of (a) preparing a reassortant influenza virus by a method according to the invention and (b) preparing a vaccine from the virus. Also, provided is a method of preparing a vaccine from a reassortant influenza virus of the invention.

Further provided is an expression system comprising one or more expression construct(s) encoding the vRNA of a reassortant influenza virus of the invention.

The Chimeric HA and NA Segments

The invention provides chimeric HA and NA segments.

Structurally, the influenza HA segment is composed of 5'- and 3'-non-coding regions (NCRs) which flank the HA segment's signal peptide (SP), transmembrane TM, cytoplasmic domain (CT) and ectodomain (see FIG. 4A). The HA ectodomain is the most important influenza antigen in influenza vaccines whilst the terminal domains (NCRs, SP, TM and CT) are of much less antigenic importance. The influenza NA segment also contains terminal domains which are the 5'- and 3'-NCRs, a CT domain and a TM domain, as well as an ectodomain, but NA does not contain a signal peptide (see FIG. 4C). The terminal domains are of much less antigenic importance than the NA ectodomain.

A skilled person can readily determine the sequences of the terminal domains within any given HA and NA segment. Furthermore, SEQ ID NOs 105-109 and SEQ ID NOs 114-118 give the sequences of the HA terminal domains of 105p30 and PR8X, respectively. SEQ ID NOs 110-114 and SEQ ID NOs 119-122 give the sequences of the terminal domains of 105p30 and PR8X, respectively. Using this sequence information a skilled person can find the corresponding domains in other HA and NA sequences.

The chimeric HA segment of the invention comprises the ectodomain from a vaccine strain and one or more of the terminal domains from a second influenza virus. The vaccine strain can be any influenza strain and is defined as the influenza strain which provides the HA ectodomain. The second influenza strain is different to the vaccine strain. The vaccine strain and the second influenza strain are preferably both influenza A strains or both influenza B strains.

The chimeric NA segment of the invention comprises the ectodomain from a first influenza strain and one or more of the terminal domains from a second influenza virus. The 'second influenza strain' is different from the 'first influenza strain'. The first and the second influenza strain are preferably both influenza A strains or both influenza B strains.

It is preferred that the chimeric HA and NA segment comprises all of the terminal domains from the second influenza strain as the inventors have shown that reassortant influenza viruses comprising such chimeric HA and/or NA proteins can grow particularly well in cell culture.

The 'second influenza strain' can be a strain which has the influenza A virus HA subtypes H1, H2, H3, H4, H5, H6, H7, H8, H9, H10, H11, H12, H13, H14, H15, H16 or H17. It may also have the influenza A virus NA subtypes N1, N2, N3, N4, N5, N6, N7, N8 or N9. It is preferred that the second influenza virus is a H1 influenza strain as the inventors have discovered that reassortant influenza viruses which contain such chimeric HA and/or NA segments grow particularly well in cell culture. Most preferably, the second influenza strain is 105p30 or PR8-X, as discussed below.

Where the chimeric HA segment comprises one or more terminal domains from 105p30, the 5'-NCR domain may have the sequence of SEQ ID NO: 105; and/or the SP of SEQ ID NO: 106; and/or the TM domain of SEQ ID NO: 107; and/or the CT domain of SEQ ID NO: 108; and/or the 3'-NCR of SEQ ID NO: 109. Preferably, the chimeric HA segment contains all of these sequences.

Where the chimeric NA segment comprises one or more terminal domains from 105p30, the 5'-NCR domain may have the sequence of SEQ ID NO: 110; and/or the CT domain of SEQ ID NO: 71; and/or the TM domain of SEQ ID NO: 112; and/or the 3'-NCR of SEQ ID NO: 113. Preferably, the chimeric NA segment contains all of these sequences.

Where the chimeric HA segment comprises one or more terminal domains from PR8-X, the 5'-NCR domain may have the sequence of SEQ ID NO: 114; and/or the SP of SEQ ID NO: 115; and/or the TM domain of SEQ ID NO: 116; and/or the CT domain of SEQ ID NO: 117; and/or the 3'-NCR of SEQ ID NO: 118. Preferably, the chimeric HA segment contains all of these sequences.

Where the chimeric NA segment comprises one or more terminal domains from PR8-X, the 5'-NCR domain may have the sequence of SEQ ID NO: 119; and/or the CT domain of SEQ ID NO: 120; and/or the TM domain of SEQ ID NO: 121; and/or the 3'-NCR of SEQ ID NO: 122. Preferably, the chimeric NA segment contains all of these sequences.

The second influenza strain can be an influenza B strain.

The ectodomain and the one or more terminal domains may all be from an influenza A virus or an influenza B virus. It is also possible to have the ectodomain from an influenza A virus and one or more of the terminal domains from an influenza B virus and vice versa. It is most preferred that all the segments in the chimeric HA or the chimeric NA segments are from influenza A strains or influenza B strains.

In some embodiments, the chimeric HA segments of the invention encode a protein which does not have tyrosine in the position corresponding to amino acid 545, when aligned to SEQ ID NO: 7.

Reassortant Viruses

The invention provides a reassortant influenza virus which comprises the chimeric HA and/or NA segments of the invention. The reassortant influenza virus comprises the HA ectodomain from a vaccine strain. The vaccine strain can be any influenza strain and is defined as the influenza strain which provides the HA ectodomain, irrespective of whether the HA ectodomain is comprised in a chimeric HA segment or not. The ectodomain of the NA segment (in a chimeric or a non-chimeric NA segment) may come from the vaccine strain or it may come from a different influenza strain.

One or more of the backbone segments (i.e. those encoding PB1, PB2, PA, NP, $M_1$, $M_2$, $NS_1$ and $NS_2$) of the reassortant influenza virus may come from a donor strain, which is an influenza virus that provides one or more of the backbone segments but which does not provide the ectodomain of the influenza HA segment. The ectodomain of the NA segment may also be provided by a donor strain or it may be provided by the vaccine strain. The reassortant influenza strains of the invention may also comprise one or more, but not all, of the backbone segments from the vaccine strain.

The donor strain may be the same as the 'second influenza strain' which provides the one or more terminal domains of the chimeric HA or NA segments. In these reassortant influenza viruses, the PA, M and/or NS segment(s) is/are preferably from the second influenza virus. The second influenza virus may also be different to the donor strain.

The reassortant influenza virus may grow to higher or similar viral titres in cell culture and/or in eggs in the same time (for example 12 hours, 24 hours, 48 hours or 72 hours) and under the same growth conditions compared to the wild-type vaccine strain. In particular, they can grow to higher or similar viral titres in MDCK cells (such as MDCK 33016) in the same time and under the same growth conditions compared to the wild-type vaccine strain. The viral titre can be determined by standard methods known to those of skill in the art. Usefully, the reassortant viruses of the invention may achieve a viral titre which is at least 5% higher, at least 10% higher, at least 20% higher, at least 50% higher, at least 100% higher, at least 200% higher, or at least 500% higher than the viral titre of the wild-type vaccine strain in the same time frame and under the same conditions. In addition, or alternatively, the reassortant influenza viruses of the invention may achieve a viral titre which is at least 5% higher, at least 10% higher, at least 20% higher, at least 50% higher, at least 100% higher, at least 200% higher, or at least 500% higher than the viral titre of a reassortant influenza virus which comprises the same viral segments expect that it does not have a chimeric HA or NA segment.

The reassortant influenza viruses may also grow to similar viral titres in the same time and under the same growth conditions compared to the wild-type vaccine strain. A similar titre in this context means that the reassortant influenza viruses grow to a titre which is within 3% of the viral titre achieved with the wild-type vaccine strain in the same time and under the same growth conditions (i.e. wild-type titre±3%).

The reassortant virus may also give HA yields which are at least 2-fold, at least 3-fold, at least 4-fold, at least 5-fold, at least 6-fold, at least 7-fold, at least 8-fold, at least 9-fold or at least 10-fold higher in cell culture and/or in eggs in the same time (for example 12 hours, 24 hours, 48 hours or 72 hours) and under the same growth conditions compared to the wild-type vaccine strain.

When the reassortant viruses of the invention are reassortants comprising the backbone segments from a single donor strain, the reassortant viruses will generally include segments from the donor strain and the vaccine strain in a ratio of 1:7, 2:6, 3:5, 4:4, 5:3, 6:2 or 7:1. Classical reassortants usually have a majority of segments from the donor strain, in particular a ratio of 6:2. Where only a single donor strain is used, it is preferred that all backbone segments are from PR8-X as such reassortant influenza viruses grow fast in cell culture.

The reassortant viruses of the invention can contain the backbone segments from two or more (i.e. three, four, five or six) donor strains. When the reassortant viruses comprise backbone segments from two donor strains, the reassortant virus will generally include segments from the first donor strain, the second donor strain and the vaccine strain in a ratio of 1:1:6, 1:2:5, 1:3:4, 1:4:3, 1:5:2, 1:6:1, 2:1:5, 2:2:4, 2:3:3, 2:4:2, 2:5:1, 3:1:2, 3:2:1, 4:1:3, 4:2:2, 4:3:1, 5:1:2, 5:2:1 or 6:1:1. The reassortant influenza viruses may also comprise viral segments from more than two, for example from three, four, five or six donor strains.

Where the reassortant influenza virus comprises backbone segments from two or three donor strains, each donor strain may provide more than one of the backbone segments of the reassortant influenza virus, but one or two of the donor strains can also provide only a single backbone segment.

Where the reassortant influenza virus comprises backbone segments from two, three, four or five donor strains, one or two of the donor strains may provide more than one of the backbone segments of the reassortant influenza virus. In general, the reassortant influenza virus cannot comprise more than six backbone segments. Accordingly, for example, if one of the donor strains provides five of the viral segments, the reassortant influenza virus can only comprise backbone segments from a total of two different donor strains.

In general a reassortant influenza virus will contain only one of each backbone segment. For example, when the influenza virus comprises the NP segment from A/California/07/09 it will not at the same time comprise the NP segment from another influenza strain.

The reassortant influenza virus may comprise the HA ectodomain from an influenza A strain. For example, the reassortant influenza virus may have the influenza A virus HA subtypes H1, H2, H3, H4, H5, H6, H7, H8, H9, H10, H11, H12, H13, H14, H15, H16 or H17. In addition, or alternatively, the reassortant influenza virus may comprise the NA ectodomain from an influenza A virus. For example, it may have the influenza A virus NA subtypes N1, N2, N3, N4, N5, N6, N7, N8 or N9. Where the vaccine strain is a seasonal influenza strain, it may have a H1 or H3 subtype. In one aspect of the invention the vaccine strain is a H1N1, a H3N2 or a H7N9 strain.

The reassortant influenza virus preferably comprises at least one backbone segment from the donor strain PR8-X. Thus, the influenza viruses of the invention may comprise one or more segments selected from: a PA segment having at least 95%, at least 96%, at least 97%, at least 98%, at least 99% or 100% identity to the sequence of SEQ ID NO: 9, a PB1 segment having at least 95%, at least 96%, at least 97%, at least 98%, at least 99% or 100% identity to the sequence of SEQ ID NO: 10, a PB2 segment having at least 95%, at least 96%, at least 97%, at least 98%, at least 99% or 100% identity to the sequence of SEQ ID NO: 11, a NP segment having at least 95%, at least 96%, at least 97%, at least 98%, at least 99% or 100% identity to the sequence of SEQ ID NO: 12, a M segment having at least 95%, at least 96%, at least 97%, at least 98%, at least 99% or 100% identity to the sequence of SEQ ID NO: 13, and/or a NS segment having at least 95%, at least 96%, at least 97%, at least 98%, at least 99% or 100% identity to the sequence of SEQ ID NO: 14. The reassortant influenza virus may comprise all of these backbone segments. This is particularly preferred as the inventors have shown that reassortant influenza viruses comprising a chimeric HA and/or NA segment in combination with this backbone grow particularly well in cell culture.

Alternatively, or in addition, the reassortant influenza virus may comprise one or more backbone viral segments from the 105p30 strain. Thus, where the reassortant influenza virus comprises one or more segments from the 105p30 strain, the viral segments may have sequences selected from: a PA segment having at least 95%, at least 96%, at least 97%, at least 98%, at least 99% or 100% identity to the sequence of SEQ ID NO: 42, a PB1 segment having at least 95%, at least 96%, at least 97%, at least 98%, at least 99% or 100% identity to the sequence of SEQ ID NO: 43, a PB2 segment having at least 95%, at least 96%, at least 97%, at least 98%, at least 99% or 100% identity to the sequence of SEQ ID NO: 44, a NP segment having at least 95%, at least 96%, at least 97%, at least 98%, at least 99% or 100% identity to the sequence of SEQ ID NO: 45, a M segment having at least 95%, at least 96%, at least 97%, at least 98%, at least 99% or 100% identity to the sequence of SEQ ID NO: 46, and/or a NS segment having at least 95%, at least 96%, at least 97%, at least 98%, at least 99% or 100% identity to the sequence of SEQ ID NO: 47. The reassortant influenza virus may comprise all of these backbone segments.

Reassortant influenza viruses with backbone segments from two or more influenza donor strains may comprise the HA segment and the PB1 segment from different influenza strains. In these reassortant influenza viruses the PB1 segment may be from donor viruses with the same influenza virus HA subtype as the vaccine strain. For example, the PB1 segment and the HA segment may both be from influenza viruses with a H1 subtype. The reassortant influenza viruses may also comprise the HA segment and the PB1 segment from different influenza strains with different influenza virus HA subtypes, wherein the PB1 segment is not from an influenza virus with a H3 HA subtype and/or wherein the HA segment is not from an influenza virus with a H1 or H5 HA subtype. For example, the PB1 segment may be from a H1 virus and/or the HA segment may be from a H3 influenza virus. Where the reassortants contain viral segments from more than one influenza donor strain, the further donor strain(s) can be any donor strain. For example, some of the viral segments may be from the A/Puerto Rico/8/34 or A/Ann Arbor/6/60 influenza strains. Reassortants containing viral segments from the A/Ann Arbor/6/60 strain may be advantageous, for example, where the reassortant virus is to be used in a live attenuated influenza vaccine.

The reassortant influenza virus may also comprise backbone segments from two or more influenza donor strains, wherein the PB1 segment is from the A/California/07/09 influenza strain. This segment may have at least 95% identity, at least 96% identity, at least 97% identity, at least 98% identity, at least 99% identity or 100% identity with the sequence of SEQ ID NO: 24. The reassortant influenza virus may have the H1 HA subtype. It will be understood that a reassortant influenza virus according to this aspect of the invention will not comprise the HA and/or NA segments from A/California/07/09.

The reassortant influenza strain may comprise the HA ectodomain and/or the NA ectodomain from an A/California/4/09 strain. Thus, for instance, the HA gene segment may encode a H1 hemagglutinin whose ectodomain is more closely related to SEQ ID NO: 70 than to SEQ ID NO: 50 (i.e. has a higher degree sequence identity when compared to SEQ ID NO: 70 than to SEQ ID NO: 50 using the same algorithm and parameters). SEQ ID NOs: 70 and 50 are 80% identical. Similarly, the NA gene may encode a N1 neuraminidase which is more closely related to SEQ ID NO: 99 than to SEQ ID NO: 51. SEQ ID NOs: 99 and 51 are 82% identical.

The reassortant influenza virus may also comprise at least one backbone viral segment from the A/California/07/09 influenza strain. When the at least one backbone viral segment is the PA segment it may have a sequence having at least 95%, at least 96%, at least 97% or at least 99% identity with the sequence of SEQ ID NO: 23. When the at least one backbone viral segment is the PB1 segment, it may have a sequence having at least 95%, at least 96%, at least 97% or at least 99% identity with the sequence of SEQ ID NO: 24. When the at least one backbone viral segment is the PB2 segment, it may have a sequence having at least 95%, at least 96%, at least 97% or at least 99% identity with the sequence of SEQ ID NO: 25. When the at least one backbone viral segment is the NP segment it may have a sequence having at least 95%, at least 96%, at least 97% or at least 99% identity with the sequence of SEQ ID NO: 26. When the at least one backbone viral segment is the M segment it may have a sequence having at least 95%, at least 96%, at least 97% or at least 99% identity with the sequence of SEQ ID NO: 27. When the at least one backbone viral segment is the NS segment it may have a sequence having at least 95%, at least 96%, at least 97% or at least 99% identity with the sequence of SEQ ID NO: 28.

Where a reassortant influenza virus comprises the PB1 segment from A/Texas/1/77, it preferably does not comprise the PA, NP or M segment from A/Puerto Rico/8/34. Where a reassortant influenza A virus comprises the PA, NP or M segment from A/Puerto Rico/8/34, it preferably does not comprise the PB1 segment from A/Texas/1/77. In some embodiments, the invention does not encompass reassortant influenza viruses which have the PB1 segment from A/Texas/1/77 and the PA, NP and M segments from A/Puerto Rico/8/34. The PB1 protein from A/Texas/1/77 may have the sequence of SEQ ID NO: 29 and the PA, NP or M proteins from A/Puerto Rico/8/34 may have the sequence of SEQ ID NOs 30, 31 or 32, respectively.

Particularly preferred are reassortant influenza viruses which comprise a chimeric HA and/or NA segment according to the invention (preferably both), the NP, PB1 and PB2 segments from 105p30 and the M, NS and PA segments from PR8-X. Also particularly preferred are reassortant influenza viruses which comprise a chimeric HA and/or NA segment according to the invention (preferably both), the PB1 segment from A/California/4/09 and the other backbone segments from PR8-X. Such reassortant influenza viruses are preferred because the inventors have found that they grow very well in cell culture and provide very good HA yields.

The backbone viral segments may encode viral proteins which are optimized for culture in the specific culture host. For example, where the reassortant influenza viruses are cultured in mammalian cells, it is advantageous to adapt at least one of the viral segments for optimal growth in the culture host. For instance, where the expression host is a canine cell, such as a MDCK cell line, the viral segments may encode proteins which have a sequence that optimises viral growth in the cell. Thus, the reassortant influenza viruses of the invention may comprise a PB2 segment which encodes a PB2 protein that has lysine in the position corresponding to amino acid 389 of SEQ ID NO: 3 when aligned to SEQ ID NO: 3 using a pairwise alignment algorithm, and/or asparagine in the position corresponding to amino acid 559 of SEQ ID NO: 3 when aligned to SEQ ID NO: 3 using a pairwise alignment algorithm. Also provided are reassortant influenza viruses in accordance with the invention in which the PA segment encodes a PA protein that has lysine in the position corresponding to amino acid 327 of SEQ ID NO: 1 when aligned to SEQ ID NO: 1 using a pairwise alignment algorithm, and/or aspartic acid in the position corresponding to amino acid 444 of SEQ ID NO: 1 when aligned to SEQ ID NO: 1, using a pairwise alignment algorithm, and/or aspartic acid in the position corresponding to amino acid 675 of SEQ ID NO: 1 when aligned to SEQ ID NO: 1, using a pairwise alignment algorithm. The reassortant influenza strains of the invention may also have a NP segment which encodes a NP protein with threonine in the position corresponding to amino acid 27 of SEQ ID NO: 4 when aligned to SEQ ID NO: 4 using a pairwise alignment algorithm, and/or asparagine in the position corresponding to amino acid 375 of SEQ ID NO: 4 when aligned to SEQ ID NO: 4, using a pairwise alignment algorithm. Variant influenza strains may also comprise two or more of these mutations. It is preferred that the variant influenza virus contains a variant PB2 protein with both of the amino acids changes identified above, and/or a PA protein which contains all three of the amino acid changes identified above, and/or a NP protein which contains both of the amino acid changes identified above. The influenza virus may be a H1 strain.

Alternatively, or in addition, the reassortant influenza viruses may comprise a PB1 segment which encodes a PB1 protein that has isoleucine in the position corresponding to amino acid 200 of SEQ ID NO: 2 when aligned to SEQ ID NO: 2 using a pairwise alignment algorithm, and/or asparagine in the position corresponding to amino acid 338 of SEQ ID NO: 2 when aligned to SEQ ID NO: 2 using a pairwise alignment algorithm, and/or isoleucine in the position corresponding to amino acid 529 of SEQ ID NO: 2 when aligned to SEQ ID NO: 2 using a pairwise alignment algorithm, and/or isoleucine in the position corresponding to amino acid 591 of SEQ ID NO: 2 when aligned to SEQ ID NO: 2 using a pairwise alignment algorithm, and/or histidine in the position corresponding to amino acid 687 of SEQ ID NO: 2 when aligned to SEQ ID NO: 2 using a pairwise alignment algorithm, and/or lysine in the position corresponding to amino acid 754 of SEQ ID NO: 2 when aligned to SEQ ID NO: 2 using a pairwise alignment algorithm.

The choice of donor strain for use in the methods of the invention can depend on the vaccine strain which is to be reassorted. As reassortants between evolutionary distant strains might not replicate well in cell culture, it is possible that the donor strain and the vaccine strain have the same HA and/or NA subtype. In other embodiments, however, the vaccine strain and the donor strain can have different HA and/or NA subtypes, and this arrangement can facilitate selection for reassortant viruses that contain the HA and/or NA segment from the vaccine strain. Therefore, although the 105p30 and PR8-X strains contain the H1 influenza subtype these donor strains can be used for vaccine strains which do not contain the H1 influenza subtype.

Thus, an influenza virus may comprises one, two, three, four, five, six or seven viral segments from the 105p30 or PR8-X strains and a HA segment which is not of the H1 subtype. The reassortant donor strains may further comprise an NA segment which is not of the N1 subtype.

Strains which can be used as vaccine strains include strains which are resistant to antiviral therapy (e.g. resistant to oseltamivir [8] and/or zanamivir), including resistant pandemic strains [9].

The reassortant influenza virus may be an influenza B virus. For example, the reassortant influenza virus may comprises the HA ectodomain from a first influenza B virus and the NP and/or PB2 segment from a second influenza B virus which is a B/Victoria/2/87-like strain. The B/Victoria/2/87-like strain may be B/Brisbane/60/08.

The reassortant influenza B virus may comprise the HA ectodomain from a first influenza B virus and the NP segment from a second influenza B virus which is not B/Lee/40 or B/Ann Arbor/1/66 or B/Panama/45/90. For example, the reassortant influenza B virus may have a NP segment which does not have the sequence of SEQ ID NOs: 80, 100, 103 or 104. The reassortant influenza B virus may also have a NP segment which does not encode the protein of SEQ ID NOs: 19, 23, 44 or 45. The reassortant influenza B virus may comprise both the NP and PB2 segments from the second influenza B virus. The second influenza B virus is preferably a B/Victoria/2/87-like strain. The B/Victoria/2/87-like strain may be B/Brisbane/60/08.

The reassortant influenza B virus may comprise the HA ectodomain from a B/Yamagata/16/88-like strain and at least one backbone segment from a B/Victoria/2/87-like strain. The reassortant influenza B virus may comprise two, three, four, five or six backbone segments from the B/Victoria/2/87-like strain. In a preferred embodiment, the reassortant influenza B virus comprises all the backbone segments from the B/Victoria/2/87-like strain. The B/Victoria/2/87-like strain may be B/Brisbane/60/08.

The reassortant influenza B virus may comprise viral segments from a B/Victoria/2/87-like strain and a B/Yamagata/16/88-like strain, wherein the ratio of segments from the B/Victoria/2/87-like strain and the B/Yamagata/16/88-like strain is 1:7, 2:6, 4:4, 5:3, 6:2 or 7:1. A ratio of 7:1, 6:2, 4:4, 3:4 or 1:7, in particular a ratio of 4:4, is preferred because such reassortant influenza B viruses grow particularly well in a culture host. The B/Victoria/2/87-like strain may be B/Brisbane/60/08. The B/Yamagata/16/88-like strain may be B/Panama/45/90. In these embodiments, the reassortant influenza B virus usually does not comprise all backbone segments from the same influenza B donor strain.

The reassortant influenza B virus may comprise:

a) the PA segment of SEQ ID NO: 71, the PB1 segment of SEQ ID NO: 72, the PB2 segment of SEQ ID NO: 73, the NP segment of SEQ ID NO: 74, the NS segment of SEQ ID NO: 76 and the M segment of SEQ ID NO: 75; or b) the PA segment of SEQ ID NO: 71, the PB1 segment of SEQ ID NO: 78, the PB2 segment of SEQ ID NO: 73, the NP segment of SEQ ID NO: 74, the NS segment of SEQ ID NO: 82 and the M segment of SEQ ID NO: 81; or
c) the PA segment of SEQ ID NO: 71, the PB1 segment of SEQ ID NO: 78, the PB2 segment of SEQ ID NO: 79, the NP segment of SEQ ID NO: 74, the NS segment of SEQ ID NO: 76 and the M segment of SEQ ID NO: 75; or
d) the PA segment of SEQ ID NO: 30, the PB1 segment of SEQ ID NO: 72, the PB2 segment of SEQ ID NO: 73, the NP segment of SEQ ID NO: 74, the NS segment of SEQ ID NO: 76 and the M segment of SEQ ID NO: 75, or
e) the PA segment of SEQ ID NO: 71, the PB1 segment of SEQ ID NO: 72, the PB2 segment of SEQ ID NO: 73, the NP segment of SEQ ID NO: 74, the NS segment of SEQ ID NO: 82 and the M segment of SEQ ID NO: 81.

Influenza B viruses currently do not display different HA subtypes, but influenza B virus strains do fall into two distinct lineages. These lineages emerged in the late 1980s and have HAs which can be antigenically and/or genetically distinguished from each other [10]. Current influenza B virus strains are either B/Victoria/2/87-like or B/Yamagata/16/88-like. These strains are usually distinguished antigenically, but differences in amino acid sequences have also been described for distinguishing the two lineages e.g. B/Yamagata/16/88-like strains often (but not always) have HA proteins with deletions at amino acid residue 164, numbered relative to the 'Lee40' HA sequence [11]. In some embodiments, the reassortant influenza B viruses of the invention may comprise viral segments from a B/Victoria/2/87-like strain. They may comprise viral segments from a B/Yamagata/16/88-like strain. Alternatively, they may comprise viral segments from a B/Victoria/2/87-like strain and a B/Yamagata/16/88-like strain.

Where the reassortant influenza B virus comprises viral segments from two or more influenza B virus strains, these viral segments may be from influenza strains which have related neuraminidases. For instance, the influenza strains which provide the viral segments may both have a B/Victoria/2/87-like neuraminidase [12] or may both have a B/Yamagata/16/88-like neuraminidase. For example, two B/Victoria/2/87-like neuraminidases may both have one or more of the following sequence characteristics: (1) not a serine at residue 27, but preferably a leucine; (2) not a glutamate at residue 44, but preferably a lysine; (3) not a threonine at residue 46, but preferably an isoleucine; (4) not a proline at residue 51, but preferably a serine; (5) not an arginine at residue 65, but preferably a histidine; (6) not a glycine at residue 70, but preferably a glutamate; (7) not a leucine at residue 73, but preferably a phenylalanine; and/or (8) not a proline at residue 88, but preferably a glutamine. Similarly, in some embodiments the neuraminidase may have a deletion at residue 43, or it may have a threonine; a deletion at residue 43, arising from a trinucleotide deletion in the NA gene, which has been reported as a characteristic of B/Victoria/2/87-like strains, although recent strains have regained Thr-43 [12]. Conversely, of course, the opposite characteristics may be shared by two B/Yamagata/16/88-like neuraminidases e.g. S27, E44, T46, P51, R65, G70, L73, and/or P88. These amino acids are numbered relative to the 'Lee40' neuraminidase sequence [13]. The reassortant influenza B virus may comprise a NA segment with the characteristics described above. Alternatively, or in addition, the reassortant influenza B virus may comprise a viral segment (other than NA) from an influenza strain with a NA segment with the characteristics described above.

The backbone viral segments of an influenza B virus which is a B/Victoria/2/87-like strain can have a higher level of identity to the corresponding viral segment from B/Victoria/2/87 than it does to the corresponding viral segment of B/Yamagata/16/88 and vice versa. For example, the NP segment of B/Panama/45/90 (which is a B/Yamagata/16/88-like strain) has 99% identity to the NP segment of B/Yamagata/16/88 and only 96% identity to the NP segment of B/Victoria/2/87.

Where the reassortant influenza B virus of the invention comprises a backbone viral segment from a B/Victoria/2/87-like strain, the viral segments may encode proteins with the following sequences. The PA protein may have at least 97% identity, at least 98%, at least 99% identity or 100% identity to the sequence of SEQ ID NO: 83. The PB1 protein may have at least 97% identity, at least 98%, at least 99% identity or 100% identity to the sequence of SEQ ID NO: 84. The PB2 protein may have at least 97%, at least 98%, at least 99% or 100% identity with the sequence of SEQ ID NO: 85. The NP protein may have at least 97% identity, at least 98%, at least 99% identity or 100% identity to the sequence of SEQ ID NO: 86. The $M_1$ protein may have at least 97% identity, at least 98%, at least 99% identity or 100% identity to the sequence of SEQ ID NO: 87. The $M_2$ protein may have at least 97% identity, at least 98%, at least 99% identity or 100% identity to the sequence of SEQ ID NO: 88. The $NS_1$ protein may have at least 97% identity, at least 98%, at least 99% identity or 100% identity to the sequence of SEQ ID NO: 89. The $NS_2$ protein may have at least 97% identity, at least 98%, at least 99% identity or 100% identity to the sequence of SEQ ID NO: 90. In some embodiments, the reassortant influenza B virus may also comprise all of these backbone segments.

Where the reassortant influenza B viruses of the invention comprise a backbone viral segment from a B/Yamagata/16/88-like strain, the viral segment may encode proteins with the following sequences. The PA protein may have at least 97% identity, at least 98%, at least 99% identity or 100% identity to the sequence of SEQ ID NO: 91. The PB1 protein may have at least 97% identity, at least 98%, at least 99% identity or 100% identity to the sequence of SEQ ID NO: 92. The PB2 protein may have at least 97%, at least 98%, at least 99% or 100% identity with the sequence of SEQ ID NO: 93. The NP protein may have at least 97% identity, at least 98%, at least 99% identity or 100% identity to the sequence of SEQ ID NO: 94. The $M_1$ protein may have at least 97% identity, at least 98%, at least 99% identity or 100% identity to the sequence of SEQ ID NO: 95. The $M_2$ protein may have at least 97% identity, at least 98%, at least 99% identity or 100% identity to the sequence of SEQ ID NO: 96. The $NS_1$ protein may have at least 97% identity, at least 98%, at least 99% identity or 100% identity to the sequence of SEQ ID NO: 97. The $NS_2$ protein may have at least 97% identity, at least 98%, at least 99% identity or 100% identity to the sequence of SEQ ID NO: 98.

The invention can be practised with donor strains having a viral segment that has at least about 70%, at least about 75%, at least about 80%, at least about 85%, at least about 90%, at least about 95% or at least about 99%, or 100% identity to a sequence of SEQ ID NOs 71-76 or 77-82. Due to the degeneracy of the genetic code, it is possible to have the same polypeptide encoded by several nucleic acids with different sequences. For example, the nucleic acid sequences of SEQ ID NOs: 33 and 34 have only 73% identity even though they encode the same viral protein. Thus, the invention may be practised with viral segments that encode the same polypeptides as the sequences of SEQ ID NOs 71-76 or 77-82.

The reassortant influenza virus may comprise segments from a vaccine strain which is an inter-pandemic (seasonal) influenza vaccine strain. It may also comprise segments from a vaccine strain which is a pandemic strain or a potentially pandemic strain. The characteristics of an influenza strain that give it the potential to cause a pandemic outbreak are: (a) it contains a new hemagglutinin compared to the hemagglutinins in currently-circulating human strains, i.e. one that has not been evident in the human population for over a decade (e.g. H2), or has not previously been seen at all in the human population (e.g. H5, H6 or H9, that have generally been found only in bird populations), such that the human population will be immunologically naïve to the strain's hemagglutinin; (b) it is capable of being transmitted horizontally in the human population; and (c) it is pathogenic to humans. A vaccine strain with H5 hemagglutinin type is preferred where the reassortant virus is used in vaccines for immunizing against pandemic influenza, such as a H5N1 strain. Other possible strains include H5N3, H9N2, H2N2, H7N1, H7N7 and H7N9, and any other emerging potentially pandemic strains. The invention is particularly suitable for producing reassortant viruses for use in vaccine for protecting against potential pandemic virus strains that can or have spread from a non-human animal population to humans, for example a swine-origin H1N1 influenza strain.

Expression Constructs

The invention provides an expression construct which encodes the chimeric HA or NA segments of the invention. Further provided are expression constructs which encode the viral segments of a reassortant influenza virus of the invention.

The invention also provides an expression construct encoding the HA and/or NA terminal domains of the chimeric HA and/or NA segments of the invention. These expression constructs are useful because the HA and NA ectodomains which need to be included in influenza vaccines change every season. The expression construct of this aspect of the invention may further encode one or more of the backbone segments. By including the terminal domains in the expression construct, it is necessary only to clone the ectodomain of the HA and/or NA segments of the circulating strain in order to provide the chimeric HA and/or NA molecule. The expression construct may comprise a restriction site between the SP and the TM domain which is useful as it facilitates cloning of the ectodomain. It is understood that the ectodomain needs to be cloned in frame with the terminal domains but this is well within the capabilities of a skilled person.

Expression constructs may be uni-directional or bi-directional expression constructs. Where more than one expression construct is used to express the viral segments of a reassortant influenza virus, it is possible to use uni-directional and/or bi-directional expression.

As influenza viruses require a protein for infectivity, it is generally preferred to use bi-directional expression constructs as this reduces the total number of expression constructs required by the host cell. Thus, the method of the invention may utilise at least one bi-directional expression construct wherein a gene or cDNA is located between an upstream pol II promoter and a downstream non-endogenous pol I promoter. Transcription of the gene or cDNA from the pol II promoter produces capped positive-sense viral mRNA which can be translated into a protein, while transcription from the non-endogenous pol I promoter produces negative-sense vRNA. The bi-directional expression construct may be a bi-directional expression vector.

Bi-directional expression constructs contain at least two promoters which drive expression in different directions (i.e. both 5' to 3' and 3' to 5') from the same construct. The two promoters can be operably linked to different strands of the same double stranded DNA. Preferably, one of the promoters is a pol I promoter and at least one of the other promoters is a pol II promoter. This is useful as the pol I promoter can be used to express uncapped vRNAs while the pol II promoter can be used to transcribe mRNAs which can subsequently be translated into proteins, thus allowing simultaneous expression of RNA and protein from the same construct. Where more than one expression construct is used within an expression system, the promoters may be a mixture of endogenous and non-endogenous promoters.

The pol I and pol II promoters used in the expression constructs may be endogenous to an organism from the same taxonomic order from which the host cell is derived. Alternatively, the promoters can be from an organism in a different taxonomic order than the host cell. The term "order" refers to conventional taxonomic ranking, and examples of orders are primates, rodentia, carnivora, marsupialia, cetacean, etc. Humans and chimpanzees are in the same taxonomic order (primates), but humans and dogs are in different orders (primates vs. carnivora). For example, the human pol I promoter can be used to express viral segments in canine cells (e.g. MDCK cells) [14].

The expression construct will typically include an RNA transcription termination sequence. The termination sequence may be an endogenous termination sequence or a termination sequence which is not endogenous to the host cell. Suitable termination sequences will be evident to those of skill in the art and include, but are not limited to, RNA polymerase I transcription termination sequence, RNA polymerase II transcription termination sequence, and ribozymes. Furthermore, the expression constructs may contain one or more polyadenylation signals for mRNAs, particularly at the end of a gene whose expression is controlled by a pol II promoter.

An expression construct may be a vector, such as a plasmid or other episomal construct. Such vectors will typically comprise at least one bacterial and/or eukaryotic origin of replication. Furthermore, the vector may comprise a selectable marker which allows for selection in prokaryotic and/or eukaryotic cells. Examples of such selectable markers are genes conferring resistance to antibiotics, such as ampicillin or kanamycin. The vector may further comprise one or more multiple cloning sites to facilitate cloning of a DNA sequence.

As an alternative, an expression construct may be a linear expression construct. Such linear expression constructs will typically not contain any amplification and/or selection sequences. However, linear constructs comprising such amplification and/or selection sequences are also within the scope of the present invention. Reference 15 describes a linear expression construct which describes individual linear expression constructs for each viral segment. It is also possible to include more than one, for example two, three four, five or six viral segments on the same linear expression construct. Such a system has been described, for example, in reference 16.

Expression constructs can be generated using methods known in the art. Such methods were described, for example, in reference 17. Where the expression construct is a linear expression construct, it is possible to linearise it before introduction into the host cell utilising a single restriction enzyme site. Alternatively, it is possible to excise the expression construct from a vector using at least two restriction enzyme sites. Furthermore, it is also possible to obtain a linear expression construct by amplifying it using a nucleic acid amplification technique (e.g. by PCR).

The expression constructs may be non-bacterial expression constructs. This means that the construct can drive expression in a eukaryotic cell of viral RNA segments encoded therein, but it does not include components which would be required for propagation of the construct in bacteria. Thus the construct will not include a bacterial origin of replication (ori), and usually will not include a bacterial selection marker (e.g. an antibiotic resistance marker). Such expression constructs are described in reference 18 which is incorporated by reference.

The expression constructs may be prepared by chemical synthesis. The expression constructs may either be prepared entirely by chemical synthesis or in part. Suitable methods for preparing expression constructs by chemical synthesis are described, for example, in reference 18.

The expression constructs of the invention can be introduced into host cells using any technique known to those of skill in the art. For example, expression constructs of the invention can be introduced into host cells by employing electroporation, DEAE-dextran, calcium phosphate precipitation, liposomes, microinjection, or microparticle-bombardment.

The expression construct(s) can be introduced into the same cell type which is subsequently used for the propagation of the influenza viruses. Alternatively, the cells into which the expression constructs are introduced and the cells used for propagation of the influenza viruses may be different.

In some embodiments, cells may be added following the introduction of the expression construct(s) into the cell, as described in reference 19. This is particularly preferred because it increases the rescue efficiency of the viruses further and can thus help to reduce the time required for viral rescue. The cells which are added may be of the same or a different cell type as the cell into which the expression construct (a) is/are introduced, but it is preferred to use cells of the same cell type as this facilitates regulatory approval and avoids conflicting culture conditions.

The invention also provides an expression system which comprises one or more of the expression constructs of the invention. The expression system may comprise one or more expression constructs which encode all the viral segments of a reassortant influenza virus of the invention.

The expression system may comprise at least two, at least three, at least four, at least five, at least six, at least seven, at least eight, at least nine, at least ten, at least eleven or at least twelve expression constructs.

Reverse Genetics

The invention is particularly suitable for producing the reassortant influenza viruses of the invention through reverse genetics techniques where the viruses are produced in culture hosts using an expression system which comprises one or more of the expression constructs of the invention. In these techniques, it is understood that the virus is produced from the expression construct(s) in the expression system.

Reverse genetics for influenza A and B viruses can be practised with 12 plasmids to express the four proteins required to initiate replication and transcription (PB1, PB2, PA and NP) and all eight viral genome segments. To reduce the number of constructs, however, a plurality of RNA polymerase I transcription cassettes (for viral RNA synthesis) can be included on a single plasmid (e.g. sequences encoding 1, 2, 3, 4, 5, 6, 7 or all 8 influenza vRNA segments), and a plurality of protein-coding regions with RNA polymerase II promoters on another plasmid (e.g. sequences encoding 1, 2, 3, 4, 5, 6, 7 or 8 influenza mRNA transcripts) [20]. It is also possible to include one or more influenza vRNA segments under control of a pol I promoter and one or more influenza protein coding regions under control of another promoter, in particular a pol II promoter, on the same plasmid. This is preferably done by using bi-directional plasmids.

Preferred aspects of the reference 20 method involve: (a) PB1, PB2 and PA mRNA-encoding regions on a single expression construct; and (b) all 8 vRNA encoding segments on a single expression construct. Including the neuraminidase (NA) and hemagglutinin (HA) segments on one expression construct and the six other viral segments on another expression construct is particularly preferred as newly emerging influenza virus strains usually have mutations in the NA and/or HA segments. Therefore, the advantage of having the HA and/or NA segments on a separate expression construct is that only the vector comprising the HA and NA sequence needs to be replaced. Thus, in one aspect of the invention the NA and/or HA segments of the vaccine strain may be included on one expression construct and the vRNA encoding segments from the donor strain(s) of the invention, excluding the HA and/or NA segment(s), are included on a different expression construct. The invention thus provides an expression construct comprising one, two, three, four, five or six vRNA encoding backbone viral segments of a donor strain of the invention. The expression construct may not comprise HA and/or NA viral segments that produce a functional HA and/or NA protein.

Known reverse genetics systems involve expressing DNA molecules which encode desired viral RNA (vRNA) molecules from pol I promoters, bacterial RNA polymerase promoters, bacteriophage polymerase promoters, etc. As influenza viruses require the presence of viral polymerase to initiate the life cycle, systems may also provide these proteins e.g. the system further comprises DNA molecules that encode viral polymerase proteins such that expression of both types of DNA leads to assembly of a complete infectious virus. It is also possible to supply the viral polymerase as a protein.

Where reverse genetics is used for the expression of influenza vRNA, it will be evident to the person skilled in the art that precise spacing of the sequence elements with reference to each other is important for the polymerase to initiate replication. It is therefore important that the DNA molecule encoding the viral RNA is positioned correctly between the pol I promoter and the termination sequence, but this positioning is well within the capabilities of those who work with reverse genetics systems.

In order to produce a recombinant virus, a cell must express all segments of the viral genome which are necessary to assemble a virion. DNA cloned into the expression constructs of the present invention preferably provides all of the viral RNA and proteins, but it is also possible to use a helper virus to provide some of the RNA and proteins, although systems which do not use a helper virus are preferred. As the influenza virus is a segmented virus, the viral genome will usually be expressed using more than one expression construct in the methods of the invention. It is also envisioned, however, to combine one or more segments or even all segments of the viral genome on a single expression construct.

In some embodiments an expression construct will also be included which leads to expression of an accessory protein in the host cell. For instance, it can be advantageous to express a non-viral serine protease (e.g. trypsin) as part of a reverse genetics system.

Cells

The culture host for use in the invention can be any eukaryotic cell that can produce the virus of interest. The invention will typically use a cell line although, for example, primary cells may be used as an alternative. The cell will typically be mammalian or avian. Suitable mammalian cells include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line [21-23]. Suitable dog cells are e.g. kidney cells, as in the CLDK and MDCK cell lines.

Further suitable cells include, but are not limited to: CHO; 293T; BHK; MRC 5; PER.C6 [24]; FRhL2; WI-38; etc. Suitable cells are widely available e.g. from the American Type Cell Culture (ATCC) collection [25], from the Coriell Cell Repositories [26], or from the European Collection of Cell Cultures (ECACC). For example, the ATCC supplies various different Vero cells under catalogue numbers CCL 81, CCL 81.2, CRL 1586 and CRL-1587, and it supplies MDCK cells under catalogue number CCL 34. PER.C6 is available from the ECACC under deposit number 96022940.

Preferred cells for use in the invention are MDCK cells [27-29], derived from Madin Darby canine kidney. The original MDCK cells are available from the ATCC as CCL 34. It is preferred that derivatives of MDCK cells are used. Such derivatives were described, for instance, in reference 27 which discloses MDCK cells that were adapted for growth in suspension culture ('MDCK 33016' or '33016-PF', deposited as DSM ACC 2219). Furthermore, reference 30 discloses MDCK-derived cells that grow in suspension in serum free culture (B-702', deposited as FERM BP-7449). In some embodiments, the MDCK cell line used may be tumorigenic. It is also envisioned to use non-tumorigenic MDCK cells. For example, reference 31 discloses non tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (ATCC PTA-6503). Reference 32 discloses MDCK cells with high susceptibility to infection, including 'MDCK.5F1' cells (ATCC CRL 12042).

The cells used in the methods of the invention are preferably cells which are suitable for producing an influenza vaccine that can be used for administration to humans. Such cells must be derived from a cell bank system which is approved for vaccine manufacture and registered with a national control authority, and must be within the maximum number of passages permitted for vaccine production (see reference 33 for a summary). Examples of suitable cells which have been approved for vaccine manufacture include MDCK cells (like MDCK 33016; see reference 27), CHO cells, Vero cells, and PER.C6 cells. The methods of the invention may not use 293T cells as these cells are not approved for vaccine manufacture.

It is possible to use a mixture of more than one cell type to practise the methods of the present invention. However, it is preferred that the methods of the invention are practised with a single cell type e.g. with monoclonal cells. Preferably, the cells used in the methods of the present invention are from a single cell line. Furthermore, the same cell line may be used for reassorting the virus and for any subsequent propagation of the virus.

Preferably, the cells are cultured in the absence of serum, to avoid a common source of contaminants. Various serum-free media for eukaryotic cell culture are known to the person skilled in the art (e.g. Iscove's medium, ultra CHO medium (BioWhittaker), EX-CELL (JRH Biosciences)). Furthermore, protein-free media may be used (e.g. PF-CHO (JRH Biosciences)). Otherwise, the cells for replication can also be cultured in the customary serum-containing media (e.g. MEM or DMEM medium with 0.5% to 10% of fetal calf serum).

The cells may be in adherent culture or in suspension.

Virus Preparation

In one embodiment, the invention provides a method for producing influenza viruses comprising steps of (a) infecting a culture host with a reassortant virus of the invention; (b) culturing the host from step (a) to produce the virus; and optionally (c) purifying the virus obtained in step (b).

The culture host may be cells or embryonated hen eggs. Where cells are used as a culture host in this aspect of the invention, it is known that cell culture conditions (e.g. temperature, cell density, pH value, etc.) are variable over a wide range subject to the cell line and the virus employed and can be adapted to the requirements of the application. The following information therefore merely represents guidelines.

As mentioned above, cells are preferably cultured in serum-free or protein-free media.

Multiplication of the cells can be conducted in accordance with methods known to those of skill in the art. For example, the cells can be cultivated in a perfusion system using ordinary support methods like centrifugation or filtration. Moreover, the cells can be multiplied according to the invention in a fed-batch system before infection. In the context of the present invention, a culture system is referred to as a fed-batch system in which the cells are initially cultured in a batch system and depletion of nutrients (or part of the nutrients) in the medium is compensated by controlled feeding of concentrated nutrients. It can be advantageous to adjust the pH value of the medium during multiplication of cells before infection to a value between pH 6.6 and pH 7.8 and especially between a value between pH 7.2 and pH 7.3. Culturing of cells preferably occurs at a temperature between 30 and 40° C. When culturing the infected cells (step ii), the cells are preferably cultured at a temperature of between 30° C. and 36° C. or between 32° C. and 34° C. or at 33° C. This is particularly preferred, as it has been shown that incubation of infected cells in this temperature range results in production of a virus that results in improved efficacy when formulated into a vaccine [34].

Oxygen partial pressure can be adjusted during culturing before infection preferably at a value between 25% and 95% and especially at a value between 35% and 60%. The values for the oxygen partial pressure stated in the context of the invention are based on saturation of air. Infection of cells occurs at a cell density of preferably about $8\text{-}25\times10^5$ cells/mL in the batch system or preferably about $5\text{-}20\times10^6$ cells/mL in the perfusion system. The cells can be infected with a viral dose (MOI value, "multiplicity of infection"; corresponds to the number of virus units per cell at the time of infection) between $10^{-8}$ and 10, preferably between 0.0001 and 0.5.

Virus may be grown on cells in adherent culture or in suspension. Microcarrier cultures can be used. In some embodiments, the cells may thus be adapted for growth in suspension.

The methods according to the invention also include harvesting and isolation of viruses or the proteins generated by them. During isolation of viruses or proteins, the cells are separated from the culture medium by standard methods like separation, filtration or ultrafiltration. The viruses or the proteins are then concentrated according to methods sufficiently known to those skilled in the art, like gradient centrifugation, filtration, precipitation, chromatography, etc., and then purified. It is also preferred according to the invention that the viruses are inactivated during or after purification. Virus inactivation can occur, for example, by β-propiolactone or formaldehyde at any point within the purification process.

The culture host may be eggs. The current standard method for influenza virus growth for vaccines uses embryonated SPF hen eggs, with virus being purified from the egg contents (allantoic fluid). It is also possible to passage a virus through eggs and subsequently propagate it in cell culture and vice versa.

Vaccine

The invention utilises virus produced according to the method to produce vaccines.

Vaccines (particularly for influenza virus) are generally based either on live virus or on inactivated virus. Inactivated vaccines may be based on whole virions, 'split' virions, or on purified surface antigens. Antigens can also be presented in the form of virosomes. The invention can be used for manufacturing any of these types of vaccine.

Where an inactivated virus is used, the vaccine may comprise whole virion, split virion, or purified surface antigens (for influenza, including hemagglutinin and, usually, also including neuraminidase). Chemical means for inactivating a virus include treatment with an effective amount of one or more of the following agents: detergents, formaldehyde, β-propiolactone, methylene blue, psoralen, carboxyfullerene (C60), binary ethylamine, acetyl ethyleneimine, or combinations thereof. Non-chemical methods of viral inactivation are known in the art, such as for example UV light or gamma irradiation.

Virions can be harvested from virus-containing fluids, e.g. allantoic fluid or cell culture supernatant, by various methods. For example, a purification process may involve zonal centrifugation using a linear sucrose gradient solution that includes detergent to disrupt the virions. Antigens may then be purified, after optional dilution, by diafiltration.

Split virions are obtained by treating purified virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses, for example are well known in the art e.g. see refs. 35-40, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, NP9, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. Examples of split influenza vaccines are the BEGRIVAC™, FLUARIX™, FLUZONE™ and FLUSHIELD™ products.

Purified influenza virus surface antigen vaccines comprise the surface antigens hemagglutinin and, typically, also neuraminidase. Processes for preparing these proteins in purified form are well known in the art. The FLUVIRIN™, AGRIPPAL™ and INFLUVAC™ products are influenza subunit vaccines.

Another form of inactivated antigen is the virosome [41] (nucleic acid free viral-like liposomal particles). Virosomes can be prepared by solubilization of virus with a detergent followed by removal of the nucleocapsid and reconstitution of the membrane containing the viral glycoproteins. An alternative method for preparing virosomes involves adding viral membrane glycoproteins to excess amounts of phospholipids, to give liposomes with viral proteins in their membrane.

The methods of the invention may also be used to produce live vaccines. Such vaccines are usually prepared by purifying virions from virion-containing fluids. For example, the fluids may be clarified by centrifugation, and stabilized with buffer (e.g. containing sucrose, potassium phosphate, and monosodium glutamate). Various forms of influenza virus vaccine are currently available (e.g. see chapters 17 & 18 of reference 42). Live virus vaccines include MedImmune's FLUMIST™ product.

The virus may be attenuated. The virus may be temperature-sensitive. The virus may be cold-adapted. These three features are particularly useful when using live virus as an antigen.

HA is the main immunogen in current inactivated influenza vaccines, and vaccine doses are standardised by reference to HA levels, typically measured by SRID. Existing vaccines typically contain about 15 mg of HA per strain, although lower doses can be used e.g. for children, or in pandemic situations, or when using an adjuvant. Fractional doses such as ½ (i.e. 7.5 mg HA per strain), ¼ and ⅛ have been used, as have higher doses (e.g. 3× or 9× doses [43,44]). Thus vaccines may include between 0.1 and 150 mg of HA per influenza strain, preferably between 0.1 and 50 mg e.g. 0.1-20 mg, 0.1-15 mg, 0.1-10 mg, 0.1-7.5 mg, 0.5-5 μg, etc. Particular doses include e.g. about 45, about 30, about 15, about 10, about 7.5, about 5, about 3.8, about 3.75, about 1.9, about 1.5, etc. per strain.

For live vaccines, dosing is measured by median tissue culture infectious dose ($TCID_{50}$) rather than HA content, and a $TCID_{50}$ of between $10^6$ and $10^8$ (preferably between $10^{65}$-$10^{75}$) per strain is typical.

Influenza strains used with the invention may have a natural HA as found in a wild-type virus, or a modified HA. For instance, it is known to modify HA to remove determinants (e.g. hyper-basic regions around the HA1/HA2 cleavage site) that cause a virus to be highly pathogenic in avian species. The use of reverse genetics facilitates such modifications.

As well as being suitable for immunizing against inter-pandemic strains, the compositions of the invention are particularly useful for immunizing against pandemic or potentially-pandemic strains. The invention is suitable for vaccinating humans as well as non-human animals.

Other strains whose antigens can usefully be included in the compositions are strains which are resistant to antiviral therapy (e.g. resistant to oseltamivir [45] and/or zanamivir), including resistant pandemic strains [46].

Compositions of the invention may include antigen(s) from one or more (e.g. 1, 2, 3, 4 or more) influenza virus strains, including influenza A virus and/or influenza B virus provided that at least one influenza strain is a reassortant influenza strain of the invention. Compositions wherein at least two, at least three or all of the antigens are from reassortant influenza strains of the invention are also envisioned. Where a vaccine includes more than one strain of influenza, the different strains are typically grown separately and are mixed after the viruses have been harvested and antigens have been prepared. Thus a process of the invention may include the step of mixing antigens from more than one influenza strain. A trivalent vaccine is typical, including antigens from two influenza A virus strains and one influenza B virus strain. A tetravalent vaccine is also useful [47], including antigens from two influenza A virus strains and two influenza B virus strains, or three influenza A virus strains and one influenza B virus strain.

Pharmaceutical Compositions

Vaccine compositions manufactured according to the invention are pharmaceutically acceptable. They usually include components in addition to the antigens e.g. they typically include one or more pharmaceutical carrier(s) and/or excipient(s). As described below, adjuvants may also be included. A thorough discussion of such components is available in reference 48.

Vaccine compositions will generally be in aqueous form. However, some vaccines may be in dry form, e.g. in the form of injectable solids or dried or polymerized preparations on a patch.

Vaccine compositions may include preservatives such as thiomersal or 2-phenoxyethanol. It is preferred, however, that the vaccine should be substantially free from (i.e. less than 5 μg/ml) mercurial material e.g. thiomersal-free [39, 49]. Vaccines containing no mercury are more preferred. An α-tocopherol succinate can be included as an alternative to mercurial compounds [39]. Preservative-free vaccines are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Vaccine compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [50], but keeping osmolality in this range is nevertheless preferred.

Vaccine compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a vaccine composition will generally be between 5.0 and 8.1, and more typically between 6.0 and 8.0 e.g. 6.5 and 7.5, or between 7.0 and 7.8. A process of the invention may therefore include a step of adjusting the pH of the bulk vaccine prior to packaging.

The vaccine composition is preferably sterile. The vaccine composition is preferably non-pyrogenic e.g. containing <1 EU (endotoxin unit, a standard measure) per dose, and preferably <0.1 EU per dose. The vaccine composition is preferably gluten-free.

Vaccine compositions of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide (CTAB'), or sodium deoxycholate, particularly for a split or surface antigen vaccine. The detergent may be present only at trace amounts. Thus the vaccine may include less than 1 mg/ml of each of octoxynol-10 and polysorbate 80. Other residual components in trace amounts could be antibiotics (e.g. neomycin, kanamycin, polymyxin B).

A vaccine composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half dose (i.e. about 0.25 ml) may be administered to children.

Compositions and kits are preferably stored at between 2° C. and 8° C. They should not be frozen. They should ideally be kept out of direct light.

Host Cell DNA

Where virus has been isolated and/or grown on a cell line, it is standard practice to minimize the amount of residual cell line DNA in the final vaccine, in order to minimize any potential oncogenic activity of the DNA.

Thus a vaccine composition prepared according to the invention preferably contains less than 10 ng (preferably less than 1 ng, and more preferably less than 100 pg) of residual host cell DNA per dose, although trace amounts of host cell DNA may be present.

It is preferred that the average length of any residual host cell DNA is less than 500 bp e.g. less than 400 bp, less than 300 bp, less than 200 bp, less than 100 bp, etc.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 51 & 52, involving a two-step treatment, first using a DNase (e.g. Benzonase), which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions [53].

Adjuvants

Compositions of the invention may advantageously include an adjuvant, which can function to enhance the immune responses (humoral and/or cellular) elicited in a subject who receives the composition. Preferred adjuvants comprise oil-in-water emulsions. Various such adjuvants are known, and they typically include at least one oil and at least one surfactant, with the oil(s) and surfactant(s) being biodegradable (metabolisable) and biocompatible. The oil droplets in the emulsion are generally less than 5 μm in diameter, and ideally have a sub-micron diameter, with these small sizes being achieved with a microfluidiser to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Another preferred oil is α-tocopherol (see below).

Mixtures of Oils can be Used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Where the vaccine contains a split virus, it is preferred that it contains free surfactant in the aqueous phase. This is advantageous as the free surfactant can exert a 'splitting effect' on the antigen, thereby disrupting any unsplit virions and/or virion aggregates that might otherwise be present. This can improve the safety of split virus vaccines [54].

Preferred emulsions have an average droplets size of <1 μm e.g. ≤750 nm, ≤500 nm, ≤400 nm, ≤300 nm, ≤250 nm, ≤220 nm, ≤200 nm, or smaller. These droplet sizes can conveniently be achieved by techniques such as microfluidisation.

Specific oil-in-water emulsion adjuvants useful with the invention include, but are not limited to:

- A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [55-57], as described in more detail in Chapter 10 of ref. 58 and chapter 12 of ref. 59. The MF59 emulsion advantageously includes citrate ions e.g. 10 mM sodium citrate buffer.
- An emulsion comprising squalene, a tocopherol, and polysorbate 80. The emulsion may include phosphate buffered saline. These emulsions may have by volume from 2 to 10% squalene, from 2 to 10% tocopherol and from 0.3 to 3% polysorbate 80, and the weight ratio of squalene:tocopherol is preferably <1 (e.g. 0.90) as this can provide a more stable emulsion. Squalene and polysorbate 80 may be present volume ratio of about 5:2 or at a weight ratio of about 11:5. Thus the three components (squalene, tocopherol, polysorbate 80) may be present at a weight ratio of 1068:1186:485 or around 55:61:25. One such emulsion ('AS03') can be made by dissolving Tween 80 in PBS to give a 2% solution, then mixing 90 ml of this solution with a mixture of (5 g of DL a tocopherol and 5 ml squalene), then microfluidising the mixture. The resulting emulsion may have submicron oil droplets e.g. with an average diameter of between 100 and 250 nm, preferably about 180 nm. The emulsion may also include a 3-de-O-acylated monophosphoryl lipid A (3d MPL). Another useful emulsion of this type may comprise, per human dose, 0.5-10 mg squalene, 0.5-11 mg tocopherol, and 0.1-4 mg polysorbate 80 [60] e.g. in the ratios discussed above.

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [61] (0.05-1% Thr-MDP, 5% squalane, 2.5% Pluronic L121 and 0.2% polysorbate 80). It can also be used without the Thr-MDP, as in the "AF" adjuvant [62] (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [63]. The emulsion may also include one or more of: alditol; a cryoprotective agent (e.g. a sugar, such as dodecylmaltoside and/or sucrose); and/or an alkylpolyglycoside. The emulsion may include a TLR4 agonist [64]. Such emulsions may be lyophilized.

An emulsion of squalene, poloxamer 105 and Abil-Care [65]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. As described in reference 66, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 67, produced by addition of aliphatic amine to desacylsaponin via the carboxyl group of glucuronic acid), dimethyidioctadecylammonium bromide and/or N,N-dioctadecyl-N,N-bis(2-hydroxyethyl)propanediamine.

An emulsion in which a saponin (e.g. QuilA or QS21) and a sterol (e.g. a cholesterol) are associated as helical micelles [68].

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [69].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [69].

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form. The antigen will generally be in an aqueous form, such that the vaccine is finally prepared by mixing two liquids. The volume ratio of the two liquids for mixing can vary (e.g. between 5:1 and 1:5) but is generally about 1:1. Where concentrations of components are given in the above descriptions of specific emulsions, these concentrations are typically for an undiluted composition, and the concentration after mixing with an antigen solution will thus decrease.

Packaging of Vaccine Compositions

Suitable containers for compositions of the invention (or kit components) include vials, syringes (e.g. disposable syringes), nasal sprays, etc. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colourless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name “Tip-Lok”™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A kit or composition may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of Treatment, and Administration of the Vaccine

The invention provides a vaccine manufactured according to the invention. These vaccine compositions are suitable for administration to human or non-human animal subjects, such as pigs or birds, and the invention provides a method of raising an immune response in a subject, comprising the step of administering a composition of the invention to the subject. The invention also provides a composition of the invention for use as a medicament, and provides the use of a composition of the invention for the manufacture of a medicament for raising an immune response in a subject.

The immune response raised by these methods and uses will generally include an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [70]. Antibody responses are typically measured by hemagglutination inhibition, by microneutralisation, by single radial immunodiffusion (SRID), and/or by single radial hemolysis (SRH). These assay techniques are well known in the art.

Compositions of the invention can be administered in various ways. The most preferred immunisation route is by intramuscular injection (e.g. into the arm or leg), but other available routes include subcutaneous injection, intranasal [71-73], oral [74], intradermal [75,76], transcutaneous, transdermal [77], etc.

Vaccines prepared according to the invention may be used to treat both children and adults. Influenza vaccines are currently recommended for use in pediatric and adult immunisation, from the age of 6 months. Thus a human subject may be less than 1 year old, 1-5 years old, 5-15 years old, 15-55 years old, or at least 55 years old. Preferred subjects for receiving the vaccines are the elderly (e.g. ≥50 years old, ≤60 years old, and preferably ≤65 years), the young (e.g. ≤5 years old), hospitalised subjects, healthcare workers, armed service and military personnel, pregnant women, the chronically ill, immunodeficient subjects, subjects who have taken an antiviral compound (e.g. an oseltamivir or zanamivir compound; see below) in the 7 days prior to receiving the vaccine, people with egg allergies and people travelling abroad. The vaccines are not suitable solely for these groups, however, and may be used more generally in a population. For pandemic strains, administration to all age groups is preferred.

Preferred compositions of the invention satisfy 1, 2 or 3 of the CPMP criteria for efficacy. In adults (18-60 years), these criteria are: (1) ≥70% seroprotection; (2) ≥40% seroconversion; and/or (3) a GMT increase of ≥2.5-fold. In elderly (>60 years), these criteria are: (1) ≥60% seroprotection; (2) ≥30% seroconversion; and/or (3) a GMT increase of ≥2-fold. These criteria are based on open label studies with at least 50 patients.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients e.g. for people who have never received an influenza vaccine before, or for vaccinating against a new HA subtype (as in a pandemic outbreak). Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine and/or a meningococcal vaccine is particularly useful in elderly patients.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3 (1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5 S)-4-acetyl amino-5-amino-3(1-ethylpropoxy)-1-cyclohexene-1-carboxylic acid, ethyl ester, phosphate (1:1), also known as oseltamivir phosphate (TAMIFLU™).

General

The term “comprising” encompasses “including” as well as “consisting” e.g. a composition “comprising” X may consist exclusively of X or may include something additional e.g. X+Y.

The word “substantially” does not exclude “completely” e.g. a composition which is “substantially free” from Y may be completely free from Y. Where necessary, the word “substantially” may be omitted from the definition of the invention.

The term “about” in relation to a numerical value x is optional and means, for example, x+10%.

The preferred pairwise alignment algorithm for use with the invention is the Needleman-Wunsch global alignment algorithm [78], using default parameters (e.g. with Gap opening penalty=10.0, and with Gap extension penalty=0.5, using the EBLOSUM62 scoring matrix). This algorithm is conveniently implemented in the needle tool in the EMBOSS package [79].

Unless specifically stated, a process comprising a step of mixing two or more components does not require any specific order of mixing. Thus components can be mixed in any order. Where there are three components then two components can be combined with each other, and then the combination may be combined with the third component, etc.

The various steps of the methods may be carried out at the same or different times, in the same or different geographical locations, e.g. countries, and by the same or different people or entities.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 80. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is taught in reference 81.

References to a percentage sequence identity between two nucleic acid sequences mean that, when aligned, that percentage of bases are the same in comparing the two sequences. This alignment and the percent homology or sequence identity can be determined using software programs known in the art, for example those described in section 7.7.18 of reference 80. A preferred alignment program is GCG Gap (Genetics Computer Group, Wisconsin, Suite Version 10.1), preferably using default parameters, which are as follows: open gap=3; extend gap=1.

Bars represent the mean plus SEM of three independent experiments. Statistical significance was determined using one-way ANOVA. The mean value of each group was compared to WT virus using Dunnett's multiple comparison test. *=P<0.05, =P<0.01, *=P<0.001; The white bars represent the results with wt A/Brisbane/10/10, the dotted column shows the results with the PR8X backbone; the hatched column shows the results with the #19 column and the grey column shows the results with the #21 backbone.

Figure 2:
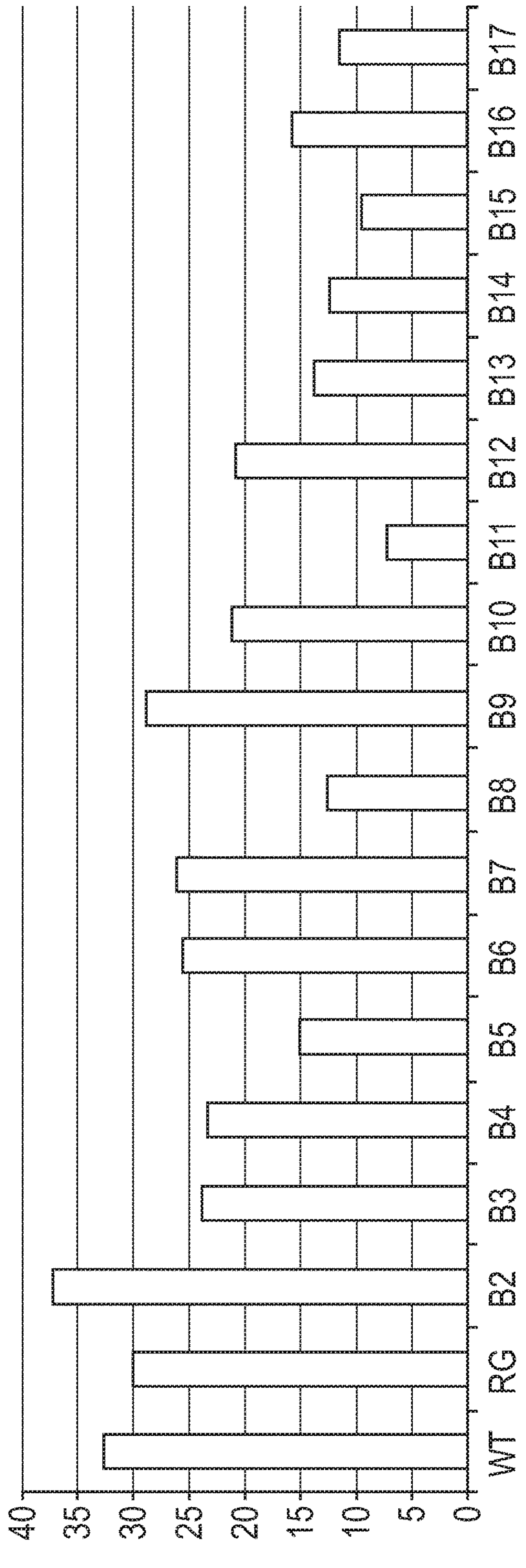

FIG. 2 compares the HA yield of different reassortant influenza B strains in MDCK cells relative to the wild-type (WT) or reverse genetics-derived (RG) B/Brisbane/60/08 strain. The viral segments of the tested influenza B viruses are shown in Table 1. The y-axis indicates the HA yield in mg/mL.

Figure 3:
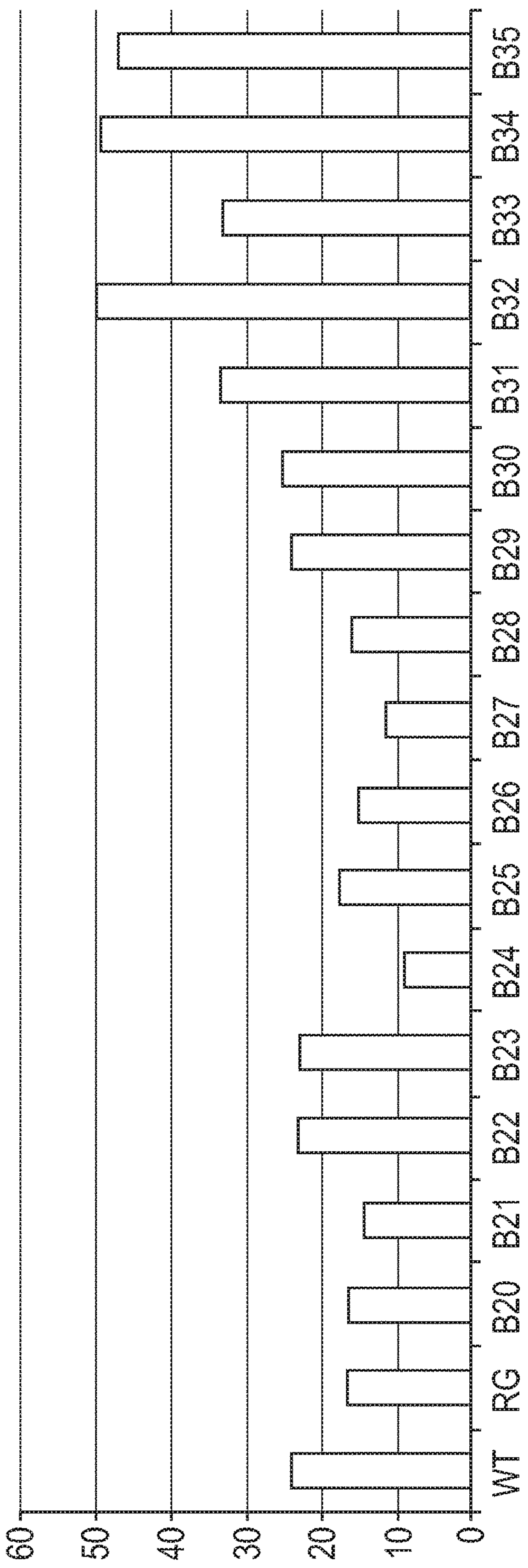

FIG. 3 compares the HA yield of different reassortant influenza B strains in MDCK cells relative to the wild-type (WT) or reverse genetics-derived (RG) B/Panama/45/90 strain. The viral segments of the tested influenza B viruses are shown in Table 1. The y-axis indicates the HA yield in mg/mL.

Figure 4A:
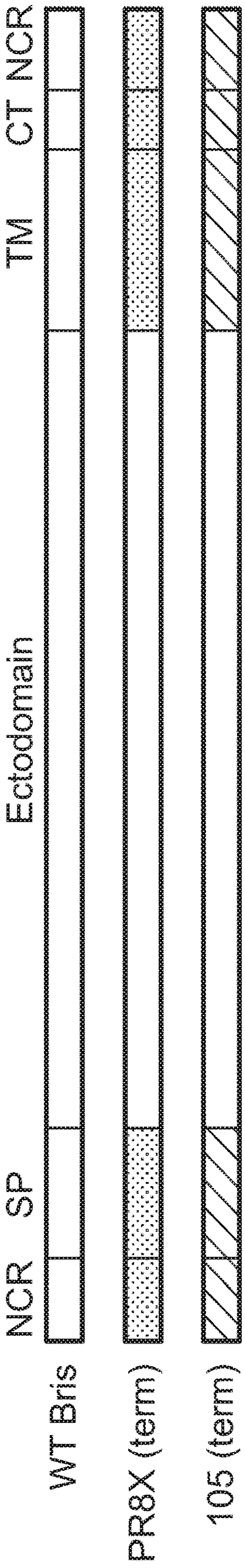
Figure 4C:
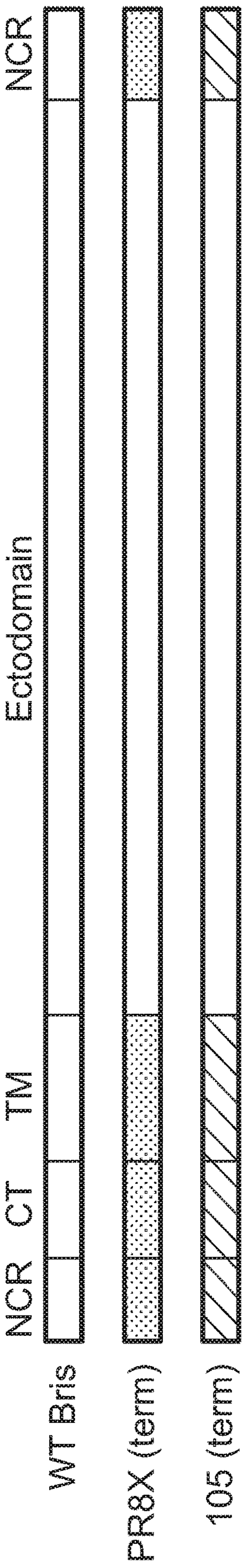
Figure 4D:
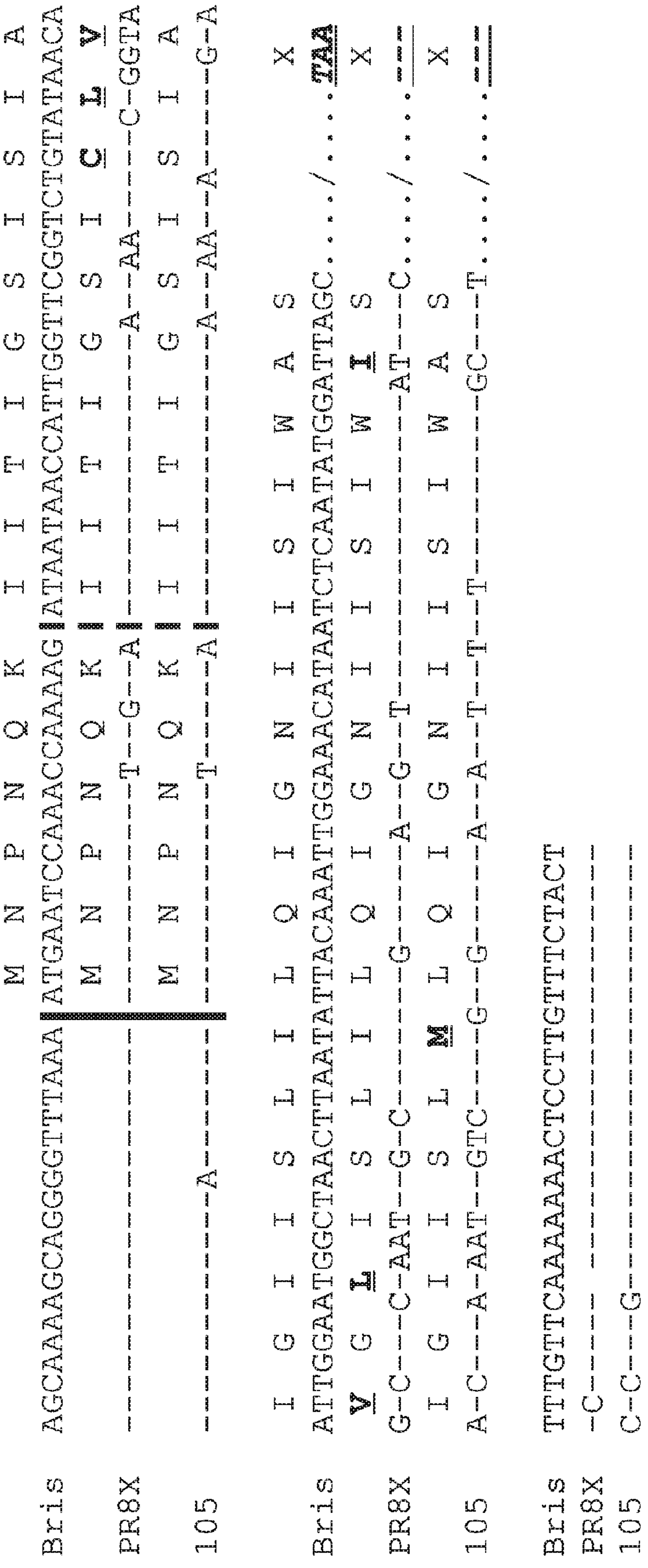

FIG. 4 (A) Schematic diagram and sequence alignment of chimeric HA constructs. The wild type A/Brisbane/10/10 HA (WT Bris) is shown in white. The terminal regions of HA, non-coding regions (NCR), signal peptide (SP), transmembrane region (TM) and cytoplasmic domain (CT), from two laboratory adapted strains of H1N1, PR8X (dotted fields) and 105p30 (hatched fields), are fused to the A/Brisbane/10/10 ectodomain to produce the chimeric HA segments shown. (B) Sequence alignment of the terminal regions of A/Brisbane/10/10 (Bris) HA (sequence accession number: EPI280335), PR8X HA (SEQ ID NO:15) and 105p30 HA (SEQ ID NO:48). Dashes represent nucleotides conserved among the strains. The 3' NCR is separated from the signal peptide sequence by the solid bar. For brevity, the ectodomain sequence is omitted (../..). The transmembrane region is separated from the cytoplasmic tail by the dashed line. The stop codon is underlined and followed by the 5' NCR. (C) Schematic diagram and sequence alignment of chimeric NA constructs. The wild type A/Brisbane/10/10 NA (WT Bris) is shown in white. The terminal regions of NA, non-coding regions (NCR), cytoplasmic domain (CT), and transmembrane region (TM) from PR8X (gray) and 105p30 (slanted lines), are grafted into the A/Brisbane/10/10 ectodomain to produce the chimeric NA segments shown. (D) Sequence alignment of the terminal regions of A/Brisbane/10/10 (Bris) NA (sequence accession number: EPI280334), PR8X NA (SEQ ID NO:16) and 105p30 NA (SEQ ID NO:49). Dashes represent nucleotides conserved among the strains. The cytoplasmic tail is separated from the 3' NCR by the solid bar and from the transmembrane region by the dashed line. For brevity, the ectodomain sequence is omitted (../..). The stop codon is underlined and followed by the 5' NCR.

Figure 5A:
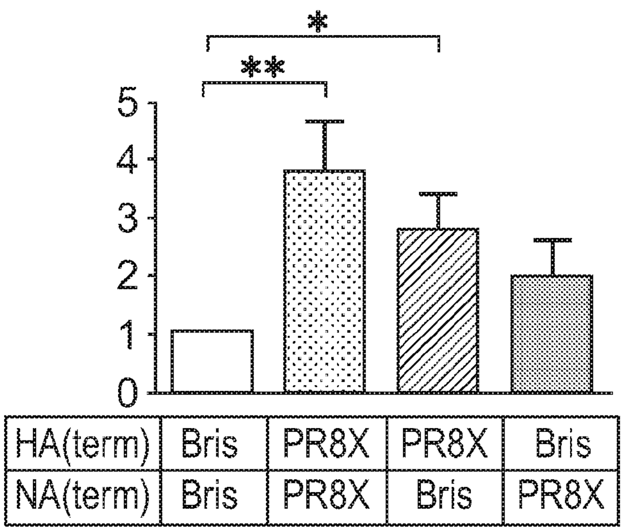
Figure 5B:
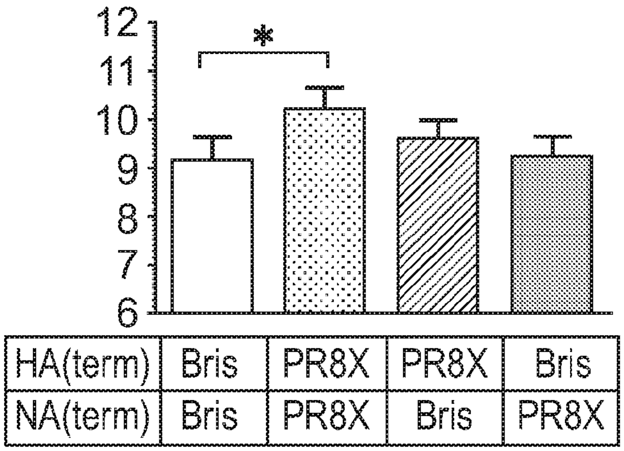
Figure 5C:
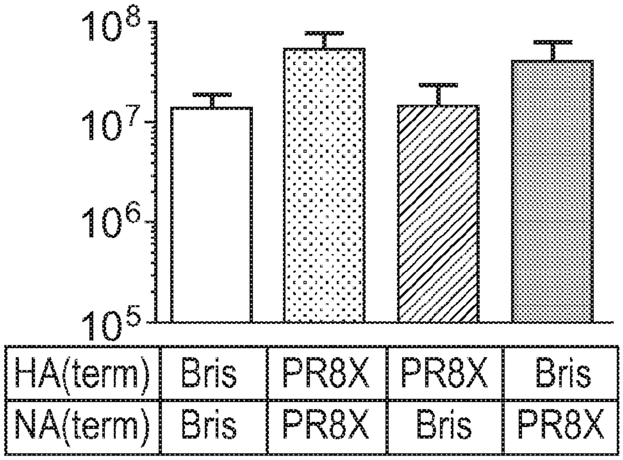

FIG. 5. PR8X(term) HA/NA segments enhance HA yield over PR8X(term) HA or NA only. MDCK 33016PF cells are infected at an MOI of 0.001 with viruses with the PR8X backbone using the indicated HA/NA gene segment combinations. (A) Fold increase as measured by HA ELISA and compared to the yield using WT A/Brisbane/10/10 HA and NA segments. The y-axis shows the fold increase in HA yield. (B) HA titer as determined using 0.5% red blood cells from guinea pigs. The y-axis shows the log 2 HA titer. (C) Virus titers 60 h post infection as determined by FFA assay. The y-axis shows the FFU/mL.

Bars represent the mean plus SEM of three independent experiments. Statistical significance was determined using one-way ANOVA. The mean value of each group is compared to Bris HA/NA using Dunnett's multiple comparison test. *=P<0.05, **=P<0.01.

Figure 6:
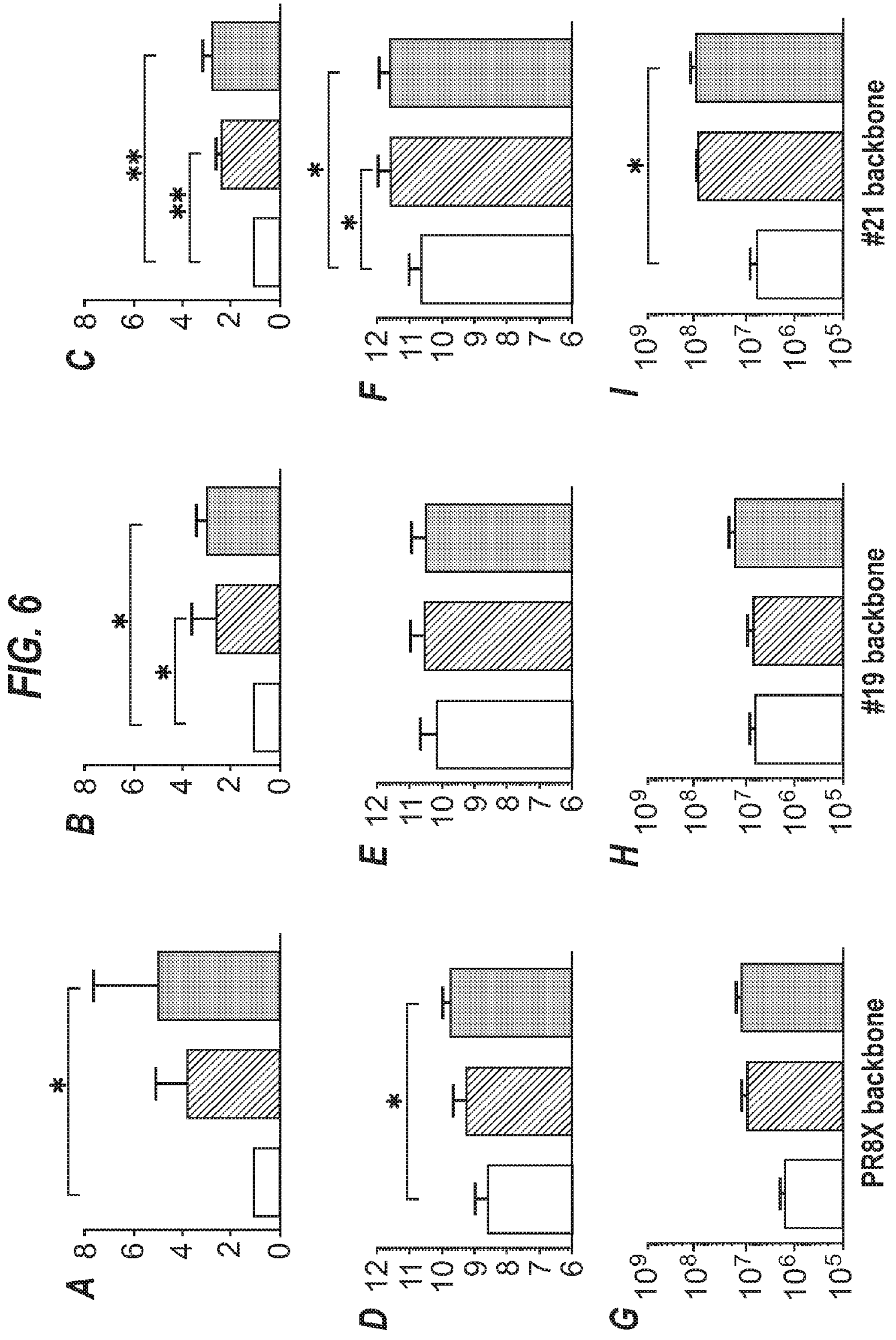

FIG. 6. Chimeric HA/NA segments enhance HA yield with all three optimized backbones. MDCK 33016PF cells are infected at an MOI of 0.001 with viruses derived from the three optimised backbones using HA and NA gene segments with the terminal regions from A/Brisbane/10/10 (Bris) (white columns), PR8X (hatched columns) and 105p30 (grey columns). Upper panels (A, B and C) show the fold increase in HA yield as measured by HA ELISA and compared to the yield using WT HA/NA segments (Bris). The y-axis shows fold increase in HA titer. Middle panels (D, E and F) show HA titers 60 h post infection as determined by HA assay. The y-axis shows log 2 HA titer. Lower panels (G, H and I) show virus titers 60 h post infection as determined by FFA assay. The y-axis shows FFU/mL.

Bars represent the mean plus SEM of three independent experiments. Statistical significance was determined using one-way ANOVA. The mean value of each group was compared to Bris HA/NA using Dunnett's multiple comparison test. *=P<0.05, **=P<0.01.

Figure 7A:
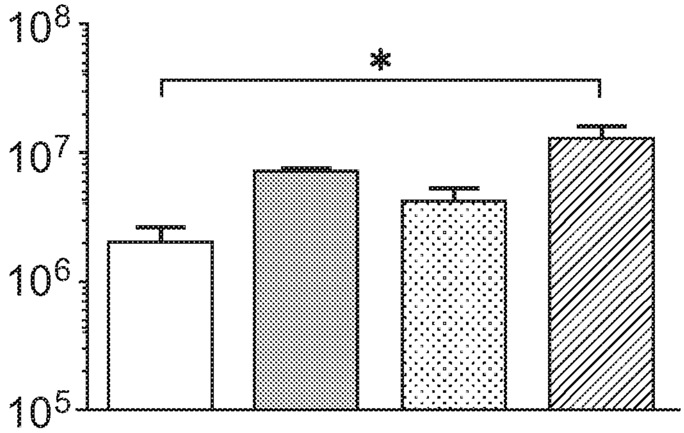
Figure 7B:
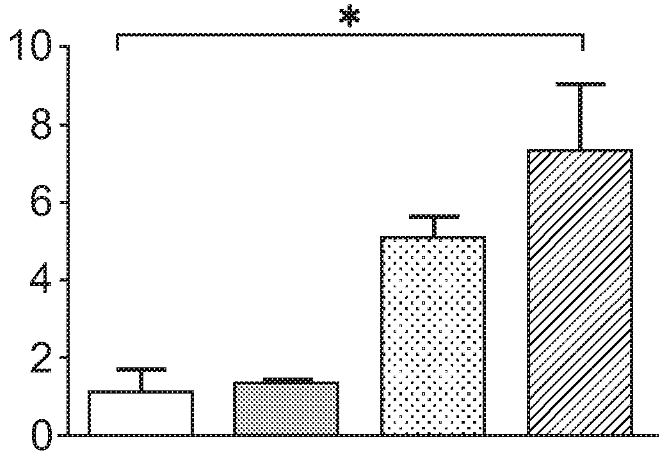

FIG. 7. Chimeric HA and NA segments enhance HA yield with #21 backbone. MDCK 33016PF cells were infected at an MOI of 0.001 with the X187 working seed (A/Victoria/210/2009 classical reassortant, white columns) and viruses derived from the #21 backbone with the indicated HA and NA gene segment combinations: terminal regions from WT A/Victoria/210/2009 (Vic, grey columns), PR8X (dotted columns) or 105 (hatched columns). (A) shows virus titers 60 h post infection as determined by FFA assay. The y-axis indicates FFU/mL (B) shows HA yield 60 h post infection as determined by HA ELISA. The y-axis indicates HA yield (mg/mL).

Bars represent the mean plus SEM of two independent experiments. Statistical significance was determined using one-way ANOVA. The mean value of each group was compared to Bris HA/NA using Dunnett's multiple comparison test. *=P<0.05.

FIG. 8. Enhanced HA content of #21 backbone-derived viruses with chimeric HA/NA segments. (A) HA yield of large scale cultures (60 mL) of MDCK 33016PF cells, infected at an MOI of 0.001 with #21 derived viruses containing HA and NA gene segments with the terminal regions from A/Brisbane/10/10 (Bris) (white columns), PR8X (hatched columns) and 105p30 (grey columns). HA yield is measured by HPLC after virus is concentrated and purified by sucrose-gradient density centrifugation. The y-axis shows μg HA/mL culture (B) Deglycosylation of HA (dHA) is performed using PNGase and viruses are subsequently separated by SDS-PAGE and viral proteins stained using SYPRO-Ruby. (C) HA content of #21 with the indicated HA and NA segments as assessed by gel densitometry assay and HPLC/BCA assay. The HA content is calculated from gel densitometry and from HPLC by dividing values from (A) over the total protein concentration in the fractions, as determined by a BCA assay. The columns show the results with HA and NA gene segments with the terminal regions from A/Brisbane/10/10 (Bris) (white columns), PR8X (hatched columns) and 105p30 (grey columns).

The y-axis shows % HA content. HA content values were compared to those of Bris(term) HA and NA (WT control), which were assigned a value of 1.

Bars represent the mean plus SEM of two independent experiments. Statistical significance is determined using one-way ANOVA. The mean value of each group was compared to Bris HA/NA using Dunnett's multiple comparison test. *=P<0.05, **=P<0.001.

MODES FOR CARRYING OUT THE INVENTION

Materials and Methods

Cells, Viruses and Plasmids 293T cells and suspension MDCK 33016PF cells are maintained as previously described [82].

The eight segments from PR8X and 105p30, the PB1 segment from A/California/07/09 and the HA/NA segments from A/Brisbane/10/10 are cloned in plasmid pKS10 for virus rescue as previously described [82]. HA terminal region chimeras are generated using overlap PCR and cloned into pKS10 as previously described [82]. Overlap PCR and Quikchange (Agilent) mutagenesis are used to generate the NA terminal region chimeras. All plasmids are sequence verified before use in rescue experiments.

Virus Growth in MDCK Cells 10 mL suspension cultures of MDCK 33016PF cultures ($1\times10^6$ cells/ml) are inoculated with virus at a multiplicity of infection (MOI) of 0.001 and incubated in TubeSpin™ Bioreactor 50 (TPP). Samples are taken at 0 and 60 hours post-infection and frozen at −80° C. until processed. Analogous methods are used for preparations of 60 mL of cultures grown in 125 ml shake flasks. Viral titers are determined using a previously described focus-formation assay [83] with slight modifications. Infectious foci are detected using an Alexa Fluor® 488-conjugated goat anti-mouse IgG (Invitrogen), and quantified with a BioSpot™ Analyzer (CTL).

HA ELISA 384 w plates (Costar) are coated 0/N with *Galanthus Nivalis* (GNA) lectin (Sigma). Plates are washed four times with wash buffer (PBS+0.05% Tween20) and blocked with 10 mM Tris-HCl+150 mM NaCl+3% Sucrose+1% BSA, pH 7.68 (blocking buffer) for 1 hr at room temperature. Three-fold serial dilutions of the samples containing a final concentration of 1% Zwittergent 3-14 (Sigma) are prepared, added in duplicate to the plates, and incubated at 37° C. for 30 minutes in a shaker. Biotinylated-IgG purified from pooled sheep antisera (NIBSC cat#11/110) raised against A/California/07/09 (antigenically similar to A/Brisbane/10/10) are added and further incubated at 37° C. for 30 minutes in a shaker. Plates are then washed four times with wash buffer and incubated with Streptavidin-Alkaline phosphatase (KPL) in wash buffer at 37° C. for 30 minutes in a shaker. Plates are washed four times with wash buffer and developed using 1 mg/ml p-Nitrophenyl Phosphate pNPP (Sigma) in DEA buffer phosphatase substrate (KPL). Plates are read after 40-50 min incubation in the dark at 405 nm using an Infinite™ 200 PRO plate reader (Tecan). Data are analyzed using GraphPad Prism software.

Hemagglutination Inhibition Assay

The Haemagglutination Inhibition Assay (HAI) is performed using ferret antisera FR-359 raised against A/California/07/09 (IRR) and a 0.75% suspension of chicken erythrocytes (Lampire Biologicals).

The hemagglutination inhibition assay (HAI) is performed as described in the World Health Organization Manual for the Laboratory Diagnosis and Virological Surveillance of Influenza. Ferret antisera FR-359 raised against A/California/07/09 (IRR) and a 0.75% suspension of chicken erythrocytes (Lampire Biologicals) prepared in phosphate-buffered saline (PBS) are used.

Sucrose Density Gradient Separation 40 mL of the harvested medum is concentrated ~16 fold by centrifugal ultrafiltration (Vivaspin 20 with 300 kD MWCO, Sartorius-Stedim Biotech) and viruses are purified. A hemagglutination assay with 0.5% guinea pig red blood cells (Cleveland Scientific) is performed to identify the fractions with the highest virion content, which are then pooled. The protein content of the pooled fractions is determined using a BCA assay (Pierce) following the manufacturer's directions.

Reversed-Phase HPLC (RP-HPLC)

Purified virions are analyzed by HPLC. The HA1 concentration is quantified using purified HA1 (a HA maturational cleavage fragment) from A/California/07/09 reagent (NIBSC cat #09/146 and 09/174) and prepared using identical methods.

SDS-PAGE and PNGaseF Deglycosylation Assay

Equal volumes from pooled virus-containing fractions are deglycosylated following the protocol of reference 3 with minor modifications. Samples are separated using 4-12% Nu-PAGE precast gels (Invitrogen), stained overnight by shaking at room temperature using SYPRO-Ruby stain (Sigma) and destained by shaking in 10% methanol for 30 mins at room temperature. Gels are scanned using a Chemidoc XRS Imager (BioRad) and analyzed using ImageJ software.

ments from PR8X. The #21 backbone contains an A/Califomia/07/09-like PB1 and the remaining backbone segments from PR8X. FIG. 1 shows the data compiled from three independent experiments that compare the HA yield (FIGS. 1A and B) and growth (FIG. 1C) of the WT virus A/Brisbane/10/10 with reassortant influenza viruses comprising these three optimized backbones (PR8X, #19 and #21) and the A/Brisbane/10/10 HA/NA segments. All reassortant influenza viruses display better performance relative to the WT A/Brisbane/10/10 virus. The virus with the #21 backbone produces the highest HA yield increase by ELISA (7.5-fold more than wild type, P<0.001) and has the highest hemagglutination (HA) (~10-fold more, P<0.001) and viral titers (~50-fold more than WT, P<0.05).

Growth Characteristics of Reassortant Influenza B Viruses

Reassortant influenza B viruses are produced by reverse genetics which contain the HA and NA proteins from various influenza strains and the other viral segments from B/Brisbane/60/08 and/or B/Panama/45/90. As a control the corresponding wild-type influenza B strain is used. These viruses are cultured either in embyronated chicken eggs or in MDCK cells. The following influenza B strains are used:

TABLE 1

| | Backbone segments | | | | | | Antigenic determinants | |
|---|---|---|---|---|---|---|---|---|
| combo # | PA | PB1 | PB2 | NP | NS | M | HA | NA |
| 1 (WT) | Brisbane | Brisbane | Brisbane | Brisbane | Brisbane | Brisbane | Brisbane | Brisbane |
| 2 | Panama | Brisbane | Brisbane | Brisbane | Brisbane | Brisbane | Brisbane | Brisbane |
| 3 | Brisbane | Panama | Brisbane | Brisbane | Brisbane | Brisbane | Brisbane | Brisbane |
| 4 | Brisbane | Brisbane | Panama | Brisbane | Brisbane | Brisbane | Brisbane | Brisbane |
| 5 | Brisbane | Brisbane | Brisbane | Panama | Brisbane | Brisbane | Brisbane | Brisbane |
| 6 | Panama | Panama | Brisbane | Brisbane | Brisbane | Brisbane | Brisbane | Brisbane |
| 7 | Panama | Brisbane | Panama | Brisbane | Brisbane | Brisbane | Brisbane | Brisbane |
| 8 | Panama | Brisbane | Brisbane | Panama | Brisbane | Brisbane | Brisbane | Brisbane |
| 9 | Brisbane | Panama | Panama | Brisbane | Brisbane | Brisbane | Brisbane | Brisbane |
| 10 | Brisbane | Panama | Brisbane | Panama | Brisbane | Brisbane | Brisbane | Brisbane |
| 11 | Brisbane | Brisbane | Panama | Panama | Brisbane | Brisbane | Brisbane | Brisbane |
| 12 | Panama | Panama | Panama | Brisbane | Brisbane | Brisbane | Brisbane | Brisbane |
| 13 | Panama | Panama | Brisbane | Panama | Brisbane | Brisbane | Brisbane | Brisbane |
| 14 | Panama | Brisbane | Panama | Panama | Brisbane | Brisbane | Brisbane | Brisbane |
| 15 | Brisbane | Panama | Panama | Panama | Brisbane | Brisbane | Brisbane | Brisbane |
| 16 | Panama | Panama | Panama | Panama | Brisbane | Brisbane | Brisbane | Brisbane |
| 17 | Panama | Panama | Panama | Panama | Panama | Panama | Brisbane | Brisbane |
| 20 | Brisbane | Panama | Panama | Panama | Panama | Panama | Panama | Panama |
| 21 | Panama | Brisbane | Panama | Panama | Panama | Panama | Panama | Panama |
| 22 | Panama | Panama | Brisbane | Panama | Panama | Panama | Panama | Panama |
| 23 | Panama | Panama | Panama | Brisbane | Panama | Panama | Panama | Panama |
| 24 | Brisbane | Brisbane | Panama | Panama | Panama | Panama | Panama | Panama |
| 25 | Brisbane | Panama | Brisbane | Panama | Panama | Panama | Panama | Panama |
| 26 | Brisbane | Panama | Panama | Brisbane | Panama | Panama | Panama | Panama |
| 27 | Panama | Brisbane | Brisbane | Panama | Panama | Panama | Panama | Panama |
| 28 | Panama | Brisbane | Panama | Brisbane | Panama | Panama | Panama | Panama |
| 29 | Panama | Panama | Brisbane | Brisbane | Panama | Panama | Panama | Panama |
| 30 | Brisbane | Brisbane | Brisbane | Panama | Panama | Panama | Panama | Panama |
| 31 | Brisbane | Brisbane | Panama | Brisbane | Panama | Panama | Panama | Panama |
| 32 | Brisbane | Panama | Brisbane | Brisbane | Panama | Panama | Panama | Panama |
| 33 | Panama | Brisbane | Brisbane | Brisbane | Panama | Panama | Panama | Panama |
| 34 | Brisbane | Brisbane | Brisbane | Brisbane | Panama | Panama | Panama | Panama |
| 35 | Brisbane | Brisbane | Brisbane | Brisbane | Brisbane | Brisbane | Panama | Panama |

Results

Three Optimized Backbones Outperform the Current Vaccine Seed Virus for Growth and HA Yield in MDCK Cell Cultures.

To overcome the limitations of using egg-derived high-growth reassortants as seed viruses for manufacturing influenza vaccines, three MDCK cell-optimized backbones (PR8-X, #19 and #21) are developed. PR8X contains all backbone segments from the cell-adapted PR8X strain. The #19 backbone contains PB1, PB2 and NP from the cell-adapted 105p30 strain, and the remaining backbone seg- The results indicate that reassortant viruses #2, #9, #30, #31, #32, #33, #34 and #35 grow equally well or even better in the culture host (see FIGS. 2 and 3) than the corresponding wild-type strain. Most of these strains comprise the NP segment from B/Brisbane/60/08 and some (in particular those which grew best) further contain the PB2 segment from B/Brisbane/60/08. All of these viruses also contain viral segments from the B/Victoria/2/87-like strain and the B/Yamagata/16/88-like strain at a ratio 7:1, 6:2, 4:4, 3:4 or 1:7.

Chimeric HA and NA Segments with Terminal Regions from Cell-Adapted Strains

Chimeric HA and NA segments are constructed that combine the non-antigenic terminal regions from HA (NCRs, signal peptide, transmembrane and cytoplasmic domains) and NA (NCRs, cytoplasmic and transmembrane domains) from PR8X and 105p30 with the ectodomain of the A/Brisbane/10/10 HA and NA segments, respectively. FIG. 4 shows a diagram of the constructs and a sequence alignment of the terminal regions of HA (panels A, B) and NA (panels C, D).

PR8X(Term) HA and NA Constructs Significantly Enhance HA Yield with the PR8X Backbone Reassortant influenza viruses are rescued which contain the PR8X backbone in combination with either the A/Brisbane/10/10 (H1N1) wt HA and NA segments, or chimeric HA and NA segments which comprise the ectodomain from A/Brisbane/10/10 and the other domains from PR8X (PR8X (term)). The growth and HA yield from the different rescued viruses is compared.

HA yield (FIG. 5A), as measured by HA ELISA, is 4-fold higher for the virus with PR8X(term) HA and NA segments than for the virus with WT HA and NA segments ($P<0.01$). Virus with the PR8X(term) HA segment and WT NA segment yields a 3-fold increase in HA compared to the virus with WT HA and NA ($P<0.05$). Virus with PR8X(term) HA and NA segments has 2-fold higher HA titers ($P<0.05$) and 4-fold higher viral titers than the virus with WT HA and NA segments (FIGS. 5B, C). Overall, these data show that viruses with chimeric PR8X(term) HA and NA segments yield more HA than viruses containing only chimeric PR8X (term) HA or NA segments.

Figure 1A:
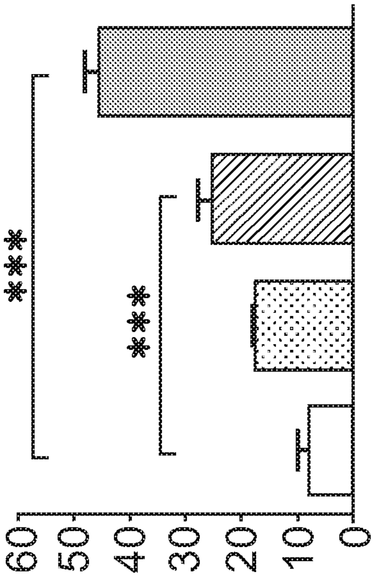
FIG. 1 Backbone-derived viruses outperform wt A/Brisbane/10/10 virus in growth and HA yield. (A) HA yield as measured by HA ELISA. The y-axis shows the HA yield (mg/mL) (B) The fold increase in HA yield by ELISA was calculated by normalizing the HA ELISA values to those of the A/Brisbane/10/10 WT virus. The y-axis shows the fold increase in HA yield. (C) HA titers using 0.5% guinea pig RBCs. The y-axis shows the log 2 HA titer. (D) Viral titers 60 h post-infection as determined by FFA assay. The y-axis shows the FFU/mL.
Figure 1B:
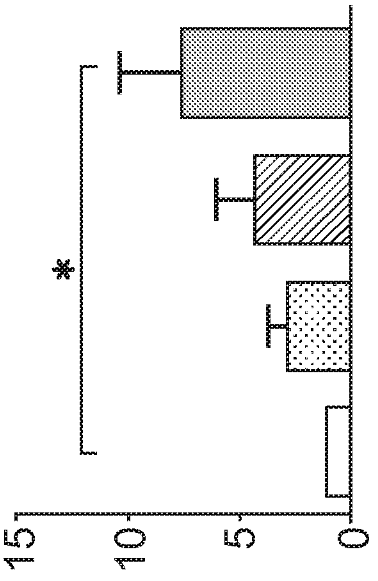
Figure 1C:
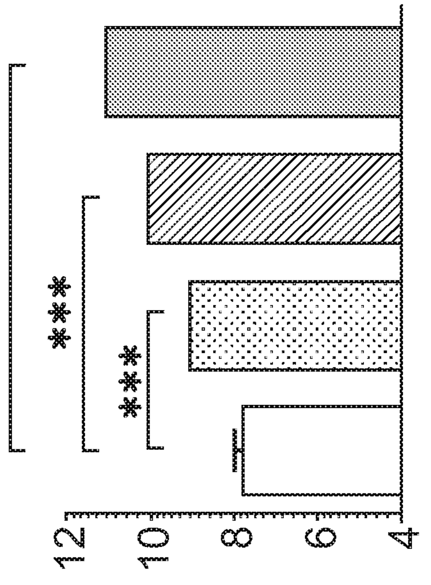
Figure 1D:
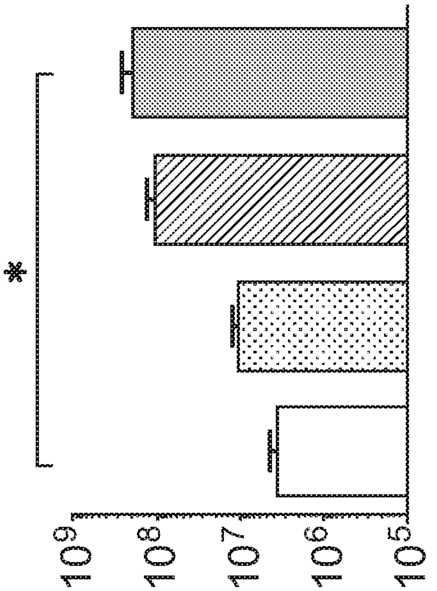

Chimeric HA and NA Constructs Enhance HA Yield with all Three Optimized Backbones The inventors next tested whether the PR8X(term) or 105p30(term) HA/NA segments can enhance growth and HA yield of the resulting viruses in all three of the optimized backbones (FIG. 1A). HA yield, as measured by ELISA and normalized to the yield from WT HA and NA segments, increase ~4-fold with PR8X(term) HA and NA segments and ~5-fold ($P<0.05$) with 105(term) HA and NA segments using the PR8X backbone (FIG. 6A). HA yield increases correlate with increases in HA titer and viral titers using the PR8X(term) and 105(term) HA and NA constructs (FIGS. 6D, G). With the #19 backbone, HA yield is ~2.5-fold higher ($P<0.05$) with the PR8X(term) HA and NA segments and ~3-fold higher ($P<0.05$) with the 105(term) HA and NA segments over virus with WT HA and NA segments (FIG. 6B). HA yield increases are not associated with increases in viral titers or HA titers (FIGS. 6E, H).

When using the #21 backbone, the inventors find significant increases with PR8X(term) and 105(term) HA and NA segments in HA yield, ~2.5-fold ($P<0.01$) and ~3-fold ($P<0.01$) respectively, HA titers (2-fold ($P<0.05$)) and viral titers over virus containing WT HA and NA segments (FIGS. 6C, F, I). Overall, these data show that using chimeric HA and NA segments with terminal regions derived from cell-adapted strains increase HA yield independent of the backbone used.

The inventors confirm that these results are not limited to a specific vaccine strain, by preparing a reassortant influenza virus which comprises the #21 backbone, the HA and NA ectodomain from A/Victoria/210/2009, and the terminal regions from WT A/Victoria/210/2009, PR8X or 105p30. The results (FIG. 7) show that reassortants which comprise chimeric HA or NA segments give better HA yields.

Sequence analyses of the viruses recovered from all backbones with WT or chimeric HA and NA segments confirmed their sequence identity with the plasmids used in virus rescue. To confirm that viruses with chimeric HA and NA segments maintain their correct antigenicity, a hemagglutination inhibition (HAI) assay is performed using ferret antisera raised against A/California/07/2009, which is antigenically similar to WT A/Brisbane/10/10. Table 2 shows, as expected, that the viruses with the chimeric HA and NA segments are antigenically indistinguishable (within 2-fold in an HAI assay) from the reference antigen that contains the WT HA and NA segments.

TABLE 2

Antigenic analysis of viruses derived from the three optimized backbones (Values represent the geometric mean of HI titers from duplicate experiments)

| Antigen | Ferret Sera FR-359 (H1N1) |
|---|---|
| A/Brisbane/10/10 | 2560 |
| PR8X + Bris(term) HA/NA | 1920 |
| PR8X + PR8X(term) HA/NA | 1920 |
| PR8X + 105(term) HA/NA | 1920 |
| #19 + Bris(term) HA/NA | 1280 |
| #19 + PR8X(term) HA/NA | 1280 |
| #19 + 105(term) HA/NA | 2560 |
| #21 + Bris(term) HA/NA | 2560 |
| #21 + PR8X(term) HA/NA | 1920 |
| #21 + 105(term) HA/NA | 1280 |
| IVR165 (H3N2) | 10> |

Increased HA Content of Viruses Containing Chimeric HA/NA Segments

Figure 8A:
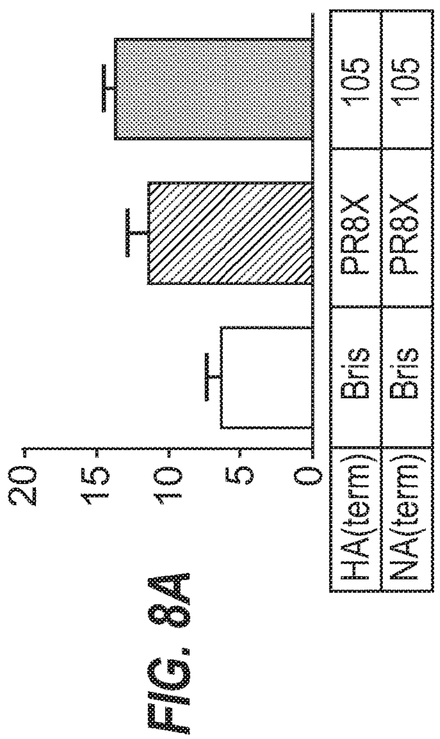

To verify further that the results observed using unpurified cell culture supernatants reflect HA yield from purified viruses, the inventors performed additional characterizations of viruses derived from the #21 backbone, which produce the highest amounts of HA (FIG. 1). To this end, large-scale amplifications (60 mL) of these viruses are performed and viruses purified using sucrose density-gradient centrifugation, as described in the methods. HA1 yield (normalized to the original culture volume of 60 mL) is determined using HPLC. Compared to viruses with wt HA/NA segments, viruses with the chimeric PR8X(term) and 105p30(term) HA/NA segments have ~1.8 fold increase (11.3 ug/mL vs 6.2 ug/mL) and a ~2.2 fold increase (13.6 ug/mL vs 6.2 ug/mL) in HA yield, respectively (FIG. 8A).

Figure 8B:
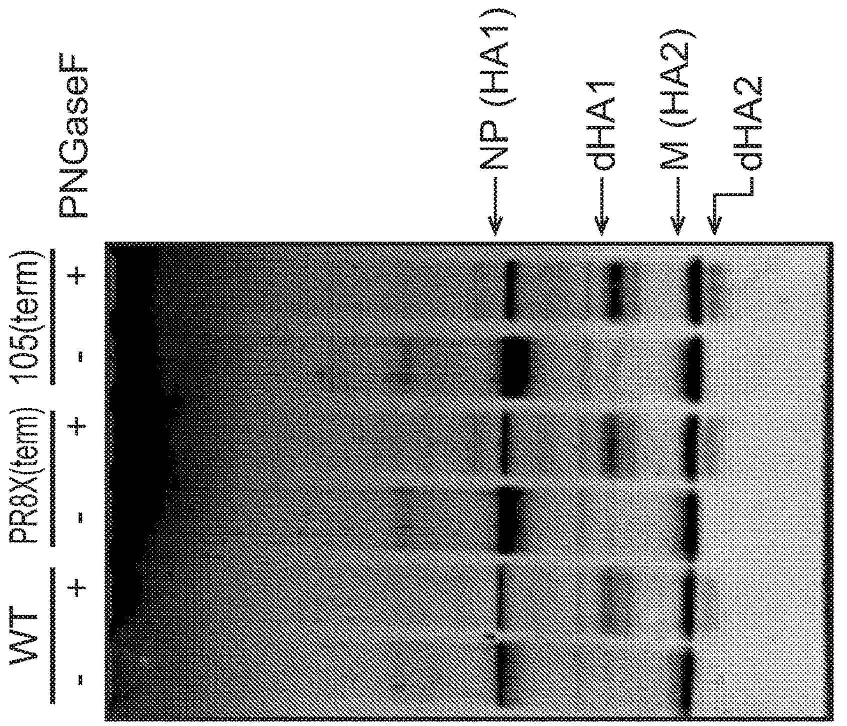
Figure 8C:
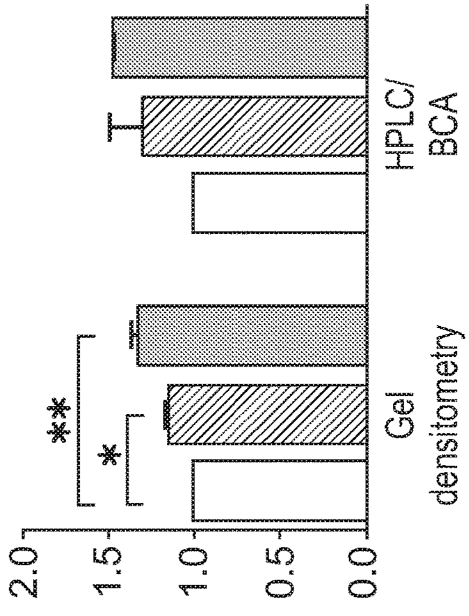

The HA content in these purified preparations is determined by using either gel densitometry or a combination of HPLC measurement of HA and total protein measurement by BCA assay. For gel densitometry determination, the pooled fractions are treated with PNGaseF, resolved by SDS-PAGE, and then stained with SYPRO-Ruby to permit accurate determination of NP, HAL M, and HA2 by densitometry. FIG. 8B shows the positions of these bands on the stained gel, and FIG. 8C shows that viruses with the PR8X (term) and 105(term) HA and NA segments had increases of 14% ($P<0.05$) and 32% ($P<0.01$), respectively, compared to viruses containing the WT HA and NA segments.

To quantitate HA1 content using the HPLC data, the HA1 values obtained by HPLC (FIG. 8A) are expressed as a fraction of the total protein content (as measured by the BCA assay) of the pooled fractions. The results in FIG. 8C show that viruses with PR8X(term) and 105(term) HA and NA segments had increased HA content of 29% and 46%, respectively, compared to WT HA and NA containing viruses.

In conclusion, these data show that the productivity of three optimized backbones for virus rescue can be enhanced by modifying the terminal regions of the HA and NA segments with those from cell-adapted strains.

It will be understood that the invention has been described by way of example only and modifications may be made whilst remaining within the scope and spirit of the invention.

SEQUENCES

SEQ ID NO: 1 (PA, PR8-X)
MEDFVRQCFNPMIVELAEKTMKEYGEDLKIETNKFAAICTHLEVCFMYSDFHFINEQGESIIVELGDPNALLKHRFE
IIEGRDRTMAWTVVNSICNTTGAEKPKFLPDLYDYKENRFIEIGVTRREVHIYYLEKANKIKSEKTHIHIFSFTGEE
MATKADYTLDEESRARIKTRLFTIRQEMASRGLWDSFRQSERGEETIEERFEITGTMRKLADQSLPPNFSSLENFRA
YVDGFEPNGYIEGKLSQMSKEVNARIEPFLKTTPRPLRLPNGPPCSQRSKFLLMDALKLSIEDPSHEGEGIPLYDAI
KCMRTFFGWKEPNVVKPHEKGINPNYLLSWKQVLAELQDIENEEKIPKTKNMKKTSQLKWALGENMAPEKVDFDDCK
DVGDLKQYDSDEPELRSLASWIQNEFNKACELTDSSWIELDEIGEDVAPIEHIASMRRNYFTSEVSHCRATEYIMKG
VYINTALLNASCAAMDDFQLIPMISKCRTKEGRRKTNLYGFIIKGRSHLRNDTDVVNFVSMEFSLTDPRLEPHKWEK
YCVLEIGDMLIRSAIGQVSRPMFLYVRTNGTSKIKMKWGMEMRRCLLQSLQQIESMIEAESSVKEKDMTKEFFENKS
ETWPIGESPKGVEESSIGKVCRTLLAKSVFNSLYASPQLEGFSAESRKLLLIVQALRDNLEPGTFDLGGLYEAIEEC
LINDPWVLLNASWFNSFLTHALS

SEQ ID NO: 2 (PB1, PR8-X)
MDVNPTLLFLKVPTQNAISTTFPYTGDPPYSHGTGTGYTMDTVNRTHQYSEKGRWTTNTETGAPQLNPIDGPLPEDN
EPSGYAQTDCVLEAMAFLEESHPGIFENSCIETMEVVQQTRVDKLTQGRQTYDWTLNRNQPAATALANTIEVFRSNG
LTANESGRLIDFLKDVMESMNKEEMGITTHFQRKRRVRDNMTKKMITQRTMGKKKQRLNKRSYLIRALTLNTMTKDA
ERGKLKRRAIATPGMQIRGFVYFVETLARSICEKLEQSGLPVGGNEKKAKLANVVRKMMTNSQDTELSFTITGDNTK
WNENQNPRMFLAMITYMTRNQPEWFRNVLSIAPIMFSNKMARLGKGYMFESKSMKLRTQIPAEMLASIDLKYFNDST
RKKIEKIRPLLIEGTASLSPGMMMGMFNMLSTVLGVSILNLGQKRYTKTTYWWDGLQSSDDFALIVNAPNHEGIQAG
VDRFYRTCKLLGINMSKKKSYINRTGTFEETSFFYRYGFVANFSMELPSFGVSGINESADMSIGVTVIKNNMINNDL
GPATAQMALQLFIKDYRYTYRCHRGDTQIQTRRSFEIKKLWEQTRSKAGLLVSDGGPNLYNIRNLHIPEVCLKWELM
DEDYQGRLCNPLNPFVSHKEIESMNNAVMMPAHGPAKNMEYDAVATTHSWIPKRNRSILNTSQRGVLEDEQMYQRCC
NLFEKFFPSSSYRRPVGISSMVEAMVSRARIDARTDFESGRIKKEEFTEIMKICSTIEELRRQK

SEQ ID NO: 3 (PB2, PR8-X)
MERIKELRNLMSQSRTREILTKTTVDHMAIIKKYTSGRQEKNPALRMKWMMAMKYPITADKRITEMIPERNEQGQTL
WSKMNDAGSDRVMVSPLAVTWWNRNGPITNTVHYPKIYKTYFERVERLKHGTFGPVHFRNQVKIRRRVDINPGHADL
SAKEAQDVIMEVVFPNEVGARILTSESQLTITKEKKEELQDCKISPLMVAYMLERELVRKTRFLPVAGGTSSVYIEV
LHLTQGTCWEQMYTPGGEVRNDDVDQSLIIAARNIVRRAAVSADPLASLLEMCHSTQIGGIRMVDILRQNPTEEQAV
DICKAAMGLRISSSFSFGGFTFKRTSGSSVKREEEVLTGNLQTLKIRVHEGYEEFTMVGRRATAILRKATRRLIQLI
VSGRDEQSIAEATIVAMVFSQEDCMIKAVRGDLNFVNRANQRLNPMHQLLRHFQKDARVLFQNWGVEPIDNVMGMIG
ILPDMTPSIEMSMRGVRISKMGVDEYSSTERVVVSIDRFLRIRDQRGNVLLSPEEVSETQGTEKLTITYSSSMMWEI
NGPESVLVNTYQWIIRNWETVKIQWSQNPTMLYNKMEFEPFQSLVPKAIRGQYSGFVRTLFQQMRDVLGTFDTAQII
KLLPFAAAPPKQSRMQFSSFTVNVRGSGMRILVRGNSPVFNYNKATKRLTVLGKDAGTLTEDPDEGTAGVESAVLRG
FLILGKEDKRYGPALSINELSNLAKGEKANVLIGQGDVVLVMKRKRDSSILTDSQTATKRIRMAIN

SEQ ID NO: 4 (NP, PR8-X)
MASQGTKRSYEQMETDGERQNATEIRASVGKMIGGIGRFYIQMCTELKLSDYEGRLIQNSLTIERMVLSAFDERRNK
YLEEHPSAGKDPKKTGGPIYRRVNGKWMRELILYDKEEIRRIWRQANNGDDATAGLTHMMIWHSNLNDATYQRTRAL
VRTGMDPRMCSLMQGSTLPRRSGAAGAAVKGVGTMVMELVRMIKRGINDRNFWRGENGRKTRIAYERMCNILKGKFQ
TAAQKAMMDQVRESRNPGNAEFEDLTFLARSALILRGSVAHKSCLPACVYGPAVASGYDFEREGYSLVGIDPFRLLQ
NSQVYSLIRPNENPAHKSQLVWMACHSAAFEDLRVLSFIKGTKVLPRGKLSTRGVQIASNENMETMESSTLELRSRY
WAIRTRSGGNTNQQRASAGQISIQPTFSVQRNLPFDRTTIMAAFNGNTEGRTSDMRTEIIRMMESARPEDVSFQGRG
VFELSDEKAASPIVPSFDMSNEGSYFFGDNAEEYDN

SEQ ID NO: 5 (M, PR8-X)
MSLLTEVETYVLSIIPSGPLKAEIAQRLEDVFAGKNTDLEVLMEWLKTRPILSPLTKGILGFVFTLTVPSERGLQRR
RFVQNALNGNGDPNNMDKAVKLYRKLKREITFHGAKEISLSYSAGALASCMGLIYNRMGAVTTEVAFGLVCATCEQI
ADSQHRSHRQMVTTTNPLIRHENRMVLASTTAKAMEQMAGSSEQAAEAMEVASQARQMVQAMRTIGTHPSSSAGLKN
DLLENLQAYQKRMGVQMQRFK

SEQ ID NO: 6 (NS, PR8-X)
MDPNTVSSFQVDCFLWHVRKRVADQELGDAPFLDRLRRDQKSLRGRGSTLGLDIKTATRAGKQIVERILKEESDEAL
KMTMASVPASRYLTDMTLEEMSRDWSMLIPKQKVAGPLCIRMDQAIMDKNIILKANFSVIFDRLETLILLRAFTEEG
AIVGEISPLPSLPGHTAEDVKNAVGVLIGGLEWNDNTVRVSETLQRFAWRSSNENGRPPLTPKQKREMAGTIRSEV

SEQ ID NO: 7 (HA, PR8-X)
MKANLLVLLCALAAADADTICIGYHTNNSTDTVDTVLEKNVTVTHSVNLLEDSHNGKLCRLKGIAPLQLGKCNIAGW
LLGNPECDPLLPVRSWSYIVETPNSENGICYPGDFIDYEELREQLSSVSSFERFEIFPKESSWPNHNTNGVTAACSH
EGKSSFYRNLLWLTEKEGSYPKLKNSYVNKKGKEVLVLWGIHHPPNSKEQQNLYQNENAYVSVVTSNYNRRFTPEIA
ERPKVRDQAGRMNYYWTLLKPGDTIIFEANGNLIAPMYAFALSRGFGSGIITSNASMHECNTKCQTPLGAINSSLPY
QNIHPVTIGECPKYVRSAKLRMVTGLRNIPSIQSRGLFGAIAGFIEGGWTGMIDGWYGYHHQNEQGSGYAADQKSTQ
NAINGITNKVNTVIEKMNIQFTAVGKEFNKLEKRMENLNKKVDDGFLDIWTYNAELLVLLENERTLEFHDSNVKNLY
EKVKSQLKNNAKEIGNGCFEFYHKCDNECMESVRNGTYDYPKYSEESKLNREKVDGVKLESMGIYQILAIYSTVASS
LVLLVSLGAISFWMCSNGSLQCRICI

SEQ ID NO: 8 (NA, PR8-X)
MNPNQKIITIGSICLVVGLISLILQIGNIISIWISHSIQTGSQNHTGICNQNIITYKNSTWVKDTTSVILTGNSSLC
PIRGWAIYSKDNSIRIGSKGDVFVIREPFISCSHLECRTFFLTQGALLNDKHSSGTVKDRSPYRALMSCPVGEAPSP
YNSRFESVAWSASACHDGMGWLTIGISGPDNGAVAVLKYNGIITETIKSWRKKILRTQESECACVNGSCFTIMTDGP
SDGLASYKIFKIEKGKVTKSIELNAPNSHYEECSCYPDTDKVMCVCRDNWHGSNRPWVSFDQNLDYQIGYICSGVFG

-continued

| SEQUENCES |
|---|
| DNPRPEDGTGSCGPVYVDGANGVKGFSYRYGNGVWIGRTKSHSSRHGFEMIWDPNGWTETDSKFSVRQDVVAMTDWS<br>GYSGSFVQHPELTGLDCMRPCFWVELIRGRPKEKTIWTSASSISFCGVNSDTVDWSWPDGAELPFSIDK |
| SEQ ID NO: 9 (PA, PR8-X)<br>AGCGAAAGCAGGTACTGATCCAAAATGGAAGATTTTGTGCGACAATGCTTCAATCCGATGATTGTCGAGCTTGCGGA<br>AAAAACAATGAAAGAGTATGGGGAGGACCTGAAAATCGAAACAAACAAATTTGCAGCAATATGCACTCACTTGGAAG<br>TATGCTTCATGTATTCAGATTTTCACTTCATCAATGAGCAAGGCGAGTCAATAATCGTAGAACTTGGTGATCCAAAT<br>GCACTTTTGAAGCACAGATTTGAAATAATCGAGGGAAGAGATCGCACAATGGCCTGGACAGTAGTAAACAGTATTTG<br>CAACACTACAGGGGCTGAGAAACCAAAGTTTCTACCAGATTTGTATGATTACAAGGAGAATAGATTTATCGAAATTG<br>GAGTAACAAGGAGAGAAGTTCACATATACTATCTGGAAAAGGCCAATAAAATTAAATCTGAGAAAACACACATCCAC<br>ATTTTCTCGTTCACTGGGGAAGAAATGGCCACAAAGGCAGACTACACTCTCGATGAAGAAAGCAGGGCTAGGATCAA<br>AACCAGACTATTCACCATAAGACAAGAAATGGCCAGCAGAGGCCTCTGGGATTCCTTTCGTCAGTCCGAGAGAGGAG<br>AAGAGACAATTGAAGAAAGGTTTGAAATCACAGGAACAATGCGCAAGCTTGCCGACCAAAGTCTCCCGCCGAACTTC<br>TCCAGCCTTGAAAATTTTAGAGCCTATGTGGATGGATTCGAACCGAACGGCTACATTGAGGGCAAGCTGTCTCAAAT<br>GTCCAAAGAAGTAAATGCTAGAATTGAACCTTTTTTGAAAACAACACCACGACCACTTAGACTTCCGAATGGGCCTC<br>CCTGTTCTCAGCGGTCCAAATTCCTGCTGATGGATGCCTTAAAATTAAGCATTGAGGACCCAAGTCATGAAGGAGAG<br>GGAATACCGCTATATGATGCAATCAAATGCATGAGAACATTCTTTGGATGGAAGGAACCCAATGTTGTTAAACCACA<br>CGAAAAGGGAATAAATCCAAATTATCTTCTGTCATGGAAGCAAGTACTGGCAGAACTGCAGGACATTGAGAATGAGG<br>AGAAAATTCCAAAGACTAAAAATATGAAGAAAACAAGTCAGCTAAAGTGGGCACTTGGTGAGAACATGGCACCAGAA<br>AAGGTAGACTTTGACGACTGTAAAGATGTAGGTGATTTGAAGCAATATGATAGTGATGAACCAGAATTGAGGTCGCT<br>TGCAAGTTGGATTCAGAATGAGTTTAACAAGGCATGCGAACTGACAGATTCAAGCTGGATAGAGCTCGATGAGATTG<br>GAGAAGATGTGGCTCCAATTGAACACATTGCAAGCATGAGAAGGAATTATTTCACATCAGAGGTGTCTCACTGCAGA<br>GCCACAGAATACATAATGAAGGGGGTGTACATCAATACTGCCTTGCTTAATGCATCTTGTGCAGCAATGGATGATTT<br>CCAATTAATTCCAATGATAAGCAAGTGTAGAACTAAGGAGGGAAGGCGAAAGACCAACTTGTATGGTTTCATCATAA<br>AAGGAAGATCCCACTTAAGGAATGACACCGACGTGGTAAACTTTGTGAGCATGGAGTTTTCTCTCACTGACCCAAGA<br>CTTGAACCACATAAATGGGAGAAGTACTGTGTTCTTGAGATAGGAGATATGCTTATAAGAAGTGCCATAGGCCAGGT<br>TTCAAGGCCCATGTTCTTGTATGTGAGAACAAATGGAACCTCAAAAATTAAAATGAAATGGGGAATGGAGATGAGGC<br>GTTGCCTCCTCCAGTCACTTCAACAAATTGAGAGTATGATTGAAGCTGAGTCCTCTGTCAAAGAGAAAGACATGACC<br>AAAGAGTTCTTTGAGAACAAATCAGAAACATGGCCCATTGGAGAGTCCCCCAAAGGAGTGGAGGAAAGTTCCATTGG<br>GAAGGTCTGCAGGACTTTATTAGCAAAGTCGGTATTCAACAGCTTGTATGCATCTCCACAACTAGAAGGATTTTCAG<br>CTGAATCAAGAAAACTGCTTCTTATCGTTCAGGCTCTTAGGGACAACCTTGAACCTGGGACCTTTGATCTTGGGGGG<br>CTATATGAAGCAATTGAGGAGTGCCTGATTAATGATCCCTGGGTTTTGCTTAATGCTTCTTGGTTCAACTCCTTCCT<br>TACACATGCATTGAGTTAGTTGTGGCAGTGCTACTATTTGCTATCCATACTGTCCAAAAAAGTACCTTGTTTCTACT |
| SEQ ID NO: 10 (PB1, PR8-X)<br>AGCGAAAGCAGGCAAACCATTTGAATGGATGTCAATCCGACCTTACTTTTCTTAAAAGTGCCAACACAAAATGCTAT<br>AAGCACAACTTTCCCTTATACTGGAGACCCTCCTTACAGCCATGGGACAGGAACAGGATACACCATGGATACTGTCA<br>ACAGGACACATCAGTACTCAGAAAAGGGAAGATGGACAACAAACACCGAAACTGGAGCACCGCAACTCAACCCGATT<br>GATGGGCCACTGCCAGAAGACAATGAACCAAGTGGTTATGCCCAAACAGATTGTGTATTGGAGGCGATGGCTTTCCT<br>TGAGGAATCCCATCCTGGTATTTTTGAAAACTCGTGTATTGAAACGATGGAGGTTGTTCAGCAAACACGAGTAGACA<br>AGCTGACACAAGGCCGACAGACCTATGACTGGACTCTAAATAGAAACCAACCTGCTGCAACAGCATTGGCCAACACA<br>ATAGAAGTGTTCAGATCAAATGGCCTCACGGCCAATGAGTCTGGAAGGCTCATAGACTTCCTTAAGGATGTAATGGA<br>GTCAATGAACAAAGAAGAAATGGGGATCACAACTCATTTTCAGAGAAAGAGACGGGTGAGAGACAATATGACTAAGA<br>AAATGATAACACAGAGAACAATGGGTAAAAAGAAGCAGAGATTGAACAAAAGGAGTTATCTAATTAGAGCATTGACC<br>CTGAACACAATGACCAAAGATGCTGAGAGAGGGAAGCTAAAACGGAGAGCAATTGCAACCCCAGGGATGCAAATAAG<br>GGGGTTTGTATACTTTGTTGAGACACTGGCAAGGAGTATATGTGAGAAACTTGAACAATCAGGGTTGCCAGTTGGAG<br>GCAATGAGAAGAAAGCAAAGTTGGCAAATGTTGTAAGGAAGATGATGACCAATTCTCAGGACACCGAACTTTCTTTC<br>ACCATCACTGGAGATAACACCAAATGGAACGAAAATCAGAATCCTCGGATGTTTTTGGCCATGATCACATATATGAC<br>CAGAAATCAGCCCGAATGGTTCAGAAATGTTCTAAGTATTGCTCCAATAATGTTCTCAAACAAAATGGCGAGACTGG<br>GAAAAGGGTATATGTTTGAGAGCAAGAGTATGAAACTTAGAACTCAAATACCTGCAGAAATGCTAGCAAGCATCGAT<br>TTGAAATATTTCAATGATTCAACAAGAAAGAAGATTGAAAAAATCCGACCGCTCTTAATAGAGGGGACTGCATCATT<br>GAGCCCTGGAATGATGATGGGCATGTTCAATATGTTAAGCACTGTATTAGGCGTCTCCATCCTGAATCTTGGACAAA<br>AGAGATACACCAAGACTACTTACTGGTGGGATGGTCTTCAATCCTCTGACGATTTTGCTCTGATTGTGAATGCACCC<br>AATCATGAAGGGATTCAAGCCGGAGTCGACAGGTTTTATCGAACCTGTAAGCTACTTGGAATCAATATGAGCAAGAA<br>AAAGTCTTACATAAACAGAACAGGTACATTTGAATTCACAAGTTTTTTCTATCGTTATGGGTTTGTTGCCAATTTCA<br>GCATGGAGCTTCCCAGTTTTGGGGTGTCTGGGATCAACGAGTCAGCGGACATGAGTATTGGAGTTACTGTCATCAAA<br>AACAATATGATAAACAATGATCTTGGTCCAGCAACAGCTCAAATGGCCCTTCAGTTGTTCATCAAAGATTACAGGTA<br>CACGTACCGATGCCATAGAGGTGACACACAAATACAAACCCGAAGATCATTTGAAATAAAGAAACTGTGGGAGCAAA<br>CCCGTTCCAAAGCTGGACTGCTGGTCTCCGACGGAGGCCCAAATTTATACAACATTAGAAATCTCCACATTCCTGAA<br>GTCTGCCTAAAATGGGAATTGATGGATGAGGATTACCAGGGGCGTTTATGCAACCCACTGAACCCATTTGTCAGCCA<br>TAAAGAAATTGAATCAATGAACAATGCAGTGATGATGCCAGCACATGGTCCAGCCAAAAACATGGAGTATGATGCTG<br>TTGCAACAACACACTCCTGGATCCCCAAAAGAAATCGATCCATCTTGAATACAAGTCAAAGAGGAGTACTTGAGGAT<br>GAACAAATGTACCAAAGGTGCTGCAATTTATTTGAAAAATTCTTCCCCAGCAGTTCATACAGAAGACCAGTCGGGAT<br>ATCCAGTATGGTGGAGGCTATGGTTTCCAGAGCCCGAATTGATGCACGGATTGATTTCGAATCTGGAAGGATAAAGA<br>AAGAAGAGTTCACTGAGATCATGAAGATCTGTTCCACCATTGAAGAGCTCAGACGGCAAAAATAGTGAATTTAGCTT<br>GTCCTTCATGAAAAAATGCCTTGTTTCTACT |
| SEQ ID NO: 11 (PB2, PR8-X)<br>AGCGAAAGCAGGTCAATTATATTCAATATGGAAAGAATAAAAGAACTAAGAAATCTAATGTCGCAGTCTCGCACCCG<br>CGAGATACTCACAAAAACCACCGTGGACCATATGGCCATAATCAAGAAGTACACATCAGGAAGACAGGAGAAGAACC<br>CAGCACTTAGGATGAAATGGATGATGGCAATGAAATATCCAATTACAGCAGACAAGAGGATAACGGAAATGATTCCT<br>GAGAGAAATGAGCAAGGACAAACTTTATGGAGTAAAATGAATGATGCCGGATCAGACCGAGTGATGGTATCACCTCT<br>GGCTGTGACATGGTGGAATAGGAATGGACCAATAACAAATACAGTTCATTATCCAAAAATCTACAAAACTTATTTTG<br>AAAGAGTAGAAAGGCTAAAGCATGGAACCTTTGGCCCTGTCCATTTTAGAAACCAAGTCAAAATACGTCGGAGAGTT<br>GACATAAATCCTGGTCATGCAGATCTCAGTGCCAAGGAGGCACAGGATGTAATCATGGAAGTTGTTTTCCCTAACGA<br>AGTGGGAGCCAGGATACTAACATCGGAATCGCAACTAACGATAACCAAAGAGAAGAAAGAAGAACTCCAGGATTGCA<br>AAATTTCTCCTTTGATGGTTGCATACATGTTGGAGAGAGAACTGGTCCGCAAAACGAGATTCCTCCCAGTGGCTGGT |

-continued

SEQUENCES

GGAACAAGCAGTGTGTACATTGAAGTGTTGCATTTGACTCAAGGAACATGCTGGGAACAGATGTATACTCCAGGAGG
GGAAGTGAGGAATGATGATGTTGATCAAAGCTTGATTATTGCTGCTAGGAACATAGTGAGAAGAGCTGCAGTATCAG
CAGATCCACTAGCATCTTTATTGGAGATGTGCCACAGCACACAGATTGGTGGAATTAGGATGGTAGACATCCTTAGG
CAGAACCCAACAGAAGAGCAAGCCGTGGATATATGCAAGGCTGCAATGGGACTGAGAATTAGCTCATCCTTCAGTTT
TGGTGGATTCACATTTAAGAGAACAAGCGGATCATCAGTCAAGAGAGAGGAAGAGGTGCTTACGGGAAATCTTCAAA
CATTGAAGATAAGAGTGCATGAGGGATATGAAGAGTTCACAATGGTTGGGAGAAGAGCAACAGCCATACTCAGAAAA
GCAACCAGGAGATTGATTCAGCTGATAGTGAGTGGGAGAGACGAACAGTCGATTGCCGAAGCAATAATTGTGGCCAT
GGTATTTTCACAAGAGGATTGTATGATAAAAGCAGTCAGAGGTGATCTGAATTTCGTCAATAGGGCGAATCAGCGAT
TGAATCCTATGCATCAACTTTTAAGACATTTTCAGAAGGATGCGAGAGTGCTTTTTCAAAATTGGGGAGTTGAACCT
ATCGACAATGTGATGGGAATGATTGGGATATTGCCCGACATGACTCCAAGCATCGAGATGTCAATGAGAGGAGTGAG
AATCAGCAAAATGGGTGTAGATGAGTACTCCAGCACGGAGAGGGTAGTGGTGAGCATTGACCGTTTTTGAGAATCC
GGGACCAACGAGGAAATGTACTACTGTCTCCCGAGGAGGTCAGTGAAACACAGGGAACAGAGAAACTGACAATAACT
TACTCATCGTCAATGATGTGGGAGATTAATGGTCCTGAATCAGTATTGGTCAATACCTATCAATGGATCATCAGAAA
CTGGGAAACTGTTAAAATTCAGTGGTCCCAGAACCCTACAATGCTATACAATAAAATGGAATTTGAACCATTTCAGT
CTTTAGTACCTAAGGCCATTAGAGGCCAATACAGTGGGTTTGTAAGAACTCTGTTCCAACAAATGAGGGATGTGCTT
GGGACATTTGATACCGCACAGATAATAAAACTTCTTCCCTTCGCAGCCGCTCCACCAAAGCAAAGTAGAATGCAGTT
CTCCTCATTTACTGTGAATGTGAGGGGATCAGGAATGAGAATACTTGTAAGGGGCAATTCTCCTGTATTCAACTATA
ACAAGGCCACGAAGAGACTCACAGTTCTCGGAAAGGATGCTGGCACTTTAACTGAAGACCCAGATGAAGGCACAGCT
GGAGTGGAGTCCGCTGTTCTGAGGGGATTCCTCATTCTGGGCAAAGAAGACAAGAGATATGGGCCAGCACTAAGCAT
CAATGAACTGAGCAACCTTGCGAAAGGAGAGAAGGCTAATGTGCTAATTGGGCAAGGAGACGTGGTGTTGGTAATGA
AACGGAAACGGGACTCTAGCATACTTACTGACAGCCAGACAGCGACCAAAAGAATTCGGATGGCCATCAATTAGTGT
CGAATAGTTTAAAAACGACCTTGTTTCTACT

SEQ ID NO: 12 (NP, PR8-X)
AGCAAAAGCAGGGTAGATAATCACTCACTGAGTGACATCAAAATCATGGCGTCTCAAGGCACCAAACGATCTTACGA
ACAGATGGAGACTGATGGAGAACGCCAGAATGCCACTGAAATCAGAGCATCCGTCGGAAAAATGATTGGTGGAATTG
GACGATTCTACATCCAAATGTGCACCGAACTCAAACTCAGTGATTATGAGGGACGGTTGATCCAAAACAGCTTAACA
ATAGAGAGAATGGTGCTCTCTGCTTTTGACGAAAGGAGAAATAAATACCTTGAAGAACATCCCAGTGCGGGAAAAGA
TCCTAAGAAAACTGGAGGACCTATATACAGGAGAGTAAACGGAAAGTGGATGAGAGAACTCATCCTTTATGACAAAG
AAGAAATAAGGCGAATCTGGCGCCAAGCTAATAATGGTGACGATGCAACGGCTGGTCTGACTCACATGATGATCTGG
CATTCCAATTTGAATGATGCAACTTATCAGAGGACAAGAGCTCTTGTTCGCACCGGAATGGATCCCAGGATGTGCTC
TCTGATGCAAGGTTCAACTCTCCCTAGGAGGTCTGGAGCCGCAGGTGCTGCAGTCAAAGGAGTTGGAACAATGGTGA
TGGAATTGGTCAGAATGATCAAACGTGGGATCAATGATCGGAACTTCTGGAGGGGTGAGAATGGACGAAAAACAAGA
ATTGCTTATGAAAGAATGTGCAACATTCTCAAAGGGAAATTTCAAACTGCTGCACAAAAAGCAATGATGGATCAAGT
GAGAGAGAGCCGGAACCCAGGGAATGCTGAGTTCGAAGATCTCACTTTTCTAGCACGGTCTGCACTCATATTGAGAG
GGTCGGTTGCTCACAAGTCCTGCCTGCCTGCCTGTGTGTATGGACCTGCCGTAGCCAGTGGGTACGACTTTGAAAGG
GAGGGATACTCTCTAGTCGGAATAGACCCTTTCAGACTGCTTCAAAACAGCCAAGTGTACAGCCTAATCAGACCAAA
TGAGAATCCAGCACACAAGAGTCAACTGGTGTGGATGGCATGCCATTCTGCCGCATTTGAAGATCTAAGAGTATTAA
GCTTCATCAAAGGGACGAAGGTGCTCCCAAGAGGGAAGCTTTCCACTAGAGGAGTTCAAATTGCTTCCAATGAAAAT
ATGGAGACTATGGAATCAAGTACACTTGAACTGAGAAGCAGGTACTGGGCCATAAGGACCAGAAGTGGAGGAAACAC
CAATCAACAGAGGGCATCTGCGGGCCAAATCAGCATACAACCTACGTTCTCAGTACAGAGAAATCTCCCTTTTGACA
GAACAACCATTATGGCAGCATTCAATGGGAATACAGAGGGGAGAACATCTGACATGAGGACCGAAATCATAAGGATG
ATGGAAAGTGCAAGACCAGAAGATGTGTCTTTCCAGGGGCGGGGAGTCTTCGAGCTCTCGGACGAAAAGGCAGCGAG
CCCGATCGTGCCTTCCTTTGACATGAGTAATGAAGGATCTTATTTCTTCGGAGACAATGCAGAGGAGTACGACAATT
AAAGAAAAATACCCTTGTTTCTACT

SEQ ID NO: 13 (M, PR8-X)
AGCAAAAGCAGGTAGATATTGAAAGATGAGTCTTCTAACCGAGGTCGAAACGTACGTACTCTCTATCATCCCGTCAG
GCCCCCTCAAAGCCGAGATCGCACAGAGACTTGAAGATGTCTTTGCAGGGAAGAACACCGATCTTGAGGTTCTCATG
GAATGGCTAAAGACAAGACCAATCCTGTCACCTCTGACTAAGGGGATTTTAGGATTTGTGTTCACGCTCACCGTGCC
CAGTGAGCGAGGACTGCAGCGTAGACGCTTTGTCCAAAATGCCCTTAATGGGAACGGGGATCCAAATAACATGGACA
AAGCAGTTAAACTGTATAGGAAGCTCAAGAGGGAGATAACATTCCATGGGGCCAAAGAAATCTCACTCAGTTATTCT
GCTGGTGCACTTGCCAGTTGTATGGGCCTCATATACAACAGGATGGGGGCTGTGACCACTGAAGTGGCATTTGGCCT
GGTATGTGCAACCTGTGAACAGATTGCTGACTCCCAGCATCGGTCTCATAGGCAAATGGTGACAACAACCAATCCAC
TAATCAGACATGAGAACAGAATGGTTTTAGCCAGCACTACAGCTAAGGCTATGGAGCAAATGGCTGGATCGAGTGAG
CAAGCAGCAGAGGCCATGGAGGTTGCTAGTCAGGCTAGACAAATGGTGCAAGCGATGAGAACCATTGGGACTCATCC
TAGCTCCAGTGCTGGTCTGAAAAATGATCTTCTTGAAAATTTGCAGGCCTATCAGAAACGAATGGGGGTGCAGATGC
AACGGTTCAAGTGATCCTCTCACTATTGCCGCAAATATCATTGGGATCTTGCACTTGACATTGTGGATTCTTGATCG
TCTTTTTTTCAAATGCATTTACCGTCGCTTTAAATACGGACTGAAAGGAGGGCCTTCTACGGAAGGAGTGCCAAAGT
CTATGAGGGAAGAATATCGAAAGGAACAGCAGAGTGCTGTGGATGCTGACGATGGTCATTTTGTCAGCATAGAGCTG
GAGTAAAAAACTACCTTGTTTCTACT

SEQ ID NO: 14 (NS, PR8-X)
AGCAAAAGCAGGGTGACAAAAACATAATGGATCCAAACACTGTGTCAAGCTTTCAGGTAGATTGCTTTCTTTGGCAT
GTCCGCAAACGAGTTGCAGACCAAGAACTAGGTGATGCCCCATTCCTTGATCGGCTTCGCCGAGATCAGAAATCCCT
AAGAGGAAGGGGCAGTACTCTCGGTCTGGACATCAAGACAGCCACACGTGCTGGAAAGCAGATAGTGGAGCGGATTC
TGAAAGAAGAATCCGATGAGGCACTTAAAATGACCATGGCCTCTGTACCTGCGTCGCGTTACCTAACTGACATGACT
CTTGAGGAAATGTCAAGGGACTGGTCCATGCTCATACCCAAGCAGAAAGTGGCAGGCCCTCTTTGTATCAGAATGGA
CCAGGCGATCATGGATAAGAACATCATACTGAAAGCGAACTTCAGTGTGATTTTTGACCGGCTGGAGACTCTAATAT
TGCTAAGGGCTTTCACCGAAGAGGGAGCAATTGTTGGCGAAATTTCACCATTGCCTTCTCTTCCAGGACATACTGCT
GAGGATGTCAAAAATGCAGTTGGAGTCCTCATCGGAGGACTTGAATGGAATGATAACACAGTTCGAGTCTCTGAAAC
TCTACAGAGATTCGCTTGGAGAAGCAGTAATGAGAATGGGAGACCTCCACTCACTCCAAAACAGAAACGAGAAATGG
CGGGAACAATTAGGTCAGAAGTTTGAAGAAATAAGATGGTTGATTGAAGAAGTGAGACACAAACTGAAGATAACAGA
GAATAGTTTTGAGCAAATAACATTTATGCAAGCCTTACATCTATTGCTTGAAGTGGAGCAAGAGATAAGAACTTTCT
CGTTTCAGCTTATTTAGTACTAAAAAACACCCTTGTTTCTACT

-continued

| SEQUENCES |
|---|

SEQ ID NO: 15 (HA, PR8-X)
AGCAAAAGCAGGGGAAAATAAAAACAACCAAAATGAAGGCAAACCTACTGGTCCTGTTATGTGCACTTGCAGCTGCA
GATGCAGACACAATATGTATAGGCTACCATACGAACAATTCAACCGACACTGTTGACACAGTACTCGAGAAGAATGT
GACAGTGACACACTCTGTTAACCTGCTCGAAGACAGCCACAACGGAAAACTATGTAGATTAAAAGGAATAGCCCCAC
TACAATTGGGGAAATGTAACATCGCCGGATGGCTCTTGGGAAACCCAGAATGCGACCCACTGCTTCCAGTGAGATCA
TGGTCCTACATTGTAGAAACACCAAACTCTGAGAATGGAATATGTTATCCAGGAGATTTCATCGACTATGAGGAGCT
GAGGGAGCAATTGAGCTCAGTGTCATCATTCGAAAGATTCGAAATATTTCCCAAAGAAAGCTCATGGCCCAACCACA
ACACAAACGGAGTAACGGCAGCATGCTCCCATGAGGGGAAAAGCAGTTTTTACAGAAATTTGCTATGGCTGACGGAG
AAGGAGGGCTCATACCCAAAGCTGAAAAATTCTTATGTGAACAAAAAAGGGAAAGAAGTCCTTGTACTGTGGGGTAT
TCATCACCCGCCTAACAGTAAGGAACAACAGAATCTCTATCAGAATGAAAATGCTTATGTCTCTGTAGTGACTTCAA
ATTATAACAGGAGATTTACCCCGGAAATAGCAGAAAGACCCAAAGTAAGAGATCAAGCTGGGAGGATGAACTATTAC
TGGACCTTGCTAAAACCCGGAGACACAATAATATTTGAGGCAAATGGAAATCTAATAGCACCAATGTATGCTTTCGC
ACTGAGTAGAGGCTTTGGGTCCGGCATCATCACCTCAAACGCATCAATGCATGAGTGTAACACGAAGTGTCAAACAC
CCCTGGGAGCTATAAACAGCAGTCTCCCTTACCAGAATATACACCCAGTCACAATAGGAGAGTGCCCAAAATACGTC
AGGAGTGCCAAATTGAGGATGGTTACAGGACTAAGGAACATTCCGTCCATTCAATCCAGAGGTCTATTTGGAGCCAT
TGCCGGTTTTATTGAAGGGGGATGGACTGGAATGATAGATGGATGGTATGGTTATCATCATCAGAATGAACAGGGAT
CAGGCTATGCAGCGGATCAAAAAAGCACACAAAATGCCATTAACGGGATTACAAACAAGGTGAACACTGTTATCGAG
AAAATGAACATTCAATTCACAGCTGTGGGTAAAGAATTCAACAAATTAGAAAAAAGGATGGAAAATTTAAATAAAAA
AGTTGATGATGGATTTCTGGACATTTGGACATATAATGCAGAATTGTTAGTTCTACTGGAAAATGAAAGGACTCTGG
AATTCCATGACTCAAATGTGAAGAATCTGTATGAGAAAGTAAAAAGCCAATTAAAGAATAATGCCAAAGAAATCGGA
AATGGATGTTTTGAGTTCTACCACAAGTGTGACAATGAATGCATGGAAAGTGTAAGAAATGGGACTTATGATTATCC
CAAATATTCAGAAGAGTCAAAGTTGAACAGGGAAAAGGTAGATGGAGTGAAATTGGAATCAATGGGGATCTATCAGA
TTCTGGCGATCTACTCAACTGTCGCCAGTTCACTGGTGCTTTTGGTCTCCCTGGGGGCAATCAGTTTCTGGATGTGT
TCTAATGGATCTTTGCAGTGCAGAATATGCATCTGAGATTAGAATTTCAGAGATATGAGGAAAAACACCCTTGTTTC
TACT

SEQ ID NO: 16 (NA, PR8-X)
AGCAAAAGCAGGGGTTTAAAATGAATCCAAATCAGAAAATAATAACCATTGGATCAATCTGTCTGGTAGTCGGACTA
ATTAGCCTAATATTGCAAATAGGGAATATAATCTCAATATGGATTAGCCATTCAATTCAAACTGGAAGTCAAAACCA
TACTGGAATATGCAACCAAAACATCATTACCTATAAAAATAGCACCTGGGTAAAGGACACAACTTCAGTGATATTAA
CCGGCAATTCATCTCTTTGTCCCATCCGTGGGTGGGCTATATACAGCAAAGACAATAGCATAAGAATTGGTTCCAAA
GGAGACGTTTTTGTCATAAGAGAGCCCTTTATTTCATGTTCTCACTTGGAATGCAGGACCTTTTTTCTGACCCAAGG
TGCCTTACTGAATGACAAGCATTCAAGTGGGACTGTTAAGGACAGAAGCCCTTATAGGGCCTTAATGAGCTGCCCTG
TCGGTGAAGCTCCGTCCCCGTACAATTCAAGATTTGAATCGGTTGCTTGGTCAGCAAGTGCATGTCATGATGGCATG
GGCTGGCTAACAATCGGAATTTCAGGTCCAGATAATGGAGCAGTGGCTGTATTAAAATACAACGGCATAATAACTGA
AACCATAAAAAGTTGGAGGAAGAAAATATTGAGGACACAAGAGTCTGAATGTGCCTGTGTAAATGGTTCATGTTTTA
CTATAATGACTGATGGCCCGAGTGATGGGCTGGCCTCGTACAAAATTTTCAAGATCGAAAAGGGGAAGGTTACTAAA
TCAATAGAGTTGAATGCACCTAATTCTCACTATGAGGAATGTTCCTGTTACCCTGATACCGACAAAGTGATGTGTGT
GTGCAGAGACAATTGGCATGGTTCGAACCGGCCATGGGTGTCTTTCGATCAAAACCTGGATTATCAAATAGGATACA
TCTGCAGTGGGGTTTTCGGTGACAACCCGCGTCCCGAAGATGGAACAGGCAGCTGTGGTCCAGTGTATGTTGATGGA
GCAAACGGAGTAAAGGGATTTTCATATAGGTATGGTAATGGTGTTTGGATAGGAAGGACCAAAAGTCACAGTTCCAG
ACATGGGTTTGAGATGATTTGGGATCCTAATGGATGGACAGAGACTGATAGTAAGTTCTCTGTGAGGCAAGATGTTG
TGGCAATGACTGATTGGTCAGGGTATAGCGGAAGTTTCGTTCAACATCCTGAGCTGACAGGGCTAGACTGTATGAGG
CCGTGCTTCTGGGTTGAATTAATCAGGGGACGACCTAAAGAAAAAACAATCTGGACTAGTGCGAGCAGCATTTCTTT
TTGTGGCGTGAATAGTGATACTGTAGATTGGTCTTGGCCAGACGGTGCTGAGTTGCCATTCAGCATTGACAAGTAGT
CTGTTCAAAAAACTCCTTGTTTCTACT

SEQ ID NO: 17 (PA, A/California/07/09)
MEDFVRQCFNPMIVELAEKAMKEYGEDPKIETNKFAAICTHLEVCFMYSDFHFIDERGESIIVESGDPNALLKHRFE
IIEGRDRIMAWTVVNSICNTTGVEKPKFLPDLYDYKENRFIEIGVTRREVHIYYLEKANKIKSEKTHIHIFSFTGEE
MATKADYTLDEESRARIKTRLFTIRQEMASRSLWDSFRQSERGEETIEEKFEITGTMRKLADQSLPPNFPSLENFRA
YVDGFEPNGCIEGKLSQMSKEVNAKIEPFLRTTPRPLRLPDGPLCHQRSKFLLMDALKLSIEDPSHEGEGIPLYDAI
KCMKTFFGWKEPNIVKPHEKGINPNYLMAWKQVLAELQDIENEEKIPRTKNMKRTSQLKWALGENMAPEKVDFDDCK
DVGDLKQYDSDEPEPRSLASWVQNEFNKACELTDSSWIELDEIGEDVAPIEHIASMRRNYFTAEVSHCRATEYIMKG
VYINTALLNASCAAMDDFQLIPMISKCRTKEGRRKTNLYGFIIKGRSHLRNDTDVVNFVSMEFSLTDPRLEPHKWEK
YCVLEIGDMLLRTAIGQVSRPMFLYVRTNGTSKIKMKWGMEMRRCLLQSLQQIESMIEAESSVKEKDMTKEFFENKS
ETWPIGESPRGVEEGSIGKVCRTLLAKSVFNSLYASPQLEGFSAESRKLLLIVQALRDNLEPGTFDLGGLYEAIEEC
LINDPWVLLNASWFNSFLTHALK SEQ ID NO: 18 (PB1, A/California/07/09)
MDVNPTLLFLKIPAQNAISTTFPYTGDPPYSHGTGTGYTMDTVNRTHQYSEKGKWTTNTETGAPQLNPIDGPLPEDN
EPSGYAQTDCVLEAMAFLEESHPGIFENSCLETMEVVQQTRVDKLTQGRQTYDWTLNRNQPAATALANTIEVFRSNG
LTANESGRLIDFLKDVMESMNKEEIEITTHFQRKRRVRDNMTKKMVTQRTIGKKKQRLNKRGYLIRALTLNTMTKDA
ERGKLKRRAIATPGMQIRGFVYFVETLARSICEKLEQSGLPVGGNEKKAKLANVVRKMMTNSQDTEISFTITGDNTK
WNENQNPRMFLAMITYITRNQPEWFRNILSMAPIMFSNKMARLGKGYMFESKRMKIRTQIPAEMLASIDLKYFNEST
KKKIEKIRPLLIDGTASLSPGMMMGMFNMLSTVLGVSILNLGQKKYTKTIYWWDGLQSSDDFALIVNAPNHEGIQAG
VDRFYRTCKLVGINMSKKKSYINKTGTFEFTSFFYRYGFVANFSMELPSFGVSGVNESADMSIGVTVIKNNMINNDL
GPATAQMALQLFIKDYRYTYRCHRGDTQIQTRRSFELKKLWDQTQSKVGLLVSDGGPNLYNIRNLHIPEVCLKWELM
DDDYRGRLCNPLNPFVSHKEIDSVNNAVVMPAHGPAKSMEYDAVATTHSWIPKRNRSILNTSQRGILEDEQMYQKCC
NLFEKFFPSSSYRRPVGISSMVEAMVSRARIDARVDFESGRIKKEEFSEIMKICSTIEELRRQK SEQ ID NO: 19 (PB2, A/California/07/09)
MERIKELRDLMSQSRTREILTKTTVDHMAIIKKYTSGRQEKNPALRMKWMMAMRYPITADKRIMDMIPERNEQGQTL
WSKTNDAGSDRVMVSPLAVTWWNRNGPTTSTVHYPKVYKTYFEKVERLKHGTFGPVHFRNQVKIRRRVDTNPGHADL
SAKEAQDVIMEVVFPNEVGARILTSESQLAITKEKKEELQDCKIAPLMVAYMLERELVRKTRFLPVAGGTGSVYIEV
LHLTQGTCWEQMYTPGGEVRNDDVDQSLIIAARNIVRRAAVSADPLASLLEMCHSTQIGGVRMVDILRQNPTEEQAV -continued

| SEQUENCES |
| --- |

DICKAAIGLRISSSFSFGGFTFKRTSGSSVKKEEEVLTGNLQTLKIRVHEGYEEFTMVGRRATAILRKATRRLIQLI
VSGRDEQSIAEAIIVAMVFSQEDCMIKAVRGDLNFVNRANQRLNPMHQLLRHFQKDAKVLFQNWGIESIDNVMGMIG
ILPDMTPSTEMSLRGIRVSKMGVDEYSSTERVVVSIDRFLRVRDQRGNVLLSPEEVSETQGTEKLTITYSSSMMWEI
NGPESVLVNTYQWIIRNWEIVKIQWSQDPTMLYNKMEFEPFQSLVPKATRSRYSGFVRTLFQQMRDVLGTFDTVQII
KLLPFAAAPPEQSRMQFSSLTVNVRGSGLRILVRGNSPVFNYNKATKRLTVLGKDAGALTEDPDEGTSGVESAVLRG
FLILGKEDKRYGPALSINELSNLAKGEKANVLIGQGDVVLVMKRKRDSSILTDSQTATKRIRMAIN

SEQ ID NO: 20 (NP, A/California/07/09)
MASQGTKRSYEQMETGGERQDATEIRASVGRMIGGIGRFYIQMCTELKLSDYDGRLIQNSITIERMVLSAFDERRNK
YLEEHPSAGKDPKKTGGPIYRRVDGKWMRELILYDKEEIRRVWRQANNGEDATAGLTHIMIWHSNLNDATYQRTRAL
VRTGMDPRMCSLMQGSTLPRRSGAAGAAVKGVGTIAMELIRMIKRGINDRNFWRGENGRRTRVAYERMCNILKGKFQ
TAAQRAMMDQVRESRNPGNAEIEDLIFLARSALILRGSVAHKSCLPACVYGLAVASGHDFEREGYSLVGIDPFKLLQ
NSQVVSLMRPN SEQ ID NO: 21 (M1, A/California/07/09)
MSLLTEVETYVLSIIPSGPLKAEIAQRLESVFAGKNTDLEALMEWLKTRPILSPLTKGILGFVFTLTVPSERGLQRR
RFVQNALNGNGDPNNMDRAVKLYKKLKREITFHGAKEVSLSYSTGALASCMGLIYNRMGTVTTEAAFGLVCATCEQI
ADSQHRSHRQMATTTNPLIRHENRMVLASTTAKAMEQMAGSSEQAAEAMEVANQTRQMVHAMRTIGTHPSSSAGLKD
DLLENLQAYQKRMGVQMQRFK SEQ ID NO: 22 (NS1, A/California/07/09)
MDSNTMSSFQVDCFLWHIRKRFADNGLGDAPFLDRLRRDQKSLKGRGNTLGLDIETATLVGKQIVEWILKEESSETL
RMTIASVPTSRYLSDMTLEEMSRDWFMLMPRQKIIGPLCVRLDQAIMEKNIVLKANFSVIFNRLETLILLRAFTEEG
AIVGEISPLPSLPGHTYEDVKNAVGVLIGGLEWNGNTVRVSENIQRFAWRNCDENGRPSLPPEQK SEQ ID NO: 23 (PA, A/California/07/09)
ATGGAAGACTTTGTGCGACAATGCTTCAATCCAATGATCGTCGAGCTTGCGGAAAAGGCAATGAAAGAATATGGGGA
AGATCCGAAAATCGAAACTAACAAGTTTGCTGCAATATGCACACATTTGGAAGTTTGTTTCATGTATTCGGATTTCC
ATTTCATCGACGAACGGGGTGAATCAATAATTGTAGAATCTGGTGACCCGAATGCACTATTGAAGCACCGATTTGAG
ATAATTGAAGGAAGAGACCGAATCATGGCCTGGACAGTGGTGAACAGTATATGTAACACAACAGGGGTAGAGAAGCC
TAAATTTCTTCCTGATTTGTATGATTACAAAGAGAACCGGTTCATTGAAATTGGAGTAACACGGAGGGAAGTCCACA
TATATTACCTAGAGAAAGCCAACAAAATAAAATCTGAGAAGACACACATTCACATCTTTTCATTCACTGGAGAGGAG
ATGGCCACCAAAGCGGACTACACCCTTGACGAAGAGAGCAGGGCAAGAATCAAAACTAGGCTTTTCACTATAAGACA
AGAAATGGCCAGTAGGAGTCTATGGGATTCCTTTCGTCAGTCCGAAAGAGGCGAAGAGACAATTGAAGAAAAATTTG
AGATTACAGGAACTATGCGCAAGCTTGCCGACCAAAGTCTCCCACCGAACTTCCCCAGCCTTGAAAACTTTAGAGCC
TATGTAGATGGATTCGAGCCGAACGGCTGCATTGAGGGCAAGCTTTCCCAAATGTCAAAAGAAGTGAACGCCAAAAT
TGAACCATTCTTGAGGACGACACCACGCCCCCTCAGATTGCCTGATGGGCCTCTTTGCCATCAGCGGTCAAAGTTCC
TGCTGATGGATGCTCTGAAATTAAGTATTGAAGACCCGAGTCACGAGGGGGAGGGAATACCACTATATGATGCAATC
AAATGCATGAAGACATTCTTTGGCTGGAAAGAGCCTAACATAGTCAAACCACATGAGAAAGGCATAAATCCCAATTA
CCTCATGGCTTGGAAGCAGGTGCTAGCAGAGCTACAGGACATTGAAAATGAAGAGAAGATCCCAAGGACAAAGAACA
TGAAGAGAACAAGCCAATTGAAGTGGGCACTCGGTGAAAATATGGCACCAGAAAAAGTAGACTTTGATGACTGCAAA
GATGTTGGAGACCTTAAACAGTATGACAGTGATGAGCCAGAGCCCAGATCTCTAGCAAGCTGGGTCCAAAATGAATT
CAATAAGGCATGTGAATTGACTGATTCAAGCTGGATAGAACTTGATGAAATAGGAGAAGATGTTGCCCCGATTGAAC
ATATCGCAAGCATGAGGAGGAACTATTTTACAGCAGAAGTGTCCCACTGCAGGGCTACTGAATACATAATGAAGGGA
GTGTACATAAATACGGCCTTGCTCAATGCATCCTGTGCAGCCATGGATGACTTTCAGCTGATCCCAATGATAAGCAA
ATGTAGGACCAAAGAAGGAAGACGGAAAACAAACCTGTATGGGTTCATTATAAAAGGAAGGTCTCATTTGAGAAATG
ATACTGATGTGGTGAACTTTGTAAGTATGGAGTTCTCACTCACTGACCCGAGACTGGAGCCACACAAATGGGAAAAA
TACTGTGTTCTTGAAATAGGAGACATGCTTCTGAGGACTGCGATAGGCCAAGTGTCGAGGCCCATGTTCCTATATGT
GAGAACCAATGGAACCTCCAAGATCAAGATGAAATGGGGCATGGAAATGAGGCGCTGCCTTCTTCAGTCTCTTCAGC
AGATTGAGAGCATGATTGAGGCCGAGTCTTCTGTCAAAGAGAAAGACATGACCAAGGAATTCTTTGAAAACAAATCG
GAAACATGGCCAATCGGAGAGTCACCCAGGGGAGTGGAGGAAGGCTCTATTGGGAAAGTGTGCAGGACCTTACTGGC
AAAATCTGTATTCAACAGTCTATATGCGTCTCCACAACTTGAGGGGTTTTCGGCTGAATCTAGAAAATTGCTTCTCA
TTGTTCAGGCACTTAGGGACAACCTGGAACCTGGAACCTTCGATCTTGGGGGGCTATATGAAGCAATCGAGGAGTGC
CTGATTAATGATCCCTGGGTTTTGCTTAATGCATCTTGGTTCAACTCCTTCCTCACACATGCACTGAAGTAG SEQ ID NO: 24 (PB1, A/California/07/09)
AGCGAAAGCAGGCAAACCATTTGAATGGATGTCAATCCGACTCTACTTTTCCTAAAAATTCCAGCGCAAAATGCCAT
AAGCACCACATTCCCTTATACTGGAGATCCTCCATACAGCCATGGAACAGGAACAGGATACACCATGGACACAGTAA
ACAGAACACACCAATACTCAGAAAAGGGAAAGTGGACGACAAACACAGAGACTGGTGCACCCCAGCTCAACCCGATT
GATGGACCACTACCTGAGGATAATGAACCAAGTGGGTATGCACAAACAGACTGTGTTCTAGAGGCTATGGCTTTCCT
TGAAGAATCCCACCCAGGAATATTTGAGAATTCATGCCTTGAAACAATGGAAGTTGTTCAACAAACAAGGGTAGATA
AACTAACTCAAGGTCGCCAGACTTATGATTGGACATTAAACAGAAATCAACCGGCAGCAACTGCATTGGCCAACACC
ATAGAAGTCTTTAGATCGAATGGCCTAACAGCTAATGAGTCAGGAAGGCTAATAGATTTCTTAAAGGATGTAATGGA
ATCAATGAACAAAGAGGAAATAGAGATAACAACCCACTTTCAAAGAAAAAGGAGAGTAAGAGACAACATGACCAAGA
AGATGGTCACGCAAAGAACAATAGGGAAGAAAAAACAAAGACTGAATAAGAGAGGCTATCTAATAAGAGCACTGACA
TTAAATACGATGACCAAAGATGCAGAGAGAGGCAAGTTAAAAAGAAGGGCTATCGCAACACCTGGGATGCAGATTAG
AGGTTTCGTATACTTTGTTGAAACTTTAGCTAGGAGCATTTGCGAAAAGCTTGAACAGTCTGGGCTCCCAGTAGGGG
GCAATGAAAAGAAGGCCAAACTGGCAAATGTTGTGAGAAAGATGATGACTAATTCACAAGACACAGAGATTTCTTTC
ACAATCACTGGGGACAACACTAAGTGGAATGAAAATCAAAATCCTCGAATGTTCCTGGCGATGATTACATATATCAC
CAGAAATCAACCCGAGTGGTTCAGAAACATCCTGAGCATGGCACCCATAATGTTCTCAAACAAAATGGCAAGACTAG
GGAAAGGGTACATGTTCGAGAGTAAAAGAATGAAGATTCGAACACAAATACCAGCAGAAATGCTAGCAAGCATTGAC
CTGAAGTACTTCAATGAATCAACAAAGAAGAAAATTGAGAAAATAAGGCCTCTTCTAATAGATGGCACAGCATCACT
GAGTCCTGGGATGATGATGGGCATGTTCAACATGCTAAGTACGGTCTTGGGAGTCTCGATACTGAATCTTGGACAAA
AGAAATACACCAAGACAATATACTGGTGGGATGGGCTCCAATCATCCGACGATTTTGCTCTCATAGTGAATGCACCA
AACCATGAGGGAATACAAGCAGGAGTGGACAGATTCTACAGGACCTGCAAGTTAGTGGGAATCAACATGAGCAAAAA
GAAGTCCTATATAAATAAGACAGGGACATTTGAATTCACAAGCTTTTTTATCGCTATGGATTTGTGGCTAATTTTA
GCATGGAGCTACCCAGCTTTGGAGTGTCTGGAGTAAATGAATCAGCTGACATGAGTATTGGAGTAACAGTGATAAAG -continued

SEQUENCES

AACAACATGATAAACAATGACCTTGGACCTGCAACGGCCCAGATGGCTCTTCAATTGTTCATCAAAGACTACAGATA
CACATATAGGTGCCATAGGGGAGACACACAAATTCAGACAAGAAGATCATTTGAGTTAAAGAAGCTGTGGGATCAAA
CCCAATCAAAGGTAGGGCTATTAGTATCAGATGGAGGACCAAACTTATACAATATACGGAATCTTCACATTCCTGAA
GTCTGCTTAAAATGGGAGCTAATGGATGATGATTATCGGGGAAGACTTTGTAATCCCCTGAATCCCTTTGTCAGTCA
TAAAGAGATTGATTCTGTAAACAATGCTGTGGTAATGCCAGCCCATGGTCCAGCCAAAAGCATGGAATATGATGCCG
TTGCAACTACACATTCCTGGATTCCCAAGAGGAATCGTTCTATTCTCAACACAAGCCAAAGGGGAATTCTTGAGGAT
GAACAGATGTACCAGAAGTGCTGCAATCTATTCGAGAAATTTTTCCCTAGCAGTTCATATAGGAGACCGGTTGGAAT
TTCTAGCATGGTGGAGGCCATGGTGTCTAGGGCCCGGATTGATGCCAGGGTCGACTTCGAGTCTGGACGGATCAAGA
AAGAAGAGTTCTCTGAGATCATGAAGATCTGTTCCACCATTGAAGAACTCAGACGGCAAAAATAATGAATTTAACTT
GTCCTTCATGAAAAAATGCCTTGTTTCTACT

SEQ ID NO: 25 (PB2, A/California/07/09)
ATGGAGAGAATAAAAGAACTGAGAGATCTAATGTCGCAGTCCCGCACTCGCGAGATACTCACTAAGACCACTGTGGA
CCATATGGCCATAATCAAAAAGTACACATCAGGAAGGCAAGAGAAGAACCCCGCACTCAGAATGAAGTGGATGATGG
CAATGAGATACCCAATTACAGCAGACAAGAGAATAATGGACATGATTCCAGAGAGGAATGAACAAGGACAAACCCTC
TGGAGCAAAACAAACGATGCTGGATCAGACCGAGTGATGGTATCACCTCTGGCCGTAACATGGTGGAATAGGAATGG
CCCAACAACAAGTACAGTTCATTACCCTAAGGTATATAAAACTTATTTCGAAAAGGTCGAAAGGTTGAAACATGGTA
CCTTCGGCCCTGTCCACTTCAGAAATCAAGTTAAAATAAGGAGGAGAGTTGATACAAACCCTGGCCATGCAGATCTC
AGTGCCAAGGAGGCACAGGATGTGATTATGGAAGTTGTTTTCCCAAATGAAGTGGGGGCAAGAATACTGACATCAGA
GTCACAGCTGGCAATAACAAAAGAGAAGAAAGAAGAGCTCCAGGATTGTAAAATTGCTCCCTTGATGGTGGCGTACA
TGCTAGAAAGAGAATTGGTCCGTAAAACAAGGTTTCTCCCAGTAGCCGGCGGAACAGGCAGTGTTTATATTGAAGTG
TTGCACTTAACCCAAGGGACGTGCTGGGAGCAGATGTACACTCCAGGAGGAGAAGTGAGAAATGATGATGTTGACCA
AAGTTTGATTATCGCTGCTAGAAACATAGTAAGAAGAGCAGCAGTGTCAGCAGACCCATTAGCATCTCTCTTGGAAA
TGTGCCACAGCACACAGATTGGAGGAGTAAGGATGGTGGACATCCTTAGACAGAATCCAACTGAGGAACAAGCCGTA
GACATATGCAAGGCAGCAATAGGGTTGAGGATTAGCTCATCTTTCAGTTTTGGTGGGTTCACTTTCAAAAGGACAAG
CGGATCATCAGTCAAGAAAGAAGAAGAAGTGCTAACGGGCAACCTCCAAACACTGAAAATAAGAGTACATGAAGGGT
ATGAAGAATTCACAATGGTTGGGAGAAGAGCAACAGCTATTCTCAGAAAGGCAACCAGGAGATTGATCCAGTTGATA
GTAAGCGGGAGAGACGAGCAGTCAATTGCTGAGGCAATAATTGTGGCCATGGTATTCTCACAGGAGGATTGCATGAT
CAAGGCAGTTAGGGGCGATCTGAACTTTGTCAATAGGGCAAACCAGCGACTGAACCCCATGCACCAACTCTTGAGGC
ATTTCCAAAAAGATGCAAAAGTGCTTTTCCAGAACTGGGGAATTGAATCCATCGACAATGTGATGGGAATGATCGGA
ATACTGCCCGACATGACCCCAAGCACGGAGATGTCGCTGAGAGGGATAAGAGTCAGCAAAATGGGAGTAGATGAATA
CTCCAGCACGGAGAGAGTGGTAGTGAGTATTGACCGATTTTTAAGGGTTAGAGATCAAAGAGGGAACGTACTATTGT
CTCCCGAAGAAGTCAGTGAAACGCAAGGAACTGAGAAGTTGACAATAACTTATTCGTCATCAATGATGTGGGAGATC
AATGGCCCTGAGTCAGTGCTAGTCAACACTTATCAATGGATAATCAGGAACTGGGAAATTGTGAAAATTCAATGGTC
ACAAGATCCCACAATGTTATACAACAAAATGGAATTTGAACCATTTCAGTCTCTTGTCCCTAAGGCAACCAGAAGCC
GGTACAGTGGATTCGTAAGGACACTGTTCCAGCAAATGCGGGATGTGCTTGGGACATTTGACACTGTCCAAATAATA
AAACTTCTCCCCTTTGCTGCTGCCCCACCAGAACAGAGTAGGATGCAATTTTCCTCATTGACTGTGAATGTGAGAGG
ATCAGGGTTGAGGATACTGGTAAGAGGCAATTCTCCAGTATTCAATTACAACAAGGCAACCAAACGACTTACAGTTC
TTGGAAAGGATGCAGGTGCATTGACTGAAGATCCAGATGAAGGCACATCTGGGGTGGAGTCTGCTGTCCTGAGAGGA
TTTCTCATTTTGGGCAAAGAAGACAAGAGATATGGCCCAGCATTAAGCATCAATGAACTGAGCAATCTTGCAAAAGG
AGAGAAGGCTAATGTGCTAATTGGGCAAGGGGACGTAGTGTTGGTAATGAAACGAAAACGGGACTCTAGCATACTTA
CTGACAGCCAGACAGCGACCAAAAGAATTCGGATGGCCATCAATTAG SEQ ID NO: 26 (NP, A/California/07/09)
ATGGCGTCTCAAGGCACCAAACGATCATATGAACAAATGGAGACTGGTGGGGAGCGCCAGGATGCCACAGAAATCAG
AGCATCTGTCGGAAGAATGATTGGTGGAATCGGGAGATTCTACATCCAAATGTGCACTGAACTCAAACTCAGTGATT
ATGATGGACGACTAATCCAGAATAGCATAACAATAGAGAGGATGGTGCTTTCTGCTTTTGATGAGAGAAGAAATAAA
TACCTAGAAGAGCATCCCAGTGCTGGGAAGGACCCTAAGAAAACAGGAGGACCCATATATAGAAGAGTAGACGGAAA
GTGGATGAGAGAACTCATCCTTTATGACAAAGAAGAAATAAGGAGAGTTTGGCGCCAAGCAAACAATGGCGAAGATG
CAACAGCAGGTCTTACTCATATCATGATTTGGCATTCCAACCTGAATGATGCCACATATCAGAGAACAAGAGCGCTT
GTTCGCACCGGAATGGATCCCAGAATGTGCTCTCTAATGCAAGGTTCAACACTTCCCAGAAGGTCTGGTGCCGCAGG
TGCTGCGGTGAAAGGAGTTGGAACAATAGCAATGGAGTTAATCAGAATGATCAAACGTGGAATCAATGACCGAAATT
TCTGGAGGGGTGAAAATGGACGAAGGACAAGGGTTGCTTATGAAAGAATGTGCAATATCCTCAAAGGAAAATTTCAA
ACAGCTGCCCAGAGGGCAATGATGGATCAAGTAAGAGAAAGTCGAAACCCAGGAAACGCTGAGATTGAAGACCTCAT
TTTCCTGGCACGGTCAGCACTCATTCTGAGGGGATCAGTTGCACATAAATCCTGCCTGCCTGCTTGTGTGTATGGGC
TTGCAGTAGCAAGTGGGCATGACTTTGAAAGGGAAGGGTACTCACTGGTCGGGATAGACCCATTCAAATTACTCCAA
AACAGCCAAGTGGTCAGCCTGATGAGACCAAATG SEQ ID NO: 27 (M, A/California/07/09)
ATGAGTCTTCTAACCGAGGTCGAAACGTACGTTCTTTCTATCATCCCGTCAGGCCCCCTCAAAGCCGAGATCGCGCA
GAGACTGGAAAGTGTCTTTGCAGGAAAGAACACAGATCTTGAGGCTCTCATGGAATGGCTAAAGACAAGACCAATCT
TGTCACCTCTGACTAAGGGAATTTTAGGATTTGTGTTCACGCTCACCGTGCCCAGTGAGCGAGGACTGCAGCGTAGA
CGCTTTGTCCAAAATGCCCTAAATGGGAATGGGGACCCGAACAACATGGATAGAGCAGTTAAACTATACAAGAAGCT
CAAAAGAGAAATAACGTTCCATGGGGCCAAGGAGGTGTCACTAAGCTATTCAACTGGTGCACTTGCCAGTTGCATGG
GCCTCATATACAACAGGATGGGAACAGTGACCACAGAAGCTGCTTTTGGTCTAGTGTGTGCCACTTGTGAACAGATT
GCTGATTCACAGCATCGGTCTCACAGACAGATGGCTACTACCACCAATCCACTAATCAGGCATGAAAACAGAATGGT
GCTGGCTAGCACTACGGCAAAGGCTATGGAACAGATGGCTGGATCGAGTGAACAGGCAGCGGAGGCCATGGAGGTTG
CTAATCAGACTAGGCAGATGGTACATGCAATGAGAACTATTGGGACTCATCCTAGCTCCAGTGCTGGTCTGAAAGAT
GACCTTCTTGAAAATTTGCAGGCCTACCAGAAGCGAATGGGAGTGCAGATGCAGCGATTCAAGTGATCCTCTCGTCA
TTGCAGCAAATATCATTGGGATCTTGCACCTGATATTGTGGATTACTGATCGTCTTTTTTTCAAATGTATTTATCGT
CGCTTTAAATACGGTTTGAAAAGAGGGCCTTCTACGGAAGGAGTGCCTGAGTCCATGAGGGAAGAATATCAACAGGA
ACAGCAGAGTGCTGTGGATGTTGACGATGGTCATTTTGTCAACATAGAGCTAGAGTAA SEQ ID NO: 28 (NS, A/California/07/09)
ATGGACTCCAACACCATGTCAAGCTTTCAGGTAGACTGTTTCCTTTGGCATATCCGCAAGCGATTTGCAGACAATGG
ATTGGGTGATGCCCCATTCCTTGATCGGCTCCGCCGAGATCAAAAGTCCTTAAAAGGAAGAGGCAACACCCTTGGCC
TCGATATCGAAACAGCCACTCTTGTTGGGAAACAAATCGTGGAATGGATCTTGAAAGAGGAATCCAGCGAGACACTT -continued

SEQUENCES

AGAATGACAATTGCATCTGTACCTACTTCGCGCTACCTTTCTGACATGACCCTCGAGGAAATGTCACGAGACTGGTT
CATGCTCATGCCTAGGCAAAAGATAATAGGCCCTCTTTGCGTGCGATTGGACCAGGCGATCATGGAAAAGAACATAG
TACTGAAAGCGAACTTCAGTGTAATCTTTAACCGATTAGAGACCTTGATACTACTAAGGGCTTTCACTGAGGAGGGA
GCAATAGTTGGAGAAATTTCACCATTACCTTCTCTTCCAGGACATACTTATGAGGATGTCAAAAATGCAGTTGGGGT
CCTCATCGGAGGACTTGAATGGAATGGTAACACGGTTCGAGTCTCTGAAAATATACAGAGATTCGCTTGGAGAAACT
GTGATGAGAATGGGAGACCTTCACTACCTCCAGAGCAGAAATGAAAAGTGGCGAGAGCAATTGGGACAGAAATTTGA
GGAAATAAGGTGGTTAATTGAAGAAATGCGGCACAGATTGAAAGCGACAGAGAATAGTTTCGAACAAATAACATTTA
TGCAAGCCTTACAACTACTGCTTGAAGTAGAACAAGAGATAAGAGCTTTCTCGTTTCAGCTTATTTAATGATAAAAA
ACACCCTTGTTTCTACTG

SEQ ID NO: 29 (A/Texas/1/77 PB1)
MDVNPTLLFLKIPAQNAISTTFPYTGDPPYSHGTGTGYTMDTVNRTHQYSEKGKWTTNTETGAPQLNPIDGPLPEDN
EPSGYAQTDCVLEAMAFLEESHPGIFENSCLETMEVVQQTRVDRLTQGRQTYDWTLNRNQPAATALANTIEVFRSNG
LTANESGRLIDFLKDVMESMDKEEIEITTHFQRKRRVRDNMTKKMVTQRTIGKKKQRVNKRSYLIRALTLNTMTKDA
ERGKLKRRAIATPGMQIRGFVYFVETLARSICEKLEQSGLPVGGNEKKAKLANVVRKMMTNSQDTELSFTITGDNTK
WNENQNPRMFLAMITYITKNQPEWFRNILSIAPIMFSNKMARLGKGYMFESKRMKLRTQIPAEMLASIDLKYFNEST
RKKIEKIRPLLIDGTASLSPGMMMGMFNMLSTVLGVSILNLGQKKYTKTTYWWDGLQSSDDFALIVNAPNHEGIQAG
VDRFYRTCKLVGINMSKKKSYINRTGTFEFTSFFYRYGFVANFSMELPSFGVSGINESADMSIGVTVIKNNMINNDL
GPATAQMALQLFIKDYRYTYRCHRGDTQIQTRRSFELKKLWEQTRSKAGLLVSDGGPNLYNIRNLHIPEVCLKWELM
DEDYQGRLCNPLNPFVSHKEIESVNNAVVMPAHGPAKSMEYDAVATTHSWIPKRNRSILNTSQRGILEDEQMYQKCC
NLFEKFFPSSSYRRPVGISSMVEAMVSRARIDARTDFESGRIKKEEFSEIMKICSTIEELRRQKQ SEQ ID NO: 30 (A/Puerto Rico/8/34 PA)
MEDFVRQCFNPMIVELAEKTMKEYGEDLKIETNKFAAICTHLEVCFMYSDFHFINEQGESIIVELGDPNALLKHRFE
IIEGRDRTMAWTVVNSICNTTGAEKPKFLPDLYDYKENRFIEIGVTRREVHIYYLEKANKIKSEKTHIHIFSFTGEE
MATKADYTLDEESRARIKTRLFTIRQEMASRGLWDSFRQSERGEETIEERFEITGTMRKLADQSLPPNFSSLENFRA
YVDGFEPNGYIEGKLSQMSKEVNARIEPFLKTTPRPLRLPNGPPCSQRSKFLLMDALKLSIEDPSHEGEGIPLYDAI
KCMRTFFGWKEPNVVKPHEKGINPNYLLSWKQVLAELQDIENEEKIPKTKNMKKTSQLKWALGENMAPEKVDFDDCK
DVGDLKQYDSDEPELRSLASWIQNEFNKACELTDSSWIELDEIGEDVAPIEHIASMRRNYFTSEVSHCRATEYIMKG
VYINTALLNASCAAMDDFQLIPMISKCRTKEGRRKTNLYGFIIKGRSHLRNDTDVVNFVSMEFSLTDPRLEPHKWEK
YCVLEIGDMLIRSAIGQVSRPMFLYVRTNGTSKIKMKWGMEMRRCLLQSLQQIESMIEAESSVKEKDMTKEFFENKS
ETWPIGESPKGVEESSIGKVCRTLLAKSVFNSLYASPQLEGFSAESRKLLLIVQALRDNLEPGTFDLGGLYEAIEEC
LINDPWVLLNASWFNSFLTHALS SEQ ID NO: 31 (A/Puerto Rico/8/34 NP)
MASQGTKRSYEQMETDGERQNATEIRASVGKMIGGIGRFYIQMCTELKLSDYEGRLIQNSLTIERMVLSAFDERRNK
YLEEHPSAGKDPKKTGGPIYRRVNGKWMRELILYDKEEIRRIWRQANNGDDATAGLTHMMIWHSNLNDATYQRTRAL
VRTGMDPRMCSLMQGSTLPRRSGAAGAAVKGVGTMVMELVRMIKRGINDRNFWRGENGRKTRIAYERMCNILKGKFQ
TAAQKAMMDQVRESRDPGNAEFEDLTFLARSALILRGSVAHKSCLPACVYGPAVASGYDFEREGYSLVGIDPFRLLQ
NSQVYSLIRPNENPAHKS SEQ ID NO: 32 (A/Puerto Rico/8/34 M)
MSLLTEVETYVLSIIPSGPLKAEIAQRLEDVFAGKNTDLEVLMEWLKTRPILSPLTKGILGFVFTLTVPSERGLQRR
RFVQNALNGNGDPNNMDKAVKLYRKLKREITFHGAKEISLSYSAGALASCMGLIYNRMGAVTTEVAFGLVCATCEQI
ADSQHRSHRQMVTTTNPLIRHENRMVLASTTAKAMEQMAGSSEQAAEAMEVASQARQMVQAMRTIGTHPSSSAGLKN
DLLENLQAYQKRMGVQMQRFK SEQ ID NO: 33 (PB2, A/New Caledonia/20/1999)
AATATGGAAAGAATAAAAGAGCTAAGGAATCTGATGTCACAATCTCGCACTCGCGAGATACTTACAAAAACTACTGT
AGACCACATGGCCATAATCAAGAAATACACATCAGGAAGACAGGAGAAAAACCCATCACTTAGAATGAAATGGATGA
TGGCAATGAAATACCCAATTACAGCAGATAAAAGGATAACGGAAATGATTCCTGAAAGAAATGAGCAAGGACAGACA
TTATGGAGTAAAGTGAATGATGCCGGATCAGACCGAGTGATGATATCACCCCTGGCTGTGACATGGTGGAACAGAAA
TGGACCAGTGGCAAGTACTATTCACTATCCAAAAATCTACAAAACTTACTTTGAAAAGGTTGAAAGGTTAAAACATG
GAACCTTTGGCCCTGTACACTTTAGAAACCAAGTCAAAATACGCCGAAGAGTCGACATAAATCCTGGTCATGCAGAC
CTCAGCGCCAAGGAGGCACAGGATGTAATTATGGAAGTTGTTTTCCCTAATGAAGTGGGAGCCAGAATACTAACATC
AGAATCGCAATTAACGATAACCAAGGAGAAAAAAGAAGAACTCCAGAATTGCAAAATTTCCCCTTTGATGGTTGCAT
ACATGTTAGAGAGGGAACTTGTCCGCAAAACGAGATTTCTCCCGGTTGCTGGTGGAACAAGCAGTGTGTACATTGAA
GTTTTGCATTTAACACAGGGGACATGCTGGGAGCAGATGTACACTCCAGGTGGGGAGGTGAGGAATGATGATGTTGA
TCAAAGCCTAATTATTGCTGCTAGGAACATAGTGAGAAGAGCTGCAGTATCAGCAGATCCACTAGCATCTTTATTAG
AAATGTGCCATAGCACACAGATTGGTGGGACAAGGATGGTGGATATTCTCAGGCAAAATCCAACAGAAGAACAAGCT
GTGGATATATGCAAAGCAGCAATGGGGCTGAGAATCAGTTCATCCTTCAGTTTTGGCGGATTCACATTTAAGAGAAC
AAGTGGATCATCAGTCAAAAGGGAGGAAGAAGTGCTCACGGGCAATCTGCAAACATTGAAGCTAACTGTGCATGAGG
GATATGAAGAGTTCACAATGGTTGGGAAAAGGGCAACAGCTATACTCAGAAAAGCAACCAGGAGATTGATTCAACTA
ATAGTGAGTGGAAGAGACGAACAGTCAATAGTCGAAGCAATAGTTGTAGCAATGGTATTCTCACAAGAAGATTGCAT
GGTAAAAGCAGTTAGAGGTGATCTGAATTTCGTTAATAGAGCGAATCAGCGGTTGAATCCCATGCATCAACTTTTGA
GACATTTTCAGAAGGATGCTAAAGTACTTTTCTTAAATTGGGGAATTGAACCTATCGACAATGTGATGGGAATGATT
GGGATATTACCTGATATGACTCCAAGTACCGAGATGTCAATGAGAGGAGTGAGAGTCAGCAAAATGGGTGTAGATGA
ATACTCCAATGCTGAAAGGGTAGTGGTGAGCATTGACCGTTTTTTGAGAGTCCGGGACCAAAGAGGAAATGTACTAC
TGTCTCCAGAGGAAGTCAGTGAAACACAGGGAACAGAGAAACTGACAATAACTTACTCTTCATCAATGATGTGGGAG
ATTAATGGCCCTGAGTCAGTGTTGATCAATACCTATCAGTGGATCATCAGAAACTGGGAGACTGTTAAAATTCAGTG
GTCTCAGAACCCTACAATGCTATACAATAAAATGGAATTCGAGCCATTTCAGTCTCTAGTCCCTAAGGCCATTAGAG
GCCAATACAGTGGGTTTGTTAGAACTCTATTTCAACAAATGAGGGATGTGCTTGGGACCTTTGACACAACTCAGATA
ATAAAACTTCTTCCCTTTGCAGCCGCTCCACCAAAGCAAAGTAGAATGCAATTCTCATCATTGACTGTGAATGTGAG
GGGATCAGGAATGAGAATACTTGTAAGGGGTAATTCTCCAGTATTCAACTACAACAAGACCACTAAGAGACTCACAG
TCCTCGGAAAGGATGCTGGCACTTTAACTGAAGACCCAGATGAAGGCACAGCTGGAGTGGAATCTGCTGTTCTAAGG
GGATTCCTCATTCTAGGCAAAGAAGATAGAAGATATGGGCCAGCATTAAGCATCAATGAATTGAGCAACCTTGCGAA -continued

| SEQUENCES |
|---|

AGGGGAAAAAGCTAATGTGCTAATTGGGCAAGGGGACGTAGTGTTGGTAATGAAACGAAAACGGGACTCTAGCATAC
TTACTGACAGCCAGACAGCGACCAAAAGAATTCGGATGGCCATCAATTAATTTCGAATAATTTAAA

SEQ ID NO: 34 (encodes the same amino acid sequence as SEQ ID NO: 33)
ATGGAACGCATTAAAGAACTGCGCAACCTGATGAGCCAGAGCCGCACCCGCGAAATTCTGACCAAAACCACCGTGGA
TCATATGGCGATTATTAAAAAATATACCAGCGGCCGCCAGGAAAAAAACCCGAGCCTGCGCATGAAATGGATGATGG
CGATGAAATATCCGATTACCGCGGATAAACGCATTACCGAAATGATTCCGGAACGCAACGAACAGGGCCAGACCCTG
TGGAGCAAAGTGAACGATGCGGGCAGCGATCGCGTGATGATTAGCCCGCTGGCGGTGACCTGGTGGAACCGCAACGG
CCCGGTGGCGAGCACCATTCATTATCCGAAAATTTATAAAACCTATTTTGAAAAAGTGGAACGCCTGAAACATGGCA
CCTTTGGCCCGGTGCATTTTCGCAACCAGGTGAAAATTCGCCGCCGCGTGGATATTAACCCGGGCCATGCGGATCTG
AGCGCGAAAGAAGCGCAGGATGTGATTATGGAAGTGGTGTTTCCGAACGAAGTGGGCGCGCGCATTCTGACCAGCGA
AAGCCAGCTGACCATTACCAAAGAAAAAAAAGAAGAACTGCAGAACTGCAAAATTAGCCCGCTGATGGTGGCGTATA
TGCTGGAACGCGAACTGGTGCGCAAAACCCGCTTTCTGCCGGTGGCGGGCGGCACCAGCAGCGTGTATATTGAAGTG
CTGCATCTGACCCAGGGCACCTGCTGGGAACAGATGTATACCCCGGGCGGCGAAGTGCGCAACGATGATGTGGATCA
GAGCCTGATTATTGCGGCGCGCAACATTGTGCGCCGCGCGGTGAGCGCGGATCCGCTGGCGAGCCTGCTGGAAA
TGTGCCATAGCACCCAGATTGGCGGCACCCGCATGGTGGATATTCTGCGCCAGAACCCGACCGAAGAACAGGCGGTG
GATATTTGCAAAGCGGCGATGGGCCTGCGCATTAGCAGCAGCTTTAGCTTTGGCGGCTTTACCTTTAAACGCACCAG
CGGCAGCAGCGTGAAACGCGAAGAAGAAGTGCTGACCGGCAACCTGCAGACCCTGAAACTGACCGTGCATGAAGGCT
ATGAAGAATTTACCATGGTGGGCAAACGCGCGACCGCGATTCTGCGCAAAGCGACCCGCCGCCTGATTCAGCTGATT
GTGAGCGGCCGCGATGAACAGAGCATTGTGGAAGCGATTGTGGTGGCGATGGTGTTTAGCCAGGAAGATTGCATGGT
GAAAGCGGTGCGCGGCGATCTGAACTTTGTGAACCGCGCGAACCAGCGCCTGAACCCGATGCATCAGCTGCTGCGCC
ATTTTCAGAAAGATGCGAAAGTGCTGTTTCTGAACTGGGGCATTGAACCGATTGATAACGTGATGGGCATGATTGGC
ATTCTGCCGGATATGACCCCGAGCACCGAAATGAGCATGCGCGGCGTGCGCGTGAGCAAAATGGGCGTGGATGAATA
TAGCAACGCGGAACGCGTGGTGGTGAGCATTGATCGCTTTCTGCGCGTGCGCGATCAGCGCGGCAACGTGCTGCTGA
GCCCGGAAGAAGTGAGCGAAACCCAGGGCACCGAAAAACTGACCATTACCTATAGCAGCAGCATGATGTGGGAAATT
AACGGCCCGGAAAGCGTGCTGATTAACACCTATCAGTGGATTATTCGCAACTGGGAAACCGTGAAAATTCAGTGGAG
CCAGAACCCGACCATGCTGTATAACAAAATGGAATTTGAACCGTTTCAGAGCCTGGTGCCGAAAGCGATTCGCGGCC
AGTATAGCGGCTTTGTGCGCACCCTGTTTCAGCAGATGCGCGATGTGCTGGGCACCTTTGATACCACCCAGATTATT
AAACTGCTGCCGTTTGCGGCGGCGCCGCCGAAACAGAGCCGCATGCAGTTTAGCAGCCTGACCGTGAACGTGCGCGG
CAGCGGCATGCGCATTCTGGTGCGCGGCAACAGCCCGGTGTTTAACTATAACAAAACCACCAAACGCCTGACCGTGC
TGGGCAAAGATGCGGGCACCCTGACCGAAGATCCGGATGAAGGCACCGCGGGCGTGGAAAGCGCGGTGCTGCGCGGC
TTTCTGATTCTGGGCAAAGAAGATCGCCGCTATGGCCCGGCGCTGAGCATTAACGAACTGAGCAACCTGGCGAAAGG
CGAAAAAGCGAACGTGCTGATTGGCCAGGGCGATGTGGTGCTGGTGATGAAACGCAAACGCGATAGCAGCATTCTGA
CCGATAGCCAGACCGCGACCAAACGCATTCGCATGGCGATTAAC SEQ ID NO: 35 (PA, A/New Caledonia/20/1999)
GATTCGAAATGGAAGATTTTGTGCGACAATGCTTCAATCCGATGATTGTCGAGCTTGCGGAAAAGGCAATGAAAGAG
TATGGAGAGGACCTGAAAATCGAAACAAACAAATTTGCAGCAATATGCACTCACTTGGAAGTATGCTTCATGTATTC
AGATTTTCATTTCATCAATGAGCAAGGCGAATCAATAATAGTAGAGCCTGAGGACCCAAATGCACTTTTAAAGCACA
GATTTGAGATAATAGAGGGACGAGATCGTACAATGGCATGGACAGTTGTAAACAGTATTTGCAACACCACAGGAGCT
GAGAAACCAAAGTTTCTGCCAGATCTGTATGATTACAAAGAGAATAGATTCATCGAGATTGGAGTGACAAGGAGGGA
AGTTCACATATACTATCTGGAAAAGGCCAACAAAATTAAATCTGAGAAGACACACATTCACATTTTCTCATTCACTG
GCGAAGAAATGGCCACAAAGGCCGATTACACTCTCGATGAAGAAAGCAGGGCTAGGATTAAAACCAGACTATTCACC
ATAAGACAAGAAATGGCAAGCAGAGGTCTTTGGGACTCCTTTCGTCAGTCCGAAAGAGGCGAAGAAACAATTGAAGA
AAGATTTGAAATCACAGGGACAATGCGCAGGCTCGCTGACCAAAGCCTTCCGCCGAACTTCTCCTGCATTGAGAATT
TTAGAGCCTATGTGGATGGATTTGAACCGAACGGCTACATTGAGGGCAAGCTTTCTCAAATGTCCAAAGAAGTAAAT
GCTAGAATTGAGCCTTTTTTGAAAACAACACCACGACCACCAATTAGACTTCCGGATGGGCCTCCTTGTTTTCAGCGGTC
AAAATTCCTGCTGATGGATTCTTTAAAATTAAGCATTGAGGATCCAAATCATGAAGGAGAGGGAATACCACTATATG
ATGCAATCAAGTGTATGAGAACATTCTTTGGATGGAAAGAACCCTCTGTTGTCAAGCCACACGGGAAGGGAATAAAT
CCGAATTATCTGCTGTCATGGAAGCAGGTATTGGAAGAGCTGCAGGACATTGAGAGTGAGGAGAAGATTCCAAGAAC
AAAAAACATGAAAAAAACGAGTCAGCTAAAGTGGGCACTTGGTGAGAACATGGCACCAGAGAAGGTGGATTTTGATG
ACTGTAAAGATATAAGCGATTTGAAGCAATATGATAGTGACGAACCTGAATTAAGGTCATTTTCAAGTTGGATCCAG
AATGAGTTCAACAAGGCATGCGAGCTGACCGATTCAATCTGGATAGAGCTCGATGAGATTGGAGAAGATGTGGCCCC
GATTGAACACATTGCAAGCATGAGAAGAAATTACTTCACAGCTGAGGTGTCCCATTGCAGAGCCACAGAATATATAA
TGAAGGGGGTATACATTAATACTGCTTTGCTTAATGCATCCTGTGCAGCAATGGATGATTTCCAACTAATTCCCATG
ATAAGCAAATGTAGAACTAAAGAGGGAAGGAGAAAGACCAATTTGTACGGCTTCATCGTAAAAGGAAGATCTCACTT
AAGGAATGACACCGATGTGGTAAACTTTGTGAGCATGGAGTTTTCCCTCACTGACCCAAGACTTGAGCCACACAAAT
GGGAGAAGTACTGTGTTCTTGAGATAGGAGATATGCTTCTAAGGAGTGCAATAGGCCAAGTGTCAAGGCCCATGTTC
TTGTATGTAAGGACAAATGGAACCTCAAAAATTAAAATGAAATGGGGAATGGAGATGAGGCGTTGCCTCCTCCAATC
CCTTCAACAAATAGAGAGCATGATTGAAGCTGAGTCCTCCGTCAAGGAGAAAGACATGACAAAAGAGTTTTTTGAGA
ATAGATCAGAAACATGGCCCATTGGAGAGTCACCAAAAGGAGTGGAAGAAGGTTCCATTGGGAAAGTATGCAGGACA
CTATTGGCTAAGTCAGTATTCAATAGTCTGTATGCATCTCCACAATTAGAAGGATTTTCAGCTGAGTCAAGAAAGTT
GCTCCTCATTGTTCAGGCTCTTAGGGACAATCTGGAACCTGGGACCTTTGATCTTGGGGGGCTATATGAAGCAATTG
AGGAGTGCCTGATTAATGATCCCTGGGTTTTGCTTAATGCTTCTTGGTTCAACTCCTTCCTAACACATGCATTGAGA
TAGCTGGGGCAATGCTACTATTTACTATCCATACTGTCCAAAAAA SEQ ID NO: 36 (PB1, A/New Caledonia/20/1999)
AATGGATGTCAATCCGACATTACTTTTCTTAAAAGTGCCAGCACAAAATGCTATAAGCACAACTTTTCCTTATACTG
GTGACCCTCCTTACAGCCATGGGACAGGAACAGGGTACACCATGGATACAGTCAACAGGACACATCAGTACTCAGAA
AGAGGAAGATGGACAAAAAATACCGAAACTGGAGCACCGCAACTCAACCCAATTGATGGGCCACTACCAAAAGACAA
TGAACCAAGTGGCTATGCCCAAACAGATTGTGTATTAGAAGCAATGGCTTTCCTTGAGGAATCCCATCCTGGTATTT
TTGAAAACTCTTGTATTGAAACAATGGAGGTTGTTCAGCAAACAAGGGTGGACAAACTGACACAAGGCAGACAGACC
TATGACTGGACTCTAAATAGGAACCAGCCTGCTGCCACAGCATTGGCCAACACTATAGAAGTGTTCAGATCAAACGG
CCTCATAGCAAATGAATCTGGGAGGCTAATAGACTTCCTTAAAGATGTAATGGAGTCGATGGACAGAGACGAAGTAG
AGATCACAACTCATTTTCAAAGAAAGAGGAGAGTGAGAGACAATGTAACTAAAAAAATGGTGACCCAAAGAACAATA
GGCAAAAAGAAACATAAATTAGACAAAAGAAGTTACCTAATTAGGGCATTAACCCTGAACACAATGACCAAAGATGC
TGAGAGGGGGAAACTAAAACGCAGAGCAATTGCAACCCCAGGAATGCAAATAAGGGGGTTTGTATACTTTGTTGAGA -continued

SEQUENCES

CACTGGCAAGAAGCATATGTGAAAAGCTTGAACAATCAGGGTTGCCAGTTGGAGGAAATGAAAAGAAAGCAAAGTTA
GCAAATGTTGTAAGGAAGATGATGACCAACTCCCAGGACACTGAAATTTCTTTCACCATCACTGGAGATAACACAAA
ATGGAACGAAAATCAAAACCCTAGAATGTTCTTGGCCATGATCACATATATAACCAAAAATCAGCCTGAATGGTTCA
GAAATATTCTAAGTATTGCTCCAATAATGTTTTCAAACAAAATGGCGAGACTAGGTAAGGGGTACATGTTTGAAAGC
AAGAGTATGAAACTGAGAACTCAAATACCTGCAGAGATGCTAGCCAACATAGATTTGAAATATTTCAATGATTCAAC
TAAAAAGAAAATTGAAAAAATCCGGCCATTATTAATAGATGGAACTGCATCATTGAGTCCTGGAATGATGATGGGCA
TGTTCAATATGTTAAGCACCGTCTTGGGCGTCTCCATTCTGAATCTTGGGCAAAAGAGATACACCAAGACTACTTAC
TGGTGGGATGGTCTTCAATCGTCTGATGATTTTGCTCTGATTGTGAATGCACCCAACTATGCAGGAATTCAAGCTGG
AGTTGACAGGTTTTATCGAACCTGTAAGCTGCTCGGAATTAATATGAGCAAAAAGAAGTCTTACATAAACAGAACAG
GTACCTTTGAGTTCACGAGCTTTTTCTATCGTTATGGGTTTGTTGCCAATTTCAGCATGGAGCTTCCTAGTTTTGGG
GTGTCTGGGGTCAATGAATCTGCAGACATGAGTATTGGAGTCACTGTCATCAAAAACAATATGATAAACAATGACCT
TGGCCCAGCAACTGCTCAAATGGCCCTTCAGTTATTTATAAAAGATTACAGGTACACGTATCGATGCCACAGAGGTG
ACACACAAATACAAACCCGGAGATCATTTGAGATAAAGAAACTATGGGACCAAACCCGCTCCAAAGCTGGGCTGTTG
GTCTCTGATGGAGGCCCCAATTTATATAACATTAGAAATCTCCATATTCCTGAAGTCTGCTTGAAATGGGAGTTGAT
GGATGAGGATTACCAGGGGCGTTTATGCAACCCATTGAACCCGTTTGTCAGTCATAAAGAGATTGAATCAGTGAACA
ATGCAGTGATGATGCCGGCACATGGTCCAGCCAAAAATATGGAGTATGACGCTGTTGCAACAACACACTCCTGGGTT
CCCAAAAGGAATCGATCCATTTTGAATACGAGCCAAAGGGGGATACTTGAGGATGAGCAAATGTATCAGAGGTGCTG
CAATTTATTTGAAAAATTCTTCCCAAGTAGCTCATACAGAAGACCAGTTGGAATATCCAGTATGGTAGAGGCTATGG
TTTCCAGAGCCCGAATTGATGCACGGATTGATTTCGAATCTGGAAGGATAAAAAAAGAGGAATTCGCTGAGATCATG
AAGACCTGTTCCACCATTGAAGACCTCAGACGGCAAAAATAGGGAATTTGGCTTGTCCTTCATGAAAA

SEQ ID NO: 37 (NP, A/New Caledonia/20/1999)
ATCACTCACTGAGTGACATCAAAGTCATGGCGTCCCAAGGCACCAAACGGTCTTACGAACAGATGGAGACTGATGGG
GAACGCCAGAATGCAACTGAAATCAGAGCATCCGTCGGAAGAATGATTGGTGGAATTGGGCGATTCTACATCCAAAT
GTGCACCGAGCTTAAACTCAATGATTATGAGGGACGACTGATCCAGAACAGCTTGACAATAGAGAGAATGGTGCTCT
CTGCTTTTGATGAGAGGAGGAATAAATATCTGGAAGAACATCCCAGCGCGGGGAAAGATCCTAAGAAAACTGGAGGA
CCCATATACAAGAGAGTAGATGGAAAGTGGGTGAGGGAACTCGTCCTTTATGACAAAGAAGAAATAAGGCGGATTTG
GCGCCAAGCCAACAATGGTGATGATGCAACGGCTGGTTTGACTCACATTATGATCTGGCATTCTAATTTGAATGATA
CAACTTACCAGAGGACAAGAGCTCTTGTCCGCACCGGAATGGATCCCAGGATGTGCTCTTTGATGCAAGGTTCAACT
CTCCCTAGAAGATCTGGAGCAGCAGGCGCTGCAGTCAAAGGAGTTGGGACAATGGTGTTGGAGTTAATCAGGATGAT
CAAACGTGGGATCAATGACCGAAACTTCTGGAGGGGTGAGAATGGAAGAAAAACAAGGATTGCTTATGAGAGAATGT
GCAACATTCTCAAAGGAAAATTTCAAACAGCTGCACAAAAAGCAATGATGGATCAAGTGAGAGAAAGCCGGAACCCA
GGAAATGCTGAGATCGAAGATCTCACTTTTCTGGCACGGTCTGCACTCATATTAAGAGGGTCAGTTGCTCACAAGTC
TTGCCTGCCTGCCTGTGTGTATGGACCAGCCGTAGCCAGTGGGTACGACTTCGAAAAAGAGGGATACTCTTTGGTAG
GGGTAGACCCTTTTAAACTGCTTCAAACCAGTCAGGTATACAGCCTAATCAGACCAAACGAGAATCCCGCACACAAG
AGTCAGTTGGTGTGGATGGCATGCAATTCTGCTGCATTTGAAGATCTAAGAGTGTCAAGCTTCATCAGAGGGACAAG
AGTACTTCCAAGGGGGAAGCTCTCCACTAGAGGAGTACAAATTGCTTCAAATGAAAACATGGATGCTATTGTATCAA
GTACTCTTGAACTGAGAAGCAGATACTGGGCCATAAGAACCAGAAGTGGAGGGAACACTAATCAACAAAGGGCCTCT
GCGGGCCAAATCAGCACACAACCTACGTTTTCTGTGCAGAGAAACCTCCCATTTGACAAAACAACCATCATGGCAGC
ATTCACTGGGAATACGGAGGGAAGAACATCAGACATGAGGGCAGAAATCATAAAGATGATGGAAAGTGCAAGACCAG
AAGAAGTGTCCTTCCAGGGGCGGGGAGTCTTTGAGCTCTCGGACGAAAGGGCAACGAACCCGATCGTGCCCTCCTTT
GACATGAGTAATGAAGGATCTTATTTCTTCGGAGACAATGCAGAGGAGTACGACAATTAATGAA SEQ ID NO: 38 (M, A/New Caledonia/20/1999)
GATGAGTCTTCTAACCGAGGTCGAAACGTACGTTCTCTCTATCGTCCCGTCAGGCCCCCTCAAAGCCGAGATCGCAC
AGAGACTTGAAAATGTCTTTGCTGGAAAGAATACCGATCTTGAGGCTCTCATGGAATGGCTAAAGACAAGACCAATC
CTGTCACCTCTGACTAAGGGGATTTTAGGATTTGTGTTCACGCTCACCGTGCCCAGTGAGCGAGGACTGCAGCGTAG
ACGCTTTGTCCAAAATGCCCTTAATGGGAATGGGGATCCAAATAATATGGACAGAGCAGTTAAACTGTATCGAAAGC
TTAAGAGGGAGATAACATTCCATGGGGCCAAAGAAATAGCACTCAGTTATTCTGCTGGTGCACTTGCCAGTTGTATG
GGACTCATATACAACAGGATGGGGGCTGTGACCACCGAATCAGCATTTGGCCTTATATGCGCAACCTGTGAACAGAT
TGCCGACTCCCAGCATAAGTCTCATAGGCAAATGGTAACAACAACCAACCCATTAATAAGACATGAGAACAGAATGG
TTCTGGCCAGCACTACAGCTAAGGCTATGGAGCAAATGGCTGGATCGAGTGAACAAGCAGCTGAGGCCATGGAGGTT
GCTAGTCAGGCCAGGCAGATGGTGCAGGCAATGAGAGCCATTGGGACTCATCCTAGCTCTAGCACTGGTCTGAAAAA
TGATCTCCTTGAAAATTTGCAGGCCTATCAGAAACGAATGGGGGTGCAGATGCAACGATTCAAGTGATCCTCTTGTT
GTTGCCGCAAGTATAATTGGGATTGTGCACCTGATATTGTGGATTATTGATCGCCTTTTTTCCAAAAGCATTTATCG
TATCTTTAAACACGGTTTAAAAAGAGGGCCTTCTACGGAAGGAGTACCAGAGTCTATGAGGGAAGAATATCGAGAGG
AACAGCAGAATGCTGTGGATGCTGACGATGGTCATTTTGTCAGCATAGAGCTAGAGTAAA SEQ ID NO: 39 (NS, A/New Caledonia/20/1999)
ATGGATTCCCACACTGTGTCAAGCTTTCAGGTAGATTGCTTCCTTTGGCATGTCCGCAAACAAGTTGCAGACCAAGA
TCTAGGCGATGCCCCATTCCTTGATCGGCTTCGCCGAGATCAGAAGTCTCTAAAGGGAAGAGGCAGCACTCTCGGTC
TGAACATCGAAACAGCCACTTGTGTTGGAAAGCAAATAGTAGAGAGGATTCTGAAAGAAGAATCCGATGAGGCATTT
AAAATGACCATGGCCTCCGCACTTGCTTCGCGGTACCTAACTGACATGACTATTGAAGAAATGTCAAGGGACTGGTT
CATGCTCATGCCCAAGCAGAAAGTGGCTGGCCCTCTTTGTGTCAGAATGGACCAGGCGATAATGGATAAGAACATCA
TACTGAAAGCGAATTTCAGTGTGATTTTTGACCGGTTGGAGAATCTGACATTACTAAGGGCTTTCACCGAAGAGGGA
GCAATTGTTGGCGAAATTTCACCATTGCCTTCTCTTCCAGGACATACTAATGAGGATGTCAAAAATGCAATTGGGGT
CCTCATCGGGGGACTTGAATGGAATGATAACACAGTTCGAGTCTCTGAAACTCTACAGAGATTCGCTTGGAGAAGCA
GTAATGAGACTGGGGGACCTCCATTCACTCCAACACAGAAACGGAAAATGGCGGGAACAATTAGGTCAGAAGTTTGA
AGAAATAAGATGGCTGATTGAAGAAGTGAGGCATAAATTGAAGACGACAGAGAATAGTTTTGAGCAAATAACATTTA
TGCAAGCATTACAGCTATTGTTTGAAGTGGAACAAGAGATTAGAACGTTTTCGTTTCAGCTTATTTAATGATAA SEQ ID NO: 40 (HA, A/New Caledonia/20/1999)
CCAAAATGAAAGCAAAACTACTGGTCCTGTTATGTACATTTACAGCTACATATGCAGACACAATATGTATAGGCTAC
CATGCCAACAACTCAACCGACACTGTTGACACAGTACTTGAGAAGAATGTGACAGTGACACACTCTGTCAACCTACT
TGAGGACAGTCACAATGGAAAACTATGTCTACTAAAAGGAATAGCCCCACTACAATTGGGTAATTGCAGCGTTGCCG
GATGGATCTTAGGAAACCCAGAATGCGAATTACTGATTTCCAAGGAATCATGGTCCTACATTGTAGAAACACCAAAT
CCTGAGAATGGAACATGTTACCCAGGGTATTTCGCCGACTATGAGGAACTGAGGGAGCAATTGAGTTCAGTATCTTC -continued

| SEQUENCES |
| --- |

ATTTGAGAGATTCGAAATATTCCCCAAAGAAAGCTCATGGCCCAACCACACCGTAACCGGAGTATCAGCATCATGCT
CCCATAATGGGAAAAGCAGTTTTTACAGAAATTTGCTATGGCTGACGGGGAAGAATGGTTTGTACCCAAACCTGAGC
AAGTCCTATGTAAACAACAAAGAGAAAGAAGTCCTTGTACTATGGGGTGTTCATCACCCGCCTAACATAGGGAACCA
AAGGGCCCTCTATCATACAGAAAATGCTTATGTCTCTGTAGTGTCTTCACATTATAGCAGAAGATTCACCCCAGAAA
TAGCCAAAAGACCCAAAGTAAGAGATCAGGAAGGAAGAATCAACTACTACTGGACTCTGCTGGAACCTGGGGATACA
ATAATATTTGAGGCAAATGGAAATCTAATAGCGCCATGGTATGCTTTTGCACTGAGTAGAGGCTTTGGATCAGGAAT
CATCACCTCAAATGCACCAATGGATGAATGTGATGCGAAGTGTCAAACACCTCAGGGAGCTATAAACAGCAGTCTTC
CTTTCCAGAATGTACACCCAGTCACAATAGGAGAGTGTCCAAAGTATGTCAGGAGTGCAAAATTAAGGATGGTTACA
GGACTAAGGAACATCCCATCCATTCAATCCAGAGGTTTGTTTGGAGCCATTGCCGGTTTCATTGAAGGGGGGTGGAC
TGGAATGGTAGATGGGTGGTATGGTTATCATCATCAGAATGAGCAAGGATCTGGCTATGCTGCAGATCAAAAAAGTA
CACAAAATGCCATTAACGGGATTACAAACAAGGTGAATTCTGTAATTGAGAAAATGAACACTCAATTCACAGCTGTG
GGCAAAGAATTCAACAAATTGGAAAGAAGGATGGAAAACTTAAATAAAAAAGTTGATGATGGGTTTCTAGACATTTG
GACATATAATGCAGAATTGTTGGTTCTACTGGAAAATGAAAGGACTTTGGATTTCCATGACTCCAATGTGAAGAATC
TGTATGAGAAAGTAAAAAGCCAATTAAAGAATAATGCCAAAGAAATAGGAAACGGGTGTTTTGAATTCTATCACAAG
TGTAACAATGAATGCATGGAGAGTGTGAAAAATGGAACTTATGACTATCCAAAATATTCCGAAGAATCAAAGTTAAA
CAGGGAGAAAATTGATGGAGTGAAATTGGAATCAATGGGAGTCTATCAGATTCTGGCGATCTACTCAACTGTCGCCA
GTTCCCTGGTTCTTTTGGTCTCCCTGGGGGCAATCAGCTTCTGGATGTGTTCCAATGGGTCTTTGCAGTGTAGAATA
TGCATCTGAGACCAGAATTTCAGAAATATAAGAA

SEQ ID NO: 41 (NA, A/New Caledonia/20/1999)
AATGAATCCAAATCAAAAAATAATAACCATTGGATCAATCAGTATAGCAATCGGAATAATTAGTCTAATGTTGCAAA
TAGGAAATATTATTTCAATATGGGCTAGTCACTCAATCCAAACTGGAAGTCAAAACCACACTGGAGTATGCAACCAA
AGAATCATCACATATGAAAACAGCACCTGGGTGAATCACACATATGTTAATATTAACAACACTAATGTTGTTGCTGG
AAAGGACAAAACTTCAGTGACATTGGCCGGCAATTCATCTCTTTGTTCTATCAGTGGATGGGCTATATACACAAAAG
ACAACAGCATAAGAATTGGCTCCAAAGGAGATGTTTTTGTCATAAGAGAACCTTTCATATCATGTTCTCACTTGGAA
TGCAGAACCTTTTTTCTGACCCAAGGTGCTCTATTAAATGACAAACATTCAAATGGGACCGTTAAGGACAGAAGTCC
TTATAGGGCCTTAATGAGCTGTCCTCTAGGTGAAGCTCCGTCCCCATACAATTCAAAGTTTGAATCAGTTGCATGGT
CAGCAAGCGCATGCCATGATGGCATGGGCTGGTTAACAATCGGAATTTCTGGTCCAGACAATGGAGCTGTGGCTGTA
CTAAAATACAACGGCATAATAACTGAAACCATAAAAAGTTGGAAAAAGCGAATATTAAGAACACAAGAGTCTGAATG
TGTCTGTGTGAACGGGTCATGTTTCACCATAATGACCGATGGCCCGAGTAATGGGGCCGCCTCGTACAAAATCTTCA
AGATCGAAAAGGGGAAGGTTACTAAATCAATAGAGTTGAATGCACCCAATTTTCATTATGAGGAATGTTCCTGTTAC
CCAGACACTGGCACAGTGATGTGTGTATGCAGGGACAACTGGCATGGTTCAAATCGACCTTGGGTGTCTTTTAATCA
AAACCTGGATTATCAAATAGGATACATCTGCAGTGGGGTGTTCGGTGACAATCCGCGTCCCAAAGATGGAGAGGGCA
GCTGTAATCCAGTGACTGTTGATGGAGCAGACGGAGTAAAGGGGTTTTCATACAAATATGGTAATGGTGTTTGGATA
GGAAGGACTAAAAGTAACAGACTTAGAAAGGGGTTTGAGATGATTTGGGATCCTAATGGATGGACAGATACCGACAG
TGATTTCTCAGTGAAACAGGATGTTGTGGCAATAACTGATTGGTCAGGGTACAGCGGAAGTTTCGTTCAACATCCTG
AGTTAACAGGATTGGACTGTATAAGACCTTGCTTCTGGGTTGAGTTAGTCAGAGGACTGCCTAGAGAAAATACAACA
ATCTGGACTAGTGGGAGCAGCATTTCTTTTTGTGGCGTAAATAGTGATACTGCAAACTGGTCTTGGCCAGACGGTGC
TGAGTTGCCGTTCACCATTGACAAGTAG SEQ ID NO: 42 (PA, 105p30)
AGCGAAAGCAGGTACTGAtTCgaAaTGGAAGATTTTGTGCGACAATGCTTCAATCCGATGATTGTCGAGCTTGCGGA
AAAGGCAATGAAAGAGTATGGAGAGGACCTGAAAATCGAAACAAACAAATTTGCAGCAATATGCACCCACTTGGAAG
TATGCTTCATGTATTCAGATTTTCATTTCATCAATGAGCAAGGCGAATCAATAATAGTAGAGCCTGAGGACCCAAAT
GCACTTTTAAAACACAGATTTGAGATAATAGAGGGGCGAGATCGTACAATGGCATGGACAGTTGTAAACAGTATTTG
CAACACCACAGGAGCTGAGAAACCAAAGTTTCTGCCAGATCTGTATGATTACAAAGAGAATAGGTTCATCGAAATTG
GAGTGACAAGGAGAGAAGTTCACATATACTATCTGGAAAAGGCCAACAAAATTAAATCTGAGAAGACACATATTCAC
ATTTTCTCATTTACTGGCGAAGAAATGGCCACAAAGGCCGATTACACTCTCGATGAAGAAAGCAGGGCTAGAATTAA
AACCAGACTATTCACCATAAGGCAAGAAATGGCAAGCAGAGGTCTTTGGGACTCCTTTCGTCAGTCCGAAAGAGGCG
AAGAGACAATTGAAGAAAGGTTTGAAATCACAGGGACAATGCGCAGGCTCGCTGATCAAAGCCTTCCGCCGAACTTC
TCCTGCATTGAGAATTTTAGAGCCTATGTGGATGGATTTGAACCGAACGGCTACATTGAGGGCAAGCTTTCTCAAAT
GTCCAAAGAAGTAAATGCTAAAATTGAGCCTTTTTTGAAAACAACACCTCGACCAATTAGACTTCCGAATGGGCCTC
CTTGTTTTCAGCGGTCAAAATTCCTGCTGATGGATTCTTTAAAATTAAGCATTGAGGATCCAAATCATGAAGGGGAG
GGAATACCACTATATGATGCAATCAAGTGTATGAGAACATTCTTTGGATGGAAAGAACCCACTGTTGTCAAGCCACA
CGAGAAGGGAATAAATCCGAATTATCTGCTGTCGTGGAAGCAGGTGTTGGAAGAGCTGCAGGACATTGAGAGTGAGG
AGAAGATTCCAAGAACAAAAAACATGAAAAAAACGAGTCAGTTAAAGTGGGCACTTGGTGAGAACATGGCACCAGAG
AAGGTGGATTTTGATGACTGTAAAGATATAAGCGATTTGAAGCAATATGATAGTGACGAACCTGAATTAAGGTCATT
TTCAAGTTGGATCCAGAATGAGTTCAACAAGGCATGCGAGCTGACCGATTCAATCTGGATAGAGCTCGATGAGATTG
GAGAAGATGTGGCCCCGATTGAACACATTGCAAGCATGAGAAGAAATTACTTCACAGCTGAGGTGTCCCATTGCAGA
GCCACTGAATATATAATGAAAGGGGTATACATTAATACTGCTTTGCTTAATGCATCCTGTGCAGCAATGGATGATTT
CCAACTAATTCCTATGATAAGCAAATGTAGAACTAAAGAGGGAAGGAGAAAGACCAATTTGTACGGCTTCATCATAA
AAGGAAGATCTCACTTAAGGAATGATACCGATGTGGTAAACTTTGTGAGCATGGAGTTTTCCCTCACTGACCCAAGA
CTTGAGCCACACAAATGGGAGAAGTACTGTGTTCTTGAGATAGGAGATATGCTTCTAAGGAGTGCAATAGGCCAAGT
GTCAAGGCCCATGTTCTTGTATGTAAGAACAAATGGAACCTCAAAAATTAAAATGAAATGGGGAATGGAGATGAGGC
GTTGCCTCCTCCAATCCCTCCAACAAATAGAGAGCATGATTGAAGCTGAGTCCTCTGTCAAGGAGAAAGACATGACA
AAAGAGTTTTTTGAGAATAGATCAGAAACATGGCCCATTGGAGAGTCACCAAAAGGAGTGGAAGAAGGTTCCATTGG
GAAAGTATGCAGGACACTATTGGCTAAATCAGTATTCAATAGTCTGTATGCATCTCCACAATTAGAAGGATTTTCAG
CTGAGTCAAGAAAGTTGCTCCTTATTGTTCAGGCTCTTAGGGACAATCTGGAACCTGGGACCTTTGATCTTGGGGGA
CTATATGAAGCAATTGAGGAGTGCCTGATTAATGATCCCTGGGTTTTGCTTAATGCTTCTTGGTTCAACTCCTTCCT
AAAACATGCATTGAGATAGCTGAGGCAATGCTACTATTTGTTATCCATACTGTCCAAAAAAGTA SEQ ID NO: 43 (PB1, 105p30)
AGCGAAAGCAGGCAAACCATTTGAATGGATGTCAATCCGACATTACTTTTCTTAAAAGTGCCAGCACAAAATGCTAT
AAGCACAACTTTTCCTTATACTGGTGACCCTCCTTACAGCCATGGAACAGGAACAGGATACACCATGGATACAGTCA
ACAGGACACATCAGTACTCAGAAAGAGGAAGATGGACGAAAAATACCGAAACTGGAGCACCGCAACTCAACCCAATT
GATGGGCCACTACCAGAAGACAATGAACCAAGTGGCTATGCCCAAACAGATTGTGTATTAGAGGCAATGGCTTTCCT
TGAAGAATCCCATCCTGGTATTTTTGAAAACTCTTGTATTGAAACAATGGAGGTTGTTCAGCAAACAAGGGTGGACA -continued

| SEQUENCES |
|---|
| AACTGACACAAGGCAGACAAACCTATGACTGGACTCTAAATAGGAACCAGCCTGCTGCCACAGCATTGGCAAACACC<br>ATAGAAGTATTCAGATCAAATGGCCTCATAGCAAATGAATCTGGAAGGCTAATAGACTTCCTTAAAGATGTAATGGA<br>GTCGATGGACAGAGACGAAGTAGAGGTCACAACTCATTTTCAAAGAAAGAGGAGAGTGAGAGACAATGTAACTAAAA<br>AAATGGTGACCCAAAGAACAATAGGAAAAAAGAAACATAAATTAGACAAAAGAAGTTACCTAATTAGGGCATTAACC<br>CTGAACACAATGACCAAAGATGCTGAGAGGGGGAAACTAAAACGCAGAGCAATTGCAACCCCAGGAATGCAAATAAG<br>GGGGTTTGTATACTTTGTTGAGACACTGGCAAGAAGCATATGTGAAAAGCTTGAACAATCAGGGTTGCCAGTTGGAG<br>GAAATGAGAAGAAAGCAAAGTTAGCAAATGTTGTAAGGAAGATGATGACCAACTCCCAGGACACTGAAATTTCTTTT<br>ACCATCACTGGAGATAACACAAAATGGAACGAAAATCAAAACCCTAGAATGTTCTTGGCCATGATCACATATATAAC<br>CAAAGATCAGCCTGAATGGTTCAGAAATATTCTAAGTATTGCTCCAATAATGTTTTCAAACAAAATGGCGAGACTAG<br>GTAGGGGGTATATGTTTGAAAGCAAGAGTATGAAACTGAGAACCCAAATACCTGCAGAGATGCTAGCCAACATAGAT<br>TTGAAATATTTCAATGATTCAACTAAAAAGAAAATTGAAAAAATTCGACCATTATTAATAGATGGAACTGCATCATT<br>GAGTCCTGGAATGATGATGGGCATGTTCAATATGTTAAGCACCGTCTTGGGCGTTTCCATTCTGAATCTTGGGCAAA<br>AAAGATACACCAAGACTACTTACTGGTGGGATGGTCTTCAATCGTCTGATGATTTTGCTTTGATTGTGAATGCACCC<br>AATTATGCAGGAATTCAAGCTGGAGTTGACAGGTTTTATCGAACCTGTAAGCTGCTCGGAATTAATATGAGCAAAAA<br>GAAGTCTTACATAAACAGAACAGGTACCTTTGAATTCACGAGCTTTTTCTATCGTTATGGGTTTGTTGCCAATTTCA<br>GCATGGAGCTTCCTAGTTTTGGGGTGTCTGGGGTCAATGAATCTGCAGACATGAGTATTGGAGTCACTGTCATCAAA<br>AACAATATGATAAACAATGACCTTGGCCCAGCAACTGCTCAAATGGCCCTTCAGTTATTTATAAAAGATTACAGGTA<br>CACTTATCGATGCCACAGAGGTGACACACAAATACAAACCCGGAGATCATTTGAAATAAAGAAACTATGGGACCAAA<br>CCCGCTCCAAAGCTGGGCTGTTGGTCTCTGATGGAGGCCCCAATTTATATAACATTAGGAATCTACATATTCCTGAA<br>GTCTGCTTGAAATGGGAGTTGATGGATGAGGATTACCAGGGGCGTTTATGCAACCCATTGAACCCGTTTGTCAGCCA<br>TAAAGAGATTGAATCAGTGAACAATGCAGTGATAATGCCGGCACATGGTCCAGCCAAAAATATGGAGTATGACGCTG<br>TTGCAACAACACACTCTTGGGTCCCCAAAAGAAATCGATCCATTTTAAACACGAGCCAAAGAGGGATACTTGAAGAT<br>GAGCAAATGTACCAAAGGTGCTGCAATTTATTTGAAAAATTCTTCCCAAGTAGCTCATACAGAAGACCAGTTGGAAT<br>ATCCAGTATGGTAGAGGCTATGGTTTCAAGAGCCCGAATTGATGCACGGATTGATTTCGAATCTGGAAGGATAAAGA<br>AAGAGGAATTCGCTGAGATCATGAAGACCTGTTCCACCATTGAAGACCTCAGACGGCAAAAATAGGGAATTTGGCTT<br>GTCCTTCATGAAAAAATGCCTTGTTTCTACT<br><br>SEQ ID NO: 44 (PB2, 105p30)<br>AGCGAAAGCAGGTCAATTATATTCAATATGGAAAGAATAAAAGAGCTAAGGAATCTGATGTCACAATCTCGCACTCG<br>CGAGATACTTACCAAAACTACTGTAGACCACATGGCCATAATAAAGAAATACACATCAGGAAGACAGGAGAAAAACC<br>CATCACTTAGGATGAAATGGATGATGGCAATGAAATACCCAATTACAGCTGATAAAAGGATAACGGAAATGATTCCT<br>GAAAGAAATGAGCAAGGACAGACACTATGGAGTAAAGTGAATGATGCCGGATCAGACCGAGTGATGATATCACCCCT<br>AGCTGTGACATGGTGGAACAGAAATGGACCAGTGGCAAACACTATCCACTATCCAAAAATCTACAAAACTTACTTTG<br>AAAAGGTTGAAAGGTTAAAACATGGAACCTTTGGCCCTGTACACTTTAGAAACCAAGTCAAAATACGCCGAAGAGTC<br>GACATAAATCCTGGTCATGCAGACCTCAGCGCCAAGGAGGCACAGGATGTAATTATGGAAGTTGTTTTCCCTAATGA<br>AGTGGGAGCCAGAATACTAACATCAGAATCGCAATTAACGATAACTAAGGAGAAAAAAGAGGAACTCCAGAATTGCA<br>AAATTTCCCCTTTGATGGTTGCATACATGTTAGAGAGGGAACTTGTCCGCAAAACAAGATTTCTCCCGGTTGCAGGT<br>GGAACAAGCAGTGTGTACATTGAAGTTTTGCATTTAACACAGGGGACATGCTGGGAGCAGATGTACACTCCAGGTGG<br>GGAGGTGAGGAATGATGATGTTGATCAAAGCCTAATTATTGCTGCTAGGAACATAGTGAGAAGAGCTGCAGTATCAG<br>CAGATCCACTAGCATCTTTATTAGAAATGTGCCATAGCACACAGATTGGTGGAACAAGGATGGTGGATATTCTCAGG<br>CAAAATCCAACAGAAGAACAAGCTGTGGACATATGCAAAGCAGCAATGGGGCTGAGAATCAGTTCATCCTTCAGTTT<br>TGGCGGATTCACATTTAAGAGAACAAGTGGATCGTCAGTCAAAAGGGAGGAAGAAGTGCTAACGGGCAATCTGCAAA<br>CATTGAAGCTAACTGTGCATGAGGGATATGAAGAATTCACAATAGTTGGGAAAAAGGCAACAGCTATACTCAGAAAA<br>GCAACCAGGAGATTGATTCAACTAATAGTGAGTGGAAGAGACGAACAGTCAATAGTCGAAGCAATAGTTGTAGCAAT<br>GGTATTCTCACAAGAAGATTGCATGGTAAAAGCGGTTAGAGGTGATCTGAATTTCGTTAATAGAGCGAATCAGCGGT<br>TGAATCCCATGCATCAACTTTTGAGACATTTTCAGAAGGATGCTAAAGTACTTTTCCTAAATTGGGGAATTGAACAT<br>ATTGACAATGTGATGGGAATGATTGGGATATTACCTGATATGACTCCAAGTACCGAGATGTCAATGAGAGGAGTGAG<br>AGTCAGCAAAATGGGTGTAGATGAATACTCCAATGCTGAAAGGGTAGTGGTAAGCATTGACCGTTTTTGAGGGTCC<br>GGGACCAAAGAGGAAATGTATTACTGTCTCCAGAGGAAGTCAGTGAAACACAAGGAACAGAGAAACTGACAATAACT<br>TACTCTTCATCATTGATGTGGGAGATTAATGGCCCTGAGTCAGTGTTGATCAATACCTACCAATGGATCATCAGAAA<br>CTGGGAGACTGTTAAAATTCAGTGGTCTCAGAACCCTACAATGCTATACAATAAAATGGAATTTGAGCCATTTCAAT<br>CTCTAGTCCCCAAGGCCATTAGAGGCCAATACAGTGGGTTTGTTAGAACTCTATTTCAACAAATGAGGGATGTGCTC<br>GGGACCTTTGACACAACTCAGATAATAAAACTTCTTCCCTTTGCAGCCGCTCCACCAAAGCAAAGTAGAATGCAATT<br>CTCGTCATTAACTGTGAATGTGAGGGGATCAGGAATGAGAATACTTGTAAGGGGTAATTCTCCAGTATTCAACTACA<br>ACAAGACCACTAAGAGACTCACAATCCTCGGAAAGGATGCTGGCACTTTAACTGAAGACCCAGATGAAGGCACAGCT<br>GGAGTGGAATCTGCTGTTTTAAGGGGATTCCTCATTCTAGGCAAAGAAGATAGAAGATATGGGCCAGCATTAAGCAT<br>CAGTGAATTGAGCAACCTTGCGAAAGGGGAGAAAGCTAATGTGCTAATTGGGCAAGGGGATGTAGTGTTGGTAATGA<br>AACGAAAACGGGACTCTAGCATACTTACTGACAGCCAGACAGCGACCAAAAGAATTCGGATGGCCATCAATTAATTT<br>CGAATAATTTAAAAACGACCTTGTTTCTACT<br><br>SEQ ID NO: 45 (NP, 105p30)<br>AGCAAAAGCAGGGTAGATAATCACTCACTGAGTGACATCAAAGTCATGGCGTCCCAAGGCACCAAACGGTCTTACGA<br>ACAGATGGAGACTGATGGGGAACGCCAGAATGCAACTGAAATCAGAGCATCCGTCGGAAGAATGATTGGGGGAATTG<br>GGCGATTCTACATCCAAATGTGCACCGAGCTTAAGCTCAATGATTATGAGGGACGACTGATCCAGAACAGCTTAACA<br>ATAGAGAGAATGGTGCTTTCTGCTTTTGATGAGAGGAGAAATAAATATCTGGAAGAACATCCCAGCGCAGGGAAAGA<br>TCCTAAGAAAACTGGAGGACCCATATACAAGAGAGTAGATGGAAAGTGGGTGAGGGAACTCGTCCTTTATGACAAAG<br>AAGAAATAAGGCGGATTTGGCGCCAAGCCAACAATGGTGATGATGCAACAGCTGGTTTGACTCACATTATGATCTGG<br>CATTCTAATTTGAATGATACAACTTACCAGAGGACAAGAGCTCTTGTCCGCACCGGAATGGATCCCAGGATGTGCTC<br>TTTGATGCAAGGTTCAACTCTCCCTAGAAGATCTGGAGCAGCAGGCGCTGCAGTCAAAGGAGTTGGGACAATGGTAT<br>TGGAGTTAATCAGGATGATCAAACGTGGGATCAACGACCGAAACTTCTGGAGGGGTGAGAATGGGAGAAAAACAAGG<br>ATTGCTTATGAGAGAATGTGCAACATTCTCAAAGGAAAATTTCAAACAGCTGCACAAAAAGCAATGATGGATCAAGT<br>GAGAGAAAGCCGGAACCCAGGAAATGCTGAGATCGAAGATCTCACTTTTCTGGCACGGTCTGCACTCATATTGAGAG<br>GATCAGTTGCTCACAAGTCTTGCCTGCCTGCTTGTGTGTATGGACCAGCCGTAGCCAGTGGGTATGACTTCGAAAAA<br>GAGGGATACTCTTTGGTGGGAGTAGACCCTTTCAAACTGCTTCAAACCAGTCAGGTATACAGCCTAATTAGACCAAA<br>CGAGAATCCCGCACACAAGAGCCAGTTGGTGTGGATGGCATGCAATTCTGCTGCATTTGAAGATCTAAGAGTGTCAA<br>GCTTCATCAGAGGGACAAGAGTACTTCCAAGGGGGAAGCTCTCCACTAGAGGAGTACAAATTGCTTCAAATGAAAAC<br>ATGGATGCTATTGTCTCAAGTACTCTTGAACTGAGAAGCAGATACTGGGCCATAAGAACCAGAAGTGGAGGGAACAC |

-continued

SEQUENCES

CAATCAACAAAGGGCCTCTGCGGGCCAAATCAGCACACAACCTACGTTTTCTGTGCAGAGAAACCTCCCATTTGACA
AAACAACCATCATGGCAGCATTCACTGGGAATACAGAGGGAAGAACATCAGACATGCGGGCAGAAATCATAAAGATG
ATGGAAAGTGCAAGACCAGAAGAAGTGTCCTTCCAGGGACGGGGAGTCTTTGAGCTCTCGGACGAAAGGGCAACGAA
CCCGATCGTGCCCTCCTTTGACATGAGTAATGAAGGATCTTATTTCTTCGGAGACAATGCAGAGGAGTACGACAATT
AATGAAAAATACCCTTGTTTCTACT

SEQ ID NO: 46 (M, 105p30)
AGCAAAAGCAGGTAGATATTGAAAGATGAGTCTTCTAACCGAGGTCGAAACGTACGTTCTCTCTATCGTCCCATCAG
GCCCCCTCAAAGCCGAGATCGCACAGAGACTTGAAGATGTATTTGCTGGAAAGAATACCGATCTTGAGGCTCTCATG
GAATGGCTAAAGACAAGACCAATCCTGTCACCTCTGACTAAGGGGATTTTAGGATTTGTGTTCACGCTCACCGTGCC
CAGTGAGCGAGGACTGCAGCGTAGACGCTTTGTCCAAAATGCCCTTAATGGGAATGGGGATCCAAATAATATGGACA
AGGCTGTCAAACTGTATCGAAAGCTTAAGAGGGAGATAACATTCCATGGGGCCAAAGAAATAGCACTCAGTTATTCT
GCTGGAGCACTTGCCAGTTGTATGGGACTCATATACAACAGGATGGGGGCTGTGACCACCGAATCAGCATTTGGCCT
TATATGTGCAACCTGTGAACAGATTGCCGACTCCCAGCATAAGTCTCATAGGCAAATGGTAACAACAACCAATCCAT
TAATAAGACATGAGAACAGAATGGTTCTGGCCAGCACTACAGCTAAGGCTATGGAGCAAATGGCTGGATCGAGTGAA
CAAGCAGCTGAGGCCATGGAGGTTGCTAGTCAGGCCAGGCAGATGGTGCAGGCAATGAGAGCCATTGGGACTCATCC
TAGCTCTAGCACTGGTCTGAAAAATGATCTCCTTGAAAATTTGCAGGCCTATCAGAAACGAATGGGGGTGCAGATGC
AACGATTCAAGTGATCCTCTTGTTGTTGCCGCAAGTATAATTGGGATTGTGCACCTGATATTGTGGATTATTGATCG
CCTTTTTTCCAAAAGCATTTATCGTATTTTTAAACACGGTTTAAAAAGAGGGCCTTCTACGGAAGGAGTACCGGAGT
CTATGAGGGAAGAATATCGAGAGGAACAGCAGAATGCTGTGGATGCTGACGATGGTCATTTTGTCAGCATAGAGCTA
GAGTAAAAAACTACCTTGTTTCTACT

SEQ ID NO: 47 (NS, 105p30)
AGCAAAAGCAGGGTGGCAAAGACATAATGGATTCCCACACTGTGTCAAGCTTTCAGGTAGATTGTTTCCTTTGGCAT
GTCCGCAAACAAGTTGCAGACCAAGATCTAGGCGATGCCCCCTTCCTTGATCGGCTTCGCCGAGATCAGAAGTCTCT
AAAGGGACGAGGCAACACTCTCGGTCTGAACATCGAAACAGCCACTTGTGTTGGAAAGCAAATAGTAGAGAGGATTC
TGAAAGAAGAATCCGATGAGACATTTAGAATGACCATGGCCTCCGCACTTGCTTCGCGGTACCTAACTGACATGACT
GTTGAAGAAATGTCAAGGGACTGGTTCATGCTCATGCCCAAGCAGAAAGTGGCTGGCCCTCTTTGTGTCAGAATGGA
CCAGGCGATAATGGATAAGAACATCATACTGAAAGCGAACTTCAGTGTGATTTTTGACCGGTTGGAGAATCTGACAT
TACTAAGGGCTTTCACCGAAGAGGGAGCAATTGTTGGCGAAATTTCACCATTGCCTTCTTTTCCAGGACATACTAAT
GAGGATGTCAAAAATGCAATTGGGGTCCTCATCGGGGGACTTGAATGGAATGATAACACAGTTCGAGTCTCTGAAGC
TCTACAGAGATTCGCTTGGAGAAGCAGTAATGAGACTGGGGGACCTCCATTCACTACAACACAGAAACGGAAAATGG
CGGGAACAATTAGGTCAGAAGTTTGAAGAAATAAGATGGCTGATTGAAGAAGTGAGGCATAAATTGAAGACGACAGA
GAGTAGTTTTGAACAAATAACATTTATGCAAGCATTACAGCTATTGTTTGAAGTGGAACAAGAGATTAGAACGTTCT
CGTTTCAGCTTATTTAATGATAAAAACACCCTTGTTTCTACT

SEQ ID NO: 48 (HA, 105p30)
AGCGAAAGCAGGGGAAAATAAAAGCAACCAAAATGAAAGTAAAACTACTGGTTCTGTTATGTACATTTACAGCTACA
TATGCAGACACAATATGTATAGGCTACCATGCCAACAACTCAACCGACACTGTTGACACAGTACTTGAGAAGAATGT
AACAGTGACACACTCTGTCAACCTACTTGAGGACAGTCACAATGGAAAACTATGTCTACTAAAAGGAATAGCCCCAC
TACAATTGGGTAATTGCAGCGTTGCCGGATGGATCTTAGGAAACCCAGAATGCGAATTACTGATTTCCAAGGAATCA
TGGTCCTACATTGTAGAAACACCAAATCCTGAGAATGGAACATGTTACCCAGGGTATTTCGCCGACTATGAGGAACT
GAGGGAGCAATTGAGTTCAGTATCTTCATTTGAAAGGTTCGAAATATTCCCCAAAGAGAGCTCATGGCCCAACCACA
CCGTAACCGGAGTATCAGCATCATGCTCCCATAACGGGAAAAGCAGTTTTTACAGAAATTTGCTATGGCTGACGGGG
AAGAATGGTTTGTACCCAAACCTGAGCAAGTCCTATGCAAACAACAAAGAGAAAGAAGTCCTTGTACTATGGGGTGT
TCATCACCCGCCTAACATAGGGGACCAAAGGGCCCTCTATCATACAGAAAATGCTTATGTCTCTGTAGTGTCTTCAC
ATTATAGCAGAAGATTCACCCCAGAAATAGCCAAAAGACCCAAGGTGAGAGACCAGGAAGGAAGAATCAACTACTAC
TGGACTCTGCTGGAACCCGGGGATACAATAATATTTGAGGCAAATGGAAATCTAATAGCGCCAAGGTATGCTTTCGC
ACTGAGTAGAGGCTTGGGATCAGGAATCATCACCTCAAATGCACCAATGGATGAATGTGATGCAAAGTGTCAAACAC
CTCAGGGAGCTATAAACAGCAGTCTTCCTTTCCAGAATGTACACCCAGTCACAATAGGAGAGTGTCCAAAGTATGTC
AGGAGTGCAAAATTAAGGATGGTTACAGGACTAAGGAACATCCCATCCATTCAATCCAGAGGTTTGTTTGGAGCAAT
TGCCGGTTTCATTGAAGGGGGGTGGACTGGAATGGTAGATGGTTGGTATGGTTATCATCATCAGAATGAGCAAGGAT
CTGGGTATGCTGCAGATCAAAAAAGCACACAAAATGCCATTAACGGGATTACAAACAAGGTGAATTCTGTAATTGAG
AAAATGAACACTCAATTCACAGCTGTGGGCAAAGAATTCAACAAATTGGAAAGAAGGATGGAAAACTTAAATAAAAA
AGTTGATGATGGGTTTCTAGACATTTGGACCTATAATGCAGAATTGTTGGTTCTACTGGAAAATGAAAGGACTTTGG
ATTTCCATGACTCCAACGTGAAGAATCTGTATGAGAAAGTAAAAAGCCAATTAAAGAATAATGCCAAAGAAATAGGA
AACGGGTGTTTTGAATTCTATCACAAGTGTAACGATGAATGCATGGAGAGTGTGAAAAATGGAACTTATGACTATCC
AAAATATTCCGAAGAATCAAAGTTAAACAGAGAGAAAATTGATGGAGTGAAATTGGAATCAATGGGAGTCTATCAGA
TTCTGGCGATCTACTCAACAGTCGCCAGTTCCCTGGTTCTTTTGGTCTCCCTGGGGGCAATCAGCTTCTGGATGTGT
TCCAATGGGTCTTTGCAGTGTAGAATATGCATCTAAGACCAGAATTTCAGAAATATAAGGAAAAACACCCTTGTTTC
TACT

SEQ ID NO: 49 (NA, 105p30)
AGCAAAAGCAGGAGTTTAAAATGAATCCAAATCAAAAAATAATAACCATTGGATCAATCAGTATAGCAATCGGAATA
ATTAGTCTAATGTTGCAAATAGGAAATATTATTTCAATATGGGCTAGTCACTCAATCCAAACTGGAAGTCAAAACCA
CACTGGAATATGCAACCAAAAAATCATCACATATGAAAACAGCACCTGGGTGAATCACACATATGTTAATATTAACA
ACACTAATGTTGTTGCTGGAAAGGACAAAACTTCAGTGACACTGGCCGGCAATTCATCTCTTTGTCCTATCAGTGGA
TGGGCTATATACACAAAAGACAACAGCATAAGAATTGGCTCCAAAGGAGATGTTTTTGTCATAAGAGAACCTTTCAT
ATCATGTTCTCACTTGGAATGCAGAACCTTTTTTCTGACCCAAGGTGCTCTATTAAATGACAAACATTCAAATGGAA
CCGTTAAGGACAGAAGTCCTTATAGGGCCTTAATGAGCTGTCCTCTAGGTGAAGCCCCGTCACCATACAATTCAAAG
TTTGAATCAGTTGCATGGTCAGCAAGCGCATGCCATGATGGCAAGGGCTGGTTAACAATCGGAATTTCTGGTCCAGA
CAATGGAGCTGTGGCTGTACTAAAATACAACGGAATAATAACTGAAACCATAAAAAGTTGGGAAAAGCGAATATTGA
GAACACAAGAGTCTGAATGTGTTTGTGTGAACGGGTCATGTTTCACCATAATGACCGATGGCCCGAGTAATGGGGCC
GCCTCGTACAAAATCTTCAAGATCGAAAAGGGGAAGGTTACTAAATCAACAGAGTTGAATGCACCCAATTTTCATTA
TGAGGAATGTTCCTGTTACCCAGACACTGGCACAGTGATGTGTGTATGCAGGGACAACTGGCATGGTTCAAATCGAC
CTTGGGTATCTTTTAATCAAAACTTGGATTATCAAATAGGATACATCTGCAGTGGAGTGTTCGGTGACAATCCGCGT
CCCAAAGATGGGAAGGGCAGCTGTAATCCAGTGACTGTTGATGGAGCAGACGGAGTTAAGGGGTTTTCATACAAATA

-continued

| SEQUENCES |
| --- |

TGGTAATGGTGTTTGGATAGGAAGGACTAAAAGTAACAGACTTAGAAAGGGGTTTGAGATGATTTGGGATCCTAATG
GATGGACAGATACCGACAGTGATTTCTCAGTGAAACAGGATGTTGTGGCAATAACTGATTGGTCAGGGTACAGCGGA
AGTTTCGTCCAACATCCTGAGTTAACAGGATTGGACTGTATAAGACCTTGCTTCTGGGTTGAGTTAGTCAGAGGACT
GCCTAGAGAAAATACAACAATCTGGACTAGTGGGAGCAGCATTTCTTTTTGTGGCGTTGATAGTGATACTGCAAATT
GGTCTTGGCCAGACGGTGCTGAGTTGCCGTTCACCATTGACAAGTAGCTCGTTGAAAAAAACTCCTTGTTTCTACT

SEQ ID NO: 50 (HA, A/Chile/1/1983)
MKAKLLVLLCALSATDADTICIGYHANNSTDTVDTVLEKNVTVTHSVNLLEDNHNGKLCKLKGIAPLQLGKCSIAGW
ILGNPECESLFSKKSWSYIAETPNSENGTCYPGYFADYEELREQLSSVSSFERFEIFPKESSWPKHNVTKGVTAACS
HKGKSSFYRNLLWLTEKNGSYPNLSKSYVNNKEKEVLVLWGVHHPSNIEDQKTIYRKENAYVSVVSSHYNRRFTPEI
AKRPKVRNQEGRINYYWTLLEPGDTIIFEANGNLIAPWYAFALSRGFGSGIITSNASMDECDAKCQTPQGAINSSLP
FQNVHPVTIGECPKYVRSTKLRMVTGLRNIPSIQSRGLFGAIAGFIEGGWTGMIDGWYGYHHQNEQGSGYAADQKST
QNAINGITNKVNSIIEKMNTQFTAVGKEFNKLEKRMENLNKKVDDGFLDIWTYNAELLVLLENERTLDFHDSNVKNL
YEKVKSQLKNNAKEIGNGCFEFYHKCNNECMESVKNGTYDYPKYSEESKLNREKIDGVKLESMGVYQILAIYSTVAS
SLVLLVSLGAISFWMCSNGSLQCRICI SEQ ID NO: 51 (NA, A/Chile/1/1983)
MNPNQKIITIGSICMTIGIISLILQIGNIISIWVSHSIQTGSQNHTGICNQRIITYENSTWVNQTYVNINNTNVVAG
KDTTSVTLAGNSSLCPIRGWAIYSKDNSIRIGSKGDVFVIREPFISCSHLECRTFFLTQGALLNDKHSNGTVKDRSP
YRALMSCPIGEAPSPYNSRFESVAWSASACHDGMGWLTIGISGPDDGAVAVLKYNGIITETIKSWRKRILRTQESEC
VCVNGSCFTIMTDGPSNGPASYRIFKIEKGKITKSIELDAPNSHYEECSCYPDTGTVMCVCRDNWHGSNRPWVSFNQ
NLDYQIGYICSGVFGDNPRPKDGKGSCDPVTVDGADGVKGFSYRYGNGVWIGRTKSNSSRKGFEMIWDPNGWTDTDS
NFLVKQDVVAMTDWSGYSGSFVQHPELTGLDCMRPCFWVELVRGRPREGTTVWTSGSSISFCGVNSDTANWSWPDGA
ELPFTIDK SEQ ID NO: 52 (NA, A/California/04/09)
MNPNQKIITIGSVCMTIGMANLILQIGNIISIWISHSIQLGNQNQIETCNQSVITYENNTWVNQTYVNISNTNFAAG
QSVVSVKLAGNSSLCPVSGWAIYSKDNSVRIGSKGDVFVIREPFISCSPLECRTFFLTQGALLNDKHSNGTIKDRSP
YRTLMSCPIGEVPSPYNSRFESVAWSASACHDGINWLTIGISGPDNGAVAVLKYNGIITDTIKSWRNNILRTQESEC
ACVNGSCFTVMTDGPSNGQASYKIFRIEKGKIVKSVEMNAPNYHYEECSCYPDSSEITCVCRDNWHGSNRPWVSFNQ
NLEYQIGYICSGIFGDNPRPNDKTGSCGPVSSNGANGVKGFSFKYGNGVWIGRTKSISSRNGFEMIWDPNGWTGTDN
NFSIKQDIVGINEWSGYSGSFVQHPELTGLDCIRPCFWVELIRGRPKENTIWTSGSSISFCGVNSDTVGWSWPDGAE
LPFTIDK SEQ ID NO: 53 (PA, A/New Caledonia/20/1999)
MEDFVRQCFNPMIVELAEKAMKEYGEDPKIETNKFAAICTHLEVCFMYSDFHFIDERGESIIVESGDPNALLKHRFE
IIEGRDRIMAWTVVNSICNTTGVEKPKFLPDLYDYKENRFIEIGVTRREVHIYYLEKANKIKSEKTHIHIFSFTGEE
MATKADYTLDEESRARIKTRLFTIRQEMASRSLWDSFRQSERGEETIEEKFEITGTMRKLADQSLPPNFPSLENFRA
YVDGFEPNGCIEGKLSQMSKEVNAKIEPFLRTTPRPLRLPDGPLCHQRSKFLLMDALKLSIEDPSHEGEGIPLYDAI
KCMKTFFGWKEPNIVKPHEKGINPNYLMAWKQVLAELQDIENEEKIPRTKNMKRTSQLKWALGENMAPEKVDFDDCK
DVGDLKQYDSDEPEPRSLASWVQNEFNKACELTDSSWIELDEIGEDVAPIEHIASMRRNYFTAEVSHCRATEYIMKG
VYINTALLNASCAAMDDFQLIPMISKCRTKEGRRKTNLYGFIIKGRSHLRNDTDVVNFVSMEFSLTDPRLEPHKWEK
YCVLEIGDMLLRTAIGQVSRPMFLYVRTNGTSKIKMKWGMEMRRCLLQSLQQIESMIEAESSVKEKDMTKEFFENKS
ETWPIGESPRGVEEGSIGKVCRTLLAKSVFNSLYASPQLEGFSAESRKLLLIVQALRDNLEPGTFDLGGLYEAIEEC
LINDPWVLLNASWFNSFLTHALK SEQ ID NO: 54 (PB1, A/New Caledonia/20/1999)
MDVNPTLLFLKVPAQNAISTTFPYTGDPPYSHGTGTGYTMDTVNRTHQYSERGRWTKNTETGAPQLNPIDGPLPKDN
EPSGYAQTDCVLEAMAFLEESHPGIFENSCIETMEVVQQTRVDKLTQGRQTYDWTLNRNQPAATALANTIEVFRSNG
LIANESGRLIDFLKDVMESMDRDEVEVTTHFQRKRRVRDNVTKKMVTQRTIGKKKHKLDKRSYLIRALTLNTMTKDA
ERGKLKRRAIATPGMQIRGFVYFVETLARSICEKLEQSGLPVGGNEKKAKLANVVRKMMTNSQDTEISFTITGDNTK
WNENQNPRMFLAMITYITKNQPEWFRNILSIAPIMESNKMARLGKGYMFESKSMKLRTQIPAEMLANIDLKYFNDST
KRKIEKIRPLLIDGTASLSPGMMMGMFNMLSTVLGVSILNLGQKRYTKTTYWWDGLQSSDDFALIVNAPNYAGIQAG
VDREYRTCKLLGINMSKKKSYINRTGTFEFTSFFYRYGFVANFSMELPSFGVSGVNESADMSIGVTVIKNNMINNDL
GPATAQMALQLFIKDYRYTYRCHRGDTQIQTRRSFEIKKLWDQTRSKAGLLVSDGGPNLYNIRNLHIPEVCLKWELM
DEDYQGRLCNPSNPFVSHKEIESVNNAVMMPAHGPAKNMEYDAVATTHSWVPKRNRSILNTSQRGILEDEQMYQRCC
NLFEKFFPSSSYRRPVGISSMVEAMVSRARIDARIDFESGRIKKEEFAEIMKTCSTIEDLRRQK SEQ ID NO: 55 (PB2, A/New Caledonia/20/1999)
MERIKELRNLMSQSRTREILTKTTVDHMAIIKKYTSGRQEKNPSLRMKWMMAMKYPITADKRITEMIPERNEQGQTL
WSKVNDAGSDRVMISPLAVTWWNRNGPVASTIHYPKIYKTYFEKVERLKHGTFGPVHFRNQVKIRRRVDINPGHADL
SAKEAQDVIMEVVFPNEVGARILTSESQLTITKEKKEELQNCKISPLMVAYMLERELVRKTRFLPVAGGTSSVYIEV
LHLTQGTCWEQMYTPGGEVRNDDVDQSLIIAARNIVRRAAVSADPLASLLEMCHSTQIGGTRMVDILRQNPTEEQAV
DICKAAMGLRISSSFSFGGFTFKRTSGSSVKREEEVLTGNLQTLKLTVHEGYEEFTMVGKRATAILRKATRRLIQLI
VSGRDEQSIVEAIVVAMVFSQEDCMVKAVRGDLNFVNRANQRLNPMHQLLRHFQKDAKVLFLNWGIEPIDNVMGMIG
ILPDMTPSTEMSMRGVRVSKMGVDEYSNAERVVVSIDRFLRVRDQRGNVLLSPEEVSETQGTEKLTITYSSSMMWEI
NGPESVLINTYQWIIRNWETVKIQWSQNPTMLYNKMEFEPFQSLVPKAIRGQYSGFVRTLFQQMRDVLGTFDTTQII
KLLPFAAAPPKQSRMQFSSLTVNVRGSGMRILVRGNSPVFNYNKTTKRLTVLGKDAGTLTEDPDEGTAGVESAVLRG
FLILGKEDRRYGPALSINELSNLAKGEKANVLIGQGDVVLVMKRKRDSSILTDSQTATKRIRMAIN SEQ ID NO: 56 (NP, A/New Caledonia/20/1999)
MASQGTKRSYEQMETDGERQNATEIRASVGRMIGGIGRFYIQMCTELKLNDYEGRLIQNSLTIERMVLSAFDERRNK
YLEEHPSAGKDPKKTGGPIYKRVDGKWVRELVLYDKEEIRRIWRQANNGDDATAGLTHIMIWHSNLNDTTYQRTRAL
VRTGMDPRMCSLMQGSTLPRRSGAAGAAVKGVGTMVLELIRMIKRGINDRNFWRGENGRKTRIAYERMCNILKGKFQ
TAAQKAMMDQVRESRNPGNAEIEDLTFLARSALILRGSVAHKSCLPACVYGPAVASGYDFEKEGYSLVGVDPFKLLQ
TSQVYSLIRPNENPAHKSQLVWMACNSAAFEDLRVSSFIRGTRVLPRGKLSTRGVQIASNENMDAIVSSTLELRSRY -continued

| SEQUENCES |
| --- |

WAIRTRSGGNTNQQRASAGQISTQPTFSVQRNLPFDKTTIMAAFTGNTEGRTSDMRAEIIKMMESARPEEVSFQGRG
VFELSDERATNPIVPSFDMSNEGSYFFGDNAEEYDN

SEQ ID NO: 57 (M1, A/New Caledonia/20/1999)
MSLLTEVETYVLSIVPSGPLKAEIAQRLENVFAGKNTDLEALMEWLKTRPILSPLTKGILGFVFTLTVPSERGLQRR
RFVQNALNGNGDPNNMDRAVKLYRKLKREITFHGAKEIALSYSAGALASCMGLIYNRMGAVTTESAFGLICATCEQI
ADSQHKSHRQMVTTTNPLIRHENRMVLASTTAKAMEQMAGSSEQAAEAMEVASQARQMVQAMRAIGTHPSSSTGLKN
DLLENLQAYQKRMGVQMQRFK SEQ ID NO: 58 (NA, A/New Caledonia/20/1999)
MNPNQKIITIGSISIAIGIISLMLQIGNIISIWASHSIQTGSQNHTGVCNQRIITYENSTWVNHTYVNINNTNVVAG
KDKTSVTLAGNSSLCSISGWAIYTKDNSIRIGSKGDVFVIREPFISCSHLECRTFFLTQGALLNDKHSNGTVKDRSP
YRALMSCPLGEAPSPYNSKFESVAWSASACHDGMGWLTIGISGPDNGAVAVLKYNGIITETIKSWKKRILRTQESEC
VCVNGSCFTIMTDGPSNGAASYKIFKIEKGKVTKSIELNAPNFHYEECSCYPDTGTVMCVCRDNWHGSNRPWVSFNQ
NLDYQIGYICSGVFGDNPRPKDGEGSCNPVTVDGADGVKGFSYKYGNGVWIGRTKSNRLRKGFEMIWDPNGWTDTDS
DFSVKQDVVAITDWSGYSGSFVQHPELTGLDCIRPCFWVELVRGLPRENTTIWTSGSSISFCGVNSDTANWSWPDGA
ELPFTIDK SEQ ID NO: 59 (PA, A/Wisconsin/67/2005)
MEDFVRQCFNPMIVELAEKAMKEYGEDLKIETNKFAAICTHLEVCFMYSDFHFINEQGESIVVELDDPNALLKHRFE
IIEGRDRTMAWTVVNSICNTTGAGKPKFLPDLYDYKENRFIEIGVTRREVHIYYLEKANKIKSENTHIHIFSFTGEE
MATKADYTLDEESRARIKTRLFTIRQEMANRGLWDSFRQSERGEETIEEKFEITGTMRRLADQSLPPNFSCLENFRA
YVDGFEPNGCIEGKLSQMSKEVNAQIEPFLKTTPRPIKLPNGPPCYQRSKFLLMDALKLSIEDPSHEGEGIPLYDAI
KCMKTFFGWKEPYIVKPHEKGINSNYLLSWKQVLSELQDIENEEKIPRTKNMKKTSQLKWALGENMAPEKVDFENCR
DISDLKQYDSDEPELRSLSSWIQNEFNKACELTDSVWIELDEIGEDVAPIEHIASMRRNYFTAEVSHCRATEYIMKG
VYINTALLNASCAAMDDFQLIPMISKCRTKEGRRKTNLYGFIIKGRSHLRNDTDVVNFVSMEFSLTDPRLEPHKWEK
YCVLEIGDMLLRSAIGQISRPMFLYVRTNGTSKVKMKWGMEMRRCLLQSLQQIESMIEAESSVKEKDMTKEFFENKS
EAWPIGESPKGVEEGSIGKVCRTLLAKSVFNSLYASPQLEGFSAESRKLLLVVQALRDNLEPGTFDLGGLYEAIEEC
LINDPWVLLNASWFNSFLTHALK SEQ ID NO: 60 (PB1, A/Wisconsin/67/2005)
MDVNPTLLFLKVPAQNAISTTFPYTGDPPYSHGTGTGYTMDTVNRTHQYSEKGKWTTNTETGAPQLNPIDGPLPEDN
EPSGYAQTDCVLEAMAFLEESHPGIFENSCLETMEAVQQTRVDRLTQGRQTYDWTLNRNQPAATALANTIEVFRSNG
LTANESGRLIDFLKDVMESMDKEEMEITTHFQRKRRVRDNMTKKMVTQRTIGKKKQRVNKRGYLIRALTLNTMTKDA
ERGKLKRRAIATPGMQIRGFVYFVETLARSICEKLEQSGLPVGGNEKKAKLANVVRKMMTNSQDTELSFTITGDNTK
WNENQNPRMFLAMITYITKNQPEWFRNILSIAPIMFSNKMARLGKGYMFESKRMKLRTQIPAEMLASIDLKYFNEST
RKKIEKIRPLLIDGTASLSPGMMMGMFNMLSTVLGVSILNLGQKKYTKTTYWWDGLQSSDDFALIVNAPNHEGIQAG
VNRFYRTCKLVGINMSKKKSYINKTGTFEFTSFFYRYGFVANFSMELPSFGVSGINESADMSIGVTVIKNNMINNDL
GPATAQMALQLFIKDYRYTYRCHRGDTQIQTRRSFELKKLWDQTQSRAGLLVSDGGPNLYNIRNLHIPEVCLKWELM
DENYRGRLCNPLNPFVSHKEIESVNNAVVMPAHGPAKSMEYDAVATTHSWIPKRNRSILNTSQRGILEDEQMYQKCC
NLFEKFFPSSSYRRPIGISSMVEAMVSRARIDARIDFESGRIKKEEFSEIMKICSTIEELRRQR SEQ ID NO: 61 (PB2, A/Wisconsin/67/2005)
MERIKELRNLMSQSRTREILTKITVDHMAIIKKYTSGRQEKNPSLRMKWMMAMKYPITADKRITEMVPERNEQGQTL
WSKMSDAGSDRVMVSPLAVTWWNRNGPVTSTVHYPKVYKTYFDKVERLKHGTFGPVHFRNQVKIRRRVDINPGHADL
SAKEAQDVIMEVVFPNEVGARILTSESQLTITKEKKEELRDCKISPLMVAYMLERELVRKTRFLPVAGGTSSIYIEV
LHLTQGTCWEQMYTPGGEVRNDDVDQSLIIAARNIVRRAAVSADPLASLLEMCHSTQIGGTRMVDILRQNPTEEQAV
DICKAAMGLRISSSFSFGGFTFKRTSGSSVKKEEEVLTGNLQTLKIRVHEGYEEFTMVGKRATAILRKATRRLVQLI
VSGRDEQSIAEAIIVAMVFSQEDCMIKAVRGDLNFVNRANQRLNPMHQLLRHFQKDAKVLFQNWGIEHIDSVMGMVG
VLPDMTPSTEMSMRGIRVSKMGVDEYSSTERVVVSIDRFLRVRDQRGNVLLSPEEVSETQGTERLTITYSSSMMWEI
NGPESVLVNTYQWIIRNWEAVKIQWSQNPAMLYNKMEFEPFQSLVPKAIRSQYSGFVRTLFQQMRDVLGTFDTTQII
KLLPFAAAPPKQSRMQFSSLTVNVRGSGMRILVRGNSPVFNYNKTTKRLTILGKDAGTLIEDPDESTSGVESAVLRG
FLIIGKEDRRYGPALSINELSNLAKGEKANVLIGQGDVVLVMKRKRDSSILTDSQTATKRIRMAIN SEQ ID NO: 62 (NP, A/Wisconsin/67/2005)
MASQGTKRSYEQMETDGDRQNATEIRASVGKMIDGIGRFYIQMCTELKLSDYEGRLIQNSLTIEKMVLSAFDERRNK
YLEEHPSAGKDPKKTGGPIYRRVDGKWMRELVLYDKEEIRRIWRQANNGEDATAGLTHIMIWHSNLNDATYQRTRAL
VRTGMDPRMCSLMQGSTLPRRSGAAGAAVKGIGTMVMELIRMVKRGINDRNFWRGENGRKTRSAYERMCNILKGKFQ
TAAQRAMVDQVRESRNPGNAEIEDLIFLARSALILRGSVAHKSCLPACVYGPAVSSGYNFEKEGYSLVGIDPFKLLQ
NSQVYSLIRPNENPAHKSQLVWMACHSAAFEDLRLLSFIRGTKVSPRGKLSTRGVQIASNENMDNMGSGTLELRSGY
WAIRTRSGGNTNQQRASAGQTSVQPTFSVQRNLPFEKSTIMAAFTGNTEGRTSDMRAEIIRMMEGAKPEEVSFRGRG
VFELSDEKATNPIVPSFDMSNEGSYFFGDNAEEYDN SEQ ID NO: 63 (M1, A/Wisconsin/67/2005)
MSLLTEVETYVLSIVPSGPLKAEIAQRLEDVFAGKNTDLEALMEWLKTRPILSPLTKGILGFVFTLTVPSERGLQRR
RFVQNALNGNGDPNNMDKAVKLYRKLKREITFHGAKEIALSYSAGALASCMGLIYNRMGAVTTEVAFGLVCATCEQI
ADSQHRSHRQMVATTNPLIRHENRMVLASTTAKAMEQMAGSSEQAAEAMEIASQARQMVQAMRAIGTHPSSSTGLRD
DLLENLQTYQKRMGVQMQRFK SEQ ID NO: 64 (M2, A/Wisconsin/67/2005)
MSLLTEVETPIRNEWGCRCNDSSDPLVVAANIIGILHLILWILDRLFFKCVYRLFKHGLKRGPSTEGVPESMREEYR
KEQQNAVDADDSHFVSIELE SEQ ID NO: 65 (NS, A/Wisconsin/67/2005)
AATGGATTCCAACACTGTGTCAAGTTTCCAGGTAGATTGCTTTCTTTGGCATATCCGGAAACAAGTTGTAGACCAAG
AACTGAGTGATGCCCCATTCCTTGATCGGCTTCGCCGAGATCAGAGGTCCCTAAGGGGAAGAGGCAATACTCTCGGT
CTAGACATCAAAGCAGCCACCCATGTTGGAAAGCAAATTGTAGAAAAGATTCTGAAAGAAGAATCTGATGAGGCACT -continued

| SEQUENCES |
|---|

TAAAATGACCATGGTCTCCACACCTGCTTCGCGATACATAACTGACATGACTATTGAGGAATTGTCAAGAAACTGGT
TCATGCTAATGCCCAAGCAGAAAGTGGAAGGACCTCTTTGCATCAGAATGGACCAGGCAATCATGGAGAAAAACATC
ATGTTGAAAGCGAATTTCAGTGTGATTTCTGACCGACTAGAGACCATAGTATTACTAAGGGCTTTCACCGAAGAGGG
AGCAATTGTTGGCGAAATCTCACCATTGCCTTCTTTTCCAGGACATACTATTGAGGATGTCAAAAATGCAATTGGGG
TCCTCATCGGAGGACTTGAATGGAATGATAACACAGTTCGAGTCTCTAAAAATCTACAGAGATTCGCTTGGAGAAGC
AGTAATGAGAATGGGGGACCTCCACTTACTCCAAAACAGAAACGGAAAATGGCGAGAACAGCTAGGTCAAAAGTTTG
AAGAGATAAGATGGCTGATTGAAGAAGTGAGACACAGACTAAAAACAACTGAAAATAGCTTTGAACAAATAACATTC
ATGCAAGCATTACAACTGCTGTTTGAAGTGGAACAGGAGATAAGAACTTTCTCATTTCAGCTTATTTAATGATAAA

SEQ ID NO: 66 (HA, A/Wisconsin/67/2005)
MKTIIALSYILCLVFAQKLPGNDNSTATLCLGHHAVPNGTIVKTITNDQIEVTNATELVQSSSTGGICDSPHQILDG
ENCTLIDALLGDPQCDGFQNKKWDLFVERSKAYSNCYPYDVPDYASLRSLVASSGTLEFNDESFNWTGVTQNGTSSS
CKRRSNNSFFSRLNWLTHLKFKYPALNVTMPNNEKFDKLYIWGVHHPVTDNDQIFLYAQASGRITVSTKRSQQTVIP
NIGSRPRIRNIPSRISIYWTIVKPGDILLINSTGNLIAPRGYFKIRSGKSSIMRSDAPIGKCNSECITPNGSIPNDK
PFQNVNRITYGACPRYVKQNTLKLATGMRNVPEKQTRGIFGAIAGFIENGWEGMVDGWYGFRHQNSEGIGQAADLKS
TQAAINQINGKLNRLIGKTNEKFHQIEKEFSEVEGRIQDLEKYVEDTKIDLWSYNAELLVALENQHTIDLTDSEMNK
LFERTKKQLRENAEDMGNGCFKIYHKCDNACIGSIRNGTYDHDVYRDEALNNRFQIKGVELKSGYKDWILWISFAIS
CFLLCVALLGFIMWACQKGNIRCNICI SEQ ID NO: 67 (NA, A/Wisconsin/67/2005)
MNPNQKIITTGSVSLTISTICFFMQIAILITTVTLHFKQYEFNSPPNNQVMLCEPTIIERNITEIVYLTNTTIEKEI
CPKLAEYRNWSKPQCNITGFAPFSKDNSIRLSAGGDIWVTREPYVSCDPDKCYQFALGQGTTLNNVHSNDTVHDRTP
YRTLLMNELGVPFHLGTKQVCIAWSSSSCHDGKAWLHVCVTGDDKNATASFIYNGRLVDSIVSWSKEILRTQESECV
CINGTCTVVMTDGSASGKADTKILFIEEGKIVHTSTLSGSAQHVEECSCYPRYLGVRCVCRDNWKGSNRPIVDINIK
DYSIVSSYVCSGLVGDTPRKNDSSSSSHCLDPNNEEGGHGVKGWAFDDGNDVWMGRTISEKLRSGYETFKVIEGWSN
PNSKLQINRQVIVDRGNRSGYSGIFSVEGKSCINRCFYVELIRGRKEETEVLWTSNSIVVFCGTSGTYGTGSWPDGA
DINLMPI SEQ ID NO: 68 (PA, 105p30)
MEDEVRQCFNPMIVELAEKAMKEYGEDPKIETNKFAAICTHLEVCFMYSDFHFIDERGESIIVESGDPNALLKHRFE
IIEGRDRIMAWTVINSICNTTGVEKPKFLPDLYDYKENRFIEIGVTRREVHIYYLEKANKIKSEKTHIHIFSFTGEE
MATKADYTLDEESRARIKTRLFTIRQEMASKSLWDSFRQSERGEETIEEKFEITGTMRKLADQSLPPNFPSLENFRA
YVDGFEPNGCIEGKLSQMSKEVNAKIEPFLRTTPRPLRLPDGPLCHQRSKFLLMDALKLSIEDPSHEGEGIPLYDAI
KCMKTFFGWKEPNIVKPHEKGINPNYLMAWKQVLAELQDIENEEKIPRTKNMKRTSQLKWALGENMAPEKVDFDDCK
DVGDLKQYDSDEPEPRSLASWVQNEFNKACELTDSSWIELDEIGEDVAPIEHIASMRRNYFTAEVSHCRATEYIMKG
VYINTALLNASCAAMDDFQLIPMISKCRTKEGRRKTNLYGFIIKGRSHLRNDTDVVNFVSMEFSLTDPRLEPHKWEK
YCVLEIGDMLLRTAIGQVSRPMFLYVRTNGTSKIKMKWGMEMRRCLLQSLQQIESMIEAESSVKEKDMTKEFFENKS
ETWPIGESPRGVEEGSIGKVCRTLLAKSVFNSLYASPQLEGFSAESRKLLLIVQALRDNLEPGTFDLGGLYEAIEEC
LINDPWVLLNASWFNSFLTHALK SEQ ID NO: 69 (M1, 105p30)
MSLLTEVETYVLSIVPSGPLKAEIAQRLENVFAGKNTDLEALMEWLKTRPILSPLTKGILGFVFTLTVPSERGLQRR
RFVQNALNGNGDPNNMDKAVKLYRKLKREITFHGAKEIALSYSAGALASCMGLIYNRMGAVTTESAFGLICATCEQI
ADSQHKSHRQMVTTTNPLIRHENRMVLASTTAKAMEQMAGSSEQAAEAMEVASQARQMVQAMRAIGTHPSSSTGLKN
DLLENLQAYQKRMGVQMQRFK SEQ ID NO: 70 (HA, A/California/04/09)
MKAILVVLLYTFATANADTLCIGYHANNSTDTVDTVLEKNVTVTHSVNLLEDKHNGKLCKLRGVAPLHLGKCNIAGW
ILGNPECESLSTASSWSYIVETPSSDNGTCYPGDFIDYEELREQLSSVSSFERFEIFPKTSSWPNHDSNKGVTAACP
HAGAKSFYKNLIWLVKKGNSYPKLSKSYINDKGKEVLVLWGIHHPSTSADQQSLYQNADTYVFVGSSRYSKKFKPEI
AIRPKVRDQEGRMNYYWTLVEPGDKITFEATGNLVVPRYAFAMERNAGSGIIISDTPVHDCNTTCQTPKGAINTSLP
FQNIHPITIGKCPKYVKSTKLRLATGLRNIPSIQSRGLFGAIAGFIEGGWTGMVDGWYGYHHQNEQGSGYAADLKST
QNAIDEITNKVNSVIEKMNTQFTAVGKEFNHLEKRIENLNKKVDDGFLDIWTYNAELLVLLENERTLDYHDSNVKNL
YEKVRSQLKNNAKEIGNGCFEFYHKCDNTCMESVKNGTYDYPKYSEEAKLNREEIDGVKLESTRIYQILAIYSTVAS
SLVLVVSLGAISFWMCSNGSLQCRICI SEQ ID NO: 71 (PA, B/Brisbane/60/08)
AGCAGAAGCGGTGCGTTTGATTTGTCATAATGGATACTTTTATTACAAGAAACTTCCAGACTACAATAATACAAAAG
GCCAAAAACACAATGGCAGAATTTAGTGAAGATCCTGAATTGCAACCAGCAATGCTATTCAATATCTGCGTCCATCT
AGAGGTTTGCTATGTAATAAGTGACATGAATTTTCTTGACGAAGAAGGAAAAGCATATACAGCATTAGAAGGACAAG
GGAAAGAACAAAACTTGAGACCACAATATGAAGTAATTGAGGGAATGCCAAGAACCATAGCATGGATGGTCCAGAGA
TCCTTAGCTCAAGAGCATGGAATAGAGACTCCCAAGTATCTGGCTGATTTGTTTGATTATAAAACCAAAAGATTTAT
AGAAGTTGGAATAACAAAGGGATTGGCTGATGATTACTTTTGGAAAAAGAAAGAAAAGTTGGGAAATAGCATGGAAC
TGATGATATTCAGCTACAATCAAGACTACTCGTTAAGTAATGAATCCTCATTGGATGAGGAAGGGAAAGGGAGAGTG
CTAAGCAGACTCACAGAACTTCAGGCTGAATTAAGTCTGAAAAATTTATGGCAAGTTCTCATAGGAGAAGAAGATGT
TGAAAAGGGAATTGATTTTAAACTTGGACAAACAATATCTAGACTAAGGGATATATCTGTTCCAGCTGGTTTCTCCA
ATTTTGAAGGAATGAGGAGCTACATAGACAATATAGACCCAAAAGGAGCAATAGAGAGAAATCTAGCAAGGATGTCT
CCCTTAGTATCAGTCACACCTAAAAAGTTAACATGGGAGGACCTAAGACCAATAGGGCCTCACATTTACGACCATGA
GCTACCAGAAGTTCCATATAATGCCTTTCTTCTAATGTCTGATGAACTGGGATTGGCCAATATGACTGAGGGAAAGT
CCAAAAAACCGAAGACATTAGCCAAAGAATGTCTAGAAAAGTACTCAACACTACGGGATCAAACTGACCCAATATTA
ATAATGAAAAGCGAAAAAGCTAACGAAAATTTCCTATGGAAGCTTTGGAGAGACTGTGTAAATACAATAAGTAATGA
GGAAACGAGTAACGAGTTACAGAAAACCAATTATGCCAAATGGGCCACAGGGGATGGATTAACATACCAGAAAATAA
TGAAAGAAGTAGCAATAGATGACGAAACAATGTGCCAAGAAGAGCCTAAAATCCCTAACAAATGTAGAGTGGCTGCT
TGGGTTCAAACAGAGATGAATCTATTGAGCACTCTGACAAGTAAAAGAGCTCTGGACCTACCAGAAATAGGGCCAGA
CATAGCACCCGTGGAGCATGTAGGAAGTGAAAGAAGGAAATACTTTGTTAATGAAATCAACTACTGTAAGGCCTCTA
CAGTTATGATGAAGTATGTGCTTTTTCACACTTCATTGTTGAATGAAAGCAATGCCAGCATGGGAAAATACAAAGTA
ATACCAATAACCAATAGAGTAGTAAATGAAAAAGGAGAAAGTTTCGACATGCTTTACGGTCTGGCGGTTAAAGGACA -continued

SEQUENCES

ATCTCATCTGAGGGGAGATACTGATGTTGTAACAGTTGTAACTTTCGAATTTAGTAGTACAGATCCAAGAGTGGACT
CAGGAAAGTGGCCAAAATATACTGTGTTTAGGATTGGCTCCCTATTTGTGAGTGGGAGGGAAAAATCTGTGTACTTG
TATTGCCGAGTGAATGGCACAAATAAGATCCAAATGAAATGGGGAATGGAAGCTAGAAGATGTTTGCTTCAATCAAT
GCAACAAATGGAGGCAATTGTTGAACAGGAATCATCAATACAAGGATATGACATGACCAAAGCCTGTTTCAAGGGAG
ACAGAGTAAATAGCCCCAAAACTTTCAGTATTGGAACTCAAGAAGGAAAACTAGTAAAAGGATCCTTTGGAAAAGCA
CTAAGAGTAATATTTACTAAATGCTTGATGCACTATGTATTTGGAAATGCCCAATTGGAGGGGTTTAGTGCCGAGTC
TAGGAGACTTCTACTGTTGATTCAAGCATTAAAGGACAGAAAGGGCCCTTGGGTGTTCGACTTAGAGGGAATGTATT
CTGGAATAGAAGAATGTATTAGCAACAACCCTTGGGTAATACAGAGTGTATACTGGTTCAATGAATGGTTGGGCTTT
GAAAAGGAGGGGAATAAAGTGTTGGAATCAGTGGATGAAATAATGGATGAATAAAAGGAAATGGTACTCAATTTGGT
ACTATTTTGTTCATTATGTATCTAAACATCCAATAAAAAGAACCAAGAATCAAAAATGCACGTGTTTCTACT

SEQ ID NO: 72 (PB1, B/Brisbane/60/08)
AGCAGAAGCGGAGCCTTTAAGATGAATATAAATCCTTATTTTCTCTTCATAGATGTGCCCGTACAGGCAGCAATTTC
AACAACATTCCCATACACTGGTGTTCCCCCTTATTCCCATGGAACAGGAACAGGCTACACAATAGACACCGTGATCA
GAACGCATGAGTACTCAAACAAGGGGAAACAGTACATTTCTGATGTTACAGGATGCACAATGGTAGATCCAACAAAT
GGACCATTACCCGAAGATAATGAGCCGAGTGCCTATGCGCAATTAGATTGCGTTTTAGAGGCTTTGGATAGAATGGA
TGAAGAACACCCAGGTCTTTTTCAAGCAGCCTCACAGAATGCTATGGAGGCCCTAATGGTCACAACTGTAGACAAAT
TAACCCAGGGGAGACAGACTTTTGATTGGACAGTATGCAGAAACCAACCTGCTGCAACGGCACTGAACACAACAATA
ACCTCTTTTAGGTTGAATGATTTAAATGGAGCCGACAAAGGTGGATTAATACCTTTTTGCCAGGATATCATTGATTC
ATTAGACCGACCTGAAATGACTTTCTTCTCAGTAAAGAATATAAAGAAAAAATTGCCTGCCAAAAACAGAAAGGGTT
TCCTCATAAAGAGGATACCAATGAAGGTAAAAGACAAAATAACCAAAGTGGAATACATCAAAAGAGCATTATCATTA
AACACAATGACAAAAGACGCTGAAAGAGGCAAACTGAAAAGAAGAGCGATTGCCACTGCTGGAATACAAATCAGAGG
GTTTGTATTAGTAGTTGAAAACTTGGCTAAAAATATATGTGAAAATCTAGAACAAAGTGGTTTACCAGTAGGTGGAA
ACGAGAAGAAAGCCAAACTGTCAAACGCAGTGGCCAAAATGCTCAGTAACTGCCCACCAGGAGGGATTAGCATGACA
GTAACAGGAGACAATACAAAATGGAATGAATGTTTAAACCCAAGAATCTTTTTGGCTATGACTGAAAGAATAACCAG
AGACAGCCCAGTTTGGTTCAGGGATTTTTGTAGTATAGCACCGGTCCTGTTCTCCAATAAGATAGCAAGATTGGGGA
AAGGGTTTATGATAACAAGCAAAACAAAAAGACTGAAGGCTCAAATACCTTGTCCTGATCTGTTTAGTATACCGTTA
GAAAGATATAATGAAGAAACAAGGGCAAAATTGAAAAAGCTAAAACCATTCTTCAATGAAGAAGGAACTGCATCTTT
GTCGCCTGGGATGATGATGGGAATGTTTAATATGCTATCTACCGTGTTGGGAGTAGCTGCACTAGGTATCAAGAACA
TTGGAAACAAAGAATACTTATGGGATGGACTGCAATCTTCTGATGATTTTGCTCTGTTTGTTAATGCAAAGGATGAA
GAAACATGTATGGAAGGAATAAACGACTTTTACCGAACATGTAAATTATTGGGAGTAAACATGAGCAAAAAGAAAAG
TTACTGTAATGAGACTGGAATGTTTGAATTTACAAGCATGTTCTACAGAGATGGATTTGTATCTAATTTTGCAATGG
AACTCCCTTCGTTTGGGGTTGCTGGAGTAAATGAATCAGCAGATATGGCAATAGGAATGACAATAATAAAGAACAAC
ATGATCAACAATGGAATGGGTCCGGCAACAGCACAAACAGCCATACAGTTATTCATAGCTGATTATAGATACACCTA
CAAATGCCACAGGGGAGATTCCAAAGTAGAAGGAAAGAGAATGAAAATCATAAAGGAGTTATGGGAAAACACTAAAG
GAAGAGATGGTCTATTAGTAGCAGATGGTGGGCCCAACATTTACAATTTGAGAAACCTGCATATCCCAGAAATAGTA
TTAAAGTATAATCTAATGGACCCTGAATACAAAGGGCGGTTACTTCATCCTCAAAATCCCTTTGTGGGACATTTGTC
TATTGAGGGCATCAAAGAGGCAGACATAACCCCAGCACATGGTCCAGTAAAGAAAATGGACTACGATGCGGTGTCTG
GAACTCATAGTTGGAGAACCAAAAGAAACAGATCTATACTAAACACTGATCAGAGGAACATGATTCTTGAGGAACAA
TGCTACGCTAAATGTTGCAACCTATTTGAGGCCTGTTTTAACAGTGCATCATACAGGAAGCCAGTGGGTCAACATAG
CATGCTTGAGGCTATGGCCCACAGATTAAGAATGGATGCACGATTAGATTATGAATCAGGGAGAATGTCAAAGGATG
ATTTTGAGAAAGCAATGGCTCACCTTGGTGAGATTGGGTACATATAAGCTTCGAAGATGTTTATGGGGTTATTGGTC
ATCATTGAATACATGCGATACACAAATGATTAAAATGAAAAAAGGCTCGTGTTTCTACT SEQ ID NO: 73 (PB2, B/Brisbane/60/08)
AGCAGAAGCGGAGCGTTTTCAAGATGACATTGGCCAAAATTGAATTGTTAAAACAACTGCTAAGGGACAATGAAGCC
AAAACAGTTTTGAAGCAAACAACGGTAGACCAATATAACATAATAAGAAAATTCAATACATCAAGGATTGAAAAGAA
TCCTTCACTAAGGATGAAGTGGGCCATGTGTTCTAATTTTCCCTTGGCTCTAACCAAGGGCGATATGGCAAACAGAA
TCCCCTTGGAATACAAAGGGATACAACTTAAAACAAATGCTGAAGACATAGGAACCAAAGGCCAAATGTGCTCAATA
GCAGCAGTTACTTGGTGGAATACATATGGACCAATAGGAGATACTGAAGGTTTCGAAAGGGTCTACGAAAGCTTTTT
TCTCAGAAAAATGAGACTTGACAACGCCACTTGGGGCCGAATAACTTTTGGCCCAGTTGAAAGAGTGAGAAAAAGGG
TACTGCTAAACCCTCTCACCAAGGAAATGCCTCCGGATGAGGCGAGCAATGTGATAATGGAAATATTGTTCCCTAAA
GAAGCAGGAATACCAAGAGAATCCACTTGGATACATAGGGAACTGATAAAAGAAAAAAGAGAAAAATTGAAAGGAAC
AATGATAACTCCAATCGTACTGGCATACATGCTTGAAAGAGAACTGGTTGCTCGAAGAAGATTCTTGCCAGTGGCAG
GAGCAACATCAGCTGAGTTCATAGAAATGCTACACTGCTTACAAGGTGAAAATTGGAGACAAATATATCACCCAGGA
GGGAATAAATTAACTGAGTCCAGGTCTCAATCAATGATAGTAGCTTGTAGAAAAATAATCAGAAGATCAATAGTCGC
TTCAAACCCACTGGAGCTAGCTGTAGAAATTGCAAACAAGACTGTGATAGATACTGAACCTTTAAAGTCATGTCTGG
CAGCCATAGACGGAGGTGATGTAGCTTGTGACATAATAAGAGCTGCATTAGGACTAAAGATCAGACAAAGACAAAGA
TTTGGACGGCTTGAGCTAAAAAGAATATCAGGAAGAGGATTCAAAAATGATGAAGAAATATTAATAGGGAACGGAAC
AATACAGAAGATTGGAATATGGGACGGGGAAGAGGAGTTCCATGTAAGATGTGGTGAATGCAGGGGAATATTAAAAA
AGAGTAAAATGAAACTGGAAAAACTACTGATAAATTCAGCCAAAAAGGAGGATATGAGAGATTTAATAATCTTATGC
ATGGTATTTTCTCAAGACACTAGGATGTTCCAAGGAGTGAGAGGAGAAATAAATTTTCTTAATCGAGCAGGCCAACT
TTTATCTCCAATGTACCAACTCCAACGATATTTTTTGAATAGAAGCAACGACCTTTTTGATCAATGGGGGTATGAGG
AATCACCCAAAGCAAGTGAACTACATGGGATAAATGAATCAATGAATGCATCTGACTATACATTGAAAGGGATTGTA
GTGACAAGAAATGTAATTGACGACTTTAGCTCTATTGAAACAGAAAAAGTATCCATAACAAAAAATCTTAGTTTAAT
AAAAAGGACTGGGGAAGTCATAATGGGAGCTAATGACGTGAGTGAATTAGAATCACAAGCACAGCTGATGATAACAT
ATGATACACCTAAAATGTGGGAAATGGGAACAACCAAAGAACTGGTGCAAAACACTTATCAATGGGTGCTAAAAAAC
TTGGTGACACTGAAGGCTCAGTTTCTTCTAGGAAAAGAGGACATGTTCCAATGGGATGCATTTGAAGCATTTGAGAG
CATAATTCCTCAGAAGATGGCTGGTCAGTACAGTGGATTTGCAAGAGCAGTGCTCAAACAAATGAGAGACCAGGAGG
TTATGAAAACTGACCAGTTCATAAAGTTGTTGCCTTTTTGTTTCTCACCACCAAAATTAAGGAGCAATGGGGAGCCT
TATCAATTCTTAAAACTTGTGTTGAAAGGAGGAGGGGAAAATTTCATCGAAGTAAGGAAAGGGTCCCCTCTATTTTC
CTATAATCCACAAACAGAAGTCCTAACTATATGCGGCAGAATGATGTCATTAAAAGGGAAAATTGAAGATGAAGAAA
GGAATAGATCAATGGGTAATGCAGTATTAGCAGGCTTTCTCGTTAGTGGCAAGTATGACCCAGATCTTGGAGATTTC
AAAACTATTGAAGAACTTGAAAAGCTGAAACCGGGGGAAAAGGCAAACATCTTACTTTATCAAGGAAAACCAGTTAA
AGTAGTTAAAAGGAAAAGGTATAGTGCTTTGTCCAATGACATTTCACAAGGAATTAAGAGACAAAGAATGACAGTTG
AGTCTATGGGGTGGGCCTTGAGCTAATATAAATTTATCCATTAATTCAATGAACGCAATTGAGTGAAAAATGCTCGT
GTTTCTACT -continued

SEQUENCES

SEQ ID NO: 74 (NP, B/Brisbane/60/08)
AGCAGAAGCACAGCATTTTCTTGTGAACTTCAAGCACCAGTAAAAGAACTGAAAATCAAAATGTCCAACATGGATAT
TGACGGTATAAACACTGGGACAATTGACAAAACACCGGAAGAAATAACTTCTGGAACCAGTGGGACAACCAGACCAA
TCATTAGACCAGCAACCCTTGCCCCACCAAGCAACAAACGAACCCGTAACCCATCCCCGGAAAGAGCAACCACAAGC
AGTGAAGATGATGTCGGAAGGAAAACCCAAAAGAAACAGACCCCGACAGAGATAAAGAAGAGCGTCTACAACATGGT
GGTGAAACTGGGCGAATTCTATAACCAGATGATGGTCAAAGCTGGACTCAATGATGACATGGAGAGAAATCTAATCC
AAAATGCGCATGCCGTGGAAAGAATTCTATTGGCTGCCACTGATGACAAGAAAACCGAGTTCCAGAAGAAAAAGAAT
GCCAGAGATGTCAAAGAAGGGAAAGAAGAAATAGATCACAACAAAACAGGAGGCACCTTTTACAAGATGGTAAGAGA
TGATAAAACCATCTACTTCAGCCCTATAAGAATTACCTTTTTAAAAGAAGAGGTGAAAACAATGTACAAAACCACCA
TGGGGAGTGATGGCTTCAGTGGACTAAATCACATAATGATTGGGCATTCACAGATGAATGATGTCTGTTTCCAAAGA
TCAAAGGCACTAAAAAGAGTTGGACTTGATCCTTCATTAATCAGTACCTTTGCGGGAAGCACAGTCCCCAGAAGATC
AGGTGCGACTGGTGTTGCAATCAAAGGAGGTGGAACCTTAGTGGCTGAAGCCATTCGATTTATAGGAAGAGCAATGG
CAGACAGAGGGCTATTGAGAGACATCAAAGCCAAGACTGCCTATGAAAAGATTCTTCTGAATCTAAAAAACAAATGC
TCTGCGCCCCAACAAAAGGCTCTAGTTGATCAAGTGATCGGAAGCAGAAATCCGGGGATTGCAGACATTGAAGATCT
AACCCTGCTTGCTCGTAGTATGGTCGTTGTTAGGCCCTCTGTGGCAAGCAAAGTGGTGCTTCCCATAAGCATTTACG
CCAAAATACCTCAACTAGGGTTCAATGTTGAAGAGTACTCTATGGTTGGGTACGAAGCCATGGCTCTTTACAATATG
GCAACACCTGTGTCCATATTAAGAATGGGAGATGATGCAAAAGATAAATCGCAATTATTCTTCATGTCTTGCTTCGG
AGCTGCCTATGAAGACCTGAGAGTTTTGTCTGCATTAACAGGCACAGAATTCAAGCCTAGATCAGCATTAAAATGCA
AGGGTTTCCATGTTCCAGCAAAGGAACAGGTAGAAGGAATGGGAGCAGCTCTGATGTCCATCAAGCTCCAGTTTTGG
GCTCCGATGACCAGATCTGGGGGGAACGAAGTAGGTGGAGACGGAGGGTCTGGCCAAATAAGCTGCAGCCCAGTGTT
TGCAGTGGAAAGACCTATTGCTCTAAGCAAGCAAGCTGTAAGAAGAATGCTGTCAATGAATATTGAGGGACGTGATG
CAGATGTCAAAGGAAATCTACTCAAGATGATGAATGACTCAATGGCTAAGAAAACCAGTGGAAATGCTTTCATTGGG
AAGAAAATGTTTCAAATATCAGACAAAAACAAAACCAATCCCATTGAAATTCCAATTAAGCAGACCATCCCCAATTT
CTTCTTTGGGAGGGACACAGCAGAGGATTATGATGACCTCGATTATTAAGGCAACAAAATAGACACTATGACTGTGA
TTGTTTCAATACGTTTGGAATGTGGGTGTTTATTCTTATTAAAATAAATATAAAAAATGCTGTTGTTTCTACT SEQ ID NO: 75 (M, B/Brisbane/60/08)
AGCAGAAGCACGCACTTTCTTAAAATGTCGCTGTTTGGAGACACAATTGCCTACCTGCTTTCATTGACAGAAGATGG
AGAAGGCAAAGCAGAACTAGCAGAAAAATTACACTGTTGGTTTGGTGGGAAAGAATTTGACCTAGACTCTGCCTTGG
AATGGATAAAAAACAAAAGATGCTTAACTGATATACAAAAAGCACTAATTGGTGCCTCTATATGCTTTTTAAAACCC
AAAGACCAGGAAAGAAAAAGAAGATTCATCACAGAGCCCTTATCAGGAATGGGAACAACAGCAACAAAAAAGAAAGG
CCTGATTCTGGCTGAGAGAAAAATGAGAAGATGTGTGAGCTTTCATGAAGCATTTGAAATAGCAGAAGGCCATGAAA
GCTCAGCGCTACTATACTGTCTCATGGTCATGTACCTGAATCCTGGAAATTATTCAATGCAAGTAAAACTAGGAACG
CTCTGTGCTTTATGCGAGAAACAAGCATCACATTCACACAGGGCTCATAGCAGAGCAGCGAGATCTTCAGTGCCTGG
AGTGAGACGAGAAATGCAGATGGTCTCAGCTATGAACACAGCAAAAACAATGAATGGAATGGGAAAAGGAGAAGACG
TCCAAAAGCTGGCAGAAGAGTTGCAAAGCAACATTGGAGTGCTGAGATCTCTTGGGGCAAGCCAAAAGAATGGGGAA
GGGATTGCAAAGGATGTAATGGAAGTGCTAAAGCAGAGCTCCATGGGAAATTCAGCTCTTGTGAAGAAATATCTATA
ATGCTCGAACCATTTCAGATTCTTACAATTTGTTCTTTTATCTTATCAGCTCTCCATTTCATGGCTTGGACAATAGG
GCATTTGAATCAAATAAAAAGAGGAATAAACATGAAAATACGAATAAAAGGTCCAAACAAAGAGACAATAAACAGAG
AGGTATCAATTTTGAGACACAGTTACCAAAAAGAAATCCAGGCCAAAGAAACAATGAAGGAAGTACTCTCTGACAAC
ATGGAGGTATTGAATGACCACATAATAATTGAGGGGCTTTCTGCCGAAGAGATAATAAAAATGGGTGAAACAGTTTT
GGAGATAGAAGAATTGCATTAAATTCAATTTTACTGTATTTCTTACTATGCATTTAAGCAAATTGTAATCAATGTCA
GCAAATAAACTGGAAAAAGTGCGTTGTTTCTACT SEQ ID NO: 76 (NS, B/Brisbane/60/08)
AGCAGAAGCAGAGGATTTGTTTAGTCACTGGCAAACAGGGAAAAATGGCGAACAACAACATGACCACAACACAAATT
GAGGTGGGTCCGGGAGCAACCAATGCCACCATAAACTTTGAAGCAGGAATTCTAGAGTGCTATGAAAGGCTTTCATG
GCAAAGAGCCCTTGACTACCCTGGTCAAGACCGCCTAAACAGACTAAAGAGAAAATTAGAGTCAAGAATAAAGACTC
ACAACAAAAGTGAGCCTGAAAGTAAAAGGATGTCCCTTGAAGAGAGAAAAGCAATTGGAGTAAAAATGATGAAAGTA
CTCCTATTTATGAATCCGTCTGCTGGAATTGAAGGGTTTGAGCCATACTGTATGAAAAGTTCCTCAAATAGCAACTG
TACGAAATACAATTGGACTGATTACCCTTCAACACCAGAGAGGTGCCTTGATGACATAGAGGAAGAACCAGAGGATG
TTGATGGCCCAACTGAAATAGTATTAAGGGACATGAACAACAAAGATGCAAGGCAAAAGATAAAGGAGGAAGTAAAC
ACTCAGAAAGAAGGGAAGTTCCGTTTGACAATAAAAAGGGATATGCGTAATGTATTGTCCTTGAGAGTGTTGGTAAA
CGGAACATTCCTCAAACACCCCAATGGACACAAGTCCTTATCAACTCTGCATAGATTGAATGCATATGACCAGAGTG
GAAGGCTTGTTGCTAAACTTGTTGCCACTGATGATCTTACAGTGGAGGATGAAGAAGATGGCCATCGGATCCTCAAC
TCACTCTTCGAGCGTCTTAATGAAGGACATTCAAAGCCAATTCGAGCAGCTGAAACTGCGGTGGGAGTCTTATCCCA
ATTTGGTCAAGAGCACCGATTATCACCAGAAGAGGGAGACAATTAGACTGGTCACGGAAGAACTTTATCTTTTAAGT
AAAAGAATTGATGATAACATACTATTCCACAAAACAGTAATAGCTAACAGCTCCATAATAGCTGACATGGTTGTATC
ATTATCATTATTAGAAACATTGTATGAAATGAAGGATGTGGTTGAAGTGTACAGCAGGCAGTGCTTGTGAATTTAAA
ATAAAAATCCTCTTGTTACTACT SEQ ID NO: 77 (PA, B/Panama/45/90)
AGCAGAAGCGGTGCGTTTGATTTGCCATAATGGATACTTTTATTACAAGAAACTTCCAGACTACAATAATACAAAAG
GCCAAAAACACAATGGCAGAATTTAGTGAAGATCCTGAATTACAACCAGCAATGCTATTCAACATCTGCGTCCATCT
AGAGGTTTGCTATGTAATAAGTGACATGAATTTTCTTGACGAAGAAGGAAAATCATATACAGCATTAGAAGGACAAG
GAAAAGAACAAAACTTGAGACCACAATATGAAGTAATTGAGGGAATGCCAAGAACCATAGCATGGATGGTCCAAAGA
TCCTTAGCTCAAGAGCATGGAATAGAGACTCCAAAGTATCTGGCTGATTTGTTTGATTATAAAACCAAGAGATTTAT
AGAAGTTGGAATAACAAAAGGATTGGCTGATGATTACTTTTGGAAAAAGAAAGAAAAGCTGGGAAATAGCATGGAAC
TGATGATATTCAGCTACAATCAAGACTATTCGTTAAGTAATGAATCCTCATTGGATGAGGAAGGGAAAGGGAGAGTG
CTAAGCAGACTCACAGAACTTCAGGCTGAATTAAGTCTGAAAAACCTATGGCAAGTTCTCATAGGAGAAGAAGATGT
TGAAAAGGGAATTGACTTTAAACTTGGACAAACAATATCTAGACTAAGGGATATATCTGTTCCAGCTGGTTTCTCCA
ATTTTGAAGGAATGAGGAGCTACATAGACAATATAGATCCTAAAGGAGCAATAGAAAGAAATCTAGCAAGGATGTCT
CCCTTAGTATCAGCCACACCTAAAAAGTTGAAATGGGAGGACCTAAGACCAATAGGGCCTCACATTTACAACCATGA
GTTACCAGAAGTTCCATATAATGCCTTTCTTCTAATGTCTGATGAATTGGGGCTGGCCAATATGACTGAGGGAAAGT
CCAAAAAACCGAAGACATTAGCCAAAGAATGTCTAGAAAAGTACTCAACACTACGGGATCAAACTGACCCAATATTA
ATAATGAAAAGCGAAAAAGCTAACGAAAATTTCCTATGGAAGCTGTGGAGGGACTGTGTAAATACAATAAGTAATGA -continued

| SEQUENCES |
|---|
| GGAAATGAGTAACGAGTTACAGAAAACCAATTATGCCAAGTGGGCCACAGGAGATGGATTAACATACCAGAAAATAA<br>TGAAAGAAGTAGCAATAGATGACGAAACAATGTGCCAAGAAGAGCCTAAAATCCCTAACAAATGTAGAGTGGCTGCT<br>TGGGTTCAAACAGAGATGAATTTATTGAGCACTCTGACAAGTAAAAGAGCTCTGGACCTACCAGAAATAGGGCCAGA<br>CGTAGCACCCGTGGAGCATGTAGGGAGTGAAAGAAGGAAATACTTTGTTAATGAAATCAACTGCTGTAAGGCCTCTA<br>CAGTTATGATGAAGTATGTGCTTTTTCACACTTCATTATTGAATGAAAGCAATGCCAGCATGGGAAAATATAAAGTA<br>ATACCAATAACCAATAGAGTAGTAAATGAAAAAGGAGAAAGTTTCGACATGCTTTATGGTCTGGCGGTTAAAGGACA<br>ATCTCATCTGAGGGGAGATACTGATGTTGTAACAGTTGTGACTTTCGAATTTAGTGGTACAGATCCCAGAGTGGACT<br>CAGGAAAGTGGCCAAAATATACTGTGTTTAGGATTGGCTCCCTATTTGTGAGTGGGAGGGAAAAATCTGTGTACCTA<br>TATTGCCGAGTGAATGGCACAAATAAGATCCAAATGAAATGGGGAATGGAAGCTAGAAGATGTCTGCTTCAATCAAT<br>GCAACAAATGGAAGCAATTGTTGAACAAGAATCATCGATACAAGGATATGACATGACCAAAGCTTGTTTCAAGGGAG<br>ACAGAGTAAATAGCCCCAAAACTTTTAGTATTGGGACTCAAGAAGGAAAACTAGTAAAAGGATCCTTTGGGAAAGCA<br>CTAAGAGTAATATTTACCAAATGTTTGATGCACTATGTATTTGGAAATGCCCAATTGGAGGGGTTTAGTGCCGAGTC<br>TAGGAGACTTCTACTGTTAATTCAAGCACTAAAGGACAGAAAGGGCCCTTGGGTGTTCGACTTAGAGGGAATGTATT<br>CTGGAATAGAAGAATGTATTAGTAACAACCCTTGGGTAATACAGAGTGCATACTGGTTCAATGAATGGTTGGGCTTT<br>GAAAAGGAGGGGAGTAAAGTATTAGAATCAGTAGATGAAATAATGAATGAATGAAAAAACATAGTACTCAATTTGGT<br>ACTATTTTGTTCATTATGTATCTAAACATCCAATAAAAAGAATCGAGAATCAAAAATGCACGTGTTTCTACT<br><br>SEQ ID NO: 78 (PB1, B/Panama/45/90)<br>AGCAGAAGCGGAGCCTTTAAGATGAATATAAATCCTTATTTTCTCTTCATAGATGTACCCATACAGGCAGCAATTTC<br>AACAACATTCCCATACACCGGTGTTCCCCCTTACTCCCATGGAACGGGAACAGGCCACACAATAGACACCGTGATCA<br>GAACACATGAGTACTCGAACAAGGGAAAACAGTATGTTTCTGACATCACAGGATGTACAATGGTAGATCCAACAAAT<br>GGGCCATTACCCGAAGACAATGAGCCGAGTGCCTATGCACAATTAGATTGCGTTCTGGAGGCTTTGGATAGAATGGA<br>TGAAGAACATCCAGGTTTGTTTCAAGCAGCCTCACAGAATGCCATGGAGGCACTAATGGTCACAACTGTAGACAAAT<br>TAACCCAGGGGAGACAGACTTTTGATTGGACAGTATGCAGAAACCAGCCTGCTGCAACGGCACTAAACACAACAATA<br>ACCTCCTTTAGGTTGAATGATTTGAATGGAGCTGACAAGGGTGGATTGGTACCCTTTTGCCAAGATATCATTGATTC<br>ATTGGACAAACCTGAAATGACTTTCTTCTCAGTAAAGAATATAAAGAAAAAATTGCCTGCTAAAAACAGAAAGGGTT<br>TCCTCATAAAGAGAATACCAATGAAAGTAAAAGACAGGATAACCAGAGTGGAATACATCAAAAGAGCATTATCATTA<br>AACACAATGACAAAAGATGCTGAAAGGGGCAAACTAAAAAGAAGAGCGATTGCAACCGCTGGAATACAAATCAGAGG<br>GTTTGTATTAGTAGTTGAAAACTTGGCTAAAAATATCTGTGAAAATCTAGAACAAAGTGGTTTGCCCGTAGGTGGAA<br>ATGAAAAGAAGGCCAAACTGTCAAATGCAGTGGCCAAAATGCTCAGTAACTGCCCACCAGGAGGGATCAGCATGACA<br>GTAACAGGAGACAATACTAAATGGAATGAATGCTTAAATCCAAGAATCTTTTTGGCTATGACTGAAAGGATAACAAG<br>AGACAGCCCAATTTGGTTCCGGGATTTTTGTAGTATAGCACCGGTCTTGTTCTCCAATAAAATAGCCAGATTGGGAA<br>AAGGATTTATGATAACAAGCAAAACAAAAAGACTGAAGGCTCAAATACCTTGTCCAGATCTGTTTAGCATACCATTA<br>GAAAGATATAATGAAGAAACAAGGGCAAAATTAAAAAAGCTGAAACCATTCTTCAATGAAGAAGGAACGGCATCTTT<br>GTCGCCTGGGATGATGATGGGAATGTTTAATATGCTATCTACCGTGTTGGGAGTAGCCGCACTAGGTATCAAAAACA<br>TTGGAAACAAAGAATATTTATGGGATGGACTGCAATCTTCTGATGATTTTGCTCTGTTTGTTAATGCAAAAGATGAA<br>GAGACATGTATGGAAGGAATAAACGACTTTTACCGAACATGTAAATTATTGGGAATAAACATGAGCAAAAAGAAAAG<br>TTACTGTAATGAAACTGGAATGTTTGAATTTACAAGCATGTTCTATAGAGATGGATTTGTATCTAATTTTGCAATGG<br>AAATTCCTTCATTTGGAGTTGCTGGAGTAAATGAATCAGCAGATATGGCAATAGGAATGACAATAATAAAGAACAAT<br>ATGATCAACAATGGGATGGGTCCAGCAACAGCACAAACAGCCATACAATTATTCATAGCTGATTATAGGTACACCTA<br>CAAATGCCACAGGGGAGATTCCAAAGTGGAAGGAAAAAGAATGAAAATTATAAAGGAGCTATGGGAAAACACTAAAG<br>GAAGAGATGGTCTGTTAGTGGCAGATGGTGGGCCCAACATTTACAATTTGAGAAACTTACATATCCCAGAAATAGTA<br>TTGAAGTACAACCTAATGGACCCTGAATACAAAGGGCGGTTACTTCATCCTCAAAATCCATTTGTAGGACATTTATC<br>TATTGAGGGCATCAAAGAAGCAGATATAACCCCAGCACATGGTCCCGTAAAGAAAATGGATTATGATGCAGTATCTG<br>GAACTCATAGTTGGAGAACCAAAAGGAACAGATCTATACTAAATACTGACCAGAGGAACATGATTCTTGAGGAACAA<br>TGCTACGCTAAGTGTTGCAACCTTTTTGAGGCCTGTTTTAATAGTGCATCATACAGGAAACCAGTAGGTCAGCACAG<br>CATGCTTGAGGCTATGGCCCACAGATTAAGAGTGGATGCACGACTAGATTATGAATCAGGAAGAATGTCAAAGGATG<br>ATTTTGAGAAAGCAATGGCTCACCTTGGTGAGATTGGGTACATATAAGCTCCGAAGATGTCTATGGGGTTATTGGTC<br>ATCATTGAATACATGTGATAAACAAATGATTAAAATGAAAAAAGGCTCGTGTTTCTACT<br><br>SEQ ID NO: 79 (PB2, B/Panama/45/90)<br>AGCAGAAGCGGAGCGTTTTCAAGATGACATTGGCTAAAATTGAATTGTTAAAACAACTGTTAAGGGACAATGAAGCC<br>AAAACAGTATTGAAACAAACAACGGTAGACCAATATAACATAATAAGAAAATTCAATACATCAAGAATTGAAAAGAA<br>CCCTTCATTGAGGATGAAGTGGGCAATGTGTTCTAATTTTCCCTTGGCTCTGACCAAGGGTGATATGGCAAACAGAA<br>TCCCCTTGGAATACAAGGGAATACAACTTAAAACAAATGCTGAAGACATAGGAACTAAAGGCCAAATGTGCTCAATA<br>GCAGCAGTTACCTGGTGGAATACATATGGACCAATAGGAGATACTGAAGGTTTCGAAAAGGTCTACGAAAGCTTTTT<br>TCTCAGAAAGATGAGACTTGACAATGCCACTTGGGGCCGAATAACTTTTGGCCCAGTTGAAAGAGTAAGAAAAAGGG<br>TACTGCTAAACCCTCTCACCAAGGAAATGCCTCCAGATGAAGCAAGTAATGTGATAATGGAAATATTGTTCCCTAAG<br>GAAGCAGGAATACCAAGAGAATCTACTTGGATACATAGGGAACTGATAAAAGAAAAAAGAGAAAAATTGAAAGGAAC<br>AATGATAACTCCCATTGTACTGGCATACATGCTTGAGAGAGAATTGGTTGCCAGAAGAAGGTTCCTGCCGGTGGCAG<br>GAGCAACATCAGCTGAGTTCATAGAAATGCTACACTGCTTACAAGGTGAAAATTGGAGACAAATATATCACCCAGGA<br>GGAAATAAACTAACTGAATCTAGGTCTCAATCGATGATTGTAGCTTGTAGAAAGATAATCAGAAGATCAATAGTCGC<br>ATCAAACCCATTAGAGCTAGCTGTAGAAATTGCAAACAAGACTGTGATAGATACTGAACCTTTAAAATCATGTCTGA<br>CAGCCATAGACGGAGGTGATGTAGCCTGTGACATAATAAGAGCTGCATTAGGACTAAAGATCAGACAAAGACAAAGA<br>TTTGGACGACTTGAACTAAAGAGAATATCAGGAAGAGGATTCAAAAATGATGAAGAAATATTAATCGGGAACGGAAC<br>AATACAGAAGATTGGAATATGGGACGGAGAAGAGGAGTTCCATGTAAGATGTGGTGAATGCAGGGGAATATTAAAAA<br>AGAGCAAAATGAGAATGGAAAAACTACTAATAAATTCAGCTAAAAAGGAAGACATGAAAGATTTAATAATCTTGTGC<br>ATGGTATTTTCTCAAGACACTAGGATGTTCCAAGGAGTGAGAGGAGAAATAAATTTTCTTAATAGAGCAGGCCAACT<br>TTTATCTCCAATGTACCAACTCCAAAGATATTTTTTGAATAGAAGCAACGATCTCTTTGATCAATGGGGGTATGAGG<br>AATCACCCAAAGCAAGTGAGCTACATGGAATAAATGAATTAATGAATGCATCTGACTACACTTTGAAAGGGGTTGTA<br>GTAACAAAAAATGTAATTGATGATTTTAGTTCTACTGAAACAGAAAAAGTATCTATAACAAAAAATCTTAGTTTAAT<br>AAAAAGGACTGGGGAAGTCATAATGGGGGCTAATGACGTAAGTGAATTAGAATCACAAGCTCAGCTAATGATAACAT<br>ATGATACACCTAAGATGTGGGAGATGGGAACAACCAAAGAACTGGTGCAAAACACCTACCAATGGGTGCTGAAAAAT<br>TTGGTAACACTGAAGGCTCAGTTTCTTCTAGGAAAAGAAGACATGTTCCAATGGGATGCATTTGAAGCATTTGAAAG<br>CATAATCCCCCAGAAGATGGCTGGCCAGTACAGTGGATTTGCAAGAGCAGTGCTCAAACAAATGAGAGACCAAGAGG<br>TTATGAAAACTGACCAGTTCATAAAGTTGTTGCCCTTTTGTTTCTCACCACCAAAATTAAGGAGAAATGGGGAGCCT<br>TATCAGTTCTTGAGGCTTGTATTGAAGGGAGGAGGAGAAAATTTCATCGAAGTAAGGAAAGGGTCCCCTCTATTCTC |

-continued

SEQUENCES

TTACAATCCACAAACAGAAGTCCTAACTATATGCGGCAGAATGATGTCATTAAAAGGGAAAATTGAAGATGAAGAAA
GGAATAGATCAATGGGGAATGCAGTATTAGCGGGCTTTCTCGTTAGTGGCAAGTATGACCCAGATCTTGGAGATTTC
AAAACTATTGAAGAACTTGAAAAGCTGAAACCGGGGGAGAAAGCAAACATCTTACTTTATCAAGGAAAGCCCGTTAA
AGTAGTTAAAAGGAAAAGATATAGTGCTTTATCCAATGACATTTCACAAGGAATTAAGAGACAAAGAATGACAGTTG
AGTCCATGGGGTGGGCCTTGAGCTAATATAAATTTATCCATTAATTCAATAAACACAATTGAGTGAAAAATGCTCGT
GTTTCTACT

SEQ ID NO: 80 (NP, B/Panama/45/90)
AGCAGAAGCACAGCATTTTCTTATTAACTTCAAGTACCAACAAAAGAACTGAAAATCAAAATGTCCAACATGGATAT
TGACGGTATCAACACTGGGACAATTGACAAAACACCGGAAGAAATAACTTCTGGAACCAGTGGGACAACCAGACCAA
TCATCAGACCAGCAACCCTTGCCCCACCAAGCAACAAACGAACCCGGAACCCATCCCCGGAAAGAGCAACCACAAGC
AGTGAAGCTGATGTCGGAAGGAAAACCCAAAAGAAACAGACCCCGACAGAGATAAAGAAGAGCGTCTACAATATGGT
AGTGAAACTGGGTGAATTCTATAACCAGATGATGGTCAAAGCTGGACTCAACGATGACATGGAGAGAAACCTAATCC
AAAATGCGCATGCTGTGGAAAGAATTCTATTGGCTGCCACTGATGACAAGAAAACTGAATTCCAGAGGAAAAAGAAT
GCCAGAGATGTCAAAGAAGGAAAAGAAGAAATAGACCACAACAAAACAGGAGGCACCTTTTACAAGATGGTAAGAGA
TGATAAAACCATCTACTTCAGCCCTATAAGAATTACCTTTTTAAAAGAAGAGGTGAAAACAATGTACAAAACCACCA
TGGGGAGTGATGGCTTCAGTGGACTAAATCACATAATGATTGGGCATTCACAGATGAATGATGTCTGTTTCCAAAGA
TCAAAGGCCCTAAAAAGAGTTGGACTTGACCCTTCATTAATCAGTACCTTTGCAGGAAGCACACTCCCCAGAAGATC
AGGTGCAACTGGTGTTGCAATCAAAGGAGGTGGAACTTTAGTGGCTGAAGCCATTCGATTTATAGGAAGAGCAATGG
CAGACAGAGGGCTATTGAGAGACATCAAAGCCAAGACTGCCTATGAAAAGATTCTTCTGAATCTAAAAAACAAATGC
TCTGCGCCCCAACAAAAGGCTCTAGTTGATCAAGTGATCGGAAGTAGAAATCCAGGGATTGCAGACATTGAAGACCT
AACCCTGCTTGCTCGTAGTATGGTCGTTGTTAGGCCCTCTGTGGCGAGCAAAGTAGTGCTTCCCATAAGCATTTATG
CTAAAATACCTCAACTAGGGTTCAATGTTGAAGAATACTCTATGGTTGGGTATGAAGCCATGGCTCTCTACAATATG
GCAACACCTGTTTCCATATTAAGAATGGGAGATGATGCAAAAGATAAATCGCAATTATTCTTCATGTCTTGCTTCGG
AGCTGCCTATGAAGACCTGAGAGTTTTGTCTGCATTAACAGGCATAGAATTCAAGCCTAGATCAGCATTAAAATGCA
AGGGTTTCCATGTTCCAGCAAAGGAACAGGTGGAAGGAATGGGGGCAGCTCTGATGTCCATCAAGCTCCAGTTTTGG
GCTCCAATGACCAGATCTGGAGGGAACGAAGTAGGTGGAGACGGAGGGTCTGGCCAAATAAGTTGCAGCCCAGTGTT
TGCAGTAGAAAGACCTATTGCTCTAAGCAAGCAAGCTGTAAGAAGAATGCTTTCAATGAATATTGAGGGACGTGATG
CAGATGTCAAAGGAAATCTACTCAAGATGATGAATGACTCAATGGCTAAGAAAACCAATGGAAATGCTTTCATTGGG
AAGAAAATGTTTCAAATATCAGACAAAAACAAAACCAATCCCGTTGAAATTCCAATTAAGCAGACCATCCCCAATTT
CTTCTTTGGGAGGGACACAGCAGAGGATTATGATGACCTCGATTATTAAAGCAACAAAATAGACACTATGACTGTGA
TTGTTTCAATACGTTTGGAATGTGGGTGTTTACTCTTATTGAAATAAATATAAAAAATGCTGTTGTTTCTACT SEQ ID NO: 81 (M, B/Panama/45/90)
AGCAGAAGCACGCACTTTCTTAAAATGTCGCTGTTTGGAGACACAATTGCCTACCTGCTTTCATTGACAGAAGATGG
AGAAGGCAAAGCAGAACTAGCAGAAAAATTACACTGTTGGTTCGGTGGGAAAGAATTTGACCTAGACTCTGCCTTGG
AATGGATAAAAAACAAAAGATGCTTAACTGATATACAGAAAGCACTAATTGGTGCCTCTATCTGCTTTTTAAAACCA
AAAGACCAAGAAAGAAAAAGAAGATTCATCACAGAGCCCCTATCAGGAATGGGAACAACAGCAACAAAAAAGAAGGG
CCTGATTCTAGCTGAGAGAAAAATGAGAAGATGTGTGAGTTTTCATGAAGCATTTGAAATAGCAGAAGGCCATGAAA
GCTCAGCGCTACTATATTGTCTCATGGTCATGTACCTGAACCCTGGAAATTATTCAATGCAAGTAAAACTAGGAACG
CTCTGTGCTTTGTGCGAGAAACAAGCATCACATTCACACAGGGCTCATAGCAGAGCAGCAAGATCTTCAGTGCCTGG
AGTGAGGCGAGAAATGCAGATGGTCTCAGCTATGAACACAGCAAAAACAATGAATGGAATGGGAAAGGGAGAAGACG
TCCAAAAACTGGCAGAAGAGCTGCAAAGCAACATTGGAGTATTGAGATCTCTTGGGGCAAGTCAAAAGAATGGGGAA
GGAATTGCAAAGGATGTGATGGAAGTGCTAAAGCAGAGCTCTATGGGAAATTCAGCTCTTGTGAAGAAATACCTATA
ATGCTCGAACCATTTCAGATTCTTTCAATTTGTTCTTTCATCTTATCAGCTCTCCATTTCATGGCTTGGACAATAGG
GCATTTGAATCAAATAAAAAGAGGAGTAAACATGAAAATACGAATAAAAAATCCAAATAAAGAGACAATAAACAGAG
AGGTATCAATTTTGAGACACAGTTACCAAAAAGAAATCCAGGCCAAAGAAACAATGAAGGAAGTACTCTCTGACAAC
ATGGAGGTATTGAGTGACCACATAGTAATTGAGGGGCTTTCTGCTGAAGAGATAATAAAAATGGGTGAAACAGTTTT
GGAGGTAGAAGAATTGCATTAAATTCAATTTTTACTGTATTTCTTGCTATGCATTTAAGCAAATTGTAATCAATGTC
AGCAAATAAACTGGAAAAAGTGCGTTGTTTCTACT SEQ ID NO: 82 (NS, B/Panama/45/90)
AGCAGAAGCAGAGGATTTGTTTAGTCACTGGCAAACGAAAAAATGGCGGACAACATGACCACAACACAAATTGAGGT
GGGTCCGGGAGCAACCAATGCCACCATAAACTTTGAAGCAGGAATTTTGGAGTGCTATGAAAGGCTTTCATGGCAAA
GAGCCCTTGACTACCCTGGTCAAGACCGCCTAAACAAACTAAAGAGAAAATTGGAATCAAGAATAAAGACTCACAAC
AAAAGTGAGCCAGAAAGTAAAAGGATGTCTCTTGAAGAGAGAAAAGCTATTGGGGTAAAAATGATGAAAGTGCTCCT
ATTTATGAACCCATCTGCTGGAGTTGAAGGGTTTGAGCCATATTGTATGAAAAATCCCTCCAATAGCAACTGTCCAG
ACTGCAATTGGGCTGATTACCCTCCAACACCAGGAAAGTACCTTGATGGCATAGAAGAAGAACCGGAGAATGTTGGT
GACTCAACTGAAATAGTATTAAGGGACATGAACAACAAAGATGCAAGGCAAAAGATAAAAGAGGAAGTAAACACTCA
GAAAGAAGGGAAATTCCGTTTGACAATAAAAAGGGATATACGTAATGTGTTGTCCTTGAGAGTGTTGGTAAACGGAA
CATTCATCAAGCACCCTAATGGATACAAGTCCTTATCAACTCTGCATAGATTGAATGCATATGACCAGAGTGGAAGA
CTTGTTGCTAAACTTGTTGCTACTGATGATCTTACAGTGGAGGATGAAGAAGATGGCCATCGGATCCTCAACTCACT
CTTCGAGCGTCTTAATGAAGGACATTCAAAGCCAATTCGAGCAGCTGAAACTGCGGTGGGAGTCTTATCCCAATTTG
GTCAAGAGCACCGATTATCACCAGAAGAGAGAGACAATTAGACTGGTTACGGAAGAACTTTATCTTTTAAGTAAAAG
AATTGATGATAACATATTGTTCCACAAAACAGTAATAGCCAACAGCTCCATAATAGCTGACATGATTGTATCATTAT
CATTATTGGAAACATTGTATGAAATGAAGGATGTGGTTGAAGTGTACAGCAGGCAGTGCTTGTGAATTTAAAATAAA
AATCCTCTTGTTACTACT SEQ ID NO: 83 (PA, B/Brisbane/60/08)
MDTFITRNFQTTIIQKAKNTMAEFSEDPELQPAMLFNICVHLEVCYVISDMNFLDEEGKAYTALEGQGKEQNLRPQY
EVIEGMPRTIAWMVQRSLAQEHGIETPKYLADLFDYKTKRFIEVGITKGLADDYFWKKKEKLGNSMELMIFSYNQDY
SLSNESSLDEEGKGRVLSRLTELQAELSLKNLWQVLIGEEDVEKGIDFKLGQTISRLRDISVPAGFSNFEGMRSYID
NIDPKGAIERNLARMSPLVSVTPKKLTWEDLRPIGPHIYDHELPEVPYNAFLLMSDELGLANMTEGKSKKPKTLAKE
CLEKYSTLRDQTDPILIMKSEKANENFLWKLWRDCVNTISNEETSNELQKTNYAKWATGDGLTYQKIMKEVAIDDET
MCQEEPKIPNKCRVAAWVQTEMNLLSTLTSKRALDLPEIGPDIAPVEHVGSERRKYFVNEINYCKASTVMMKYVLFH
TSLLNESNASMGKYKVIPITNRVVNEKGESFDMLYGLAVKGQSHLRGDTDVVTVVTFEFSSTDPRVDSGKWPKYTVF
RIGSLFVSGREKSVYLYCRVNGTNKIQMKWGMEARRCLLQSMQQMEAIVEQESSIQGYDMTKACFKGDRVNSPKTFS -continued

SEQUENCES

IGTQEGKLVKGSFGKALRVIFTKCLMHYVFGNAQLEGFSAESRRLLLLIQALKDRKGPWVFDLEGMYSGIEECISNN
PWVIQSVYWFNEWLGFEKEGNKVLESVDEIMDE

SEQ ID NO: 84 (PB1, B/Brisbane/60/08)
MNINPYFLFIDVPVQAAISTTFPYTGVPPYSHGTGTGYTIDTVIRTHEYSNKGKQYISDVTGCTMVDPTNGPLPEDN
EPSAYAQLDCVLEALDRMDEEHPGLFQAASQNAMEALMVTTVDKLTQGRQTFDWTVCRNQPAATALNTTITSFRLND
LNGADKGGLIPFCQDIIDSLDRPEMTFFSVKNIKKKLPAKNRKGFLIKRIPMKVKDKITKVEYIKRALSLNTMTKDA
ERGKLKRRAIATAGIQIRGFVLVVENLAKNICENLEQSGLPVGGNEKKAKLSNAVAKMLSNCPPGGISMTVTGDNTK
WNECLNPRIFLAMTERITRDSPVWFRDFCSIAPVLFSNKIARLGKGFMITSKTKRLKAQIPCPDLFSIPLERYNEET
RAKLKKLKPFFNEEGTASLSPGMMMGMFNMLSTVLGVAALGIKNIGNKEYLWDGLQSSDDFALFVNAKDEETCMEGI
NDFYRTCKLLGVNMSKKKSYCNETGMFEFTSMFYRDGFVSNFAMELPSFGVAGVNESADMAIGMTIIKNNMINNGMG
PATAQTAIQLFIADYRYTYKCHRGDSKVEGKRMKIIKELWENTKGRDGLLVADGGPNIYNLRNLHIPEIVLKYNLMD
PEYKGRLLHPQNPFVGHLSIEGIKEADITPAHGPVKKMDYDAVSGTHSWRTKRNRSILNTDQRNMILEEQCYAKCCN
LFEACFNSASYRKPVGQHSMLEAMAHRLRMDARLDYESGRMSKDDFEKAMAHLGEIGYI SEQ ID NO: 85 (PB2, B/Brisbane/60/08)
MTLAKIELLKQLLRDNEAKTVLKQTTVDQYNIIRKFNTSRIEKNPSLRMKWAMCSNFPLALTKGDMANRIPLEYKGI
QLKTNAEDIGTKGQMCSIAAVTWWNTYGPIGDTEGFERVYESFFLRKMRLDNATWGRITFGPVERVRKRVLLNPLTK
EMPPDEASNVIMEILFPKEAGIPRESTWIHRELIKEKREKLKGTMITPIVLAYMLERELVARRRFLPVAGATSAEFI
EMLHCLQGENWRQIYHPGGNKLTESRSQSMIVACRKIIRRSIVASNPLELAVEIANKTVIDTEPLKSCLAAIDGGDV
ACDIIRAALGLKIRQRQRFGRLELKRISGRGFKNDEEILIGNGTIQKIGIWDGEEEFHVRCGECRGILKKSKMKLEK
LLINSAKKEDMRDLIILCMVFSQDTRMFQGVRGEINFLNRAGQLLSPMYQLQRYFLNRSNDLFDQWGYEESPKASEL
HGINESMNASDYTLKGIVVTRNVIDDFSSIETEKVSITKNLSLIKRTGEVIMGANDVSELESQAQLMITYDTPKMWE
MGTTKELVQNTYQWVLKNLVTLKAQFLLGKEDMFQWDAFEAFESIIPQKMAGQYSGFARAVLKQMRDQEVMKTDQFI
KLLPFCFSPPKLRSNGEPYQFLKLVLKGGGENFIEVRKGSPLFSYNPQTEVLTICGRMMSLKGKIEDEERNRSMGNA
VLAGFLVSGKYDPDLGDFKTIEELEKLKPGEKANILLYQGKPVKVVKRKRYSALSNDISQGIKRQRMTVESMGWALS SEQ ID NO: 86 (NP, B/Brisbane/60/08)
MSNMDIDGINTGTIDKTPEEITSGTSGTTRPIIRPATLAPPSNKRTRNPSPERATTSSEDDVGRKTQKKQTPTEIKK
SVYNMVVKLGEFYNQMMVKAGLNDDMERNLIQNAHAVERILLAATDDKKTEFQKKKNARDVKEGKEEIDHNKTGGTF
YKMVRDDKTIYFSPIRITFLKEEVKTMYKTTMGSDGFSGLNHIMIGHSQMNDVCFQRSKALKRVGLDPSLISTFAGS
TVPRRSGATGVAIKGGGTLVAEAIRFIGRAMADRGLLRDIKAKTAYEKILLNLKNKCSAPQQKALVDQVIGSRNPGI
ADIEDLTLLARSMVVVRPSVASKVVLPISIYAKIPQLGFNVEEYSMVGYEAMALYNMATPVSILRMGDDAKDKSQLF
FMSCFGAAYEDLRVLSALTGTEFKPRSALKCKGFHVPAKEQVEGMGAALMSIKLQFWAPMTRSGGNEVGGDGGSGQI
SCSPVFAVERPIALSKQAVRRMLSMNIEGRDADVKGNLLKMMNDSMAKKTSGNAFIGKKMFQISDKNKTNPIEIPIK
QTIPNFFFGRDTAEDYDDLDY SEQ ID NO: 87 ($M_1$, B/Brisbane/60/08)
MSLFGDTIAYLLSLTEDGEGKAELAEKLHCWFGGKEFDLDSALEWIKNKRCLTDIQKALIGASICFLKPKDQERKRR
FITEPLSGMGTTATKKKGLILAERKMRRCVSFHEAFEIAEGHESSALLYCLMVMYLNPGNYSMQVKLGTLCALCEKQ
ASHSHRAHSRAARSSVPGVRREMQMVSAMNTAKTMNGMGKGEDVQKLAEELQSNIGVLRSLGASQKNGEGIAKDVME
VLKQSSMGNSALVKKYL SEQ ID NO: 88 ($M_2$, B/Brisbane/60/08)
MLEPFQILTICSFILSALHFMAWTIGHLNQIKRGINMKIRIKGPNKETINREVSILRHSYQKEIQAKETMKEVLSDN
MEVLNDHIIIEGLSAEEIIKMGETVLEIEELH SEQ ID NO: 89 ($NS_1$, B/Brisbane/60/08)
MANNNMTTTQIEVGPGATNATINFEAGILECYERLSWQRALDYPGQDRLNRLKRKLESRIKTHNKSEPESKRMSLEE
RKAIGVKMMKVLLFMNPSAGIEGFEPYCMKSSSNSNCTKYNWTDYPSTPERCLDDIEEEPEDVDGPTEIVLRDMNNK
DARQKIKEEVNTQKEGKFRLTIKRDMRNVLSLRVLVNGTFLKHPNGHKSLSTLHRLNAYDQSGRLVAKLVATDDLTV
EDEEDGHRILNSLFERLNEGHSKPIRAAETAVGVLSQFGQEHRLSPEEGDN SEQ ID NO: 90 (NS2, B/Brisbane/60/08)
MANNNMTTTQIEWRMKKMAIGSSTHSSSVLMKDIQSQFEQLKLRWESYPNLVKSTDYHQKRETIRLVTEELYLLSKR
IDDNILFHKTVIANSSIIADMVVSLSLLETLYEMKDVVEVYSRQCL SEQ ID NO: 91 (PA, B/Panama/45/90)
MDTFITRNFQTTIIQKAKNTMAEFSEDPELQPAMLFNICVHLEVCYVISDMNFLDEEGKSYTALEGQGKEQNLRPQY
EVIEGMPRTIAWMVQRSLAQEHGIETPKYLADLFDYKTKRFIEVGITKGLADDYFWKKKEKLGNSMELMIFSYNQDY
SLSNESSLDEEGKGRVLSRLTELQAELSLKNLWQVLIGEEDVEKGIDFKLGQTISRLRDISVPAGFSNFEGMRSYID
NIDPKGAIERNLARMSPLVSATPKKLKWEDLRPIGPHIYNHELPEVPYNAFLLMSDELGLANMTEGKSKKPKTLAKE
CLEKYSTLRDQTDPILIMKSEKANENFLWKLWRDCVNTISNEEMSNELQKTNYAKWATGDGLTYQKIMKEVAIDDET
MCQEEPKIPNKCRVAAWVQTEMNLLSTLTSKRALDLPEIGPDVAPVEHVGSERRKYFVNEINCCKASTVMMKYVLFH
TSLLNESNASMGKYKVIPITNRVVNEKGESFDMLYGLAVKGQSHLRGDTDVVTVVTFEFSGTDPRVDSGKWPKYTVF
RIGSLFVSGREKSVYLYCRVNGTNKIQMKWGMEARRCLLQSMQQMEAIVEQESSIQGYDMTKACFKGDRVNSPKTFS
IGTQEGKLVKGSFGKALRVIFTKCLMHYVEGNAQLEGFSAESRRLLLLIQALKDRKGPWVFDLEGMYSGIEECISNN
PWVIQSAYWFNEWLGFEKEGSKVLESVDEIMNE SEQ ID NO: 92 (PB1, B/Panama/45/90)
MNINPYFLFIDVPIQAAISTTFPYTGVPPYSHGTGTGHTIDTVIRTHEYSNKGKQYVSDITGCTMVDPTNGPLPEDN
EPSAYAQLDCVLEALDRMDEEHPGLFQAASQNAMEALMVTTVDKLTQGRQTFDWTVCRNQPAATALNTTITSFRLND
LNGADKGGLVPFCQDIIDSLDKPEMTFFSVKNIKKKLPAKNRKGFLIKRIPMKVKDRITRVEYIKRALSLNTMTKDA
ERGKLKRRAIATAGIQIRGFVLVVENLAKNICENLEQSGLPVGGNEKKAKLSNAVAKMLSNCPPGGISMTVTGDNTK
WNECLNPRIFLAMTERITRDSPIWERDFCSIAPVLFSNKIARLGKGFMITSKTKRLKAQIPCPDLFSIPLERYNEET
RAKLKKLKPFFNEEGTASLSPGMMMGMFNMLSTVLGVAALGIKNIGNKEYLWDGLQSSDDFALFVNAKDEETCMEGI
NDFYRTCKLLGINMSKKKSYCNETGMFEFTSMFYRDGFVSNFAMEIPSFGVAGVNESADMAIGMTIIKNNMINNGMG -continued

SEQUENCES

PATAQTAIQLFIADYRYTYKCHRGDSKVEGKRMKIIKELWENTKGRDGLLVADGGPNIYNLRNLHIPEIVLKYNLMD
PEYKGRLLHPQNPFVGHLSIEGIKEADITPAHGPVKKMDYDAVSGTHSWRTKRNRSILNTDQRNMILEEQCYAKCCN
LFEACFNSASYRKPVGQHSMLEAMAHRLRVDARLDYESGRMSKDDFEKAMAHLGEIGYI

SEQ ID NO: 93 (PB2, B/Panama/45/90)
MTLAKIELLKQLLRDNEAKTVLKQTTVDQYNIIRKFNTSRIEKNPSLRMKWAMCSNFPLALTKGDMANRIPLEYKGI
QLKTNAEDIGTKGQMCSIAAVTWWNTYGPIGDTEGFEKVYESFFLRKMRLDNATWGRITFGPVERVRKRVLLNPLTK
EMPPDEASNVIMEILFPKEAGIPRESTWIHRELIKEKREKLKGTMITPIVLAYMLERELVARRRFLPVAGATSAEFI
EMLHCLQGENWRQIYHPGGNKLTESRSQSMIVACRKIIRRSIVASNPLELAVEIANKTVIDTEPLKSCLTAIDGGDV
ACDIIRAALGLKIRQRQRFGRLELKRISGRGFKNDEEILIGNGTIQKIGIWDGEEEFHVRCGECRGILKKSKMRMEK
LLINSAKKEDMKDLIILCMVFSQDTRMFQGVRGEINFLNRAGQLLSPMYQLQRYFLNRSNDLFDQWGYEESPKASEL
HGINELMNASDYTLKGVVVTKNVIDDFSSTETEKVSITKNLSLIKRTGEVIMGANDVSELESQAQLMITYDTPKMWE
MGTTKELVQNTYQWVLKNLVTLKAQFLLGKEDMFQWDAFEAFESIIPQKMAGQYSGFARAVLKQMRDQEVMKTDQFI
KLLPFCFSPPKLRRNGEPYQFLRLVLKGGGENFIEVRKGSPLFSYNPQTEVLTICGRMMSLKGKIEDEERNRSMGNA
VLAGFLVSGKYDPDLGDFKTIEELEKLKPGEKANILLYQGKPVKVVKRKRYSALSNDISQGIKRQRMTVESMGWALS SEQ ID NO: 94 (NP, B/Panama/45/90)
MSNMDIDGINTGTIDKTPEEITSGTSGTTRPIIRPATLAPPSNKRTRNPSPERATTSSEADVGRKTQKKQTPTEIKK
SVYNMVVKLGEFYNQMMVKAGLNDDMERNLIQNAHAVERILLAATDDKKTEFQRKKNARDVKEGKEEIDHNKTGGTF
YKMVRDDKTIYFSPIRITFLKEEVKTMYKTTMGSDGFSGLNHIMIGHSQMNDVCFQRSKALKRVGLDPSLISTFAGS
TLPRRSGATGVAIKGGGTLVAEAIRFIGRAMADRGLLRDIKAKTAYEKILLNLKNKCSAPQQKALVDQVIGSRNPGI
ADIEDLTLLARSMVVVRPSVASKVVLPISIYAKIPQLGFNVEEYSMVGYEAMALYNMATPVSILRMGDDAKDKSQLF
FMSCFGAAYEDLRVLSALTGIEFKPRSALKCKGFHVPAKEQVEGMGAALMSIKLQFWAPMTRSGGNEVGGDGGSGQI
SCSPVFAVERPIALSKQAVRRMLSMNIEGRDADVKGNLLKMMNDSMAKKTNGNAFIGKKMFQISDKNKTNPVEIPIK
QTIPNFFFGRDTAEDYDDLDY SEQ ID NO: 95 ($M_1$, B/Panama/45/90)
MSLFGDTIAYLLSLTEDGEGKAELAEKLHCWFGGKEFDLDSALEWIKNKRCLTDIQKALIGASICFLKPKDQERKRR
FITEPLSGMGTTATKKKGLILAERKMRRCVSFHEAFEIAEGHESSALLYCLMVMYLNPGNYSMQVKLGTLCALCEKQ
ASHSHRAHSRAARSSVPGVRREMQMVSAMNTAKTMNGMGKGEDVQKLAEELQSNIGVLRSLGASQKNGEGIAKDVME
VLKQSSMGNSALVKKYL SEQ ID NO: 96 ($M_2$, B/Panama/45/90)
MLEPFQILSICSFILSALHFMAWTIGHLNQIKRGVNMKIRIKNPNKETINREVSILRHSYQKEIQAKETMKEVLSDN
MEVLSDHIVIEGLSAEEIIKMGETVLEVEELH SEQ ID NO: 97 ($NS_1$, B/Panama/45/90)
MADNMTTTQIEVGPGATNATINFEAGILECYERLSWQRALDYPGQDRLNKLKRKLESRIKTHNKSEPESKRMSLEER
KAIGVKMMKVLLFMNPSAGVEGFEPYCMKNPSNSNCPDCNWADYPPTPGKYLDGIEEEPENVGDSTEIVLRDMNNKD
ARQKIKEEVNTQKEGKFRLTIKRDIRNVLSLRVLVNGTFIKHPNGYKSLSTLHRLNAYDQSGRLVAKLVATDDLTVE
DEEDGHRILNSLFERLNEGHSKPIRAAETAVGVLSQFGQEHRLSPEERDN SEQ ID NO: 98 ($NS_2$, B/Panama/45/90)
MADNMTTTQIEWRMKKMAIGSSTHSSSVLMKDIQSQFEQLKLRWESYPNLVKSTDYHQKRETIRLVTEELYLLSKRI
DDNILFHKTVIANSSIIADMIVSLSLLETLYEMKDVVEVYSRQCL SEQ ID NO: 99 (NA, A/California/04/09)
MNPNQKIITIGSVCMTIGMANLILQIGNIISIWISHSIQLGNQNQIETCNQSVITYENNTWVNQTYVNISNTNFAAG
QSVVSVKLAGNSSLCPVSGWAIYSKDNSVRIGSKGDVFVIREPFISCSPLECRTFFLTQGALLNDKHSNGTIKDRSP
YRTLMSCPIGEVPSPYNSRFESVAWSASACHDGINWLTIGISGPDNGAVAVLKYNGIITDTIKSWRNNILRTQESEC
ACVNGSCFTVMTDGPSNGQASYKIFRIEKGKIVKSVEMNAPNYHYEECSCYPDSSEITCVCRDNWHGSNRPWVSFNQ
NLEYQIGYICSGIFGDNPRPNDKTGSCGPVSSNGANGVKGFSFKYGNGVWIGRTKSISSRNGFEMIWDPNGWTGTDN
NFSIKQDIVGINEWSGYSGSFVQHPELTGLDCIRPCFWVELIRGRPKENTIWTSGSSISFCGVNSDTVGWSWPDGAE
LPFTIDK SEQ ID NO: 100 (NP, B/Lee/40)
AGCATTTTCTTGTGAGCTTCGAGCACTAATAAAACTGAAAATCAAAATGTCCAACATGGATATTGACAGTATAAATA
CCGGAACAATCGATAAAAAACCAGAAGAACTGACTCCCGGAACCAGTGGGGCAACCAGACCAATCATCAAGCCAGCA
ACCCTTGCTCCGCCAAGCAACAAACGAACCCGAAATCCATCCCCAGAAAGGACAACCACAAGCAGTGAAACCGATAT
CGGAAGGAAAATCCAAAAGAAACAAACCCCAACAGAGATAAAGAAGAGCGTCTACAACATGGTGGTAAAGCTGGGTG
AATTCTACAACCAGATGATGGTCAAAGCTGGACTTAATGATGACATGGAAAGGAATCTAATCCAAAATGCACAAGCT
GTGGAGAGAATCCTATTGGCTGCAACTGATGACAAGAAAACTGAATACCAAAAGAAAAGGAATGCCAGAGATGTCAA
AGAAGGGAAGGAAGAAATAGACCACAACAAGACAGGAGGCACCTTTTATAAGATGGTAAGAGATGATAAAACCATCT
ACTTCAGCCCTATAAAAATTACCTTTTTAAAAGAAGAGGTGAAAACAATGTACAAGACCACCATGGGGAGTGATGGT
TTCAGTGGACTAAATCACATTATGATTGGACATTCACAGATGAACGATGTCTGTTTCCAAAGATCAAAGGCACTGAA
AAGGGTTGGACTTGACCCTTCATTAATCAGTACTTTTGCCGGAAGCACACTACCCAGAAGATCAGGTACAACTGGTG
TTGCAATCAAAGGAGGTGGAACTTTAGTGGCAGAAGCCATTCGATTTATAGGAAGAGCAATGGCAGACAGAGGGCTA
CTGAGAGACATCAAGGCCAAGACAGCCTATGAAAAGATTCTTCTGAATCTGAAAAACAAGTGCTCTGCGCCCCAACA
AAAGGCTCTAGTTGATCAAGTGATCGGAAGTAGGAACCCAGGGATTGCAGACATAGAAGACCTAACTCTGCTTGCCA
GAAGCATGATAGTTGTCAGACCCTCTGTAGCGAGCAAAGTGGTGCTTCCCATAAGCATTTATGCTAAAATACCTCAA
CTAGGATTCAATATCGAAGAATACTCTATGGTTGGGTATGAAGCCATGGCTCTTTATAATATGGCAACACCTGTTTC
CATATTAAGAATGGGAGATGACGCAAAAGATAAATCTCAACTATTCTTCATGTCGTGCTTCGGAGCTGCCTATGAAG
ATCTAAGAGTGTTATCTGCACTAACGGGCACCGAATTTAAGCCTAGATCAGCACTAAAATGCAAGGGTTTCCATGTC
CCGGCTAAGGAGCAAGTAGAAGGAATGGGGGCAGCTCTGATGTCCATCAAGCTTCAGTTCTGGGCCCCAATGACCAG
ATCTGGAGGGAATGAAGTAAGTGGAGAAGGAGGGTCTGGTCAAATAAGTTGCAGCCCTGTGTTTGCAGTAGAAAGAC
CTATTGCTCTAAGCAAGCAAGCTGTAAGAAGAATGCTGTCAATGAACGTTGAAGGACGTGATGCAGATGTCAAAGGA
AATCTACTCAAAATGATGAATGATTCGATGGCAAAGAAAACCAGTGGAAATGCTTTCATTGGGAAGAAAATGTTTCA -continued

| SEQUENCES |
|---|

AATATCAGACAAAAACAAAGTCAATCCCATTGAGATTCCAATTAAGCAGACCATCCCCAGTTTCTTCTTTGGGAGGG
ACACAGCAGAGGATTATGATGACCTCGATTATTAAAGCAATAAAATAGACACTATGGCTGTGACTGTTTCAGTACGT
TTGGGATGTGGGTGTTTACTCTTATTGAAATAAATGTAAAA

SEQ ID NO: 101 (NP, B/Ann Arbor/1/66)
MSNMDIDGTNTGTIDKTPEEITSGTSGATRPIIKPATLAPPSNKRTRNPSPERATTSSEAIVGRRTQKKQTPTEIKK
SVYNMVVKLGEFYNQMMVKAGLNDDMERNLIQNAHAVERILLAATDDKKTEYQKKKNARDVKEGKEEIDHNKTGGTF
YKMVRDDKTIYFSPIRITFLKEEVKTMYKTTMGSDGFSGLNHIMIGHSQMNDVCFQRSKALKRVGLDPSLISTFAGS
TLPRRSGATGVAIKGGGTLVAEAIRFIGRAMADRGLLRDIRAKTAYEKILLNLKNKCSAPQQKALVDQVIGSRNPGI
ADIEDLTLLARSMVVVRPSVASKVVLPISINAKIPQLGFNVEEYSMVGYEAMALYNMATPVSILRMGDDAKDKSQLF
FMSCFGAAYEDQRVLSALTGTEFKPRSALKCKGFHVPAKEQVEGMGAALMSIKLQFWAPMTRSGGNEVGGDGGSGQI
SCSPVFAVERPIALSKQAVRRMLSMNIEGRDADVKGNLLKMMNDSMAKKTNGNAFIGKKMFQISDKNKINPVDIPIK
QTIPNFFFGRDTAEDYDDLDY SEQ ID NO: 102 (NP, B/Ann Arbor/1/66)
MSNMDIDGINTGTIDKTPEEITSGTSGATRPIIKPATLAPPSNKRTRNPSPERAATSSEADVGRRTQKKQTPTEIKK
SVYNMVVKLGEFYNQMMVKAGLNDDMERNLIQNAHAAERILLAATDDKKTEFQKKKNARDVKEGKEEIDHNKTGGTF
YKMVRDDKTIYFSPIRITFLKEEVKTMYKTTMGSDGFSGLNHIMIGHSQMNDVCFQRSKALKRVGLDPSLISTFAGS
TLPRRSGATGVAIKGGGTLVAEAIRFIGRAMADRGLLRDIRAKTAYEKILLNLKNKCSAPQQKALVDQVIGSRNPGI
ADIEDLTLLARSMVVVRPSVASKVVLPISINAKIPQLGFNVEEYSMVGYEAMALYNMATPVSILRMGDDAKDKSQLF
FMSCFGAAYEDQRVLSALTGTEFKHRSALKCKGFHVPAKEQVEGMGAALMSIKLQFWAPMTRSGGNEVGGDGGSGQI
SCSPVFAVERPIALSKQAVRRMLSMNIEGRDADVKGNLLKMMNDSMTKKTNGNAFIGKKMFQISDKNKTNPIEIPIK
QTIPNFFFGRDTAEDYDDLDY SEQ ID NO: 103 (NP, B/Ann Arbor/1/66)
AGCAGAAGCACAGCATTTTCTTGTGAACTTCAAGTACCAACAAAAACTGAAAATCAAAATGTCCAACATGGATATTG
ACGGCATCAACACTGGAACAATTGACAAAACACCAGAAGAAATAACTTCCGGAACCAGTGGGGCAACCAGACCAATC
ATCAAGCCAGCAACCCTTGCCCCACCAAGCAATAAACGAACCCGAAACCCATCCCCAGAAAGGGCAACCACAAGCAG
CGAAGCGATTGTCGGAAGGAGAACCCAAAAGAAACAAACCCCGACAGAGATAAAGAAGAGCGTCTACAATATGGTAG
TGAAACTGGGTGAATTCTACAACCAGATGATGGTCAAAGCTGGACTCAACGATGACATGGAGAGAAACCTAATCCAA
AATGCACATGCTGTGGAAAGAATTCTATTGGCTGCTACTGATGACAAGAAAACTGAATACCAAAAGAAAAAGAATGC
CAGAGATGTCAAAGAAGGGAAAGAAGAAATAGACCACAACAAAACAGGAGGCACCTTTTATAAGATGGTAAGAGATG
ATAAAACCATCTACTTCAGCCCTATAAGAATTACCTTTTTAAAAGAAGAGGTGAAAACAATGTACAAGACCACCATG
GGGAGTGATGGTTTCAGTGGACTAAATCACATCATGATTGGGCATTCACAGATGAACGATGTCTGTTTCCAAAGATC
AAAGGCACTAAAAAGAGTTGGACTTGACCCTTCATTAATCAGTACTTTTGCAGGAAGCACACTCCCCAGAAGATCAG
GTGCAACTGGTGTTGCGATCAAAGGAGGTGGAACTTTAGTGGCAGAAGCCATTCGATTTATAGGAAGAGCAATGGCA
GACAGAGGGCTATTGAGAGACATCAGAGCCAAGACGGCCTATGAAAAGATTCTTCTGAATCTGAAAAACAAGTGCTC
TGCGCCCCAACAAAAGGCTCTAGTTGATCAAGTGATCGGAAGTAGAAACCCAGGGATTGCAGACATAGAAGACCTAA
CCCTGCTTGCCCGAAGCATGGTCGTTGTCAGGCCCTCTGTAGCGAGCAAAGTGGTGCTTCCCATAAGCATTAATGCT
AAAATACCTCAACTAGGGTTCAATGTTGAAGAATACTCTATGGTTGGGTATGAAGCCATGGCTCTTTATAATATGGC
AACACCTGTTTCCATATTAAGAATGGGAGACGATGCAAAAGATAAATCACAATTATTCTTCATGTCTTGCTTTGGAG
CTGCCTATGAAGACCAAAGAGTTTTGTCTGCACTAACCGGCACAGAATTCAAGCCTAGGTCAGCATTAAAGTGCAAG
GGTTTCCACGTTCCAGCAAAGGAGCAAGTGGAAGGAATGGGGGCAGCTCTGATGTCCATCAAGCTCCAGTTTTGGGC
CCCAATGACCAGATCTGGGGGGAACGAAGTAGGTGGAGACGGAGGGTCTGGTCAAATAAGTTGCAGCCCCGTGTTTG
CAGTAGAGAGACCTATTGCTCTAAGCAAGCAAGCTGTAAGAAGAATGCTGTCAATGAATATTGAGGGACGTGATGCA
GATGTCAAAGGAAATCTACTCAAGATGATGAATGATTCAATGGCTAAGAAAACCAATGGAAATGCTTTCATTGGGAA
GAAAATGTTTCAAATATCAGACAAAAACAAAATCAATCCCGTTGATATTCCAATTAAGCAGACCATCCCCAATTTCT
TCTTTGGGAGGGACACAGCAGAGGATTATGATGACCTCGATTATTAAAGCAACAAAATAGACACTATGGCTGTGACT
GTTTCAGTACGTTTGGAATGTGGGTGTTTACTCTTATTGAAATAAATGTAAAAAATGCTGTTGTTTCTACT SEQ ID NO: 104 (NP, B/Ann Arbor/1/66)
AGCAGAAGCACAGCATTTTCTTGTGAACTTCAAGTACCAACAAAAACTGAAAATCAAAATGTCCAACATGGATATTG
ACGGCATCAACACTGGAACAATTGACAAAACACCAGAAGAAATAACTTCCGGAACCAGTGGGGCAACCAGACCAATC
ATCAAACCAGCAACCCTTGCCCCACCAAGCAACAAACGAACCCGAAACCCATCCCCGGAAAGGGCAGCCACAAGCAG
TGAAGCTGATGTCGGAAGGAGAACCCAAAAGAAACAAACCCCGACAGAGATAAAGAAGAGCGTCTACAATATGGTAG
TGAAACTGGGTGAATTCTACAACCAGATGATGGTCAAAGCTGGACTCAACGATGACATGGAGAGAAACCTAATCCAA
AATGCACATGCTGCGGAAAGAATTCTATTGGCTGCTACTGATGACAAGAAAACTGAATTCCAAAAGAAAAAGAATGC
CAGAGATGTCAAAGAAGGGAAAGAAGAAATAGACCACAACAAAACAGGAGGCACCTTTTACAAGATGGTAAGAGATG
ATAAAACCATCTACTTCAGCCCTATAAGAATTACCTTTTTAAAAGAAGAGGTGAAAACAATGTACAAAACCACCATG
GGGAGTGATGGTTTCAGTGGACTAAATCACATCATGATTGGGCATTCACAGATGAACGATGTCTGTTTCCAAAGATC
AAAGGCACTAAAAAGAGTTGGACTTGACCCTTCATTAATCAGTACTTTTGCAGGAAGCACACTCCCCAGAAGATCAG
GTGCAACTGGTGTTGCGATCAAAGGAGGTGGAACTTTAGTGGCAGAAGCCATTCGATTTATAGGAAGAGCAATGGCA
GACAGAGGGCTATTGAGAGACATCAGAGCCAAGACGGCCTATGAAAAGATTCTTCTGAATCTGAAAAACAAGTGCTC
TGCGCCCCAACAAAAGGCTCTAGTTGATCAAGTGATCGGAAGTAGAAATCCAGGGATTGCAGACATAGAAGACCTAA
CCCTGCTTGCCCGAAGCATGGTCGTTGTCAGGCCCTCTGTAGCGAGCAAAGTGGTGCTTCCCATAAGCATTAATGCC
AAAATACCTCAACTAGGGTTCAATGTTGAAGAATACTCTATGGTTGGGTATGAAGCCATGGCTCTTTATAATATGGC
AACACCTGTTTCCATATTAAGAATGGGAGACGATGCAAAAGATAAATCACAATTATTCTTCATGTCTTGCTTCGGAG
CTGCCTATGAAGACCAAAGAGTTTTGTCTGCACTAACAGGCACAGAATTCAAGCATAGGTCAGCATTAAAGTGCAAG
GGTTTCCACGTTCCAGCAAAGGAGCAAGTGGAAGGAATGGGGGCAGCTCTGATGTCCATCAAGCTCCAGTTTTGGGC
TCCAATGACCAGATCTGGGGGGAATGAAGTAGGTGGAGACGGAGGGTCTGGTCAAATAAGTTGCAGCCCCGTGTTTG
CAGTAGAAAGACCTATTGCTCTAAGCAAGCAAGCTGTAAGAAGAATGCTGTCAATGAATATTGAGGGACGTGATGCA
GATGTCAAAGGAAATCTACTCAAGATGATGAATGATTCAATGACTAAGAAAACCAATGGAAATGCTTTCATTGGGAA
GAAAATGTTTCAAATATCAGACAAAAACAAAACCAATCCCATTGAGATTCCAATTAAGCAGACCATCCCCAATTTCT
TCTTTGGGAGGGACACAGCAGAGGATTATGATGACCTCGATTATTAAAGCAACAAAATAGACACTATGGCTGTGACT
GTTTCAGTACGTTTGGAATGTGGGTGTTTACTTTTATTGAAATAAATGTAAAAAATGCTGTTGTTTCTACT -continued

| SEQUENCES |
| --- |
| SEQ ID NO: 105 (5'-R4NCR, 105p30)<br>AGCAAAAGCAGGGGAAAATAAAAGCAACCAAA |
| SEQ ID NO: 106 (HA SP, 105p30)<br>ATGAAAGTAAAACTACTGGTTCTGTTATGTACATTTACAGCTACATATGCA |
| SEQ ID NO: 107 (HA TM domain, 105p30)<br>AGATTCTGGCGATCTACTCAACAGTCGCCAGTTCCCTGGTTCTTTTGGTCTCCCTGGGGGCAATCAGCTTCTGGATG |
| SEQ ID NO: 108 (HA CT domain, 105p30)<br>TGTTCCAATGGGTCTTTGCAGTGTAGAATATGCATCTAA |
| SEQ ID NO: 109 (HA 3'-NCR, 105p30)<br>GACCAGAATTTCAGAAATATAAGGAAAAACACCCTTGTTTCTACT |
| SEQ ID NO: 110 (NA 5'-NCR, 105p30)<br>AGCAAAAGCAGGAGTTTAAA |
| SEQ ID NO: 111 (NA CT, 105p30)<br>ATGAATCCAAATCAAAAA |
| SEQ ID NO: 112 (NA TM domain, 105p30)<br>ATAATAACCATTGGATCAATCAGTATAGCAATCGGAATAATTAGTCTAATGTTGCAAATAGGAAATATTATTTCAAT<br>ATGGGCTAGT |
| SEQ ID NO: 113 (NA 3'-NCR, 105p30)<br>CTCGTTGAAAAAAACTCCTTGTTTCTACT |
| SEQ ID NO: 114 (5'-HA NCR, PR8-X)<br>AGCAAAAGCAGGGGAAAATAAAAACAACCAAA |
| SEQ ID NO: 115 (HASP, PR8-X)<br>ATGAAGGCAAACCTACTGGTCCTGTTATGTGCACTTGCAGCTGCAGATGCA |
| SEQ ID NO: 116 (HA TM domain, PR8-A)<br>CAGATTCTGGCGATCTACTCAACTGTCGCCAGTTCACTGGTGCTTTTGGTCTCCCTGGGGGCAATCAGTTTCTGGAT<br>G |
| SEQ ID NO: 117 (HA CT domain, PR8-A)<br>TGTTCTAATGGATCTTTGCAGTGCAGAATATGCATCTGA |
| SEQ ID NO: 118 (HA 3'-NCR, PR8-X)<br>GATTAGAATTTCAGAGATATGAGGAAAAACACCCTTGTTTCTACT |
| SEQ ID NO: 119 (NA 5'-NCR, PR8-X)<br>AGCAAAAGCAGGGGTTTAAA |
| SEQ ID NO: 120 (NA CT, PR8-X)<br>ATGAATCCAAATCAGAAA |
| SEQ ID NO: 121 (NA TM domain, PR8-X)<br>ATAATAACCATTGGATCAATCTGTCTGGTAGTCGGACTAATTAGCCTAATATTGCAAATAGGGAATATAATCTCAAT<br>ATGGATTAGC |
| SEQ ID NO: 122 (NA 3'-NCR, PR8-X)<br>TCTGTTCAAAAAACTCCTTGTTTCTACT |

REFERENCES

[1] WO2007/002008
[2] WO2007/124327
[3] Harvey et al. (2011) *J. Virol,* 85(12):6086-6-90
[4] Harvey et al. (2010) *Vaccine,* 23; 28(50):8008-14
[5] Jing et al. (2012) *Vaccine* 13; 30(28):4144-52
[6] Hai et al. (2011) *J. Virol.,* 85(14):6832.
[7] Flandorfer et al. (2003) *J. Virol.* 2003, 77(17):9116
[8] Herlocher et al. (2004) *J Infect Dis* 190(9):1627-30.
[9] Le et al. (2005) *Nature* 437(7062):1108.
[10] Rota et al. (1992) *J Gen Virol* 73:2737-42.
[11] GenBank sequence GI:325176.
[12] McCullers et al. (1999) *J Virol* 73:7343-8.
[13] GenBank sequence GI:325237.
[14] WO2010/133964
[15] WO2009/000891
[16] U.S. provisional application No. 61/273,151
[17] Sambrook et al, Molecular Cloning: A Laboratory Manual, 2 ed., 1989, Cold Spring Harbor Press, Cold Spring Harbor, N. Y
[18] WO2011/012999
[19] WO2011048560
[20] Neumann et al. (2005) Proc Natl Acad Sci USA 102: 16825-9
[21] Kistner et al. (1998) Vaccine 16:960-8.
[22] Kistner et al. (1999) Dev Biol Stand 98:101-110.
[23] Bruhl et al. (2000) Vaccine 19:1149-58.
[24] Pau et al. (2001) Vaccine 19:2716-21.
[25] http://www.atcc.org/

[26] http://locus.umdnj.edu/
[27] WO97/37000.
[28] Brands et al. (1999) Dev Biol Stand 98:93-100.
[29] Halperin et al. (2002) Vaccine 20:1240-7.
[30] EP-A-1260581 (WO01/64846)
[31] WO2006/071563
[32] WO2005/113758
[33] Grachev et al. (1998) Biologicals; 26(3):175-93.
[34] WO97/37001
[35] WO02/28422.
[36] WO02/067983.
[37] WO02/074336.
[38] WO01/21151.
[39] WO02/097072.
[40] WO2005/113756.
[41] Huckriede et al. (2003) *Methods Enzymol* 373:74-91.
[42] Vaccines. (eds. Plotkins & Orenstein). 4th edition, 2004, ISBN: 0-7216-9688-0
[43] Treanor et al. (1996) *J Infect Dis* 173:1467-70.
[44] Keitel et al. (1996) *Clin Diagn Lab Immunol* 3:507-10.
[45] Herlocher et al. (2004) *J Infect Dis* 190(9):1627-30.
[46] Le et al. (2005) *Nature* 437(7062):1108.
[47] WO2008/068631.
[48] Gennaro (2000) *Remington: The Science and Practice of Pharmacy.* 20th edition, ISBN: 0683306472.
[49] Banzhoff (2000) *Immunology Letters* 71:91-96.
[50] Nony et al. (2001) *Vaccine* 27:3645-51.
[51] EP-B-0870508.
[52] U.S. Pat. No. 5,948,410.
[53] WO2007/052163.
[54] WO2007/052061
[55] WO90/14837.
[56] Podda & Del Giudice (2003) *Expert Rev Vaccines* 2:197-203.
[57] Podda (2001) *Vaccine* 19: 2673-2680.
[58] *Vaccine Design: The Subunit and Adjuvant Approach* (eds. Powell & Newman) Plenum Press 1995 (ISBN 0-306-44867-X).
[59] *Vaccine Adjuvants: Preparation Methods and Research Protocols* (Volume 42 of *Methods in Molecular Medicine* series). ISBN: 1-59259-083-7. Ed. O'Hagan.
[60] WO2008/043774.
[61] Allison & Byars (1992) *Res Immunol* 143:519-25.
[62] Hariharan et al. (1995) *Cancer Res* 55:3486-9.
[63] US-2007/014805.
[64] US-2007/0191314.
[65] Suli et al. (2004) *Vaccine* 22(25-26):3464-9.
[66] WO95/11700.
[67] U.S. Pat. No. 6,080,725.
[68] WO2005/097181.
[69] WO2006/113373.
[70] Potter & Oxford (1979) *Br Med Bull* 35: 69-75.
[71] Greenbaum et al. (2004) *Vaccine* 22:2566-77.
[72] Zurbriggen et al (2003) *Expert Rev Vaccines* 2:295-304.
[73] Piascik (2003) *J Am Pharm Assoc* (Wash D.C.). 43:728-30.
[74] Mann et al. (2004) *Vaccine* 22:2425-9.
[75] Halperin et al (1979) *Am J Public Health* 69:1247-50.
[76] Herbert et al. (1979) *J Infect Dis* 140:234-8.
[77] Chen et al. (2003) *Vaccine* 21:2830-6.
[78] Needleman & Wunsch (1970) *J Mol. Biol.* 48, 443-453.
[79] Rice et al. (2000) *Trends Genet* 16:276-277.
[80] *Current Protocols in Molecular Biology* (F. M. Ausubel et al., eds., 1987) Supplement 30.
[81] Smith & Waterman (1981) *Adv. Appl. Math.* 2: 482-489.
[82] Suphaphiphat et at (2010) *Virol J.;* 14; 7:157
[83] Okuno et al. (1990) *Clin Microbiol;* 28(6): 1308-13.

The invention claimed is:

1. A chimeric influenza hemagglutinin polynucleotide segment comprising an ectodomain, a 5'-non-coding region (5'-NCR), a 3'-non-coding region (3'-NCR), a signal peptide domain (SP), a transmembrane domain (TM), and a cytoplasmic domain (CT), wherein the ectodomain is from a first influenza strain which is an influenza A strain, and one or more of the 5'-NCR, 3'-NCR, SP, TM, and CT are from a second influenza strain selected from the group consisting of 105p30 and PR8-X, and wherein the 5'-NCR comprises SEQ ID NO:105 or SEQ ID NO:114, the 3'-NCR comprises SEQ ID NO:109 or SEQ ID NO:118, the SP comprises SEQ ID NO:106 or SEQ ID NO:115, the TM comprises SEQ ID NO:107 or SEQ ID NO:116, and the CT comprises SEQ ID NO:108 or SEQ ID NO:117.

2. The chimeric influenza hemagglutinin polynucleotide segment of claim 1, wherein the ectodomain is from an influenza A strain which is not an H1 or H3 strain.

3. The chimeric influenza hemagglutinin polynucleotide segment of claim 1, comprising one or more of the 5'-NCR of SEQ ID NO:105, the 3'-NCR of SEQ ID NO:109, the SP of SEQ ID NO:106, the TM of SEQ ID NO:107, and the CT of SEQ ID NO:108.

4. The chimeric influenza hemagglutinin polynucleotide segment of claim 1, comprising one or more of the 5'-NCR of SEQ ID NO:114, the 3'-NCR of SEQ ID NO:118, the SP of SEQ ID NO:115, the TM of SEQ ID NO:116, and the CT of SEQ ID NO:117.

5. The chimeric influenza hemagglutinin polynucleotide segment of claim 1, comprising the 5'-NCR of SEQ ID NO:105, the 3'-NCR of SEQ ID NO:109, the SP of SEQ ID NO:106, the TM of SEQ ID NO:107, and the CT of SEQ ID NO:108.

6. The chimeric influenza hemagglutinin polynucleotide segment of claim 1, comprising the 5'-NCR of SEQ ID NO:114, the 3'-NCR of SEQ ID NO:118, the SP of SEQ ID NO:115, the TM of SEQ ID NO:116, and the CT of SEQ ID NO:117.

7. The chimeric influenza hemagglutinin polynucleotide segment of claim 1, wherein the chimeric influenza hemagglutinin polynucleotide segment encodes a protein that does not have tyrosine in the position corresponding to amino acid 545, when aligned to SEQ ID NO:7.

* * * * *

SEQUENCE LISTING

```
<160> NUMBER OF SEQ ID NOS: 143

<210> SEQ ID NO 1
<211> LENGTH: 716
<212> TYPE: PRT
<213> ORGANISM: Influenza A Virus

<400> SEQUENCE: 1

Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Ile Val Glu
    50                  55                  60

Leu Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140
```

-continued

```
Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asn
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Leu
385                 390                 395                 400

Arg Ser Leu Ala Ser Trp Ile Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ser
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Ile Arg Ser Ala Ile Gly Gln Val Ser Arg Pro
545                 550                 555                 560
```

Met Phe Leu Tyr Val Arg Thr Asn Gly Thr Ser Lys Ile Lys Met Lys
565 570 575

Trp Gly Met Glu Met Arg Arg Cys Leu Leu Gln Ser Leu Gln Gln Ile
580 585 590

Glu Ser Met Ile Glu Ala Glu Ser Ser Val Lys Glu Lys Asp Met Thr
595 600 605

Lys Glu Phe Phe Glu Asn Lys Ser Glu Thr Trp Pro Ile Gly Glu Ser
610 615 620

Pro Lys Gly Val Glu Glu Ser Ser Ile Gly Lys Val Cys Arg Thr Leu
625 630 635 640

Leu Ala Lys Ser Val Phe Asn Ser Leu Tyr Ala Ser Pro Gln Leu Glu
645 650 655

Gly Phe Ser Ala Glu Ser Arg Lys Leu Leu Leu Ile Val Gln Ala Leu
660 665 670

Arg Asp Asn Leu Glu Pro Gly Thr Phe Asp Leu Gly Gly Leu Tyr Glu
675 680 685

Ala Ile Glu Glu Cys Leu Ile Asn Asp Pro Trp Val Leu Leu Asn Ala
690 695 700

Ser Trp Phe Asn Ser Phe Leu Thr His Ala Leu Ser
705 710 715

<210> SEQ ID NO 2
<211> LENGTH: 757
<212> TYPE: PRT
<213> ORGANISM: Influenza A Virus

<400> SEQUENCE: 2

Met Asp Val Asn Pro Thr Leu Leu Phe Leu Lys Val Pro Thr Gln Asn
1 5 10 15

Ala Ile Ser Thr Thr Phe Pro Tyr Thr Gly Asp Pro Pro Tyr Ser His
20 25 30

Gly Thr Gly Thr Gly Tyr Thr Met Asp Thr Val Asn Arg Thr His Gln
35 40 45

Tyr Ser Glu Lys Gly Arg Trp Thr Thr Asn Thr Glu Thr Gly Ala Pro
50 55 60

Gln Leu Asn Pro Ile Asp Gly Pro Leu Pro Glu Asp Asn Glu Pro Ser
65 70 75 80

Gly Tyr Ala Gln Thr Asp Cys Val Leu Glu Ala Met Ala Phe Leu Glu
85 90 95

Glu Ser His Pro Gly Ile Phe Glu Asn Ser Cys Ile Glu Thr Met Glu
100 105 110

Val Val Gln Gln Thr Arg Val Asp Lys Leu Thr Gln Gly Arg Gln Thr
115 120 125

Tyr Asp Trp Thr Leu Asn Arg Asn Gln Pro Ala Ala Thr Ala Leu Ala
130 135 140

Asn Thr Ile Glu Val Phe Arg Ser Asn Gly Leu Thr Ala Asn Glu Ser
145 150 155 160

Gly Arg Leu Ile Asp Phe Leu Lys Asp Val Met Glu Ser Met Asn Lys
165 170 175

Glu Glu Met Gly Ile Thr Thr His Phe Gln Arg Lys Arg Arg Val Arg
180 185 190

Asp Asn Met Thr Lys Lys Met Ile Thr Gln Arg Thr Met Gly Lys Lys
195 200 205

Lys Gln Arg Leu Asn Lys Arg Ser Tyr Leu Ile Arg Ala Leu Thr Leu
210 215 220

-continued

```
Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Met
625                 630                 635                 640
```

```
Asn Asn Ala Val Met Met Pro Ala His Gly Pro Ala Lys Asn Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Val Leu Glu Asp Glu Gln Met
        675                 680                 685

Tyr Gln Arg Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
            740                 745                 750

Leu Arg Arg Gln Lys
        755


<210> SEQ ID NO 3
<211> LENGTH: 759
<212> TYPE: PRT
<213> ORGANISM: Influenza A Virus

<400> SEQUENCE: 3

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Lys
65                  70                  75                  80

Met Asn Asp Ala Gly Ser Asp Arg Val Met Val Ser Pro Leu Ala Val
                85                  90                  95

Thr Trp Trp Asn Arg Asn Gly Pro Ile Thr Asn Thr Val His Tyr Pro
            100                 105                 110

Lys Ile Tyr Lys Thr Tyr Phe Glu Arg Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255
```

-continued

```
Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Val Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Arg Val Leu Phe Gln Asn
        435                 440                 445

Trp Gly Val Glu Pro Ile Asp Asn Val Met Gly Met Ile Gly Ile Leu
    450                 455                 460

Pro Asp Met Thr Pro Ser Ile Glu Met Ser Met Arg Gly Val Arg Ile
465                 470                 475                 480

Ser Lys Met Gly Val Asp Glu Tyr Ser Ser Thr Glu Arg Val Val Val
                485                 490                 495

Ser Ile Asp Arg Phe Leu Arg Ile Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Lys Gln Ser Arg Met Gln Phe Ser Ser Phe Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670
```

```
Gly Thr Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755


<210> SEQ ID NO 4
<211> LENGTH: 498
<212> TYPE: PRT
<213> ORGANISM: Influenza A Virus

<400> SEQUENCE: 4

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285
```

```
Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Leu Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Asn Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 5
<211> LENGTH: 252
<212> TYPE: PRT
<213> ORGANISM: Influenza A Virus

<400> SEQUENCE: 5

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160
```

Ser His Arg Gln Met Val Thr Thr Thr Asn Pro Leu Ile Arg His Glu
165 170 175

Asn Arg Met Val Leu Ala Ser Thr Thr Ala Lys Ala Met Glu Gln Met
180 185 190

Ala Gly Ser Ser Glu Gln Ala Ala Glu Ala Met Glu Val Ala Ser Gln
195 200 205

Ala Arg Gln Met Val Gln Ala Met Arg Thr Ile Gly Thr His Pro Ser
210 215 220

Ser Ser Ala Gly Leu Lys Asn Asp Leu Leu Glu Asn Leu Gln Ala Tyr
225 230 235 240

Gln Lys Arg Met Gly Val Gln Met Gln Arg Phe Lys
245 250

<210> SEQ ID NO 6
<211> LENGTH: 230
<212> TYPE: PRT
<213> ORGANISM: Influenza A Virus

<400> SEQUENCE: 6

Met Asp Pro Asn Thr Val Ser Ser Phe Gln Val Asp Cys Phe Leu Trp
1 5 10 15

His Val Arg Lys Arg Val Ala Asp Gln Glu Leu Gly Asp Ala Pro Phe
20 25 30

Leu Asp Arg Leu Arg Arg Asp Gln Lys Ser Leu Arg Gly Arg Gly Ser
35 40 45

Thr Leu Gly Leu Asp Ile Lys Thr Ala Thr Arg Ala Gly Lys Gln Ile
50 55 60

Val Glu Arg Ile Leu Lys Glu Glu Ser Asp Glu Ala Leu Lys Met Thr
65 70 75 80

Met Ala Ser Val Pro Ala Ser Arg Tyr Leu Thr Asp Met Thr Leu Glu
85 90 95

Glu Met Ser Arg Asp Trp Ser Met Leu Ile Pro Lys Gln Lys Val Ala
100 105 110

Gly Pro Leu Cys Ile Arg Met Asp Gln Ala Ile Met Asp Lys Asn Ile
115 120 125

Ile Leu Lys Ala Asn Phe Ser Val Ile Phe Asp Arg Leu Glu Thr Leu
130 135 140

Ile Leu Leu Arg Ala Phe Thr Glu Glu Gly Ala Ile Val Gly Glu Ile
145 150 155 160

Ser Pro Leu Pro Ser Leu Pro Gly His Thr Ala Glu Asp Val Lys Asn
165 170 175

Ala Val Gly Val Leu Ile Gly Gly Leu Glu Trp Asn Asp Asn Thr Val
180 185 190

Arg Val Ser Glu Thr Leu Gln Arg Phe Ala Trp Arg Ser Ser Asn Glu
195 200 205

Asn Gly Arg Pro Pro Leu Thr Pro Lys Gln Lys Arg Glu Met Ala Gly
210 215 220

Thr Ile Arg Ser Glu Val
225 230

<210> SEQ ID NO 7
<211> LENGTH: 565
<212> TYPE: PRT
<213> ORGANISM: Influenza A Virus

<400> SEQUENCE: 7

```
Met Lys Ala Asn Leu Leu Val Leu Leu Cys Ala Leu Ala Ala Ala Asp
1               5                   10                  15

Ala Asp Thr Ile Cys Ile Gly Tyr His Thr Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415
```

-continued

```
Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Glu Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 8
<211> LENGTH: 454
<212> TYPE: PRT
<213> ORGANISM: Influenza A Virus

<400> SEQUENCE: 8

Met Asn Pro Asn Gln Lys Ile Ile Thr Ile Gly Ser Ile Cys Leu Val
1               5                   10                  15

Val Gly Leu Ile Ser Leu Ile Leu Gln Ile Gly Asn Ile Ile Ser Ile
            20                  25                  30

Trp Ile Ser His Ser Ile Gln Thr Gly Ser Gln Asn His Thr Gly Ile
        35                  40                  45

Cys Asn Gln Asn Ile Ile Thr Tyr Lys Asn Ser Thr Trp Val Lys Asp
    50                  55                  60

Thr Thr Ser Val Ile Leu Thr Gly Asn Ser Ser Leu Cys Pro Ile Arg
65                  70                  75                  80

Gly Trp Ala Ile Tyr Ser Lys Asp Asn Ser Ile Arg Ile Gly Ser Lys
                85                  90                  95

Gly Asp Val Phe Val Ile Arg Glu Pro Phe Ile Ser Cys Ser His Leu
            100                 105                 110

Glu Cys Arg Thr Phe Phe Leu Thr Gln Gly Ala Leu Leu Asn Asp Lys
        115                 120                 125

His Ser Ser Gly Thr Val Lys Asp Arg Ser Pro Tyr Arg Ala Leu Met
    130                 135                 140

Ser Cys Pro Val Gly Glu Ala Pro Ser Pro Tyr Asn Ser Arg Phe Glu
145                 150                 155                 160

Ser Val Ala Trp Ser Ala Ser Ala Cys His Asp Gly Met Gly Trp Leu
                165                 170                 175

Thr Ile Gly Ile Ser Gly Pro Asp Asn Gly Ala Val Ala Val Leu Lys
            180                 185                 190

Tyr Asn Gly Ile Ile Thr Glu Thr Ile Lys Ser Trp Arg Lys Lys Ile
        195                 200                 205

Leu Arg Thr Gln Glu Ser Glu Cys Ala Cys Val Asn Gly Ser Cys Phe
    210                 215                 220
```

Thr Ile Met Thr Asp Gly Pro Ser Asp Gly Leu Ala Ser Tyr Lys Ile
225 230 235 240

Phe Lys Ile Glu Lys Gly Lys Val Thr Lys Ser Ile Glu Leu Asn Ala
245 250 255

Pro Asn Ser His Tyr Glu Glu Cys Ser Cys Tyr Pro Asp Thr Asp Lys
260 265 270

Val Met Cys Val Cys Arg Asp Asn Trp His Gly Ser Asn Arg Pro Trp
275 280 285

Val Ser Phe Asp Gln Asn Leu Asp Tyr Gln Ile Gly Tyr Ile Cys Ser
290 295 300

Gly Val Phe Gly Asp Asn Pro Arg Pro Glu Asp Gly Thr Gly Ser Cys
305 310 315 320

Gly Pro Val Tyr Val Asp Gly Ala Asn Gly Val Lys Gly Phe Ser Tyr
325 330 335

Arg Tyr Gly Asn Gly Val Trp Ile Gly Arg Thr Lys Ser His Ser Ser
340 345 350

Arg His Gly Phe Glu Met Ile Trp Asp Pro Asn Gly Trp Thr Glu Thr
355 360 365

Asp Ser Lys Phe Ser Val Arg Gln Asp Val Val Ala Met Thr Asp Trp
370 375 380

Ser Gly Tyr Ser Gly Ser Phe Val Gln His Pro Glu Leu Thr Gly Leu
385 390 395 400

Asp Cys Met Arg Pro Cys Phe Trp Val Glu Leu Ile Arg Gly Arg Pro
405 410 415

Lys Glu Lys Thr Ile Trp Thr Ser Ala Ser Ser Ile Ser Phe Cys Gly
420 425 430

Val Asn Ser Asp Thr Val Asp Trp Ser Trp Pro Asp Gly Ala Glu Leu
435 440 445

Pro Phe Ser Ile Asp Lys
450

<210> SEQ ID NO 9
<211> LENGTH: 2233
<212> TYPE: DNA
<213> ORGANISM: Influenza A Virus

<400> SEQUENCE: 9
agcgaaagca ggtactgatc caaaatggaa gattttgtgc gacaatgctt caatccgatg 60
attgtcgagc ttgcggaaaa aacaatgaaa gagtatgggg aggacctgaa aatcgaaaca 120
aacaaatttg cagcaatatg cactcacttg gaagtatgct tcatgtattc agattttcac 180
ttcatcaatg agcaaggcga gtcaataatc gtagaacttg gtgatccaaa tgcacttttg 240
aagcacagat ttgaaataat cgagggaaga gatcgcacaa tggcctggac agtagtaaac 300
agtatttgca acactacagg ggctgagaaa ccaaagtttc taccagattt gtatgattac 360
aaggagaata gatttatcga aattggagta acaaggagag aagttcacat atactatctg 420
gaaaaggcca ataaaattaa atctgagaaa acacacatcc acattttctc gttcactggg 480
gaagaaatgg ccacaaaggc agactacact ctcgatgaag aaagcagggc taggatcaaa 540
accagactat tcaccataag acaagaaatg gccagcagag gcctctggga ttcctttcgt 600
cagtccgaga gaggagaaga gacaattgaa gaaaggtttg aaatcacagg aacaatgcgc 660
aagcttgccg accaaagtct cccgccgaac ttctccagcc ttgaaaattt tagagcctat 720
gtggatggat tcgaaccgaa cggctacatt gagggcaagc tgtctcaaat gtccaaagaa 780

-continued gtaaatgcta gaattgaacc ttttttgaaa acaacaccac gaccacttag acttccgaat 840
gggcctccct gttctcagcg gtccaaattc ctgctgatgg atgccttaaa attaagcatt 900
gaggacccaa gtcatgaagg agagggaata ccgctatatg atgcaatcaa atgcatgaga 960
acattctttg gatggaagga acccaatgtt gttaaaccac acgaaaaggg aataaatcca 1020
aattatcttc tgtcatggaa gcaagtactg gcagaactgc aggacattga gaatgaggag 1080
aaaattccaa agactaaaaa tatgaagaaa acaagtcagc taaagtgggc acttggtgag 1140
aacatggcac cagaaaaggt agactttgac gactgtaaag atgtaggtga tttgaagcaa 1200
tatgatagtg atgaaccaga attgaggtcg cttgcaagtt ggattcagaa tgagtttaac 1260
aaggcatgcg aactgacaga ttcaagctgg atagagctcg atgagattgg agaagatgtg 1320
gctccaattg aacacattgc aagcatgaga aggaattatt tcacatcaga ggtgtctcac 1380
tgcagagcca cagaatacat aatgaagggg gtgtacatca atactgcctt gcttaatgca 1440
tcttgtgcag caatggatga tttccaatta attccaatga taagcaagtg tagaactaag 1500
gagggaaggc gaaagaccaa cttgtatggt ttcatcataa aaggaagatc ccacttaagg 1560
aatgacaccg acgtggtaaa ctttgtgagc atggagtttt ctctcactga cccaagactt 1620
gaaccacata aatgggagaa gtactgtgtt cttgagatag gagatatgct tataagaagt 1680
gccataggcc aggtttcaag gcccatgttc ttgtatgtga gaacaaatgg aacctcaaaa 1740
attaaaatga aatggggaat ggagatgagg cgttgcctcc tccagtcact tcaacaaatt 1800
gagagtatga ttgaagctga gtcctctgtc aaagagaaag acatgaccaa agagttcttt 1860
gagaacaaat cagaaacatg gcccattgga gagtccccca aaggagtgga ggaaagttcc 1920
attgggaagg tctgcaggac tttattagca aagtcggtat tcaacagctt gtatgcatct 1980
ccacaactag aaggattttc agctgaatca agaaaactgc ttcttatcgt tcaggctctt 2040
agggacaacc ttgaacctgg gacctttgat cttgggggc tatatgaagc aattgaggag 2100
tgcctgatta atgatccctg ggttttgctt aatgcttctt ggttcaactc cttccttaca 2160
catgcattga gttagttgtg gcagtgctac tatttgctat ccatactgtc caaaaaagta 2220
ccttgtttct act 2233

<210> SEQ ID NO 10
<211> LENGTH: 2341
<212> TYPE: DNA
<213> ORGANISM: Influenza A Virus

<400> SEQUENCE: 10
agcgaaagca ggcaaaccat ttgaatggat gtcaatccga ccttactttt cttaaaagtg 60
ccaacacaaa atgctataag cacaactttc ccttatactg gagaccctcc ttacagccat 120
gggacaggaa caggatacac catggatact gtcaacagga cacatcagta ctcagaaaag 180
ggaagatgga caacaaacac cgaaactgga gcaccgcaac tcaacccgat tgatgggcca 240
ctgccagaag acaatgaacc aagtggttat gcccaaacag attgtgtatt ggaggcgatg 300
gctttccttg aggaatccca tcctggtatt tttgaaaact cgtgtattga aacgatggag 360
gttgttcagc aaacacgagt agacaagctg acacaaggcc gacagaccta tgactggact 420
ctaaatagaa accaacctgc tgcaacagca ttggccaaca caatagaagt gttcagatca 480
aatggcctca cggccaatga gtctggaagg ctcatagact tccttaagga tgtaatggag 540
tcaatgaaca aagaagaaat ggggatcaca actcattttc agagaaagag acgggtgaga 600
gacaatatga ctaagaaaat gataacacag agaacaatgg gtaaaaagaa gcagagattg 660
aacaaaagga gttatctaat tagagcattg accctgaaca caatgaccaa agatgctgag 720
agagggaagc taaaacggag agcaattgca accccaggga tgcaaataag gggtttgta 780 tactttgttg agacactggc aaggagtata tgtgagaaac ttgaacaatc agggttgcca 840
gttggaggca atgagaagaa agcaaagttg gcaaatgttg taaggaagat gatgaccaat 900
tctcaggaca ccgaactttc tttcaccatc actggagata acaccaaatg gaacgaaaat 960
cagaatcctc ggatgttttt ggccatgatc acatatatga ccagaaatca gcccgaatgg 1020
ttcagaaatg ttctaagtat tgctccaata atgttctcaa acaaaatggc gagactggga 1080
aaagggtata tgtttgagag caagagtatg aaacttagaa ctcaaatacc tgcagaaatg 1140
ctagcaagca tcgatttgaa atatttcaat gattcaacaa gaaagaagat tgaaaaaatc 1200
cgaccgctct taatagaggg gactgcatca ttgagccctg gaatgatgat gggcatgttc 1260
aatatgttaa gcactgtatt aggcgtctcc atcctgaatc ttggacaaaa gagatacacc 1320
aagactactt actggtggga tggtcttcaa tcctctgacg attttgctct gattgtgaat 1380
gcacccaatc atgaagggat tcaagccgga gtcgacaggt tttatcgaac ctgtaagcta 1440
cttggaatca atatgagcaa gaaaaagtct tacataaaca gaacaggtac atttgaattc 1500
acaagttttt tctatcgtta tgggtttgtt gccaatttca gcatggagct tcccagtttt 1560
ggggtgtctg ggatcaacga gtcagcggac atgagtattg gagttactgt catcaaaaac 1620
aatatgataa acaatgatct tggtccagca acagctcaaa tggcccttca gttgttcatc 1680
aaagattaca ggtacacgta ccgatgccat agaggtgaca cacaaataca aacccgaaga 1740
tcatttgaaa taaagaaact gtgggagcaa acccgttcca aagctggact gctggtctcc 1800
gacggaggcc caaatttata caacattaga aatctccaca ttcctgaagt ctgcctaaaa 1860
tgggaattga tggatgagga ttaccagggg cgtttatgca acccactgaa cccatttgtc 1920
agccataaag aaattgaatc aatgaacaat gcagtgatga tgccagcaca tggtccagcc 1980
aaaaacatgg agtatgatgc tgttgcaaca acacactcct ggatccccaa aagaaatcga 2040
tccatcttga atacaagtca aagaggagta cttgaggatg aacaaatgta ccaaaggtgc 2100
tgcaatttat ttgaaaaatt cttccccagc agttcataca gaagaccagt cgggatatcc 2160
agtatggtgg aggctatggt ttccagagcc cgaattgatg cacggattga tttcgaatct 2220
ggaaggataa agaaagaaga gttcactgag atcatgaaga tctgttccac cattgaagag 2280
ctcagacggc aaaaatagtg aatttagctt gtccttcatg aaaaaatgcc ttgtttctac 2340
t 2341

<210> SEQ ID NO 11
<211> LENGTH: 2341
<212> TYPE: DNA
<213> ORGANISM: Influenza A Virus

<400> SEQUENCE: 11
agcgaaagca ggtcaattat attcaatatg gaaagaataa aagaactaag aaatctaatg 60
tcgcagtctc gcacccgcga gatactcaca aaaaccaccg tggaccatat ggccataatc 120
aagaagtaca catcaggaag acaggagaag aacccagcac ttaggatgaa atggatgatg 180
gcaatgaaat atccaattac agcagacaag aggataacgg aaatgattcc tgagagaaat 240
gagcaaggac aaactttatg gagtaaaatg aatgatgccg gatcagaccg agtgatggta 300
tcacctctgg ctgtgacatg gtggaatagg aatggaccaa taacaaatac agttcattat 360

```
ccaaaaatct acaaaactta ttttgaaaga gtagaaaggc taaagcatgg aacctttggc    420
cctgtccatt ttagaaacca agtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taaccaaaga gaagaaagaa    600
gaactccagg attgcaaaat ttctcctttg atggttgcat acatgttgga gagagaactg    660
gtccgcaaaa cgagattcct cccagtggct ggtggaacaa gcagtgtgta cattgaagtg    720
ttgcatttga ctcaaggaac atgctgggaa cagatgtata ctccaggagg ggaagtgagg    780
aatgatgatg ttgatcaaag cttgattatt gctgctagga acatagtgag aagagctgca    840
gtatcagcag atccactagc atctttattg gagatgtgcc acagcacaca gattggtgga    900
attaggatgg tagacatcct taggcagaac ccaacagaag agcaagccgt ggatatatgc    960
aaggctgcaa tgggactgag aattagctca tccttcagtt ttggtggatt cacatttaag   1020
agaacaagcg gatcatcagt caagagagag gaagaggtgc ttacgggaaa tcttcaaaca   1080
ttgaagataa gagtgcatga gggatatgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtca gaggtgatct gaatttcgtc aatagggcga atcagcgatt gaatcctatg   1320
catcaacttt taagacattt tcagaaggat gcgagagtgc tttttcaaaa ttggggagtt   1380
gaacctatcg acaatgtgat gggaatgatt gggatattgc ccgacatgac tccaagcatc   1440
gagatgtcaa tgagaggagt gagaatcagc aaaatgggtg tagatgagta ctccagcacg   1500
gagagggtag tggtgagcat tgaccgtttt ttgagaatcc gggaccaacg aggaaatgta   1560
ctactgtctc ccgaggaggt cagtgaaaca cagggaacag agaaactgac aataacttac   1620
tcatcgtcaa tgatgtggga gattaatggt cctgaatcag tattggtcaa tacctatcaa   1680
tggatcatca gaaactggga aactgttaaa attcagtggt cccagaaccc tacaatgcta   1740
tacaataaaa tggaatttga accatttcag tctttagtac ctaaggccat tagaggccaa   1800
tacagtgggt ttgtaagaac tctgttccaa caaatgaggg atgtgcttgg gacatttgat   1860
accgcacaga taataaaact tcttcccttc gcagccgctc caccaaagca aagtagaatg   1920
cagttctcct catttactgt gaatgtgagg ggatcaggaa tgagaatact tgtaaggggc   1980
aattctcctg tattcaacta taacaaggcc acgaagagac tcacagttct cggaaaggat   2040
gctggcactt taactgaaga cccagatgaa ggcacagctg gagtggagtc cgctgttctg   2100
aggggattcc tcattctggg caaagaagac aagagatatg ggccagcact aagcatcaat   2160
gaactgagca accttgcgaa aggagagaag gctaatgtgc taattgggca aggagacgtg   2220
gtgttggtaa tgaaacggaa acgggactct agcatactta ctgacagcca gacagcgacc   2280
aaaagaattc ggatggccat caattagtgt cgaatagttt aaaaacgacc ttgtttctac   2340
t                                                                   2341
```

<210> SEQ ID NO 12
<211> LENGTH: 1565
<212> TYPE: DNA
<213> ORGANISM: Influenza A Virus

<400> SEQUENCE: 12

```
agcaaaagca gggtagataa tcactcactg agtgacatca aaatcatggc gtctcaaggc     60
```

-continued accaaacgat cttacgaaca gatggagact gatggagaac gccagaatgc cactgaaatc 120
agagcatccg tcggaaaaat gattggtgga attggacgat tctacatcca aatgtgcacc 180
gaactcaaac tcagtgatta tgagggacgg ttgatccaaa acagcttaac aatagagaga 240
atggtgctct ctgcttttga cgaaaggaga aataaatacc ttgaagaaca tcccagtgcg 300
ggaaaagatc ctaagaaaac tggaggacct atatacagga gagtaaacgg aaagtggatg 360
agagaactca tcctttatga caaagaagaa ataaggcgaa tctggcgcca agctaataat 420
ggtgacgatg caacggctgg tctgactcac atgatgatct ggcattccaa tttgaatgat 480
gcaacttatc agaggacaag agctcttgtt cgcaccggaa tggatcccag gatgtgctct 540
ctgatgcaag gttcaactct ccctaggagg tctggagccg caggtgctgc agtcaaagga 600
gttggaacaa tggtgatgga attggtcaga atgatcaaac gtgggatcaa tgatcggaac 660
ttctggaggg gtgagaatgg acgaaaaaca agaattgctt atgaaagaat gtgcaacatt 720
ctcaaaggga aatttcaaac tgctgcacaa aaagcaatga tggatcaagt gagagagagc 780
cggaacccag ggaatgctga gttcgaagat ctcacttttc tagcacggtc tgcactcata 840
ttgagagggt cggttgctca caagtcctgc ctgcctgcct gtgtgtatgg acctgccgta 900
gccagtgggt acgactttga aagggaggga tactctctag tcggaataga ccctttcaga 960
ctgcttcaaa acagccaagt gtacagccta atcagaccaa atgagaatcc agcacacaag 1020
agtcaactgg tgtggatggc atgccattct gccgcatttg aagatctaag agtattaagc 1080
ttcatcaaag ggacgaaggt gctcccaaga gggaagcttt ccactagagg agttcaaatt 1140
gcttccaatg aaaatatgga gactatggaa tcaagtacac ttgaactgag aagcaggtac 1200
tgggccataa ggaccagaag tggaggaaac accaatcaac agagggcatc tgcgggccaa 1260
atcagcatac aacctacgtt ctcagtacag agaaatctcc cttttgacag aacaaccatt 1320
atggcagcat tcaatgggaa tacagagggg agaacatctg acatgaggac cgaaatcata 1380
aggatgatgg aaagtgcaag accagaagat gtgtctttcc aggggcgggg agtcttcgag 1440
ctctcggacg aaaaggcagc gagcccgatc gtgccttcct ttgacatgag taatgaagga 1500
tcttatttct tcggagacaa tgcagaggag tacgacaatt aaagaaaaat acccttgttt 1560
ctact 1565

<210> SEQ ID NO 13
<211> LENGTH: 1027
<212> TYPE: DNA
<213> ORGANISM: Influenza A Virus

<400> SEQUENCE: 13
agcaaaagca ggtagatatt gaaagatgag tcttctaacc gaggtcgaaa cgtacgtact 60
ctctatcatc ccgtcaggcc ccctcaaagc cgagatcgca cagagacttg aagatgtctt 120
tgcagggaag aacaccgatc ttgaggttct catggaatgg ctaaagacaa gaccaatcct 180
gtcacctctg actaagggga ttttaggatt tgtgttcacg ctcaccgtgc ccagtgagcg 240
aggactgcag cgtagacgct ttgtccaaaa tgcccttaat gggaacgggg atccaaataa 300
catggacaaa gcagttaaac tgtataggaa gctcaagagg gagataacat tccatggggc 360
caaagaaatc tcactcagtt attctgctgg tgcacttgcc agttgtatgg gcctcatata 420
caacaggatg gggctgtga ccactgaagt ggcatttggc ctggtatgtg caacctgtga 480
acagattgct gactcccagc atcggtctca taggcaaatg gtgacaacaa ccaatccact 540
aatcagacat gagaacagaa tggttttagc cagcactaca gctaaggcta tggagcaaat 600
ggctggatcg agtgagcaag cagcagaggc catggaggtt gctagtcagg ctagacaaat 660
ggtgcaagcg atgagaacca ttgggactca tcctagctcc agtgctggtc tgaaaaatga 720
tcttcttgaa aatttgcagg cctatcagaa acgaatgggg gtgcagatgc aacggttcaa 780
gtgatcctct cactattgcc gcaaatatca ttgggatctt gcacttgaca ttgtggattc 840
ttgatcgtct ttttttcaaa tgcatttacc gtcgctttaa atacggactg aaaggagggc 900
cttctacgga aggagtgcca aagtctatga gggaagaata tcgaaaggaa cagcagagtg 960
ctgtggatgc tgacgatggt cattttgtca gcatagagct ggagtaaaaa actaccttgt 1020
ttctact 1027

<210> SEQ ID NO 14
<211> LENGTH: 890
<212> TYPE: DNA
<213> ORGANISM: Influenza A Virus

<400> SEQUENCE: 14
agcaaaagca gggtgacaaa aacataatgg atccaaacac tgtgtcaagc tttcaggtag 60
attgctttct ttggcatgtc cgcaaacgag ttgcagacca agaactaggt gatgccccat 120
tccttgatcg gcttcgccga gatcagaaat ccctaagagg aaggggcagt actctcggtc 180
tggacatcaa gacagccaca cgtgctggaa agcagatagt ggagcggatt ctgaaagaag 240
aatccgatga ggcacttaaa atgaccatgg cctctgtacc tgcgtcgcgt tacctaactg 300
acatgactct tgaggaaatg tcaagggact ggtccatgct catacccaag cagaaagtgg 360
caggccctct ttgtatcaga atggaccagg cgatcatgga taagaacatc atactgaaag 420
cgaacttcag tgtgattttt gaccggctgg agactctaat attgctaagg gctttcaccg 480
aagagggagc aattgttggc gaaatttcac cattgccttc tcttccagga catactgctg 540
aggatgtcaa aaatgcagtt ggagtcctca tcggaggact tgaatggaat gataacacag 600
ttcgagtctc tgaaactcta cagagattcg cttggagaag cagtaatgag aatgggagac 660
ctccactcac tccaaaacag aaacgagaaa tggcgggaac aattaggtca gaagtttgaa 720
gaaataagat ggttgattga agaagtgaga cacaaactga agataacaga gaatagtttt 780
gagcaaataa catttatgca agccttacat ctattgcttg aagtggagca agagataaga 840
actttctcgt ttcagcttat ttagtactaa aaaacaccct tgtttctact 890

<210> SEQ ID NO 15
<211> LENGTH: 1775
<212> TYPE: DNA
<213> ORGANISM: Influenza A Virus

<400> SEQUENCE: 15
agcaaaagca ggggaaaata aaaacaacca aaatgaaggc aaacctactg gtcctgttat 60
gtgcacttgc agctgcagat gcagacacaa tatgtatagg ctaccatacg aacaattcaa 120
ccgacactgt tgacacagta ctcgagaaga atgtgacagt gacacactct gttaacctgc 180
tcgaagacag ccacaacgga aaactatgta gattaaaagg aatagcccca ctacaattgg 240
ggaaatgtaa catcgccgga tggctcttgg gaaacccaga atgcgaccca ctgcttccag 300
tgagatcatg gtcctacatt gtagaaacac caaactctga gaatggaata tgttatccag 360
gagatttcat cgactatgag gagctgaggg agcaattgag ctcagtgtca tcattcgaaa 420
gattcgaaat atttcccaaa gaaagctcat ggcccaacca caacacaaac ggagtaacgg 480

```
cagcatgctc ccatgagggg aaaagcagtt tttacagaaa tttgctatgg ctgacggaga    540

aggagggctc atacccaaag ctgaaaaatt cttatgtgaa caaaaaaggg aaagaagtcc    600

ttgtactgtg ggtattcat cacccgccta acagtaagga acaacagaat ctctatcaga    660

atgaaaatgc ttatgtctct gtagtgactt caaattataa caggagattt accccggaaa    720

tagcagaaag acccaaagta agagatcaag ctgggaggat gaactattac tggaccttgc    780

taaaacccgg agacacaata atatttgagg caaatggaaa tctaatagca ccaatgtatg    840

ctttcgcact gagtagaggc tttgggtccg gcatcatcac ctcaaacgca tcaatgcatg    900

agtgtaacac gaagtgtcaa acacccctgg gagctataaa cagcagtctc ccttaccaga    960

atatacaccc agtcacaata ggagagtgcc caaaatacgt caggagtgcc aaattgagga   1020

tggttacagg actaaggaac attccgtcca ttcaatccag aggtctattt ggagccattg   1080

ccggttttat tgaaggggga tggactggaa tgatagatgg atggtatggt tatcatcatc   1140

agaatgaaca gggatcaggc tatgcagcgg atcaaaaaag cacacaaaat gccattaacg   1200

ggattacaaa caaggtgaac actgttatcg agaaaatgaa cattcaattc acagctgtgg   1260

gtaaagaatt caacaaatta gaaaaaagga tggaaaattt aaataaaaaa gttgatgatg   1320

gatttctgga catttggaca tataatgcag aattgttagt tctactggaa aatgaaagga   1380

ctctggaatt ccatgactca aatgtgaaga atctgtatga gaaagtaaaa agccaattaa   1440

agaataatgc caaagaaatc ggaaatggat gttttgagtt ctaccacaag tgtgacaatg   1500

aatgcatgga aagtgtaaga aatgggactt atgattatcc caaatattca gaagagtcaa   1560

agttgaacag ggaaaaggta gatggagtga aattggaatc aatggggatc tatcagattc   1620

tggcgatcta ctcaactgtc gccagttcac tggtgctttt ggtctccctg ggggcaatca   1680

gtttctggat gtgttctaat ggatctttgc agtgcagaat atgcatctga gattagaatt   1740

tcagagatat gaggaaaaac acccttgttt ctact                              1775
```

<210> SEQ ID NO 16
<211> LENGTH: 1413
<212> TYPE: DNA
<213> ORGANISM: Influenza A Virus

<400> SEQUENCE: 16

```
agcaaaagca ggggtttaaa atgaatccaa atcagaaaat aataaccatt ggatcaatct     60

gtctggtagt cggactaatt agcctaatat tgcaaatagg gaatataatc tcaatatgga    120

ttagccattc aattcaaact ggaagtcaaa accatactgg aatatgcaac caaaacatca    180

ttacctataa aaatagcacc tgggtaaagg acacaacttc agtgatatta accggcaatt    240

catctctttg tcccatccgt gggtgggcta tatacagcaa agacaatagc ataagaattg    300

gttccaaagg agacgttttt gtcataagag agccctttat ttcatgttct cacttggaat    360

gcaggacctt ttttctgacc caaggtgcct tactgaatga caagcattca agtgggactg    420

ttaaggacag aagcccttat agggccttaa tgagctgccc tgtcggtgaa gctccgtccc    480

cgtacaattc aagatttgaa tcggttgctt ggtcagcaag tgcatgtcat gatggcatgg    540

gctggctaac aatcggaatt tcaggtccag ataatggagc agtggctgta ttaaaataca    600

acggcataat aactgaaacc ataaaaagtt ggaggaagaa aatattgagg acacaagagt    660

ctgaatgtgc ctgtgtaaat ggttcatgtt ttactataat gactgatggc ccgagtgatg    720

ggctggcctc gtacaaaatt ttcaagatcg aaaaggggaa ggttactaaa tcaatagagt    780

tgaatgcacc taattctcac tatgaggaat gttcctgtta ccctgatacc gacaaagtga    840
```

tgtgtgtgtg cagagacaat tggcatggtt cgaaccggcc atgggtgtct ttcgatcaaa 900
acctggatta tcaaatagga tacatctgca gtggggtttt cggtgacaac ccgcgtcccg 960
aagatggaac aggcagctgt ggtccagtgt atgttgatgg agcaaacgga gtaaagggat 1020
tttcatatag gtatggtaat ggtgtttgga taggaaggac caaaagtcac agttccagac 1080
atgggtttga gatgatttgg gatcctaatg gatggacaga gactgatagt aagttctctg 1140
tgaggcaaga tgttgtggca atgactgatt ggtcagggta tagcggaagt ttcgttcaac 1200
atcctgagct gacagggcta gactgtatga ggccgtgctt ctgggttgaa ttaatcaggg 1260
gacgacctaa agaaaaaaca atctggacta gtgcgagcag catttctttt tgtggcgtga 1320
atagtgatac tgtagattgg tcttggccag acggtgctga gttgccattc agcattgaca 1380
agtagtctgt tcaaaaaact ccttgtttct act 1413

<210> SEQ ID NO 17
<211> LENGTH: 716
<212> TYPE: PRT
<213> ORGANISM: Influenza A Virus

<400> SEQUENCE: 17

Met Glu Asp Phe Val Arg Gln Cys Phe Asn Pro Met Ile Val Glu Leu
1 5 10 15

Ala Glu Lys Ala Met Lys Glu Tyr Gly Glu Asp Pro Lys Ile Glu Thr
20 25 30

Asn Lys Phe Ala Ala Ile Cys Thr His Leu Glu Val Cys Phe Met Tyr
35 40 45

Ser Asp Phe His Phe Ile Asp Glu Arg Gly Glu Ser Ile Ile Val Glu
50 55 60

Ser Gly Asp Pro Asn Ala Leu Leu Lys His Arg Phe Glu Ile Ile Glu
65 70 75 80

Gly Arg Asp Arg Ile Met Ala Trp Thr Val Val Asn Ser Ile Cys Asn
85 90 95

Thr Thr Gly Val Glu Lys Pro Lys Phe Leu Pro Asp Leu Tyr Asp Tyr
100 105 110

Lys Glu Asn Arg Phe Ile Glu Ile Gly Val Thr Arg Arg Glu Val His
115 120 125

Ile Tyr Tyr Leu Glu Lys Ala Asn Lys Ile Lys Ser Glu Lys Thr His
130 135 140

Ile His Ile Phe Ser Phe Thr Gly Glu Glu Met Ala Thr Lys Ala Asp
145 150 155 160

Tyr Thr Leu Asp Glu Glu Ser Arg Ala Arg Ile Lys Thr Arg Leu Phe
165 170 175

Thr Ile Arg Gln Glu Met Ala Ser Arg Ser Leu Trp Asp Ser Phe Arg
180 185 190

Gln Ser Glu Arg Gly Glu Glu Thr Ile Glu Glu Lys Phe Glu Ile Thr
195 200 205

Gly Thr Met Arg Lys Leu Ala Asp Gln Ser Leu Pro Pro Asn Phe Pro
210 215 220

Ser Leu Glu Asn Phe Arg Ala Tyr Val Asp Gly Phe Glu Pro Asn Gly
225 230 235 240

Cys Ile Glu Gly Lys Leu Ser Gln Met Ser Lys Glu Val Asn Ala Lys
245 250 255

Ile Glu Pro Phe Leu Arg Thr Thr Pro Arg Pro Leu Arg Leu Pro Asp
260 265 270

-continued

```
Gly Pro Leu Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Asn Ile Val Lys Pro His Glu Lys Gly Ile Asn Pro Asn Tyr Leu Met
                325                 330                 335

Ala Trp Lys Gln Val Leu Ala Glu Leu Gln Asp Ile Glu Asn Glu Glu
            340                 345                 350

Lys Ile Pro Arg Thr Lys Asn Met Lys Arg Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Pro
385                 390                 395                 400

Arg Ser Leu Ala Ser Trp Val Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Thr Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Arg Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685
```

Ala Ile Glu Glu Cys Leu Ile Asn Asp Pro Trp Val Leu Leu Asn Ala
690 695 700

Ser Trp Phe Asn Ser Phe Leu Thr His Ala Leu Lys
705 710 715

<210> SEQ ID NO 18
<211> LENGTH: 757
<212> TYPE: PRT
<213> ORGANISM: Influenza A Virus

<400> SEQUENCE: 18

Met Asp Val Asn Pro Thr Leu Leu Phe Leu Lys Ile Pro Ala Gln Asn
1 5 10 15

Ala Ile Ser Thr Thr Phe Pro Tyr Thr Gly Asp Pro Pro Tyr Ser His
20 25 30

Gly Thr Gly Thr Gly Tyr Thr Met Asp Thr Val Asn Arg Thr His Gln
35 40 45

Tyr Ser Glu Lys Gly Lys Trp Thr Thr Asn Thr Glu Thr Gly Ala Pro
50 55 60

Gln Leu Asn Pro Ile Asp Gly Pro Leu Pro Glu Asp Asn Glu Pro Ser
65 70 75 80

Gly Tyr Ala Gln Thr Asp Cys Val Leu Glu Ala Met Ala Phe Leu Glu
85 90 95

Glu Ser His Pro Gly Ile Phe Glu Asn Ser Cys Leu Glu Thr Met Glu
100 105 110

Val Val Gln Gln Thr Arg Val Asp Lys Leu Thr Gln Gly Arg Gln Thr
115 120 125

Tyr Asp Trp Thr Leu Asn Arg Asn Gln Pro Ala Ala Thr Ala Leu Ala
130 135 140

Asn Thr Ile Glu Val Phe Arg Ser Asn Gly Leu Thr Ala Asn Glu Ser
145 150 155 160

Gly Arg Leu Ile Asp Phe Leu Lys Asp Val Met Glu Ser Met Asn Lys
165 170 175

Glu Glu Ile Glu Ile Thr Thr His Phe Gln Arg Lys Arg Arg Val Arg
180 185 190

Asp Asn Met Thr Lys Lys Met Val Thr Gln Arg Thr Ile Gly Lys Lys
195 200 205

Lys Gln Arg Leu Asn Lys Arg Gly Tyr Leu Ile Arg Ala Leu Thr Leu
210 215 220

Asn Thr Met Thr Lys Asp Ala Glu Arg Gly Lys Leu Lys Arg Arg Ala
225 230 235 240

Ile Ala Thr Pro Gly Met Gln Ile Arg Gly Phe Val Tyr Phe Val Glu
245 250 255

Thr Leu Ala Arg Ser Ile Cys Glu Lys Leu Glu Gln Ser Gly Leu Pro
260 265 270

Val Gly Gly Asn Glu Lys Lys Ala Lys Leu Ala Asn Val Val Arg Lys
275 280 285

Met Met Thr Asn Ser Gln Asp Thr Glu Ile Ser Phe Thr Ile Thr Gly
290 295 300

Asp Asn Thr Lys Trp Asn Glu Asn Gln Asn Pro Arg Met Phe Leu Ala
305 310 315 320

Met Ile Thr Tyr Ile Thr Arg Asn Gln Pro Glu Trp Phe Arg Asn Ile
325 330 335

Leu Ser Met Ala Pro Ile Met Phe Ser Asn Lys Met Ala Arg Leu Gly
340 345 350

```
Lys Gly Tyr Met Phe Glu Ser Lys Arg Met Lys Ile Arg Thr Gln Ile
        355                 360                 365

Pro Ala Glu Met Leu Ala Ser Ile Asp Leu Lys Tyr Phe Asn Glu Ser
    370                 375                 380

Thr Lys Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Ile Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Val Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Asp Gln Thr Gln Ser Lys Val Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Asp Asp Tyr Arg Gly Arg Leu
    610                 615                 620

Cys Asn Pro Leu Asn Pro Phe Val Ser His Lys Glu Ile Asp Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Val Asp Phe Glu Ser Gly Arg Ile Lys
                725                 730                 735

Lys Glu Glu Phe Ser Glu Ile Met Lys Ile Cys Ser Thr Ile Glu Glu
            740                 745                 750

Leu Arg Arg Gln Lys
        755
```

<210> SEQ ID NO 19
<211> LENGTH: 759
<212> TYPE: PRT
<213> ORGANISM: Influenza A Virus

<400> SEQUENCE: 19

Met Glu Arg Ile Lys Glu Leu Arg Asp Leu Met Ser Gln Ser Arg Thr
1 5 10 15

Arg Glu Ile Leu Thr Lys Thr Thr Val Asp His Met Ala Ile Ile Lys
20 25 30

Lys Tyr Thr Ser Gly Arg Gln Glu Lys Asn Pro Ala Leu Arg Met Lys
35 40 45

Trp Met Met Ala Met Arg Tyr Pro Ile Thr Ala Asp Lys Arg Ile Met
50 55 60

Asp Met Ile Pro Glu Arg Asn Glu Gln Gly Gln Thr Leu Trp Ser Lys
65 70 75 80

Thr Asn Asp Ala Gly Ser Asp Arg Val Met Val Ser Pro Leu Ala Val
85 90 95

Thr Trp Trp Asn Arg Asn Gly Pro Thr Thr Ser Thr Val His Tyr Pro
100 105 110

Lys Val Tyr Lys Thr Tyr Phe Glu Lys Val Glu Arg Leu Lys His Gly
115 120 125

Thr Phe Gly Pro Val His Phe Arg Asn Gln Val Lys Ile Arg Arg Arg
130 135 140

Val Asp Thr Asn Pro Gly His Ala Asp Leu Ser Ala Lys Glu Ala Gln
145 150 155 160

Asp Val Ile Met Glu Val Val Phe Pro Asn Glu Val Gly Ala Arg Ile
165 170 175

Leu Thr Ser Glu Ser Gln Leu Ala Ile Thr Lys Glu Lys Lys Glu Glu
180 185 190

Leu Gln Asp Cys Lys Ile Ala Pro Leu Met Val Ala Tyr Met Leu Glu
195 200 205

Arg Glu Leu Val Arg Lys Thr Arg Phe Leu Pro Val Ala Gly Gly Thr
210 215 220

Gly Ser Val Tyr Ile Glu Val Leu His Leu Thr Gln Gly Thr Cys Trp
225 230 235 240

Glu Gln Met Tyr Thr Pro Gly Gly Glu Val Arg Asn Asp Asp Val Asp
245 250 255

Gln Ser Leu Ile Ile Ala Ala Arg Asn Ile Val Arg Arg Ala Ala Val
260 265 270

Ser Ala Asp Pro Leu Ala Ser Leu Leu Glu Met Cys His Ser Thr Gln
275 280 285

Ile Gly Gly Val Arg Met Val Asp Ile Leu Arg Gln Asn Pro Thr Glu
290 295 300

Glu Gln Ala Val Asp Ile Cys Lys Ala Ala Ile Gly Leu Arg Ile Ser
305 310 315 320

Ser Ser Phe Ser Phe Gly Gly Phe Thr Phe Lys Arg Thr Ser Gly Ser
325 330 335

Ser Val Lys Lys Glu Glu Glu Val Leu Thr Gly Asn Leu Gln Thr Leu
340 345 350

Lys Ile Arg Val His Glu Gly Tyr Glu Glu Phe Thr Met Val Gly Arg
355 360 365

Arg Ala Thr Ala Ile Leu Arg Lys Ala Thr Arg Arg Leu Ile Gln Leu
370 375 380

```
Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu Ser Ile Asp Asn Val Met Gly Met Ile Gly Ile Leu
    450                 455                 460

Pro Asp Met Thr Pro Ser Thr Glu Met Ser Leu Arg Gly Ile Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Ile Val
545                 550                 555                 560

Lys Ile Gln Trp Ser Gln Asp Pro Thr Met Leu Tyr Asn Lys Met Glu
                565                 570                 575

Phe Glu Pro Phe Gln Ser Leu Val Pro Lys Ala Thr Arg Ser Arg Tyr
            580                 585                 590

Ser Gly Phe Val Arg Thr Leu Phe Gln Gln Met Arg Asp Val Leu Gly
        595                 600                 605

Thr Phe Asp Thr Val Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Leu Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ser Gly Val Glu Ser
        675                 680                 685

Ala Val Leu Arg Gly Phe Leu Ile Leu Gly Lys Glu Asp Lys Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755
```

<210> SEQ ID NO 20
<211> LENGTH: 319
<212> TYPE: PRT
<213> ORGANISM: Influenza A Virus

<400> SEQUENCE: 20

Met Ala Ser Gln Gly Thr Lys Arg Ser Tyr Glu Gln Met Glu Thr Gly
1 5 10 15

Gly Glu Arg Gln Asp Ala Thr Glu Ile Arg Ala Ser Val Gly Arg Met
20 25 30

Ile Gly Gly Ile Gly Arg Phe Tyr Ile Gln Met Cys Thr Glu Leu Lys
35 40 45

Leu Ser Asp Tyr Asp Gly Arg Leu Ile Gln Asn Ser Ile Thr Ile Glu
50 55 60

Arg Met Val Leu Ser Ala Phe Asp Glu Arg Arg Asn Lys Tyr Leu Glu
65 70 75 80

Glu His Pro Ser Ala Gly Lys Asp Pro Lys Lys Thr Gly Gly Pro Ile
85 90 95

Tyr Arg Arg Val Asp Gly Lys Trp Met Arg Glu Leu Ile Leu Tyr Asp
100 105 110

Lys Glu Glu Ile Arg Arg Val Trp Arg Gln Ala Asn Asn Gly Glu Asp
115 120 125

Ala Thr Ala Gly Leu Thr His Ile Met Ile Trp His Ser Asn Leu Asn
130 135 140

Asp Ala Thr Tyr Gln Arg Thr Arg Ala Leu Val Arg Thr Gly Met Asp
145 150 155 160

Pro Arg Met Cys Ser Leu Met Gln Gly Ser Thr Leu Pro Arg Arg Ser
165 170 175

Gly Ala Ala Gly Ala Ala Val Lys Gly Val Gly Thr Ile Ala Met Glu
180 185 190

Leu Ile Arg Met Ile Lys Arg Gly Ile Asn Asp Arg Asn Phe Trp Arg
195 200 205

Gly Glu Asn Gly Arg Arg Thr Arg Val Ala Tyr Glu Arg Met Cys Asn
210 215 220

Ile Leu Lys Gly Lys Phe Gln Thr Ala Ala Gln Arg Ala Met Met Asp
225 230 235 240

Gln Val Arg Glu Ser Arg Asn Pro Gly Asn Ala Glu Ile Glu Asp Leu
245 250 255

Ile Phe Leu Ala Arg Ser Ala Leu Ile Leu Arg Gly Ser Val Ala His
260 265 270

Lys Ser Cys Leu Pro Ala Cys Val Tyr Gly Leu Ala Val Ala Ser Gly
275 280 285

His Asp Phe Glu Arg Glu Gly Tyr Ser Leu Val Gly Ile Asp Pro Phe
290 295 300

Lys Leu Leu Gln Asn Ser Gln Val Val Ser Leu Met Arg Pro Asn
305 310 315

<210> SEQ ID NO 21
<211> LENGTH: 252
<212> TYPE: PRT
<213> ORGANISM: Influenza A Virus

<400> SEQUENCE: 21

Met Ser Leu Leu Thr Glu Val Glu Thr Tyr Val Leu Ser Ile Ile Pro
1 5 10 15

Ser Gly Pro Leu Lys Ala Glu Ile Ala Gln Arg Leu Glu Ser Val Phe
20 25 30

Ala Gly Lys Asn Thr Asp Leu Glu Ala Leu Met Glu Trp Leu Lys Thr
35 40 45

-continued

```
Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Lys Lys Leu Lys Arg Glu Ile Thr Phe His Gly Ala
            100                 105                 110

Lys Glu Val Ser Leu Ser Tyr Ser Thr Gly Ala Leu Ala Ser Cys Met
        115                 120                 125

Gly Leu Ile Tyr Asn Arg Met Gly Thr Val Thr Thr Glu Ala Ala Phe
    130                 135                 140

Gly Leu Val Cys Ala Thr Cys Glu Gln Ile Ala Asp Ser Gln His Arg
145                 150                 155                 160

Ser His Arg Gln Met Ala Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Asn Gln
        195                 200                 205

Thr Arg Gln Met Val His Ala Met Arg Thr Ile Gly Thr His Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250
```

<210> SEQ ID NO 22
<211> LENGTH: 219
<212> TYPE: PRT
<213> ORGANISM: Influenza A Virus

<400> SEQUENCE: 22

```
Met Asp Ser Asn Thr Met Ser Ser Phe Gln Val Asp Cys Phe Leu Trp
1               5                   10                  15

His Ile Arg Lys Arg Phe Ala Asp Asn Gly Leu Gly Asp Ala Pro Phe
            20                  25                  30

Leu Asp Arg Leu Arg Arg Asp Gln Lys Ser Leu Lys Gly Arg Gly Asn
        35                  40                  45

Thr Leu Gly Leu Asp Ile Glu Thr Ala Thr Leu Val Gly Lys Gln Ile
    50                  55                  60

Val Glu Trp Ile Leu Lys Glu Glu Ser Ser Glu Thr Leu Arg Met Thr
65                  70                  75                  80

Ile Ala Ser Val Pro Thr Ser Arg Tyr Leu Ser Asp Met Thr Leu Glu
                85                  90                  95

Glu Met Ser Arg Asp Trp Phe Met Leu Met Pro Arg Gln Lys Ile Ile
            100                 105                 110

Gly Pro Leu Cys Val Arg Leu Asp Gln Ala Ile Met Glu Lys Asn Ile
        115                 120                 125

Val Leu Lys Ala Asn Phe Ser Val Ile Phe Asn Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Tyr Glu Asp Val Lys Asn
                165                 170                 175
```

Ala Val Gly Val Leu Ile Gly Gly Leu Glu Trp Asn Gly Asn Thr Val
180 185 190

Arg Val Ser Glu Asn Ile Gln Arg Phe Ala Trp Arg Asn Cys Asp Glu
195 200 205

Asn Gly Arg Pro Ser Leu Pro Pro Glu Gln Lys
210 215

<210> SEQ ID NO 23
<211> LENGTH: 2151
<212> TYPE: DNA
<213> ORGANISM: Influenza A Virus

<400> SEQUENCE: 23
atggaagact ttgtgcgaca atgcttcaat ccaatgatcg tcgagcttgc ggaaaaggca 60
atgaaagaat atggggaaga tccgaaaatc gaaactaaca agtttgctgc aatatgcaca 120
catttggaag tttgtttcat gtattcggat ttccatttca tcgacgaacg ggtgaatca 180 ataattgtag aatctggtga cccgaatgca ctattgaagc accgatttga gataattgaa 240
ggaagagacc gaatcatggc ctggacagtg gtgaacagta tatgtaacac aacaggggta 300
gagaagccta aatttcttcc tgatttgtat gattacaaag agaaccggtt cattgaaatt 360
ggagtaacac ggagggaagt ccacatatat tacctagaga aagccaacaa aataaaatct 420
gagaagacac acattcacat cttttcattc actggagagg agatggccac caaagcggac 480
tacacccttg acgaagagag cagggcaaga atcaaaacta ggcttttcac tataagacaa 540
gaaatggcca gtaggagtct atgggattcc tttcgtcagt ccgaaagagg cgaagagaca 600
attgaagaaa aatttgagat tacaggaact atgcgcaagc ttgccgacca aagtctccca 660
ccgaacttcc ccagccttga aaactttaga gcctatgtag atggattcga gccgaacggc 720
tgcattgagg gcaagctttc ccaaatgtca aaagaagtga acgccaaaat tgaaccattc 780
ttgaggacga caccacgccc cctcagattg cctgatgggc ctctttgcca tcagcggtca 840
aagttcctgc tgatggatgc tctgaaatta agtattgaag acccgagtca cgagggggag 900
ggaataccac tatatgatgc aatcaaatgc atgaagacat tctttggctg gaaagagcct 960
aacatagtca aaccacatga gaaaggcata aatcccaatt acctcatggc ttggaagcag 1020
gtgctagcag agctacagga cattgaaaat gaagagaaga tcccaaggac aaagaacatg 1080
aagagaacaa gccaattgaa gtgggcactc ggtgaaaata tggcaccaga aaaagtagac 1140
tttgatgact gcaaagatgt tggagacctt aaacagtatg acagtgatga gccagagccc 1200
agatctctag caagctgggt ccaaaatgaa ttcaataagg catgtgaatt gactgattca 1260
agctggatag aacttgatga aataggagaa gatgttgccc cgattgaaca tatcgcaagc 1320
atgaggagga actattttac agcagaagtg tcccactgca gggctactga atacataatg 1380
aagggagtgt acataaatac ggccttgctc aatgcatcct gtgcagccat ggatgacttt 1440
cagctgatcc caatgataag caaatgtagg accaaagaag gaagacggaa aacaaacctg 1500
tatgggttca ttataaaagg aaggtctcat ttgagaaatg atactgatgt ggtgaacttt 1560
gtaagtatgg agttctcact cactgacccg agactggagc cacacaaatg ggaaaaatac 1620
tgtgttcttg aaataggaga catgctcttg aggactgcga taggccaagt gtcgaggccc 1680
atgttcctat atgtgagaac caatggaacc tccaagatca agatgaaatg gggcatggaa 1740
atgaggcgct gccttcttca gtctcttcag cagattgaga gcatgattga ggccgagtct 1800
tctgtcaaag agaaagacat gaccaaggaa ttctttgaaa acaaatcgga aacatggcca 1860

-continued atcggagagt cacccagggg agtggaggaa ggctctattg ggaaagtgtg caggacctta 1920
ctggcaaaat ctgtattcaa cagtctatat gcgtctccac aacttgaggg gttttcggct 1980
gaatctagaa aattgcttct cattgttcag gcacttaggg acaacctgga acctggaacc 2040
ttcgatcttg gggggctata tgaagcaatc gaggagtgcc tgattaatga tccctgggtt 2100
ttgcttaatg catcttggtt caactccttc ctcacacatg cactgaagta g 2151

<210> SEQ ID NO 24
<211> LENGTH: 2341
<212> TYPE: DNA
<213> ORGANISM: Influenza A Virus

<400> SEQUENCE: 24
agcgaaagca ggcaaaccat ttgaatggat gtcaatccga ctctactttt cctaaaaatt 60
ccagcgcaaa atgccataag caccacattc ccttatactg gagatcctcc atacagccat 120
ggaacaggaa caggatacac catggacaca gtaaacagaa cacaccaata ctcagaaaag 180
ggaaagtgga cgacaaacac agagactggt gcaccccagc tcaacccgat tgatggacca 240
ctacctgagg ataatgaacc aagtgggtat gcacaaacag actgtgttct agaggctatg 300
gctttccttg aagaatccca cccaggaata tttgagaatt catgccttga aacaatggaa 360
gttgttcaac aaacaagggt agataaacta actcaaggtc gccagactta tgattggaca 420
ttaaacagaa atcaaccggc agcaactgca ttggccaaca ccatagaagt ctttagatcg 480
aatggcctaa cagctaatga gtcaggaagg ctaatagatt tcttaaagga tgtaatggaa 540
tcaatgaaca aagaggaaat agagataaca acccactttc aaagaaaaag gagagtaaga 600
gacaacatga ccaagaagat ggtcacgcaa agaacaatag ggaagaaaaa acaaagactg 660
aataagagag gctatctaat aagagcactg acattaaata cgatgaccaa agatgcagag 720
agaggcaagt taaaaagaag ggctatcgca acacctggga tgcagattag aggtttcgta 780
tactttgttg aaactttagc taggagcatt tgcgaaaagc ttgaacagtc tgggctccca 840
gtagggggca atgaaaagaa ggccaaactg gcaaatgttg tgagaaagat gatgactaat 900
tcacaagaca cagagatttc tttcacaatc actggggaca acactaagtg gaatgaaaat 960
caaaatcctc gaatgttcct ggcgatgatt acatatatca ccagaaatca acccgagtgg 1020
ttcagaaaca tcctgagcat ggcacccata atgttctcaa acaaaatggc aagactaggg 1080
aaagggtaca tgttcgagag taaaagaatg aagattcgaa cacaaatacc agcagaaatg 1140
ctagcaagca ttgacctgaa gtacttcaat gaatcaacaa agaagaaaat tgagaaaata 1200
aggcctcttc taatagatgg cacagcatca ctgagtcctg ggatgatgat gggcatgttc 1260
aacatgctaa gtacggtctt gggagtctcg atactgaatc ttggacaaaa gaaatacacc 1320
aagacaatat actggtggga tgggctccaa tcatccgacg attttgctct catagtgaat 1380
gcaccaaacc atgagggaat acaagcagga gtggacagat tctacaggac ctgcaagtta 1440
gtgggaatca acatgagcaa aaagaagtcc tatataaata agacagggac atttgaattc 1500
acaagctttt tttatcgcta tggatttgtg gctaatttta gcatggagct acccagcttt 1560
ggagtgtctg gagtaaatga atcagctgac atgagtattg gagtaacagt gataaagaac 1620
aacatgataa acaatgacct tggacctgca acggcccaga tggctcttca attgttcatc 1680
aaagactaca gatacacata taggtgccat aggggagaca cacaaattca gacaagaaga 1740
tcatttgagt taaagaagct gtgggatcaa acccaatcaa aggtagggct attagtatca 1800

-continued gatggaggac caaacttata caatatacgg aatcttcaca ttcctgaagt ctgcttaaaa 1860
tgggagctaa tggatgatga ttatcgggga agactttgta atcccctgaa tccctttgtc 1920
agtcataaag agattgattc tgtaaacaat gctgtggtaa tgccagccca tggtccagcc 1980
aaaagcatgg aatatgatgc cgttgcaact acacattcct ggattcccaa gaggaatcgt 2040
tctattctca acacaagcca aaggggaatt cttgaggatg aacagatgta ccagaagtgc 2100
tgcaatctat tcgagaaatt tttccctagc agttcatata ggagaccggt tggaatttct 2160
agcatggtgg aggccatggt gtctagggcc cggattgatg ccagggtcga cttcgagtct 2220
ggacggatca agaaagaaga gttctctgag atcatgaaga tctgttccac cattgaagaa 2280
ctcagacggc aaaaataatg aatttaactt gtccttcatg aaaaaatgcc ttgtttctac 2340
t 2341

<210> SEQ ID NO 25
<211> LENGTH: 2280
<212> TYPE: DNA
<213> ORGANISM: Influenza A Virus

<400> SEQUENCE: 25
atggagagaa taaaagaact gagagatcta atgtcgcagt cccgcactcg cgagatactc 60
actaagacca ctgtggacca tatggccata atcaaaaagt acacatcagg aaggcaagag 120
aagaaccccg cactcagaat gaagtggatg atggcaatga gatacccaat tacagcagac 180
aagagaataa tggacatgat tccagagagg aatgaacaag gacaaaccct ctggagcaaa 240
acaaacgatg ctggatcaga ccgagtgatg gtatcacctc tggccgtaac atggtggaat 300
aggaatggcc caacaacaag tacagttcat taccctaagg tatataaaac ttatttcgaa 360
aaggtcgaaa ggttgaaaca tggtaccttc ggccctgtcc acttcagaaa tcaagttaaa 420
ataaggagga gagttgatac aaaccctggc catgcagatc tcagtgccaa ggaggcacag 480
gatgtgatta tggaagttgt tttcccaaat gaagtggggg caagaatact gacatcagag 540
tcacagctgg caataacaaa agagaagaaa gaagagctcc aggattgtaa aattgctccc 600
ttgatggtgg cgtacatgct agaaagagaa ttggtccgta aaacaaggtt tctcccagta 660
gccggcggaa caggcagtgt ttatattgaa gtgttgcact taacccaagg gacgtgctgg 720
gagcagatgt acactccagg aggagaagtg agaaatgatg atgttgacca aagtttgatt 780
atcgctgcta gaaacatagt aagaagagca gcagtgtcag cagacccatt agcatctctc 840
ttggaaatgt gccacagcac acagattgga ggagtaagga tggtggacat ccttagacag 900
aatccaactg aggaacaagc cgtagacata tgcaaggcag caatagggtt gaggattagc 960
tcatctttca gttttggtgg gttcactttc aaaaggacaa gcggatcatc agtcaagaaa 1020
gaagaagaag tgctaacggg caacctccaa acactgaaaa taagagtaca tgaagggtat 1080
gaagaattca caatggttgg gagaagagca acagctattc tcagaaaggc aaccaggaga 1140
ttgatccagt tgatagtaag cgggagagac gagcagtcaa ttgctgaggc aataattgtg 1200
gccatggtat tctcacagga ggattgcatg atcaaggcag ttaggggcga tctgaacttt 1260
gtcaataggg caaaccagcg actgaacccc atgcaccaac tcttgaggca tttccaaaaa 1320
gatgcaaaag tgcttttcca gaactgggga attgaatcca tcgacaatgt gatgggaatg 1380
atcggaatac tgcccgacat gaccccaagc acggagatgt cgctgagagg gataagagtc 1440
agcaaaatgg gagtagatga atactccagc acggagagag tggtagtgag tattgaccga 1500
tttttaaggg ttagagatca aagagggaac gtactattgt ctcccgaaga agtcagtgaa 1560
acgcaaggaa ctgagaagtt gacaataact tattcgtcat caatgatgtg ggagatcaat 1620
ggccctgagt cagtgctagt caacacttat caatggataa tcaggaactg ggaaattgtg 1680
aaaattcaat ggtcacaaga tcccacaatg ttatacaaca aaatggaatt tgaaccattt 1740
cagtctcttg tccctaaggc aaccagaagc cggtacagtg gattcgtaag gacactgttc 1800
cagcaaatgc gggatgtgct tgggacattt gacactgtcc aaataataaa acttctcccc 1860
tttgctgctg ccccaccaga acagagtagg atgcaatttt cctcattgac tgtgaatgtg 1920
agaggatcag ggttgaggat actggtaaga ggcaattctc cagtattcaa ttacaacaag 1980
gcaaccaaac gacttacagt tcttggaaag gatgcaggtg cattgactga agatccagat 2040
gaaggcacat ctggggtgga gtctgctgtc ctgagaggat ttctcatttt gggcaaagaa 2100
gacaagagat atggcccagc attaagcatc aatgaactga gcaatcttgc aaaaggagag 2160
aaggctaatg tgctaattgg gcaaggggac gtagtgttgg taatgaaacg aaaacgggac 2220
tctagcatac ttactgacag ccagacagcg accaaaagaa ttcggatggc catcaattag 2280

<210> SEQ ID NO 26
<211> LENGTH: 958
<212> TYPE: DNA
<213> ORGANISM: Influenza A Virus

<400> SEQUENCE: 26
atggcgtctc aaggcaccaa acgatcatat gaacaaatgg agactggtgg ggagcgccag 60
gatgccacag aaatcagagc atctgtcgga agaatgattg gtggaatcgg gagattctac 120
atccaaatgt gcactgaact caaactcagt gattatgatg gacgactaat ccagaatagc 180
ataacaatag agaggatggt gctttctgct tttgatgaga gaagaaataa atacctagaa 240
gagcatccca gtgctgggaa ggaccctaag aaaacaggag gacccatata tagaagagta 300
gacggaaagt ggatgagaga actcatcctt tatgacaaag aagaaataag gagagtttgg 360
cgccaagcaa acaatggcga agatgcaaca gcaggtctta ctcatatcat gatttggcat 420
tccaacctga atgatgccac atatcagaga acaagagcgc ttgttcgcac cggaatggat 480
cccagaatgt gctctctaat gcaaggttca acacttccca gaaggtctgg tgccgcaggt 540
gctgcggtga aaggagttgg aacaatagca atggagttaa tcagaatgat caaacgtgga 600
atcaatgacc gaaatttctg gaggggtgaa aatggacgaa ggacaagggt tgcttatgaa 660
agaatgtgca atatcctcaa aggaaaattt caaacagctg cccagagggc aatgatggat 720
caagtaagag aaagtcgaaa cccaggaaac gctgagattg aagacctcat tttcctggca 780
cggtcagcac tcattctgag gggatcagtt gcacataaat cctgcctgcc tgcttgtgtg 840
tatgggcttg cagtagcaag tgggcatgac tttgaaaggg aagggtactc actggtcggg 900
atagacccat tcaaattact ccaaaacagc caagtggtca gcctgatgag accaaatg 958

<210> SEQ ID NO 27
<211> LENGTH: 982
<212> TYPE: DNA
<213> ORGANISM: Influenza A Virus

<400> SEQUENCE: 27
atgagtcttc taaccgaggt cgaaacgtac gttctttcta tcatcccgtc aggccccctc 60
aaagccgaga tcgcgcagag actggaaagt gtctttgcag gaaagaacac agatcttgag 120
gctctcatgg aatggctaaa gacaagacca atcttgtcac ctctgactaa gggaatttta 180
ggatttgtgt tcacgctcac cgtgcccagt gagcgaggac tgcagcgtag acgctttgtc 240
caaaatgccc taaatgggaa tggggacccg aacaacatgg atagagcagt taaactatac 300
aagaagctca aaagagaaat aacgttccat ggggccaagg aggtgtcact aagctattca 360
actggtgcac ttgccagttg catgggcctc atatacaaca ggatgggaac agtgaccaca 420
gaagctgctt ttggtctagt gtgtgccact tgtgaacaga ttgctgattc acagcatcgg 480
tctcacagac agatggctac taccaccaat ccactaatca ggcatgaaaa cagaatggtg 540
ctggctagca ctacggcaaa ggctatggaa cagatggctg gatcgagtga acaggcagcg 600
gaggccatgg aggttgctaa tcagactagg cagatggtac atgcaatgag aactattggg 660
actcatccta gctccagtgc tggtctgaaa gatgaccttc ttgaaaattt gcaggcctac 720
cagaagcgaa tgggagtgca gatgcagcga ttcaagtgat cctctcgtca ttgcagcaaa 780
tatcattggg atcttgcacc tgatattgtg gattactgat cgtctttttt tcaaatgtat 840
ttatcgtcgc tttaaatacg gtttgaaaag agggccttct acggaaggag tgcctgagtc 900
catgagggaa gaatatcaac aggaacagca gagtgctgtg gatgttgacg atggtcattt 960
tgtcaacata gagctagagt aa 982

<210> SEQ ID NO 28
<211> LENGTH: 865
<212> TYPE: DNA
<213> ORGANISM: Influenza A Virus

<400> SEQUENCE: 28
atggactcca acaccatgtc aagctttcag gtagactgtt tcctttggca tatccgcaag 60
cgatttgcag acaatggatt gggtgatgcc ccattccttg atcggctccg ccgagatcaa 120
aagtccttaa aaggaagagg caacaccctt ggcctcgata tcgaaacagc cactcttgtt 180
gggaaacaaa tcgtggaatg gatcttgaaa gaggaatcca gcgagacact tagaatgaca 240
attgcatctg tacctacttc gcgctacctt tctgacatga ccctcgagga aatgtcacga 300
gactggttca tgctcatgcc taggcaaaag ataataggcc ctctttgcgt gcgattggac 360
caggcgatca tggaaaagaa catagtactg aaagcgaact tcagtgtaat ctttaaccga 420
ttagagacct tgatactact aagggctttc actgaggagg gagcaatagt tggagaaatt 480
tcaccattac cttctcttcc aggacatact tatgaggatg tcaaaaatgc agttggggtc 540
ctcatcggag gacttgaatg gaatggtaac acggttcgag tctctgaaaa tatacagaga 600
ttcgcttgga gaaactgtga tgagaatggg agaccttcac tacctccaga gcagaaatga 660
aaagtggcga gagcaattgg gacagaaatt tgaggaaata aggtggttaa ttgaagaaat 720
gcggcacaga ttgaaagcga cagagaatag tttcgaacaa ataacattta tgcaagcctt 780
acaactactg cttgaagtag aacaagagat aagagctttc tcgtttcagc ttatttaatg 840
ataaaaaaca cccttgtttc tactg 865

<210> SEQ ID NO 29
<211> LENGTH: 758
<212> TYPE: PRT
<213> ORGANISM: Influenza A Virus

<400> SEQUENCE: 29

Met Asp Val Asn Pro Thr Leu Leu Phe Leu Lys Ile Pro Ala Gln Asn
1 5 10 15

Ala Ile Ser Thr Thr Phe Pro Tyr Thr Gly Asp Pro Pro Tyr Ser His
20 25 30

```
Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Arg Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Ile Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Val Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Arg Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Thr Tyr Trp Trp Asp Gly Leu Gln Ser Ser Asp Asp Phe Ala
        435                 440                 445
```

```
Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Met Lys Ile Cys Ser Thr Ile Glu Glu
            740                 745                 750

Leu Arg Arg Gln Lys Gln
        755
```

<210> SEQ ID NO 30
<211> LENGTH: 716
<212> TYPE: PRT
<213> ORGANISM: Influenza A Virus

<400> SEQUENCE: 30

```
Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Ile Val Glu
    50                  55                  60
```

```
Leu Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asn
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Leu
385                 390                 395                 400

Arg Ser Leu Ala Ser Trp Ile Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ser
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480
```

-continued

```
Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Ile Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Ser Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Ser
705                 710                 715
```

<210> SEQ ID NO 31
<211> LENGTH: 326
<212> TYPE: PRT
<213> ORGANISM: Influenza A Virus

<400> SEQUENCE: 31

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140
```

-continued

```
Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asp Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser
                325


<210> SEQ ID NO 32
<211> LENGTH: 252
<212> TYPE: PRT
<213> ORGANISM: Influenza A Virus

<400> SEQUENCE: 32

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
```

-continued 180 185 190

Ala Gly Ser Ser Glu Gln Ala Ala Glu Ala Met Glu Val Ala Ser Gln
195 200 205

Ala Arg Gln Met Val Gln Ala Met Arg Thr Ile Gly Thr His Pro Ser
210 215 220

Ser Ser Ala Gly Leu Lys Asn Asp Leu Leu Glu Asn Leu Gln Ala Tyr
225 230 235 240

Gln Lys Arg Met Gly Val Gln Met Gln Arg Phe Lys
245 250

<210> SEQ ID NO 33
<211> LENGTH: 2299
<212> TYPE: DNA
<213> ORGANISM: Influenza A Virus

<400> SEQUENCE: 33
aatatggaaa gaataaaaga gctaaggaat ctgatgtcac aatctcgcac tcgcgagata 60
cttacaaaaa ctactgtaga ccacatggcc ataatcaaga aatacacatc aggaagacag 120
gagaaaaacc catcacttag aatgaaatgg atgatggcaa tgaaataccc aattacagca 180
gataaaagga taacggaaat gattcctgaa agaaatgagc aaggacagac attatggagt 240
aaagtgaatg atgccggatc agaccgagtg atgatatcac ccctggctgt gacatggtgg 300
aacagaaatg gaccagtggc aagtactatt cactatccaa aaatctacaa aacttacttt 360
gaaaaggttg aaaggttaaa acatggaacc tttggccctg tacactttag aaaccaagtc 420
aaaatacgcc gaagagtcga cataaatcct ggtcatgcag acctcagcgc caaggaggca 480
caggatgtaa ttatggaagt tgttttccct aatgaagtgg gagccagaat actaacatca 540
gaatcgcaat taacgataac caaggagaaa aaagaagaac tccagaattg caaaatttcc 600
cctttgatgg ttgcatacat gttagagagg gaacttgtcc gcaaaacgag atttctcccg 660
gttgctggtg gaacaagcag tgtgtacatt gaagttttgc atttaacaca ggggacatgc 720
tgggagcaga tgtacactcc aggtggggag gtgaggaatg atgatgttga tcaaagccta 780
attattgctg ctaggaacat agtgagaaga gctgcagtat cagcagatcc actagcatct 840
ttattagaaa tgtgccatag cacacagatt ggtgggacaa ggatggtgga tattctcagg 900
caaaatccaa cagaagaaca agctgtggat atatgcaaag cagcaatggg gctgagaatc 960
agttcatcct tcagttttgg cggattcaca tttaagagaa caagtggatc atcagtcaaa 1020
agggaggaag aagtgctcac gggcaatctg caaacattga agctaactgt gcatgaggga 1080
tatgaagagt tcacaatggt tgggaaaagg gcaacagcta tactcagaaa agcaaccagg 1140
agattgattc aactaatagt gagtggaaga gacgaacagt caatagtcga agcaatagtt 1200
gtagcaatgg tattctcaca agaagattgc atggtaaaag cagttagagg tgatctgaat 1260
ttcgttaata gagcgaatca gcggttgaat cccatgcatc aacttttgag acattttcag 1320
aaggatgcta aagtactttt cttaaattgg ggaattgaac ctatcgacaa tgtgatggga 1380
atgattggga tattacctga tatgactcca agtaccgaga tgtcaatgag aggagtgaga 1440
gtcagcaaaa tgggtgtaga tgaatactcc aatgctgaaa gggtagtggt gagcattgac 1500 cgtttttga gagtccggga ccaaagagga aatgtactac tgtctccaga ggaagtcagt 1560
gaaacacagg gaacagagaa actgacaata acttactctt catcaatgat gtgggagatt 1620
aatggccctg agtcagtgtt gatcaatacc tatcagtgga tcatcagaaa ctgggagact 1680
gttaaaattc agtggtctca gaaccctaca atgctataca ataaaatgga attcgagcca 1740
tttcagtctc tagtccctaa ggccattaga ggccaataca gtgggtttgt tagaactcta 1800
tttcaacaaa tgagggatgt gcttgggacc tttgacacaa ctcagataat aaaacttctt 1860
ccctttgcag ccgctccacc aaagcaaagt agaatgcaat tctcatcatt gactgtgaat 1920
gtgaggggat caggaatgag aatacttgta aggggtaatt ctccagtatt caactacaac 1980
aagaccacta agagactcac agtcctcgga aaggatgctg gcactttaac tgaagaccca 2040
gatgaaggca cagctggagt ggaatctgct gttctaaggg gattcctcat tctaggcaaa 2100
gaagatagaa gatatgggcc agcattaagc atcaatgaat tgagcaacct tgcgaaaggg 2160
gaaaaagcta atgtgctaat tgggcaaggg gacgtagtgt tggtaatgaa acgaaaacgg 2220
gactctagca tacttactga cagccagaca gcgaccaaaa gaattcggat ggccatcaat 2280
taatttcgaa taatttaaa 2299

<210> SEQ ID NO 34
<211> LENGTH: 2277
<212> TYPE: DNA
<213> ORGANISM: Influenza A Virus

<400> SEQUENCE: 34
atggaacgca ttaaagaact gcgcaacctg atgagccaga gccgcacccg cgaaattctg 60
accaaaacca ccgtggatca tatggcgatt attaaaaaat ataccagcgg ccgccaggaa 120
aaaaacccga gcctgcgcat gaaatggatg atggcgatga aatatccgat taccgcggat 180
aaacgcatta ccgaaatgat tccggaacgc aacgaacagg gccagaccct gtggagcaaa 240
gtgaacgatg cgggcagcga tcgcgtgatg attagcccgc tggcggtgac ctggtggaac 300
cgcaacggcc cggtggcgag caccattcat tatccgaaaa tttataaaac ctattttgaa 360
aaagtggaac gcctgaaaca tggcaccttt ggcccggtgc attttcgcaa ccaggtgaaa 420
attcgccgcc gcgtggatat taacccgggc catgcggatc tgagcgcgaa agaagcgcag 480
gatgtgatta tggaagtggt gtttccgaac gaagtgggcg cgcgcattct gaccagcgaa 540
agccagctga ccattaccaa agaaaaaaaa gaagaactgc agaactgcaa aattagcccg 600
ctgatggtgg cgtatatgct ggaacgcgaa ctggtgcgca aaacccgctt tctgccggtg 660
gcgggcggca ccagcagcgt gtatattgaa gtgctgcatc tgacccaggg cacctgctgg 720
gaacagatgt ataccccggg cggcgaagtg cgcaacgatg atgtggatca gagcctgatt 780
attgcggcgc gcaacattgt gcgccgcgcg gcggtgagcg cggatccgct ggcgagcctg 840
ctggaaatgt gccatagcac ccagattggc ggcacccgca tggtggatat tctgcgccag 900
aacccgaccg aagaacaggc ggtggatatt tgcaaagcgg cgatgggcct gcgcattagc 960
agcagcttta gctttggcgg ctttaccttt aaacgcacca gcggcagcag cgtgaaacgc 1020
gaagaagaag tgctgaccgg caacctgcag accctgaaac tgaccgtgca tgaaggctat 1080
gaagaattta ccatggtggg caaacgcgcg accgcgattc tgcgcaaagc gacccgccgc 1140
ctgattcagc tgattgtgag cggccgcgat gaacagagca ttgtggaagc gattgtggtg 1200
gcgatggtgt ttagccagga agattgcatg gtgaaagcgg tgcgcggcga tctgaacttt 1260
gtgaaccgcg cgaaccagcg cctgaacccg atgcatcagc tgctgcgcca ttttcagaaa 1320
gatgcgaaag tgctgtttct gaactggggc attgaaccga ttgataacgt gatgggcatg 1380
attggcattc tgccggatat gaccccgagc accgaaatga gcatgcgcgg cgtgcgcgtg 1440
agcaaaatgg gcgtggatga atatagcaac gcggaacgcg tggtggtgag cattgatcgc 1500

-continued

```
tttctgcgcg tgcgcgatca gcgcggcaac gtgctgctga gcccggaaga agtgagcgaa   1560

acccagggca ccgaaaaact gaccattacc tatagcagca gcatgatgtg ggaaattaac   1620

ggcccggaaa gcgtgctgat taacacctat cagtggatta ttcgcaactg ggaaaccgtg   1680

aaaattcagt ggagccagaa cccgaccatg ctgtataaca aaatggaatt tgaaccgttt   1740

cagagcctgg tgccgaaagc gattcgcggc cagtatagcg gctttgtgcg caccctgttt   1800

cagcagatgc gcgatgtgct gggcaccttt gataccaccc agattattaa actgctgccg   1860

tttgcggcgg cgccgccgaa acagagccgc atgcagttta gcagcctgac cgtgaacgtg   1920

cgcggcagcg gcatgcgcat tctggtgcgc ggcaacagcc cggtgtttaa ctataacaaa   1980

accaccaaac gcctgaccgt gctgggcaaa gatgcgggca ccctgaccga agatccggat   2040

gaaggcaccg cgggcgtgga aagcgcggtg ctgcgcggct ttctgattct gggcaaagaa   2100

gatcgccgct atggcccggc gctgagcatt aacgaactga gcaacctggc gaaaggcgaa   2160

aaagcgaacg tgctgattgg ccagggcgat gtggtgctgg tgatgaaacg caaacgcgat   2220

agcagcattc tgaccgatag ccagaccgcg accaaacgca ttcgcatggc gattaac      2277
```

<210> SEQ ID NO 35
<211> LENGTH: 2201
<212> TYPE: DNA
<213> ORGANISM: Influenza A Virus

<400> SEQUENCE: 35

```
gattcgaaat ggaagatttt gtgcgacaat gcttcaatcc gatgattgtc gagcttgcgg     60

aaaaggcaat gaaagagtat ggagaggacc tgaaaatcga aacaaacaaa tttgcagcaa    120

tatgcactca cttggaagta tgcttcatgt attcagattt tcatttcatc aatgagcaag    180

gcgaatcaat aatagtagag cctgaggacc caaatgcact tttaaagcac agatttgaga    240

taatagaggg acgagatcgt acaatggcat ggacagttgt aaacagtatt tgcaacacca    300

caggagctga gaaaccaaag tttctgccag atctgtatga ttacaaagag aatagattca    360

tcgagattgg agtgacaagg agggaagttc acatatacta tctggaaaag gccaacaaaa    420

ttaaatctga gaagacacac attcacattt tctcattcac tggcgaagaa atggccacaa    480

aggccgatta cactctcgat gaagaaagca gggctaggat taaaaccaga ctattcacca    540

taagacaaga aatggcaagc agaggtcttt gggactcctt tcgtcagtcc gaaagaggcg    600

aagaaacaat tgaagaaaga tttgaaatca cagggacaat gcgcaggctc gctgaccaaa    660

gccttccgcc gaacttctcc tgcattgaga attttagagc ctatgtggat ggatttgaac    720

cgaacggcta cattgagggc aagctttctc aaatgtccaa agaagtaaat gctagaattg    780

agcctttttt gaaaacaaca ccacgaccaa ttagacttcc ggatgggcct ccttgttttc    840

agcggtcaaa attcctgctg atggattctt taaaattaag cattgaggat ccaaatcatg    900

aaggagaggg aataccacta tatgatgcaa tcaagtgtat gagaacattc tttggatgga    960

aagaaccctc tgttgtcaag ccacacggga agggaataaa tccgaattat ctgctgtcat   1020

ggaagcaggt attggaagag ctgcaggaca ttgagagtga ggagaagatt ccaagaacaa   1080

aaaacatgaa aaaaacgagt cagctaaagt gggcacttgg tgagaacatg gcaccagaga   1140

aggtggattt tgatgactgt aaagatataa gcgatttgaa gcaatatgat agtgacgaac   1200

ctgaattaag gtcattttca agttggatcc agaatgagtt caacaaggca tgcgagctga   1260

ccgattcaat ctggatagag ctcgatgaga ttggagaaga tgtggccccg attgaacaca   1320

ttgcaagcat gagaagaaat tacttcacag ctgaggtgtc ccattgcaga gccacagaat   1380
```

atataatgaa gggggtatac attaatactg ctttgcttaa tgcatcctgt gcagcaatgg 1440
atgatttcca actaattccc atgataagca aatgtagaac taaagaggga aggagaaaga 1500
ccaatttgta cggcttcatc gtaaaaggaa gatctcactt aaggaatgac accgatgtgg 1560
taaactttgt gagcatggag ttttccctca ctgacccaag acttgagcca cacaaatggg 1620
agaagtactg tgttcttgag ataggagata tgcttctaag gagtgcaata ggccaagtgt 1680
caaggcccat gttcttgtat gtaaggacaa atggaacctc aaaaattaaa atgaaatggg 1740
gaatggagat gaggcgttgc ctcctccaat cccttcaaca aatagagagc atgattgaag 1800
ctgagtcctc cgtcaaggag aaagacatga caaaagagtt ttttgagaat agatcagaaa 1860
catggcccat tggagagtca ccaaaaggag tggaagaagg ttccattggg aaagtatgca 1920
ggacactatt ggctaagtca gtattcaata gtctgtatgc atctccacaa ttagaaggat 1980
tttcagctga gtcaagaaag ttgctcctca ttgttcaggc tcttagggac aatctggaac 2040
ctgggacctt tgatcttggg gggctatatg aagcaattga ggagtgcctg attaatgatc 2100
cctgggtttt gcttaatgct tcttggttca actccttcct aacacatgca ttgagatagc 2160
tggggcaatg ctactattta ctatccatac tgtccaaaaa a 2201

<210> SEQ ID NO 36
<211> LENGTH: 2301
<212> TYPE: DNA
<213> ORGANISM: Influenza A Virus

<400> SEQUENCE: 36
aatggatgtc aatccgacat tacttttctt aaaagtgcca gcacaaaatg ctataagcac 60
aacttttcct tatactggtg accctcctta cagccatggg acaggaacag ggtacaccat 120
ggatacagtc aacaggacac atcagtactc agaaagagga agatggacaa aaaataccga 180
aactggagca ccgcaactca acccaattga tgggccacta ccaaaagaca atgaaccaag 240
tggctatgcc caaacagatt gtgtattaga agcaatggct ttccttgagg aatcccatcc 300
tggtattttt gaaaactctt gtattgaaac aatggaggtt gttcagcaaa caagggtgga 360
caaactgaca caaggcagac agacctatga ctggactcta aataggaacc agcctgctgc 420
cacagcattg gccaacacta tagaagtgtt cagatcaaac ggcctcatag caaatgaatc 480
tgggaggcta atagacttcc ttaaagatgt aatggagtcg atggacagag acgaagtaga 540
gatcacaact cattttcaaa gaaagaggag agtgagagac aatgtaacta aaaaaatggt 600
gacccaaaga acaataggca aaaagaaaca taaattagac aaaagaagtt acctaattag 660
ggcattaacc ctgaacacaa tgaccaaaga tgctgagagg gggaaactaa aacgcagagc 720
aattgcaacc ccaggaatgc aaataagggg gtttgtatac tttgttgaga cactggcaag 780
aagcatatgt gaaaagcttg aacaatcagg gttgccagtt ggaggaaatg aaaagaaagc 840
aaagttagca aatgttgtaa ggaagatgat gaccaactcc caggacactg aaatttcttt 900
caccatcact ggagataaca caaaatggaa cgaaaatcaa aaccctagaa tgttcttggc 960
catgatcaca tatataacca aaaatcagcc tgaatggttc agaaatattc taagtattgc 1020
tccaataatg ttttcaaaca aaatggcgag actaggtaag ggtacatgt ttgaaagcaa 1080
gagtatgaaa ctgagaactc aaatacctgc agagatgcta gccaacatag atttgaaata 1140
tttcaatgat tcaactaaaa agaaaattga aaaaatccgg ccattattaa tagatggaac 1200
tgcatcattg agtcctggaa tgatgatggg catgttcaat atgttaagca ccgtcttggg 1260

```
cgtctccatt ctgaatcttg ggcaaaagag atacaccaag actacttact ggtgggatgg   1320

tcttcaatcg tctgatgatt ttgctctgat tgtgaatgca cccaactatg caggaattca   1380

agctggagtt gacaggtttt atcgaacctg taagctgctc ggaattaata tgagcaaaaa   1440

gaagtcttac ataaacagaa caggtacctt tgagttcacg agctttttct atcgttatgg   1500

gtttgttgcc aatttcagca tggagcttcc tagttttggg gtgtctgggg tcaatgaatc   1560

tgcagacatg agtattggag tcactgtcat caaaaacaat atgataaaca atgaccttgg   1620

cccagcaact gctcaaatgg cccttcagtt atttataaaa gattacaggt acacgtatcg   1680

atgccacaga ggtgacacac aaatacaaac ccggagatca tttgagataa agaaactatg   1740

ggaccaaacc cgctccaaag ctgggctgtt ggtctctgat ggaggcccca atttatataa   1800

cattagaaat ctccatattc ctgaagtctg cttgaaatgg gagttgatgg atgaggatta   1860

ccaggggcgt ttatgcaacc cattgaaccc gtttgtcagt cataaagaga ttgaatcagt   1920

gaacaatgca gtgatgatgc cggcacatgg tccagccaaa aatatggagt atgacgctgt   1980

tgcaacaaca cactcctggg ttcccaaaag gaatcgatcc attttgaata cgagccaaag   2040

ggggatactt gaggatgagc aaatgtatca gaggtgctgc aatttatttg aaaaattctt   2100

cccaagtagc tcatacagaa gaccagttgg aatatccagt atggtagagg ctatggtttc   2160

cagagcccga attgatgcac ggattgattt cgaatctgga aggataaaaa aagaggaatt   2220

cgctgagatc atgaagacct gttccaccat tgaagacctc agacggcaaa aatagggaat   2280

ttggcttgtc cttcatgaaa a                                             2301
```

```
<210> SEQ ID NO 37
<211> LENGTH: 1527
<212> TYPE: DNA
<213> ORGANISM: Influenza A Virus

<400> SEQUENCE: 37

atcactcact gagtgacatc aaagtcatgg cgtcccaagg caccaaacgg tcttacgaac     60

agatggagac tgatggggaa cgccagaatg caactgaaat cagagcatcc gtcggaagaa    120

tgattggtgg aattgggcga ttctacatcc aaatgtgcac cgagcttaaa ctcaatgatt    180

atgagggacg actgatccag aacagcttga caatagagag aatggtgctc tctgcttttg    240

atgagaggag gaataaatat ctggaagaac atcccagcgc ggggaaagat cctaagaaaa    300

ctggaggacc catatacaag agagtagatg gaaagtgggt gagggaactc gtcctttatg    360

acaaagaaga aataaggcgg atttggcgcc aagccaacaa tggtgatgat gcaacggctg    420

gtttgactca cattatgatc tggcattcta atttgaatga tacaacttac cagaggacaa    480

gagctcttgt ccgcaccgga atggatccca ggatgtgctc tttgatgcaa ggttcaactc    540

tccctagaag atctggagca gcaggcgctg cagtcaaagg agttgggaca atggtgttgg    600

agttaatcag gatgatcaaa cgtgggatca atgaccgaaa cttctggagg ggtgagaatg    660

gaagaaaaac aaggattgct tatgagagaa tgtgcaacat tctcaaagga aaatttcaaa    720

cagctgcaca aaaagcaatg atggatcaag tgagagaaag ccggaaccca ggaaatgctg    780

agatcgaaga tctcactttt ctggcacggt ctgcactcat attaagaggg tcagttgctc    840

acaagtcttg cctgcctgcc tgtgtgtatg gaccagccgt agccagtggg tacgacttcg    900

aaaaagaggg atactctttg gtaggggtag acccttttaa actgcttcaa accagtcagg    960

tatacagcct aatcagacca aacgagaatc ccgcacacaa gagtcagttg gtgtggatgg   1020

catgcaattc tgctgcattt gaagatctaa gagtgtcaag cttcatcaga gggacaagag   1080
```

tacttccaag ggggaagctc tccactagag gagtacaaat tgcttcaaat gaaaacatgg 1140
atgctattgt atcaagtact cttgaactga gaagcagata ctgggccata agaaccagaa 1200
gtggagggaa cactaatcaa caaagggcct ctgcgggcca aatcagcaca caacctacgt 1260
tttctgtgca gagaaacctc ccatttgaca aaacaaccat catggcagca ttcactggga 1320
atacggaggg aagaacatca gacatgaggg cagaaatcat aaagatgatg gaaagtgcaa 1380
gaccagaaga agtgtccttc caggggcggg gagtctttga gctctcggac gaaagggcaa 1440
cgaacccgat cgtgccctcc tttgacatga gtaatgaagg atcttatttc ttcggagaca 1500
atgcagagga gtacgacaat taatgaa 1527

<210> SEQ ID NO 38
<211> LENGTH: 984
<212> TYPE: DNA
<213> ORGANISM: Influenza A Virus

<400> SEQUENCE: 38
gatgagtctt ctaaccgagg tcgaaacgta cgttctctct atcgtcccgt caggccccct 60
caaagccgag atcgcacaga gacttgaaaa tgtctttgct ggaaagaata ccgatcttga 120
ggctctcatg gaatggctaa agacaagacc aatcctgtca cctctgacta aggggatttt 180
aggatttgtg ttcacgctca ccgtgcccag tgagcgagga ctgcagcgta gacgctttgt 240
ccaaaatgcc cttaatggga atggggatcc aaataatatg gacagagcag ttaaactgta 300
tcgaaagctt aagagggaga taacattcca tggggccaaa gaaatagcac tcagttattc 360
tgctggtgca cttgccagtt gtatgggact catatacaac aggatggggg ctgtgaccac 420
cgaatcagca tttggcctta tatgcgcaac ctgtgaacag attgccgact cccagcataa 480
gtctcatagg caaatggtaa caacaaccaa cccattaata agacatgaga acagaatggt 540
tctggccagc actacagcta aggctatgga gcaaatggct ggatcgagtg aacaagcagc 600
tgaggccatg gaggttgcta gtcaggccag gcagatggtg caggcaatga gagccattgg 660
gactcatcct agctctagca ctggtctgaa aaatgatctc cttgaaaatt tgcaggccta 720
tcagaaacga atgggggtgc agatgcaacg attcaagtga tcctcttgtt gttgccgcaa 780
gtataattgg gattgtgcac ctgatattgt ggattattga tcgccttttt tccaaaagca 840
tttatcgtat ctttaaacac ggtttaaaaa gagggccttc tacggaagga gtaccagagt 900
ctatgaggga agaatatcga gaggaacagc agaatgctgt ggatgctgac gatggtcatt 960
ttgtcagcat agagctagag taaa 984

<210> SEQ ID NO 39
<211> LENGTH: 844
<212> TYPE: DNA
<213> ORGANISM: Influenza A Virus

<400> SEQUENCE: 39
atggattccc acactgtgtc aagctttcag gtagattgct tcctttggca tgtccgcaaa 60
caagttgcag accaagatct aggcgatgcc ccattccttg atcggcttcg ccgagatcag 120
aagtctctaa agggaagagg cagcactctc ggtctgaaca tcgaaacagc cacttgtgtt 180
ggaaagcaaa tagtagagag gattctgaaa gaagaatccg atgaggcatt taaaatgacc 240
atggcctccg cacttgcttc gcggtaccta actgacatga ctattgaaga aatgtcaagg 300
gactggttca tgctcatgcc caagcagaaa gtggctggcc ctctttgtgt cagaatggac 360

-continued

```
caggcgataa tggataagaa catcatactg aaagcgaatt tcagtgtgat ttttgaccgg    420

ttggagaatc tgacattact aagggctttc accgaagagg gagcaattgt tggcgaaatt    480

tcaccattgc cttctcttcc aggacatact aatgaggatg tcaaaaatgc aattggggtc    540

ctcatcgggg gacttgaatg gaatgataac acagttcgag tctctgaaac tctacagaga    600

ttcgcttgga gaagcagtaa tgagactggg ggacctccat tcactccaac acagaaacgg    660

aaaatggcgg gaacaattag gtcagaagtt tgaagaaata agatggctga ttgaagaagt    720

gaggcataaa ttgaagacga cagagaatag ttttgagcaa ataacattta tgcaagcatt    780

acagctattg tttgaagtgg aacaagagat tagaacgttt tcgtttcagc ttatttaatg    840

ataa                                                                 844
```

<210> SEQ ID NO 40
<211> LENGTH: 1728
<212> TYPE: DNA
<213> ORGANISM: Influenza A Virus

<400> SEQUENCE: 40

```
ccaaaatgaa agcaaaacta ctggtcctgt tatgtacatt tacagctaca tatgcagaca     60

caatatgtat aggctaccat gccaacaact caaccgacac tgttgacaca gtacttgaga    120

agaatgtgac agtgacacac tctgtcaacc tacttgagga cagtcacaat ggaaaactat    180

gtctactaaa aggaatagcc ccactacaat tgggtaattg cagcgttgcc ggatggatct    240

taggaaaccc agaatgcgaa ttactgattt ccaaggaatc atggtcctac attgtagaaa    300

caccaaatcc tgagaatgga acatgttacc cagggtattt cgccgactat gaggaactga    360

gggagcaatt gagttcagta tcttcatttg agagattcga aatattcccc aaagaaagct    420

catggcccaa ccacaccgta accggagtat cagcatcatg ctcccataat gggaaaagca    480

gtttttacag aaatttgcta tggctgacgg ggaagaatgg tttgtaccca aacctgagca    540

agtcctatgt aaacaacaaa gagaaagaag tccttgtact atggggtgtt catcacccgc    600

ctaacatagg gaaccaaagg gccctctatc atacagaaaa tgcttatgtc tctgtagtgt    660

cttcacatta tagcagaaga ttcaccccag aaatagccaa aagacccaaa gtaagagatc    720

aggaaggaag aatcaactac tactggactc tgctggaacc tggggataca ataatatttg    780

aggcaaatgg aaatctaata gcgccatggt atgcttttgc actgagtaga ggctttggat    840

caggaatcat cacctcaaat gcaccaatgg atgaatgtga tgcgaagtgt caaacacctc    900

agggagctat aaacagcagt cttcctttcc agaatgtaca cccagtcaca ataggagagt    960

gtccaaagta tgtcaggagt gcaaaattaa ggatggttac aggactaagg aacatcccat   1020

ccattcaatc cagaggtttg tttggagcca ttgccggttt cattgaaggg gggtggactg   1080

gaatggtaga tgggtggtat ggttatcatc atcagaatga gcaaggatct ggctatgctg   1140

cagatcaaaa aagtacacaa aatgccatta acgggattac aaacaaggtg aattctgtaa   1200

ttgagaaaat gaacactcaa ttcacagctg tgggcaaaga attcaacaaa ttggaaagaa   1260

ggatggaaaa cttaaataaa aaagttgatg atgggtttct agacatttgg acatataatg   1320

cagaattgtt ggttctactg gaaaatgaaa ggactttgga tttccatgac tccaatgtga   1380

agaatctgta tgagaaagta aaaagccaat taaagaataa tgccaaagaa ataggaaacg   1440

ggtgttttga attctatcac aagtgtaaca atgaatgcat ggagagtgtg aaaaatggaa   1500

cttatgacta tccaaaatat tccgaagaat caaagttaaa cagggagaaa attgatggag   1560

tgaaattgga atcaatggga gtctatcaga ttctggcgat ctactcaact gtcgccagtt   1620
```

-continued ccctggttct tttggtctcc ctgggggcaa tcagcttctg gatgtgttcc aatgggtctt 1680
tgcagtgtag aatatgcatc tgagaccaga atttcagaaa tataagaa 1728

<210> SEQ ID NO 41
<211> LENGTH: 1414
<212> TYPE: DNA
<213> ORGANISM: Influenza A Virus

<400> SEQUENCE: 41
aatgaatcca aatcaaaaaa taataaccat tggatcaatc agtatagcaa tcggaataat 60
tagtctaatg ttgcaaatag gaaatattat ttcaatatgg gctagtcact caatccaaac 120
tggaagtcaa aaccacactg gagtatgcaa ccaaagaatc atcacatatg aaaacagcac 180
ctgggtgaat cacacatatg ttaatattaa caacactaat gttgttgctg gaaaggacaa 240
aacttcagtg acattggccg gcaattcatc tctttgttct atcagtggat gggctatata 300
cacaaaagac aacagcataa gaattggctc caaaggagat gtttttgtca taagagaacc 360
tttcatatca tgttctcact tggaatgcag aacctttttt ctgacccaag gtgctctatt 420
aaatgacaaa cattcaaatg ggaccgttaa ggacagaagt ccttataggg ccttaatgag 480
ctgtcctcta ggtgaagctc cgtccccata caattcaaag tttgaatcag ttgcatggtc 540
agcaagcgca tgccatgatg gcatgggctg gttaacaatc ggaatttctg gtccagacaa 600
tggagctgtg gctgtactaa aatacaacgg cataataact gaaaccataa aaagttggaa 660
aaagcgaata ttaagaacac aagagtctga atgtgtctgt gtgaacgggt catgtttcac 720
cataatgacc gatggcccga gtaatggggc cgcctcgtac aaaatcttca agatcgaaaa 780
ggggaaggtt actaaatcaa tagagttgaa tgcacccaat tttcattatg aggaatgttc 840
ctgttaccca gacactggca cagtgatgtg tgtatgcagg gacaactggc atggttcaaa 900
tcgaccttgg gtgtctttta atcaaaacct ggattatcaa ataggataca tctgcagtgg 960
ggtgttcggt gacaatccgc gtcccaaaga tggagagggc agctgtaatc cagtgactgt 1020
tgatggagca gacggagtaa aggggttttc atacaaatat ggtaatggtg tttggatagg 1080
aaggactaaa agtaacagac ttagaaaggg gtttgagatg atttgggatc ctaatggatg 1140
gacagatacc gacagtgatt tctcagtgaa acaggatgtt gtggcaataa ctgattggtc 1200
agggtacagc ggaagtttcg ttcaacatcc tgagttaaca ggattggact gtataagacc 1260
ttgcttctgg gttgagttag tcagaggact gcctagagaa aatacaacaa tctggactag 1320
tgggagcagc atttcttttt gtggcgtaaa tagtgatact gcaaactggt cttggccaga 1380
cggtgctgag ttgccgttca ccattgacaa gtag 1414

<210> SEQ ID NO 42
<211> LENGTH: 2220
<212> TYPE: DNA
<213> ORGANISM: Influenza A Virus

<400> SEQUENCE: 42
agcgaaagca ggtactgatt cgaaatggaa gattttgtgc gacaatgctt caatccgatg 60
attgtcgagc ttgcggaaaa ggcaatgaaa gagtatggag aggacctgaa aatcgaaaca 120
aacaaatttg cagcaatatg cacccacttg gaagtatgct tcatgtattc agattttcat 180
ttcatcaatg agcaaggcga atcaataata gtagagcctg aggacccaaa tgcactttta 240
aaacacagat ttgagataat agaggggcga gatcgtacaa tggcatggac agttgtaaac 300

-continued

```
agtatttgca acaccacagg agctgagaaa ccaaagtttc tgccagatct gtatgattac    360

aaagagaata ggttcatcga aattggagtg acaaggagag aagttcacat atactatctg    420

gaaaaggcca acaaaattaa atctgagaag acacatattc acattttctc atttactggc    480

gaagaaatgg ccacaaaggc cgattacact ctcgatgaag aaagcagggc tagaattaaa    540

accagactat tcaccataag gcaagaaatg gcaagcagag gtctttggga ctcctttcgt    600

cagtccgaaa gaggcgaaga gacaattgaa gaaaggtttg aaatcacagg gacaatgcgc    660

aggctcgctg atcaaagcct tccgccgaac ttctcctgca ttgagaattt tagagcctat    720

gtggatggat ttgaaccgaa cggctacatt gagggcaagc tttctcaaat gtccaaagaa    780

gtaaatgcta aaattgagcc tttttgaaa acaacacctc gaccaattag acttccgaat    840

gggcctcctt gttttcagcg gtcaaaattc ctgctgatgg attctttaaa attaagcatt    900

gaggatccaa atcatgaagg ggagggaata ccactatatg atgcaatcaa gtgtatgaga    960

acattctttg gatggaaaga acccactgtt gtcaagccac acgagaaggg aataaatccg   1020

aattatctgc tgtcgtggaa gcaggtgttg gaagagctgc aggacattga gagtgaggag   1080

aagattccaa gaacaaaaaa catgaaaaaa acgagtcagt taaagtgggc acttggtgag   1140

aacatggcac cagagaaggt ggattttgat gactgtaaag atataagcga tttgaagcaa   1200

tatgatagtg acgaacctga attaaggtca ttttcaagtt ggatccagaa tgagttcaac   1260

aaggcatgcg agctgaccga ttcaatctgg atagagctcg atgagattgg agaagatgtg   1320

gccccgattg aacacattgc aagcatgaga agaaattact tcacagctga ggtgtcccat   1380

tgcagagcca ctgaatatat aatgaaaggg gtatacatta atactgcttt gcttaatgca   1440

tcctgtgcag caatggatga tttccaacta attcctatga taagcaaatg tagaactaaa   1500

gagggaagga gaaagaccaa tttgtacggc ttcatcataa aaggaagatc tcacttaagg   1560

aatgataccg atgtggtaaa ctttgtgagc atggagtttt ccctcactga cccaagactt   1620

gagccacaca aatgggagaa gtactgtgtt cttgagatag gagatatgct tctaaggagt   1680

gcaataggcc aagtgtcaag gcccatgttc ttgtatgtaa gaacaaatgg aacctcaaaa   1740

attaaaatga aatggggaat ggagatgagg cgttgcctcc tccaatccct ccaacaaata   1800

gagagcatga ttgaagctga gtcctctgtc aaggagaaag acatgacaaa agagtttttt   1860

gagaatagat cagaaacatg gcccattgga gagtcaccaa aaggagtgga agaaggttcc   1920

attgggaaag tatgcaggac actattggct aaatcagtat tcaatagtct gtatgcatct   1980

ccacaattag aaggattttc agctgagtca agaaagttgc tccttattgt tcaggctctt   2040

agggacaatc tggaacctgg gacctttgat cttgggggac tatatgaagc aattgaggag   2100

tgcctgatta atgatccctg ggttttgctt aatgcttctt ggttcaactc cttcctaaaa   2160

catgcattga gatagctgag gcaatgctac tatttgttat ccatactgtc caaaaaagta   2220
```

<210> SEQ ID NO 43
<211> LENGTH: 2341
<212> TYPE: DNA
<213> ORGANISM: Influenza A Virus

<400> SEQUENCE: 43

```
agcgaaagca ggcaaaccat ttgaatggat gtcaatccga cattactttt cttaaaagtg     60

ccagcacaaa atgctataag cacaactttt ccttatactg gtgaccctcc ttacagccat    120

ggaacaggaa caggatacac catggataca gtcaacagga cacatcagta ctcagaaaga    180

ggaagatgga cgaaaaatac cgaaactgga gcaccgcaac tcaacccaat tgatgggcca    240
```

-continued

```
ctaccagaag acaatgaacc aagtggctat gcccaaacag attgtgtatt agaggcaatg    300
gctttccttg aagaatccca tcctggtatt tttgaaaact cttgtattga aacaatggag    360
gttgttcagc aaacaagggt ggacaaactg acacaaggca gacaaaccta tgactggact    420
ctaaatagga accagcctgc tgccacagca ttggcaaaca ccatagaagt attcagatca    480
aatggcctca tagcaaatga atctggaagg ctaatagact tccttaaaga tgtaatggag    540
tcgatggaca gagacgaagt agaggtcaca actcattttc aaagaaagag gagagtgaga    600
gacaatgtaa ctaaaaaaat ggtgacccaa agaacaatag gaaaaaagaa acataaatta    660
gacaaaagaa gttacctaat tagggcatta accctgaaca caatgaccaa agatgctgag    720
agggggaaac taaaacgcag agcaattgca accccaggaa tgcaaataag gggGtttgta    780
tactttgttg agacactggc aagaagcata tgtgaaaagc ttgaacaatc agggttgcca    840
gttggaggaa atgagaagaa agcaaagtta gcaaatgttg taaggaagat gatgaccaac    900
tcccaggaca ctgaaatttc ttttaccatc actggagata acacaaaatg gaacgaaaat    960
caaaacccta gaatgttctt ggccatgatc acatatataa ccaaagatca gcctgaatgg   1020
ttcagaaata ttctaagtat tgctccaata atgttttcaa acaaaatggc gagactaggt   1080
agggggtata tgtttgaaag caagagtatg aaactgagaa cccaaatacc tgcagagatg   1140
ctagccaaca tagatttgaa atatttcaat gattcaacta aaaagaaaat tgaaaaaatt   1200
cgaccattat taatagatgg aactgcatca ttgagtcctg gaatgatgat gggcatgttc   1260
aatatgttaa gcaccgtctt gggcgtttcc attctgaatc ttgggcaaaa aagatacacc   1320
aagactactt actggtggga tggtcttcaa tcgtctgatg attttgcttt gattgtgaat   1380
gcacccaatt atgcaggaat tcaagctgga gttgacaggt tttatcgaac ctgtaagctg   1440
ctcggaatta atatgagcaa aaagaagtct tacataaaca gaacaggtac ctttgaattc   1500
acgagctttt tctatcgtta tgggtttgtt gccaatttca gcatggagct tcctagtttt   1560
ggggtgtctg gggtcaatga atctgcagac atgagtattg gagtcactgt catcaaaaac   1620
aatatgataa acaatgacct tggcccagca actgctcaaa tggcccttca gttatttata   1680
aaagattaca ggtacactta tcgatgccac agaggtgaca cacaaataca aacccggaga   1740
tcatttgaaa taaagaaact atgggaccaa acccgctcca aagctgggct gttggtctct   1800
gatggaggcc ccaatttata taacattagg aatctacata ttcctgaagt ctgcttgaaa   1860
tgggagttga tggatgagga ttaccagggg cgtttatgca acccattgaa cccgtttgtc   1920
agccataaag agattgaatc agtgaacaat gcagtgataa tgccggcaca tggtccagcc   1980
aaaaatatgg agtatgacgc tgttgcaaca acacactctt gggtccccaa aagaaatcga   2040
tccattttaa acacgagcca aagagggata cttgaagatg agcaaatgta ccaaaggtgc   2100
tgcaatttat ttgaaaaatt cttcccaagt agctcataca gaagaccagt tggaatatcc   2160
agtatggtag aggctatggt ttcaagagcc cgaattgatg cacggattga tttcgaatct   2220
ggaaggataa agaaagagga attcgctgag atcatgaaga cctgttccac cattgaagac   2280
ctcagacggc aaaaataggg aatttggctt gtccttcatg aaaaaatgcc ttgtttctac   2340
t                                                                   2341
```

<210> SEQ ID NO 44
<211> LENGTH: 2341
<212> TYPE: DNA
<213> ORGANISM: Influenza A Virus

<400> SEQUENCE: 44
agcgaaagca ggtcaattat attcaatatg gaaagaataa aagagctaag gaatctgatg 60
tcacaatctc gcactcgcga gatacttacc aaaactactg tagaccacat ggccataata 120
aagaaataca catcaggaag acaggagaaa aacccatcac ttaggatgaa atggatgatg 180
gcaatgaaat acccaattac agctgataaa aggataacgg aaatgattcc tgaaagaaat 240
gagcaaggac agacactatg gagtaaagtg aatgatgccg gatcagaccg agtgatgata 300
tcacccctag ctgtgacatg gtggaacaga aatggaccag tggcaaacac tatccactat 360
ccaaaaatct acaaaactta ctttgaaaag gttgaaaggt taaaacatgg aacctttggc 420
cctgtacact ttagaaacca agtcaaaata cgccgaagag tcgacataaa tcctggtcat 480
gcagacctca gcgccaagga ggcacaggat gtaattatgg aagttgtttt ccctaatgaa 540
gtgggagcca gaatactaac atcagaatcg caattaacga taactaagga gaaaaaagag 600
gaactccaga attgcaaaat ttcccctttg atggttgcat acatgttaga gagggaactt 660
gtccgcaaaa caagatttct cccggttgca ggtggaacaa gcagtgtgta cattgaagtt 720
ttgcatttaa cacaggggac atgctgggag cagatgtaca ctccaggtgg ggaggtgagg 780
aatgatgatg ttgatcaaag cctaattatt gctgctagga acatagtgag aagagctgca 840
gtatcagcag atccactagc atctttatta gaaatgtgcc atagcacaca gattggtgga 900
acaaggatgg tggatattct caggcaaaat ccaacagaag aacaagctgt ggacatatgc 960
aaagcagcaa tggggctgag aatcagttca tccttcagtt ttggcggatt cacatttaag 1020
agaacaagtg gatcgtcagt caaaagggag gaagaagtgc taacgggcaa tctgcaaaca 1080
ttgaagctaa ctgtgcatga gggatatgaa gaattcacaa tagttgggaa aaaggcaaca 1140
gctatactca gaaaagcaac caggagattg attcaactaa tagtgagtgg aagagacgaa 1200
cagtcaatag tcgaagcaat agttgtagca atggtattct cacaagaaga ttgcatggta 1260
aaagcggtta gaggtgatct gaatttcgtt aatagagcga atcagcggtt gaatcccatg 1320
catcaacttt tgagacattt tcagaaggat gctaaagtac ttttcctaaa ttggggaatt 1380
gaacatattg acaatgtgat gggaatgatt gggatattac ctgatatgac tccaagtacc 1440
gagatgtcaa tgagaggagt gagagtcagc aaaatgggtg tagatgaata ctccaatgct 1500
gaaagggtag tggtaagcat tgaccgtttt ttgagggtcc gggaccaaag aggaaatgta 1560
ttactgtctc cagaggaagt cagtgaaaca caaggaacag agaaactgac aataacttac 1620
tcttcatcat tgatgtggga gattaatggc cctgagtcag tgttgatcaa tacctaccaa 1680
tggatcatca gaaactggga gactgttaaa attcagtggt ctcagaaccc tacaatgcta 1740
tacaataaaa tggaatttga gccatttcaa tctctagtcc ccaaggccat tagaggccaa 1800
tacagtgggt ttgttagaac tctatttcaa caaatgaggg atgtgctcgg gacctttgac 1860
acaactcaga taataaaact tcttcccttt gcagccgctc caccaaagca aagtagaatg 1920
caattctcgt cattaactgt gaatgtgagg ggatcaggaa tgagaatact tgtaaggggt 1980
aattctccag tattcaacta caacaagacc actaagagac tcacaatcct cggaaaggat 2040
gctggcactt taactgaaga cccagatgaa ggcacagctg gagtggaatc tgctgtttta 2100
aggggattcc tcattctagg caaagaagat agaagatatg ggccagcatt aagcatcagt 2160
gaattgagca accttgcgaa aggggagaaa gctaatgtgc taattgggca aggggatgta 2220
gtgttggtaa tgaaacgaaa acgggactct agcatactta ctgacagcca gacagcgacc 2280
aaaagaattc ggatggccat caattaattt cgaataattt aaaaacgacc ttgtttctac 2340
t 2341

<210> SEQ ID NO 45
<211> LENGTH: 1565
<212> TYPE: DNA
<213> ORGANISM: Influenza A Virus

<400> SEQUENCE: 45
agcaaaagca gggtagataa tcactcactg agtgacatca aagtcatggc gtcccaaggc 60
accaaacggt cttacgaaca gatggagact gatggggaac gccagaatgc aactgaaatc 120
agagcatccg tcggaagaat gattggggga attgggcgat tctacatcca aatgtgcacc 180
gagcttaagc tcaatgatta tgagggacga ctgatccaga acagcttaac aatagagaga 240
atggtgcttt ctgcttttga tgagaggaga aataaatatc tggaagaaca tcccagcgca 300
gggaaagatc ctaagaaaac tggaggaccc atatacaaga gagtagatgg aaagtgggtg 360
agggaactcg tcctttatga caaagaagaa ataaggcgga tttggcgcca agccaacaat 420
ggtgatgatg caacagctgg tttgactcac attatgatct ggcattctaa tttgaatgat 480
acaacttacc agaggacaag agctcttgtc cgcaccggaa tggatcccag gatgtgctct 540
ttgatgcaag gttcaactct ccctagaaga tctggagcag caggcgctgc agtcaaagga 600
gttgggacaa tggtattgga gttaatcagg atgatcaaac gtgggatcaa cgaccgaaac 660
ttctggaggg gtgagaatgg gagaaaaaca aggattgctt atgagagaat gtgcaacatt 720
ctcaaaggaa aatttcaaac agctgcacaa aaagcaatga tggatcaagt gagagaaagc 780
cggaacccag gaaatgctga gatcgaagat ctcacttttc tggcacggtc tgcactcata 840
ttgagaggat cagttgctca caagtcttgc ctgcctgctt gtgtgtatgg accagccgta 900
gccagtgggt atgacttcga aaaagaggga tactctttgg tgggagtaga ccctttcaaa 960
ctgcttcaaa ccagtcaggt atacagccta attagaccaa acgagaatcc cgcacacaag 1020
agccagttgg tgtggatggc atgcaattct gctgcatttg aagatctaag agtgtcaagc 1080
ttcatcagag ggacaagagt acttccaagg gggaagctct ccactagagg agtacaaatt 1140
gcttcaaatg aaaacatgga tgctattgtc tcaagtactc ttgaactgag aagcagatac 1200
tgggccataa gaaccagaag tggagggaac accaatcaac aaagggcctc tgcgggccaa 1260
atcagcacac aacctacgtt ttctgtgcag agaaacctcc catttgacaa aacaaccatc 1320
atggcagcat tcactgggaa tacagaggga agaacatcag acatgcgggc agaaatcata 1380
aagatgatgg aaagtgcaag accagaagaa gtgtccttcc agggacgggg agtctttgag 1440
ctctcggacg aaagggcaac gaacccgatc gtgccctcct ttgacatgag taatgaagga 1500
tcttatttct tcggagacaa tgcagaggag tacgacaatt aatgaaaaat acccttgttt 1560
ctact 1565

<210> SEQ ID NO 46
<211> LENGTH: 1027
<212> TYPE: DNA
<213> ORGANISM: Influenza A Virus

<400> SEQUENCE: 46
agcaaaagca ggtagatatt gaaagatgag tcttctaacc gaggtcgaaa cgtacgttct 60
ctctatcgtc ccatcaggcc ccctcaaagc cgagatcgca cagagacttg aagatgtatt 120
tgctggaaag aataccgatc ttgaggctct catggaatgg ctaaagacaa gaccaatcct 180
gtcacctctg actaagggga ttttaggatt tgtgttcacg ctcaccgtgc ccagtgagcg 240
aggactgcag cgtagacgct ttgtccaaaa tgcccttaat gggaatgggg atccaaataa 300
tatggacaag gctgtcaaac tgtatcgaaa gcttaagagg gagataacat tccatggggc 360
caaagaaata gcactcagtt attctgctgg agcacttgcc agttgtatgg gactcatata 420
caacaggatg gggctgtga ccaccgaatc agcatttggc cttatatgtg caacctgtga 480
acagattgcc gactcccagc ataagtctca taggcaaatg gtaacaacaa ccaatccatt 540
aataagacat gagaacagaa tggttctggc cagcactaca gctaaggcta tggagcaaat 600
ggctggatcg agtgaacaag cagctgaggc catggaggtt gctagtcagg ccaggcagat 660
ggtgcaggca atgagagcca ttgggactca tcctagctct agcactggtc tgaaaaatga 720
tctccttgaa aatttgcagg cctatcagaa acgaatgggg gtgcagatgc aacgattcaa 780
gtgatcctct tgttgttgcc gcaagtataa ttgggattgt gcacctgata ttgtggatta 840
ttgatcgcct tttttccaaa agcatttatc gtatttttaa acacggttta aaaagagggc 900
cttctacgga aggagtaccg gagtctatga gggaagaata tcgagaggaa cagcagaatg 960
ctgtggatgc tgacgatggt cattttgtca gcatagagct agagtaaaaa actaccttgt 1020
ttctact 1027

<210> SEQ ID NO 47
<211> LENGTH: 889
<212> TYPE: DNA
<213> ORGANISM: Influenza A Virus

<400> SEQUENCE: 47
agcaaaagca gggtggcaaa gacataatgg attcccacac tgtgtcaagc tttcaggtag 60
attgtttcct ttggcatgtc cgcaaacaag ttgcagacca agatctaggc gatgccccct 120
tccttgatcg gcttcgccga gatcagaagt ctctaaaggg acgaggcaac actctcggtc 180
tgaacatcga aacagccact tgtgttggaa agcaaatagt agagaggatt ctgaaagaag 240
aatccgatga gacatttaga atgaccatgg cctccgcact tgcttcgcgg tacctaactg 300
acatgactgt tgaagaaatg tcaagggact ggttcatgct catgcccaag cagaaagtgg 360
ctggccctct ttgtgtcaga atggaccagg cgataatgga taagaacatc atactgaaag 420
cgaacttcag tgtgattttt gaccggttgg agaatctgac attactaagg gctttcaccg 480
aagagggagc aattgttggc gaaatttcac cattgccttc ttttccagga catactaatg 540
aggatgtcaa aaatgcaatt ggggtcctca tcgggggact tgaatggaat gataacacag 600
ttcgagtctc tgaagctcta cagagattcg cttggagaag cagtaatgag actgggggac 660
ctccattcac tacaacacag aaacggaaaa tggcgggaac aattaggtca gaagtttgaa 720
gaaataagat ggctgattga agaagtgagg cataaattga agacgacaga gagtagtttt 780
gaacaaataa catttatgca agcattacag ctattgtttg aagtggaaca agagattaga 840
acgttctcgt ttcagcttat ttaatgataa aaacaccctt gtttctact 889

<210> SEQ ID NO 48
<211> LENGTH: 1775
<212> TYPE: DNA
<213> ORGANISM: Influenza A Virus

<400> SEQUENCE: 48
agcgaaagca ggggaaaata aaagcaacca aaatgaaagt aaaactactg gttctgttat 60
gtacatttac agctacatat gcagacacaa tatgtatagg ctaccatgcc aacaactcaa 120

-continued ccgacactgt tgacacagta cttgagaaga atgtaacagt gacacactct gtcaacctac 180
ttgaggacag tcacaatgga aaactatgtc tactaaaagg aatagcccca ctacaattgg 240
gtaattgcag cgttgccgga tggatcttag gaaacccaga atgcgaatta ctgatttcca 300
aggaatcatg gtcctacatt gtagaaacac caaatcctga gaatggaaca tgttacccag 360
ggtatttcgc cgactatgag gaactgaggg agcaattgag ttcagtatct tcatttgaaa 420
ggttcgaaat attccccaaa gagagctcat ggcccaacca caccgtaacc ggagtatcag 480
catcatgctc ccataacggg aaaagcagtt tttacagaaa tttgctatgg ctgacgggga 540
agaatggttt gtacccaaac ctgagcaagt cctatgcaaa caacaaagag aaagaagtcc 600
ttgtactatg ggtgttcat cacccgccta acatagggga ccaaagggcc ctctatcata 660
cagaaaatgc ttatgtctct gtagtgtctt cacattatag cagaagattc accccagaaa 720
tagccaaaag acccaaggtg agagaccagg aaggaagaat caactactac tggactctgc 780
tggaacccgg ggatacaata atatttgagg caaatggaaa tctaatagcg ccaaggtatg 840
ctttcgcact gagtagaggc ttgggatcag gaatcatcac ctcaaatgca ccaatggatg 900
aatgtgatgc aaagtgtcaa acacctcagg gagctataaa cagcagtctt cctttccaga 960
atgtacaccc agtcacaata ggagagtgtc caaagtatgt caggagtgca aaattaagga 1020
tggttacagg actaaggaac atcccatcca ttcaatccag aggtttgttt ggagcaattg 1080
ccggtttcat tgaagggggg tggactggaa tggtagatgg ttggtatggt tatcatcatc 1140
agaatgagca aggatctggg tatgctgcag atcaaaaaag cacacaaaat gccattaacg 1200
ggattacaaa caaggtgaat tctgtaattg agaaaatgaa cactcaattc acagctgtgg 1260
gcaaagaatt caacaaattg gaaagaagga tggaaaactt aaataaaaaa gttgatgatg 1320
ggtttctaga catttggacc tataatgcag aattgttggt tctactggaa aatgaaagga 1380
ctttggattt ccatgactcc aacgtgaaga atctgtatga gaaagtaaaa agccaattaa 1440
agaataatgc caaagaaata ggaaacgggt gttttgaatt ctatcacaag tgtaacgatg 1500
aatgcatgga gagtgtgaaa aatggaactt atgactatcc aaaatattcc gaagaatcaa 1560
agttaaacag agagaaaatt gatggagtga aattggaatc aatgggagtc tatcagattc 1620
tggcgatcta ctcaacagtc gccagttccc tggttctttt ggtctccctg gggcaatca 1680 gcttctggat gtgttccaat gggtctttgc agtgtagaat atgcatctaa gaccagaatt 1740
tcagaaatat aaggaaaaac acccttgttt ctact 1775

<210> SEQ ID NO 49
<211> LENGTH: 1462
<212> TYPE: DNA
<213> ORGANISM: Influenza A Virus

<400> SEQUENCE: 49
agcaaaagca ggagtttaaa atgaatccaa atcaaaaaat aataaccatt ggatcaatca 60
gtatagcaat cggaataatt agtctaatgt tgcaaatagg aaatattatt tcaatatggg 120
ctagtcactc aatccaaact ggaagtcaaa accacactgg aatatgcaac caaaaaatca 180
tcacatatga aaacagcacc tgggtgaatc acacatatgt taatattaac aacactaatg 240
ttgttgctgg aaaggacaaa acttcagtga cactggccgg caattcatct ctttgtccta 300
tcagtggatg ggctatatac acaaaagaca acagcataag aattggctcc aaaggagatg 360
tttttgtcat aagagaacct ttcatatcat gttctcactt ggaatgcaga accttttttc 420

-continued

```
tgacccaagg tgctctatta aatgacaaac attcaaatgg aaccgttaag gacagaagtc    480

cttatagggc cttaatgagc tgtcctctag gtgaagcccc gtcaccatac aattcaaagt    540

ttgaatcagt tgcatggtca gcaagcgcat gccatgatgg caagggctgg ttaacaatcg    600

gaatttctgg tccagacaat ggagctgtgg ctgtactaaa atacaacgga ataataactg    660

aaaccataaa aagttgggaa aagcgaatat tgagaacaca agagtctgaa tgtgtttgtg    720

tgaacgggtc atgtttcacc ataatgaccg atggcccgag taatggggcc gcctcgtaca    780

aaatcttcaa gatcgaaaag ggaaggtta ctaaatcaac agagttgaat gcacccaatt     840

ttcattatga ggaatgttcc tgttacccag acactggcac agtgatgtgt gtatgcaggg    900

acaactggca tggttcaaat cgaccttggg tatcttttaa tcaaaacttg gattatcaaa    960

taggatacat ctgcagtgga gtgttcggtg acaatccgcg tcccaaagat gggaagggca   1020

gctgtaatcc agtgactgtt gatggagcag acggagttaa ggggttttca tacaaatatg   1080

gtaatggtgt ttggatagga aggactaaaa gtaacagact tagaaagggg tttgagatga   1140

tttgggatcc taatggatgg acagataccg acagtgattt ctcagtgaaa caggatgttg   1200

tggcaataac tgattggtca gggtacagcg gaagtttcgt ccaacatcct gagttaacag   1260

gattggactg tataagacct tgcttctggg ttgagttagt cagaggactg cctagagaaa   1320

atacaacaat ctggactagt gggagcagca tttctttttg tggcgttgat agtgatactg   1380

caaattggtc ttggccagac ggtgctgagt tgccgttcac cattgacaag tagctcgttg   1440

aaaaaaactc cttgtttcta ct                                            1462
```

<210> SEQ ID NO 50
<211> LENGTH: 566
<212> TYPE: PRT
<213> ORGANISM: Influenza A Virus

<400> SEQUENCE: 50

```
Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Asn His Asn Gly Lys Leu Cys Lys Leu Lys Gly Ile
    50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Lys His Asn
    130                 135                 140

Val Thr Lys Gly Val Thr Ala Ala Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
            180                 185                 190
```

```
Leu Trp Gly Val His His Pro Ser Asn Ile Glu Asp Gln Lys Thr Ile
        195                 200                 205

Tyr Arg Lys Glu Asn Ala Tyr Val Ser Val Val Ser Ser His Tyr Asn
    210                 215                 220

Arg Arg Phe Thr Pro Glu Ile Ala Lys Arg Pro Lys Val Arg Asn Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Ile Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 51
<211> LENGTH: 470
<212> TYPE: PRT
<213> ORGANISM: Influenza A Virus
```

-continued

<400> SEQUENCE: 51

Met Asn Pro Asn Gln Lys Ile Ile Thr Ile Gly Ser Ile Cys Met Thr
1 5 10 15

Ile Gly Ile Ile Ser Leu Ile Leu Gln Ile Gly Asn Ile Ile Ser Ile
20 25 30

Trp Val Ser His Ser Ile Gln Thr Gly Ser Gln Asn His Thr Gly Ile
35 40 45

Cys Asn Gln Arg Ile Ile Thr Tyr Glu Asn Ser Thr Trp Val Asn Gln
50 55 60

Thr Tyr Val Asn Ile Asn Asn Thr Asn Val Val Ala Gly Lys Asp Thr
65 70 75 80

Thr Ser Val Thr Leu Ala Gly Asn Ser Ser Leu Cys Pro Ile Arg Gly
85 90 95

Trp Ala Ile Tyr Ser Lys Asp Asn Ser Ile Arg Ile Gly Ser Lys Gly
100 105 110

Asp Val Phe Val Ile Arg Glu Pro Phe Ile Ser Cys Ser His Leu Glu
115 120 125

Cys Arg Thr Phe Phe Leu Thr Gln Gly Ala Leu Leu Asn Asp Lys His
130 135 140

Ser Asn Gly Thr Val Lys Asp Arg Ser Pro Tyr Arg Ala Leu Met Ser
145 150 155 160

Cys Pro Ile Gly Glu Ala Pro Ser Pro Tyr Asn Ser Arg Phe Glu Ser
165 170 175

Val Ala Trp Ser Ala Ser Ala Cys His Asp Gly Met Gly Trp Leu Thr
180 185 190

Ile Gly Ile Ser Gly Pro Asp Asp Gly Ala Val Ala Val Leu Lys Tyr
195 200 205

Asn Gly Ile Ile Thr Glu Thr Ile Lys Ser Trp Arg Lys Arg Ile Leu
210 215 220

Arg Thr Gln Glu Ser Glu Cys Val Cys Val Asn Gly Ser Cys Phe Thr
225 230 235 240

Ile Met Thr Asp Gly Pro Ser Asn Gly Pro Ala Ser Tyr Arg Ile Phe
245 250 255

Lys Ile Glu Lys Gly Lys Ile Thr Lys Ser Ile Glu Leu Asp Ala Pro
260 265 270

Asn Ser His Tyr Glu Glu Cys Ser Cys Tyr Pro Asp Thr Gly Thr Val
275 280 285

Met Cys Val Cys Arg Asp Asn Trp His Gly Ser Asn Arg Pro Trp Val
290 295 300

Ser Phe Asn Gln Asn Leu Asp Tyr Gln Ile Gly Tyr Ile Cys Ser Gly
305 310 315 320

Val Phe Gly Asp Asn Pro Arg Pro Lys Asp Gly Lys Gly Ser Cys Asp
325 330 335

Pro Val Thr Val Asp Gly Ala Asp Gly Val Lys Gly Phe Ser Tyr Arg
340 345 350

Tyr Gly Asn Gly Val Trp Ile Gly Arg Thr Lys Ser Asn Ser Ser Arg
355 360 365

Lys Gly Phe Glu Met Ile Trp Asp Pro Asn Gly Trp Thr Asp Thr Asp
370 375 380

Ser Asn Phe Leu Val Lys Gln Asp Val Val Ala Met Thr Asp Trp Ser
385 390 395 400

Gly Tyr Ser Gly Ser Phe Val Gln His Pro Glu Leu Thr Gly Leu Asp
405 410 415

Cys Met Arg Pro Cys Phe Trp Val Glu Leu Val Arg Gly Arg Pro Arg
420 425 430

Glu Gly Thr Thr Val Trp Thr Ser Gly Ser Ser Ile Ser Phe Cys Gly
435 440 445

Val Asn Ser Asp Thr Ala Asn Trp Ser Trp Pro Asp Gly Ala Glu Leu
450 455 460

Pro Phe Thr Ile Asp Lys
465 470

<210> SEQ ID NO 52
<211> LENGTH: 469
<212> TYPE: PRT
<213> ORGANISM: Influenza A Virus

<400> SEQUENCE: 52

Met Asn Pro Asn Gln Lys Ile Ile Thr Ile Gly Ser Val Cys Met Thr
1 5 10 15

Ile Gly Met Ala Asn Leu Ile Leu Gln Ile Gly Asn Ile Ile Ser Ile
20 25 30

Trp Ile Ser His Ser Ile Gln Leu Gly Asn Gln Asn Gln Ile Glu Thr
35 40 45

Cys Asn Gln Ser Val Ile Thr Tyr Glu Asn Asn Thr Trp Val Asn Gln
50 55 60

Thr Tyr Val Asn Ile Ser Asn Thr Asn Phe Ala Ala Gly Gln Ser Val
65 70 75 80

Val Ser Val Lys Leu Ala Gly Asn Ser Ser Leu Cys Pro Val Ser Gly
85 90 95

Trp Ala Ile Tyr Ser Lys Asp Asn Ser Val Arg Ile Gly Ser Lys Gly
100 105 110

Asp Val Phe Val Ile Arg Glu Pro Phe Ile Ser Cys Ser Pro Leu Glu
115 120 125

Cys Arg Thr Phe Phe Leu Thr Gln Gly Ala Leu Leu Asn Asp Lys His
130 135 140

Ser Asn Gly Thr Ile Lys Asp Arg Ser Pro Tyr Arg Thr Leu Met Ser
145 150 155 160

Cys Pro Ile Gly Glu Val Pro Ser Pro Tyr Asn Ser Arg Phe Glu Ser
165 170 175

Val Ala Trp Ser Ala Ser Ala Cys His Asp Gly Ile Asn Trp Leu Thr
180 185 190

Ile Gly Ile Ser Gly Pro Asp Asn Gly Ala Val Ala Val Leu Lys Tyr
195 200 205

Asn Gly Ile Ile Thr Asp Thr Ile Lys Ser Trp Arg Asn Asn Ile Leu
210 215 220

Arg Thr Gln Glu Ser Glu Cys Ala Cys Val Asn Gly Ser Cys Phe Thr
225 230 235 240

Val Met Thr Asp Gly Pro Ser Asn Gly Gln Ala Ser Tyr Lys Ile Phe
245 250 255

Arg Ile Glu Lys Gly Lys Ile Val Lys Ser Val Glu Met Asn Ala Pro
260 265 270

Asn Tyr His Tyr Glu Glu Cys Ser Cys Tyr Pro Asp Ser Ser Glu Ile
275 280 285

Thr Cys Val Cys Arg Asp Asn Trp His Gly Ser Asn Arg Pro Trp Val
290 295 300

Ser Phe Asn Gln Asn Leu Glu Tyr Gln Ile Gly Tyr Ile Cys Ser Gly 305 310 315 320

Ile Phe Gly Asp Asn Pro Arg Pro Asn Asp Lys Thr Gly Ser Cys Gly
325 330 335

Pro Val Ser Ser Asn Gly Ala Asn Gly Val Lys Gly Phe Ser Phe Lys
340 345 350

Tyr Gly Asn Gly Val Trp Ile Gly Arg Thr Lys Ser Ile Ser Ser Arg
355 360 365

Asn Gly Phe Glu Met Ile Trp Asp Pro Asn Gly Trp Thr Gly Thr Asp
370 375 380

Asn Asn Phe Ser Ile Lys Gln Asp Ile Val Gly Ile Asn Glu Trp Ser
385 390 395 400

Gly Tyr Ser Gly Ser Phe Val Gln His Pro Glu Leu Thr Gly Leu Asp
405 410 415

Cys Ile Arg Pro Cys Phe Trp Val Glu Leu Ile Arg Gly Arg Pro Lys
420 425 430

Glu Asn Thr Ile Trp Thr Ser Gly Ser Ser Ile Ser Phe Cys Gly Val
435 440 445

Asn Ser Asp Thr Val Gly Trp Ser Trp Pro Asp Gly Ala Glu Leu Pro
450 455 460

Phe Thr Ile Asp Lys
465

<210> SEQ ID NO 53
<211> LENGTH: 716
<212> TYPE: PRT
<213> ORGANISM: Influenza A Virus

<400> SEQUENCE: 53

Met Glu Asp Phe Val Arg Gln Cys Phe Asn Pro Met Ile Val Glu Leu
1 5 10 15

Ala Glu Lys Ala Met Lys Glu Tyr Gly Glu Asp Pro Lys Ile Glu Thr
20 25 30

Asn Lys Phe Ala Ala Ile Cys Thr His Leu Glu Val Cys Phe Met Tyr
35 40 45

Ser Asp Phe His Phe Ile Asp Glu Arg Gly Glu Ser Ile Ile Val Glu
50 55 60

Ser Gly Asp Pro Asn Ala Leu Leu Lys His Arg Phe Glu Ile Ile Glu
65 70 75 80

Gly Arg Asp Arg Ile Met Ala Trp Thr Val Val Asn Ser Ile Cys Asn
85 90 95

Thr Thr Gly Val Glu Lys Pro Lys Phe Leu Pro Asp Leu Tyr Asp Tyr
100 105 110

Lys Glu Asn Arg Phe Ile Glu Ile Gly Val Thr Arg Arg Glu Val His
115 120 125

Ile Tyr Tyr Leu Glu Lys Ala Asn Lys Ile Lys Ser Glu Lys Thr His
130 135 140

Ile His Ile Phe Ser Phe Thr Gly Glu Glu Met Ala Thr Lys Ala Asp
145 150 155 160

Tyr Thr Leu Asp Glu Glu Ser Arg Ala Arg Ile Lys Thr Arg Leu Phe
165 170 175

Thr Ile Arg Gln Glu Met Ala Ser Arg Ser Leu Trp Asp Ser Phe Arg
180 185 190

Gln Ser Glu Arg Gly Glu Glu Thr Ile Glu Glu Lys Phe Glu Ile Thr
195 200 205

-continued

```
Gly Thr Met Arg Lys Leu Ala Asp Gln Ser Leu Pro Pro Asn Phe Pro
    210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Lys
                245                 250                 255

Ile Glu Pro Phe Leu Arg Thr Thr Pro Arg Pro Leu Arg Leu Pro Asp
            260                 265                 270

Gly Pro Leu Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Asn Ile Val Lys Pro His Glu Lys Gly Ile Asn Pro Asn Tyr Leu Met
                325                 330                 335

Ala Trp Lys Gln Val Leu Ala Glu Leu Gln Asp Ile Glu Asn Glu Glu
            340                 345                 350

Lys Ile Pro Arg Thr Lys Asn Met Lys Arg Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Pro
385                 390                 395                 400

Arg Ser Leu Ala Ser Trp Val Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Thr Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Arg Gly Val Glu Glu Gly Ser Ile Gly Lys Val Cys Arg Thr Leu
```

```
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Lys
705                 710                 715


<210> SEQ ID NO 54
<211> LENGTH: 757
<212> TYPE: PRT
<213> ORGANISM: Influenza A Virus

<400> SEQUENCE: 54

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Arg Gly Arg Trp Thr Lys Asn Thr Glu Thr Gly Ala Pro
    50                  55                  60

Gln Leu Asn Pro Ile Asp Gly Pro Leu Pro Lys Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Ile Ala Asn Glu Ser
145                 150                 155                 160

Gly Arg Leu Ile Asp Phe Leu Lys Asp Val Met Glu Ser Met Asp Arg
                165                 170                 175

Asp Glu Val Glu Val Thr Thr His Phe Gln Arg Lys Arg Arg Val Arg
            180                 185                 190

Asp Asn Val Thr Lys Lys Met Val Thr Gln Arg Thr Ile Gly Lys Lys
        195                 200                 205

Lys His Lys Leu Asp Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285
```

-continued

Met Met Thr Asn Ser Gln Asp Thr Glu Ile Ser Phe Thr Ile Thr Gly
290 295 300

Asp Asn Thr Lys Trp Asn Glu Asn Gln Asn Pro Arg Met Phe Leu Ala
305 310 315 320

Met Ile Thr Tyr Ile Thr Lys Asn Gln Pro Glu Trp Phe Arg Asn Ile
325 330 335

Leu Ser Ile Ala Pro Ile Met Phe Ser Asn Lys Met Ala Arg Leu Gly
340 345 350

Lys Gly Tyr Met Phe Glu Ser Lys Ser Met Lys Leu Arg Thr Gln Ile
355 360 365

Pro Ala Glu Met Leu Ala Asn Ile Asp Leu Lys Tyr Phe Asn Asp Ser
370 375 380

Thr Lys Arg Lys Ile Glu Lys Ile Arg Pro Leu Leu Ile Asp Gly Thr
385 390 395 400

Ala Ser Leu Ser Pro Gly Met Met Met Gly Met Phe Asn Met Leu Ser
405 410 415

Thr Val Leu Gly Val Ser Ile Leu Asn Leu Gly Gln Lys Arg Tyr Thr
420 425 430

Lys Thr Thr Tyr Trp Trp Asp Gly Leu Gln Ser Ser Asp Asp Phe Ala
435 440 445

Leu Ile Val Asn Ala Pro Asn Tyr Ala Gly Ile Gln Ala Gly Val Asp
450 455 460

Arg Phe Tyr Arg Thr Cys Lys Leu Leu Gly Ile Asn Met Ser Lys Lys
465 470 475 480

Lys Ser Tyr Ile Asn Arg Thr Gly Thr Phe Glu Phe Thr Ser Phe Phe
485 490 495

Tyr Arg Tyr Gly Phe Val Ala Asn Phe Ser Met Glu Leu Pro Ser Phe
500 505 510

Gly Val Ser Gly Val Asn Glu Ser Ala Asp Met Ser Ile Gly Val Thr
515 520 525

Val Ile Lys Asn Asn Met Ile Asn Asn Asp Leu Gly Pro Ala Thr Ala
530 535 540

Gln Met Ala Leu Gln Leu Phe Ile Lys Asp Tyr Arg Tyr Thr Tyr Arg
545 550 555 560

Cys His Arg Gly Asp Thr Gln Ile Gln Thr Arg Arg Ser Phe Glu Ile
565 570 575

Lys Lys Leu Trp Asp Gln Thr Arg Ser Lys Ala Gly Leu Leu Val Ser
580 585 590

Asp Gly Gly Pro Asn Leu Tyr Asn Ile Arg Asn Leu His Ile Pro Glu
595 600 605

Val Cys Leu Lys Trp Glu Leu Met Asp Glu Asp Tyr Gln Gly Arg Leu
610 615 620

Cys Asn Pro Ser Asn Pro Phe Val Ser His Lys Glu Ile Glu Ser Val
625 630 635 640

Asn Asn Ala Val Met Met Pro Ala His Gly Pro Ala Lys Asn Met Glu
645 650 655

Tyr Asp Ala Val Ala Thr Thr His Ser Trp Val Pro Lys Arg Asn Arg
660 665 670

Ser Ile Leu Asn Thr Ser Gln Arg Gly Ile Leu Glu Asp Glu Gln Met
675 680 685

Tyr Gln Arg Cys Cys Asn Leu Phe Glu Lys Phe Phe Pro Ser Ser Ser
690 695 700

Tyr Arg Arg Pro Val Gly Ile Ser Ser Met Val Glu Ala Met Val Ser 705 710 715 720

Arg Ala Arg Ile Asp Ala Arg Ile Asp Phe Glu Ser Gly Arg Ile Lys
725 730 735

Lys Glu Glu Phe Ala Glu Ile Met Lys Thr Cys Ser Thr Ile Glu Asp
740 745 750

Leu Arg Arg Gln Lys
755

<210> SEQ ID NO 55
<211> LENGTH: 759
<212> TYPE: PRT
<213> ORGANISM: Influenza A Virus

<400> SEQUENCE: 55

Met Glu Arg Ile Lys Glu Leu Arg Asn Leu Met Ser Gln Ser Arg Thr
1 5 10 15

Arg Glu Ile Leu Thr Lys Thr Thr Val Asp His Met Ala Ile Ile Lys
20 25 30

Lys Tyr Thr Ser Gly Arg Gln Glu Lys Asn Pro Ser Leu Arg Met Lys
35 40 45

Trp Met Met Ala Met Lys Tyr Pro Ile Thr Ala Asp Lys Arg Ile Thr
50 55 60

Glu Met Ile Pro Glu Arg Asn Glu Gln Gly Gln Thr Leu Trp Ser Lys
65 70 75 80

Val Asn Asp Ala Gly Ser Asp Arg Val Met Ile Ser Pro Leu Ala Val
85 90 95

Thr Trp Trp Asn Arg Asn Gly Pro Val Ala Ser Thr Ile His Tyr Pro
100 105 110

Lys Ile Tyr Lys Thr Tyr Phe Glu Lys Val Glu Arg Leu Lys His Gly
115 120 125

Thr Phe Gly Pro Val His Phe Arg Asn Gln Val Lys Ile Arg Arg Arg
130 135 140

Val Asp Ile Asn Pro Gly His Ala Asp Leu Ser Ala Lys Glu Ala Gln
145 150 155 160

Asp Val Ile Met Glu Val Val Phe Pro Asn Glu Val Gly Ala Arg Ile
165 170 175

Leu Thr Ser Glu Ser Gln Leu Thr Ile Thr Lys Glu Lys Lys Glu Glu
180 185 190

Leu Gln Asn Cys Lys Ile Ser Pro Leu Met Val Ala Tyr Met Leu Glu
195 200 205

Arg Glu Leu Val Arg Lys Thr Arg Phe Leu Pro Val Ala Gly Gly Thr
210 215 220

Ser Ser Val Tyr Ile Glu Val Leu His Leu Thr Gln Gly Thr Cys Trp
225 230 235 240

Glu Gln Met Tyr Thr Pro Gly Gly Glu Val Arg Asn Asp Asp Val Asp
245 250 255

Gln Ser Leu Ile Ile Ala Ala Arg Asn Ile Val Arg Arg Ala Ala Val
260 265 270

Ser Ala Asp Pro Leu Ala Ser Leu Leu Glu Met Cys His Ser Thr Gln
275 280 285

Ile Gly Gly Thr Arg Met Val Asp Ile Leu Arg Gln Asn Pro Thr Glu
290 295 300

Glu Gln Ala Val Asp Ile Cys Lys Ala Ala Met Gly Leu Arg Ile Ser
305 310 315 320

-continued

```
Ser Ser Phe Ser Phe Gly Gly Phe Thr Phe Lys Arg Thr Ser Gly Ser
                325                 330                 335

Ser Val Lys Arg Glu Glu Glu Val Leu Thr Gly Asn Leu Gln Thr Leu
            340                 345                 350

Lys Leu Thr Val His Glu Gly Tyr Glu Glu Phe Thr Met Val Gly Lys
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Val Glu Ala Ile Val Val
385                 390                 395                 400

Ala Met Val Phe Ser Gln Glu Asp Cys Met Val Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Leu Asn
        435                 440                 445

Trp Gly Ile Glu Pro Ile Asp Asn Val Met Gly Met Ile Gly Ile Leu
    450                 455                 460

Pro Asp Met Thr Pro Ser Thr Glu Met Ser Met Arg Gly Val Arg Val
465                 470                 475                 480

Ser Lys Met Gly Val Asp Glu Tyr Ser Asn Ala Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Ile Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Thr Gln Ile Ile Lys Leu Leu Pro Phe Ala Ala Ala
    610                 615                 620

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Thr Thr Lys Arg Leu Thr Val Leu Gly Lys Asp Ala
            660                 665                 670

Gly Thr Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Arg Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
```

```
            740                 745                 750

Arg Ile Arg Met Ala Ile Asn
        755


<210> SEQ ID NO 56
<211> LENGTH: 498
<212> TYPE: PRT
<213> ORGANISM: Influenza A Virus

<400> SEQUENCE: 56

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Ile Gly Gly Ile Gly Arg Phe Tyr Ile Gln Met Cys Thr Glu Leu Lys
        35                  40                  45

Leu Asn Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Lys Arg Val Asp Gly Lys Trp Val Arg Glu Leu Val Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Ile Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Leu Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Ile Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Lys Glu Gly Tyr Ser Leu Val Gly Val Asp Pro Phe
    290                 295                 300

Lys Leu Leu Gln Thr Ser Gln Val Tyr Ser Leu Ile Arg Pro Asn Glu
305                 310                 315                 320

Asn Pro Ala His Lys Ser Gln Leu Val Trp Met Ala Cys Asn Ser Ala
                325                 330                 335

Ala Phe Glu Asp Leu Arg Val Ser Ser Phe Ile Arg Gly Thr Arg Val
            340                 345                 350
```

```
Leu Pro Arg Gly Lys Leu Ser Thr Arg Gly Val Gln Ile Ala Ser Asn
        355                 360                 365

Glu Asn Met Asp Ala Ile Val Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Thr Gln Pro Thr Phe Ser Val Gln Arg
                405                 410                 415

Asn Leu Pro Phe Asp Lys Thr Thr Ile Met Ala Ala Phe Thr Gly Asn
            420                 425                 430

Thr Glu Gly Arg Thr Ser Asp Met Arg Ala Glu Ile Ile Lys Met Met
        435                 440                 445

Glu Ser Ala Arg Pro Glu Glu Val Ser Phe Gln Gly Arg Gly Val Phe
    450                 455                 460

Glu Leu Ser Asp Glu Arg Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn


<210> SEQ ID NO 57
<211> LENGTH: 252
<212> TYPE: PRT
<213> ORGANISM: Influenza A Virus

<400> SEQUENCE: 57

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asn Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Ser Ala Phe
    130                 135                 140

Gly Leu Ile Cys Ala Thr Cys Glu Gln Ile Ala Asp Ser Gln His Lys
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Ala Ile Gly Thr His Pro Ser
    210                 215                 220
```

Ser Ser Thr Gly Leu Lys Asn Asp Leu Leu Glu Asn Leu Gln Ala Tyr
225 230 235 240

Gln Lys Arg Met Gly Val Gln Met Gln Arg Phe Lys
245 250

<210> SEQ ID NO 58
<211> LENGTH: 470
<212> TYPE: PRT
<213> ORGANISM: Influenza A Virus

<400> SEQUENCE: 58

Met Asn Pro Asn Gln Lys Ile Ile Thr Ile Gly Ser Ile Ser Ile Ala
1 5 10 15

Ile Gly Ile Ile Ser Leu Met Leu Gln Ile Gly Asn Ile Ile Ser Ile
20 25 30

Trp Ala Ser His Ser Ile Gln Thr Gly Ser Gln Asn His Thr Gly Val
35 40 45

Cys Asn Gln Arg Ile Ile Thr Tyr Glu Asn Ser Thr Trp Val Asn His
50 55 60

Thr Tyr Val Asn Ile Asn Asn Thr Asn Val Val Ala Gly Lys Asp Lys
65 70 75 80

Thr Ser Val Thr Leu Ala Gly Asn Ser Ser Leu Cys Ser Ile Ser Gly
85 90 95

Trp Ala Ile Tyr Thr Lys Asp Asn Ser Ile Arg Ile Gly Ser Lys Gly
100 105 110

Asp Val Phe Val Ile Arg Glu Pro Phe Ile Ser Cys Ser His Leu Glu
115 120 125

Cys Arg Thr Phe Phe Leu Thr Gln Gly Ala Leu Leu Asn Asp Lys His
130 135 140

Ser Asn Gly Thr Val Lys Asp Arg Ser Pro Tyr Arg Ala Leu Met Ser
145 150 155 160

Cys Pro Leu Gly Glu Ala Pro Ser Pro Tyr Asn Ser Lys Phe Glu Ser
165 170 175

Val Ala Trp Ser Ala Ser Ala Cys His Asp Gly Met Gly Trp Leu Thr
180 185 190

Ile Gly Ile Ser Gly Pro Asp Asn Gly Ala Val Ala Val Leu Lys Tyr
195 200 205

Asn Gly Ile Ile Thr Glu Thr Ile Lys Ser Trp Lys Lys Arg Ile Leu
210 215 220

Arg Thr Gln Glu Ser Glu Cys Val Cys Val Asn Gly Ser Cys Phe Thr
225 230 235 240

Ile Met Thr Asp Gly Pro Ser Asn Gly Ala Ala Ser Tyr Lys Ile Phe
245 250 255

Lys Ile Glu Lys Gly Lys Val Thr Lys Ser Ile Glu Leu Asn Ala Pro
260 265 270

Asn Phe His Tyr Glu Glu Cys Ser Cys Tyr Pro Asp Thr Gly Thr Val
275 280 285

Met Cys Val Cys Arg Asp Asn Trp His Gly Ser Asn Arg Pro Trp Val
290 295 300

Ser Phe Asn Gln Asn Leu Asp Tyr Gln Ile Gly Tyr Ile Cys Ser Gly
305 310 315 320

Val Phe Gly Asp Asn Pro Arg Pro Lys Asp Gly Glu Gly Ser Cys Asn
325 330 335

Pro Val Thr Val Asp Gly Ala Asp Gly Val Lys Gly Phe Ser Tyr Lys
340 345 350

Tyr Gly Asn Gly Val Trp Ile Gly Arg Thr Lys Ser Asn Arg Leu Arg
355 360 365

Lys Gly Phe Glu Met Ile Trp Asp Pro Asn Gly Trp Thr Asp Thr Asp
370 375 380

Ser Asp Phe Ser Val Lys Gln Asp Val Val Ala Ile Thr Asp Trp Ser
385 390 395 400

Gly Tyr Ser Gly Ser Phe Val Gln His Pro Glu Leu Thr Gly Leu Asp
405 410 415

Cys Ile Arg Pro Cys Phe Trp Val Glu Leu Val Arg Gly Leu Pro Arg
420 425 430

Glu Asn Thr Thr Ile Trp Thr Ser Gly Ser Ser Ile Ser Phe Cys Gly
435 440 445

Val Asn Ser Asp Thr Ala Asn Trp Ser Trp Pro Asp Gly Ala Glu Leu
450 455 460

Pro Phe Thr Ile Asp Lys
465 470

<210> SEQ ID NO 59
<211> LENGTH: 716
<212> TYPE: PRT
<213> ORGANISM: Influenza A Virus

<400> SEQUENCE: 59

Met Glu Asp Phe Val Arg Gln Cys Phe Asn Pro Met Ile Val Glu Leu
1 5 10 15

Ala Glu Lys Ala Met Lys Glu Tyr Gly Glu Asp Leu Lys Ile Glu Thr
20 25 30

Asn Lys Phe Ala Ala Ile Cys Thr His Leu Glu Val Cys Phe Met Tyr
35 40 45

Ser Asp Phe His Phe Ile Asn Glu Gln Gly Glu Ser Ile Val Val Glu
50 55 60

Leu Asp Asp Pro Asn Ala Leu Leu Lys His Arg Phe Glu Ile Ile Glu
65 70 75 80

Gly Arg Asp Arg Thr Met Ala Trp Thr Val Val Asn Ser Ile Cys Asn
85 90 95

Thr Thr Gly Ala Gly Lys Pro Lys Phe Leu Pro Asp Leu Tyr Asp Tyr
100 105 110

Lys Glu Asn Arg Phe Ile Glu Ile Gly Val Thr Arg Arg Glu Val His
115 120 125

Ile Tyr Tyr Leu Glu Lys Ala Asn Lys Ile Lys Ser Glu Asn Thr His
130 135 140

Ile His Ile Phe Ser Phe Thr Gly Glu Glu Met Ala Thr Lys Ala Asp
145 150 155 160

Tyr Thr Leu Asp Glu Glu Ser Arg Ala Arg Ile Lys Thr Arg Leu Phe
165 170 175

Thr Ile Arg Gln Glu Met Ala Asn Arg Gly Leu Trp Asp Ser Phe Arg
180 185 190

Gln Ser Glu Arg Gly Glu Glu Thr Ile Glu Glu Lys Phe Glu Ile Thr
195 200 205

Gly Thr Met Arg Arg Leu Ala Asp Gln Ser Leu Pro Pro Asn Phe Ser
210 215 220

Cys Leu Glu Asn Phe Arg Ala Tyr Val Asp Gly Phe Glu Pro Asn Gly
225 230 235 240

Cys Ile Glu Gly Lys Leu Ser Gln Met Ser Lys Glu Val Asn Ala Gln

```
                245                 250                 255

Ile Glu Pro Phe Leu Lys Thr Thr Pro Arg Pro Ile Lys Leu Pro Asn
            260                 265                 270

Gly Pro Pro Cys Tyr Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Tyr Ile Val Lys Pro His Glu Lys Gly Ile Asn Ser Asn Tyr Leu Leu
                325                 330                 335

Ser Trp Lys Gln Val Leu Ser Glu Leu Gln Asp Ile Glu Asn Glu Glu
            340                 345                 350

Lys Ile Pro Arg Thr Lys Asn Met Lys Lys Thr Ser Gln Leu Lys Trp
        355                 360                 365

Ala Leu Gly Glu Asn Met Ala Pro Glu Lys Val Asp Phe Glu Asn Cys
    370                 375                 380

Arg Asp Ile Ser Asp Leu Lys Gln Tyr Asp Ser Asp Glu Pro Glu Leu
385                 390                 395                 400

Arg Ser Leu Ser Ser Trp Ile Gln Asn Glu Phe Asn Lys Ala Cys Glu
                405                 410                 415

Leu Thr Asp Ser Val Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Ser Ala Ile Gly Gln Ile Ser Arg Pro
545                 550                 555                 560

Met Phe Leu Tyr Val Arg Thr Asn Gly Thr Ser Lys Val Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Ala Trp Pro Ile Gly Glu Ser
    610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Val Val Gln Ala Leu
            660                 665                 670
```

```
Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Lys
705                 710                 715


<210> SEQ ID NO 60
<211> LENGTH: 757
<212> TYPE: PRT
<213> ORGANISM: Influenza A Virus

<400> SEQUENCE: 60

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Ala Val Gln Gln Thr Arg Val Asp Arg Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Val Asn Lys Arg Gly Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
```

-continued

```
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Arg Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asn
    450                 455                 460

Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Asp Gln Thr Gln Ser Arg Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asn Tyr Arg Gly Arg Leu
    610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Ile Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Met Lys Ile Cys Ser Thr Ile Glu Glu
            740                 745                 750
```

```
Leu Arg Arg Gln Arg
        755


<210> SEQ ID NO 61
<211> LENGTH: 759
<212> TYPE: PRT
<213> ORGANISM: Influenza A Virus

<400> SEQUENCE: 61

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ser Leu Arg Met Lys
        35                  40                  45

Trp Met Met Ala Met Lys Tyr Pro Ile Thr Ala Asp Lys Arg Ile Thr
    50                  55                  60

Glu Met Val Pro Glu Arg Asn Glu Gln Gly Gln Thr Leu Trp Ser Lys
65                  70                  75                  80

Met Ser Asp Ala Gly Ser Asp Arg Val Met Val Ser Pro Leu Ala Val
                85                  90                  95

Thr Trp Trp Asn Arg Asn Gly Pro Val Thr Ser Thr Val His Tyr Pro
            100                 105                 110

Lys Val Tyr Lys Thr Tyr Phe Asp Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Arg Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Ile Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Thr Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Lys Glu Glu Glu Val Leu Thr Gly Asn Leu Gln Thr Leu
            340                 345                 350

Lys Ile Arg Val His Glu Gly Tyr Glu Glu Phe Thr Met Val Gly Lys
```

```
        355                 360                 365

Arg Ala Thr Ala Ile Leu Arg Lys Ala Thr Arg Arg Leu Val Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu His Ile Asp Ser Val Met Gly Met Val Gly Val Leu
    450                 455                 460

Pro Asp Met Thr Pro Ser Thr Glu Met Ser Met Arg Gly Ile Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Arg Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Ala Val
545                 550                 555                 560

Lys Ile Gln Trp Ser Gln Asn Pro Ala Met Leu Tyr Asn Lys Met Glu
                565                 570                 575

Phe Glu Pro Phe Gln Ser Leu Val Pro Lys Ala Ile Arg Ser Gln Tyr
            580                 585                 590

Ser Gly Phe Val Arg Thr Leu Phe Gln Gln Met Arg Asp Val Leu Gly
        595                 600                 605

Thr Phe Asp Thr Thr Gln Ile Ile Lys Leu Leu Pro Phe Ala Ala Ala
    610                 615                 620

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Thr Thr Lys Arg Leu Thr Ile Leu Gly Lys Asp Ala
            660                 665                 670

Gly Thr Leu Ile Glu Asp Pro Asp Glu Ser Thr Ser Gly Val Glu Ser
        675                 680                 685

Ala Val Leu Arg Gly Phe Leu Ile Ile Gly Lys Glu Asp Arg Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755
```

<210> SEQ ID NO 62

-continued

<211> LENGTH: 498
<212> TYPE: PRT
<213> ORGANISM: Influenza A Virus

<400> SEQUENCE: 62

Met Ala Ser Gln Gly Thr Lys Arg Ser Tyr Glu Gln Met Glu Thr Asp
1 5 10 15

Gly Asp Arg Gln Asn Ala Thr Glu Ile Arg Ala Ser Val Gly Lys Met
20 25 30

Ile Asp Gly Ile Gly Arg Phe Tyr Ile Gln Met Cys Thr Glu Leu Lys
35 40 45

Leu Ser Asp Tyr Glu Gly Arg Leu Ile Gln Asn Ser Leu Thr Ile Glu
50 55 60

Lys Met Val Leu Ser Ala Phe Asp Glu Arg Arg Asn Lys Tyr Leu Glu
65 70 75 80

Glu His Pro Ser Ala Gly Lys Asp Pro Lys Lys Thr Gly Gly Pro Ile
85 90 95

Tyr Arg Arg Val Asp Gly Lys Trp Met Arg Glu Leu Val Leu Tyr Asp
100 105 110

Lys Glu Glu Ile Arg Arg Ile Trp Arg Gln Ala Asn Asn Gly Glu Asp
115 120 125

Ala Thr Ala Gly Leu Thr His Ile Met Ile Trp His Ser Asn Leu Asn
130 135 140

Asp Ala Thr Tyr Gln Arg Thr Arg Ala Leu Val Arg Thr Gly Met Asp
145 150 155 160

Pro Arg Met Cys Ser Leu Met Gln Gly Ser Thr Leu Pro Arg Arg Ser
165 170 175

Gly Ala Ala Gly Ala Ala Val Lys Gly Ile Gly Thr Met Val Met Glu
180 185 190

Leu Ile Arg Met Val Lys Arg Gly Ile Asn Asp Arg Asn Phe Trp Arg
195 200 205

Gly Glu Asn Gly Arg Lys Thr Arg Ser Ala Tyr Glu Arg Met Cys Asn
210 215 220

Ile Leu Lys Gly Lys Phe Gln Thr Ala Ala Gln Arg Ala Met Val Asp
225 230 235 240

Gln Val Arg Glu Ser Arg Asn Pro Gly Asn Ala Glu Ile Glu Asp Leu
245 250 255

Ile Phe Leu Ala Arg Ser Ala Leu Ile Leu Arg Gly Ser Val Ala His
260 265 270

Lys Ser Cys Leu Pro Ala Cys Val Tyr Gly Pro Ala Val Ser Ser Gly
275 280 285

Tyr Asn Phe Glu Lys Glu Gly Tyr Ser Leu Val Gly Ile Asp Pro Phe
290 295 300

Lys Leu Leu Gln Asn Ser Gln Val Tyr Ser Leu Ile Arg Pro Asn Glu
305 310 315 320

Asn Pro Ala His Lys Ser Gln Leu Val Trp Met Ala Cys His Ser Ala
325 330 335

Ala Phe Glu Asp Leu Arg Leu Leu Ser Phe Ile Arg Gly Thr Lys Val
340 345 350

Ser Pro Arg Gly Lys Leu Ser Thr Arg Gly Val Gln Ile Ala Ser Asn
355 360 365

Glu Asn Met Asp Asn Met Gly Ser Gly Thr Leu Glu Leu Arg Ser Gly
370 375 380

Tyr Trp Ala Ile Arg Thr Arg Ser Gly Gly Asn Thr Asn Gln Gln Arg 385 390 395 400

Ala Ser Ala Gly Gln Thr Ser Val Gln Pro Thr Phe Ser Val Gln Arg
405 410 415

Asn Leu Pro Phe Glu Lys Ser Thr Ile Met Ala Ala Phe Thr Gly Asn
420 425 430

Thr Glu Gly Arg Thr Ser Asp Met Arg Ala Glu Ile Ile Arg Met Met
435 440 445

Glu Gly Ala Lys Pro Glu Glu Val Ser Phe Arg Gly Arg Gly Val Phe
450 455 460

Glu Leu Ser Asp Glu Lys Ala Thr Asn Pro Ile Val Pro Ser Phe Asp
465 470 475 480

Met Ser Asn Glu Gly Ser Tyr Phe Phe Gly Asp Asn Ala Glu Glu Tyr
485 490 495

Asp Asn

<210> SEQ ID NO 63
<211> LENGTH: 252
<212> TYPE: PRT
<213> ORGANISM: Influenza A Virus

<400> SEQUENCE: 63

Met Ser Leu Leu Thr Glu Val Glu Thr Tyr Val Leu Ser Ile Val Pro
1 5 10 15

Ser Gly Pro Leu Lys Ala Glu Ile Ala Gln Arg Leu Glu Asp Val Phe
20 25 30

Ala Gly Lys Asn Thr Asp Leu Glu Ala Leu Met Glu Trp Leu Lys Thr
35 40 45

Arg Pro Ile Leu Ser Pro Leu Thr Lys Gly Ile Leu Gly Phe Val Phe
50 55 60

Thr Leu Thr Val Pro Ser Glu Arg Gly Leu Gln Arg Arg Arg Phe Val
65 70 75 80

Gln Asn Ala Leu Asn Gly Asn Gly Asp Pro Asn Asn Met Asp Lys Ala
85 90 95

Val Lys Leu Tyr Arg Lys Leu Lys Arg Glu Ile Thr Phe His Gly Ala
100 105 110

Lys Glu Ile Ala Leu Ser Tyr Ser Ala Gly Ala Leu Ala Ser Cys Met
115 120 125

Gly Leu Ile Tyr Asn Arg Met Gly Ala Val Thr Thr Glu Val Ala Phe
130 135 140

Gly Leu Val Cys Ala Thr Cys Glu Gln Ile Ala Asp Ser Gln His Arg
145 150 155 160

Ser His Arg Gln Met Val Ala Thr Thr Asn Pro Leu Ile Arg His Glu
165 170 175

Asn Arg Met Val Leu Ala Ser Thr Thr Ala Lys Ala Met Glu Gln Met
180 185 190

Ala Gly Ser Ser Glu Gln Ala Ala Glu Ala Met Glu Ile Ala Ser Gln
195 200 205

Ala Arg Gln Met Val Gln Ala Met Arg Ala Ile Gly Thr His Pro Ser
210 215 220

Ser Ser Thr Gly Leu Arg Asp Asp Leu Leu Glu Asn Leu Gln Thr Tyr
225 230 235 240

Gln Lys Arg Met Gly Val Gln Met Gln Arg Phe Lys
245 250

-continued

<210> SEQ ID NO 64
<211> LENGTH: 97
<212> TYPE: PRT
<213> ORGANISM: Influenza A Virus

<400> SEQUENCE: 64

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Asn Ile
            20                  25                  30

Ile Gly Ile Leu His Leu Ile Leu Trp Ile Leu Asp Arg Leu Phe Phe
        35                  40                  45

Lys Cys Val Tyr Arg Leu Phe Lys His Gly Leu Lys Arg Gly Pro Ser
    50                  55                  60

Thr Glu Gly Val Pro Glu Ser Met Arg Glu Glu Tyr Arg Lys Glu Gln
65                  70                  75                  80

Gln Asn Ala Val Asp Ala Asp Asp Ser His Phe Val Ser Ile Glu Leu
                85                  90                  95

Glu

<210> SEQ ID NO 65
<211> LENGTH: 846
<212> TYPE: DNA
<213> ORGANISM: Influenza A Virus

<400> SEQUENCE: 65
aatggattcc aacactgtgt caagtttcca ggtagattgc tttctttggc atatccggaa 60
acaagttgta gaccaagaac tgagtgatgc cccattcctt gatcggcttc gccgagatca 120
gaggtcccta aggggaagag gcaatactct cggtctagac atcaaagcag ccacccatgt 180
tggaaagcaa attgtagaaa agattctgaa agaagaatct gatgaggcac ttaaaatgac 240
catggtctcc acacctgctt cgcgatacat aactgacatg actattgagg aattgtcaag 300
aaactggttc atgctaatgc ccaagcagaa agtggaagga cctctttgca tcagaatgga 360
ccaggcaatc atggagaaaa acatcatgtt gaaagcgaat ttcagtgtga tttctgaccg 420
actagagacc atagtattac taagggcttt caccgaagag ggagcaattg ttggcgaaat 480
ctcaccattg ccttcttttc caggacatac tattgaggat gtcaaaaatg caattggggt 540
cctcatcgga ggacttgaat ggaatgataa cacagttcga gtctctaaaa atctacagag 600
attcgcttgg agaagcagta atgagaatgg gggacctcca cttactccaa aacagaaacg 660
gaaaatggcg agaacagcta ggtcaaaagt ttgaagagat aagatggctg attgaagaag 720
tgagacacag actaaaaaca actgaaaata gctttgaaca aataacattc atgcaagcat 780
tacaactgct gtttgaagtg gaacaggaga taagaacttt ctcatttcag cttatttaat 840
gataaa 846

<210> SEQ ID NO 66
<211> LENGTH: 566
<212> TYPE: PRT
<213> ORGANISM: Influenza A Virus

<400> SEQUENCE: 66

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

-continued

```
His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asp Glu Ser Phe Asn Trp Thr
    130                 135                 140

Gly Val Thr Gln Asn Gly Thr Ser Ser Ser Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
```

```
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565


<210> SEQ ID NO 67
<211> LENGTH: 469
<212> TYPE: PRT
<213> ORGANISM: Influenza A Virus

<400> SEQUENCE: 67

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Lys Asn Ala Thr Ala Ser Phe Ile Tyr Asn
        195                 200                 205

Gly Arg Leu Val Asp Ser Ile Val Ser Trp Ser Lys Glu Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255
```

```
Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Leu Gly Val Arg
        275                 280                 285

Cys Val Cys Arg Asp Asn Trp Lys Gly Ser Asn Arg Pro Ile Val Asp
    290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Lys Val Ile Glu Gly Trp Ser
    370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465
```

<210> SEQ ID NO 68
<211> LENGTH: 716
<212> TYPE: PRT
<213> ORGANISM: Influenza A Virus

<400> SEQUENCE: 68

```
Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asp Glu Arg Gly Glu Ser Ile Ile Val Glu
    50                  55                  60

Ser Gly Asp Pro Asn Ala Leu Leu Lys His Arg Phe Glu Ile Ile Glu
65                  70                  75                  80

Gly Arg Asp Arg Ile Met Ala Trp Thr Val Ile Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160
```

-continued

```
Tyr Thr Leu Asp Glu Glu Ser Arg Ala Arg Ile Lys Thr Arg Leu Phe
                165                 170                 175

Thr Ile Arg Gln Glu Met Ala Ser Lys Ser Leu Trp Asp Ser Phe Arg
            180                 185                 190

Gln Ser Glu Arg Gly Glu Glu Thr Ile Glu Glu Lys Phe Glu Ile Thr
        195                 200                 205

Gly Thr Met Arg Lys Leu Ala Asp Gln Ser Leu Pro Pro Asn Phe Pro
    210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Lys
                245                 250                 255

Ile Glu Pro Phe Leu Arg Thr Thr Pro Arg Pro Leu Arg Leu Pro Asp
            260                 265                 270

Gly Pro Leu Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Asn Ile Val Lys Pro His Glu Lys Gly Ile Asn Pro Asn Tyr Leu Met
                325                 330                 335

Ala Trp Lys Gln Val Leu Ala Glu Leu Gln Asp Ile Glu Asn Glu Glu
            340                 345                 350

Lys Ile Pro Arg Thr Lys Asn Met Lys Arg Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Pro
385                 390                 395                 400

Arg Ser Leu Ala Ser Trp Val Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Thr Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575
```

```
Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Arg Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Lys
705                 710                 715
```

<210> SEQ ID NO 69
<211> LENGTH: 252
<212> TYPE: PRT
<213> ORGANISM: Influenza A Virus

<400> SEQUENCE: 69

```
Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asn Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Ser Ala Phe
    130                 135                 140

Gly Leu Ile Cys Ala Thr Cys Glu Gln Ile Ala Asp Ser Gln His Lys
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Ala Ile Gly Thr His Pro Ser
    210                 215                 220

Ser Ser Thr Gly Leu Lys Asn Asp Leu Leu Glu Asn Leu Gln Ala Tyr
225                 230                 235                 240
```

```
Gln Lys Arg Met Gly Val Gln Met Gln Arg Phe Lys
                245                 250


<210> SEQ ID NO 70
<211> LENGTH: 566
<212> TYPE: PRT
<213> ORGANISM: Influenza A Virus

<400> SEQUENCE: 70

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
```

```
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 71
<211> LENGTH: 2305
<212> TYPE: DNA
<213> ORGANISM: Influenza B Virus

<400> SEQUENCE: 71

agcagaagcg gtgcgtttga tttgtcataa tggatacttt tattacaaga aacttccaga      60

ctacaataat acaaaaggcc aaaaacacaa tggcagaatt tagtgaagat cctgaattgc     120

aaccagcaat gctattcaat atctgcgtcc atctagaggt ttgctatgta ataagtgaca     180

tgaattttct tgacgaagaa ggaaaagcat atacagcatt agaaggacaa gggaaagaac     240

aaaacttgag accacaatat gaagtaattg agggaatgcc aagaaccata gcatggatgg     300

tccagagatc cttagctcaa gagcatggaa tagagactcc caagtatctg gctgatttgt     360

ttgattataa aaccaaaaga tttatagaag ttggaataac aaagggattg gctgatgatt     420

acttttggaa aaagaaagaa aagttgggaa atagcatgga actgatgata ttcagctaca     480

atcaagacta ctcgttaagt aatgaatcct cattggatga ggaagggaaa gggagagtgc     540

taagcagact cacagaactt caggctgaat taagtctgaa aaatttatgg caagttctca     600

taggagaaga agatgttgaa aagggaattg attttaaact tggacaaaca atatctagac     660

taagggatat atctgttcca gctggtttct ccaattttga aggaatgagg agctacatag     720

acaatataga cccaaaagga gcaatagaga gaaatctagc aaggatgtct cccttagtat     780

cagtcacacc taaaaagtta acatgggagg acctaagacc aatagggcct cacatttacg     840

accatgagct accagaagtt ccatataatg cctttcttct aatgtctgat gaactgggat     900
```

-continued tggccaatat gactgaggga aagtccaaaa aaccgaagac attagccaaa gaatgtctag 960
aaaagtactc aacactacgg gatcaaactg acccaatatt aataatgaaa agcgaaaaag 1020
ctaacgaaaa tttcctatgg aagctttgga gagactgtgt aaatacaata agtaatgagg 1080
aaacgagtaa cgagttacag aaaaccaatt atgccaaatg ggccacaggg gatggattaa 1140
cataccagaa aataatgaaa gaagtagcaa tagatgacga aacaatgtgc caagaagagc 1200
ctaaaatccc taacaaatgt agagtggctg cttgggttca aacagagatg aatctattga 1260
gcactctgac aagtaaaaga gctctggacc taccagaaat agggccagac atagcacccg 1320
tggagcatgt aggaagtgaa agaaggaaat actttgttaa tgaaatcaac tactgtaagg 1380
cctctacagt tatgatgaag tatgtgcttt ttcacacttc attgttgaat gaaagcaatg 1440
ccagcatggg aaaatacaaa gtaataccaa taaccaatag agtagtaaat gaaaaaggag 1500
aaagtttcga catgctttac ggtctggcgg ttaaaggaca atctcatctg aggggagata 1560
ctgatgttgt aacagttgta actttcgaat ttagtagtac agatccaaga gtggactcag 1620
gaaagtggcc aaaatatact gtgtttagga ttggctccct atttgtgagt gggagggaaa 1680
aatctgtgta cttgtattgc cgagtgaatg gcacaaataa gatccaaatg aaatggggaa 1740
tggaagctag aagatgtttg cttcaatcaa tgcaacaaat ggaggcaatt gttgaacagg 1800
aatcatcaat acaaggatat gacatgacca aagcctgttt caagggagac agagtaaata 1860
gccccaaaac tttcagtatt ggaactcaag aaggaaaact agtaaaagga tcctttggaa 1920
aagcactaag agtaatattt actaaatgct tgatgcacta tgtatttgga aatgcccaat 1980
tggaggggtt tagtgccgag tctaggagac ttctactgtt gattcaagca ttaaaggaca 2040
gaaagggccc ttgggtgttc gacttagagg gaatgtattc tggaatagaa gaatgtatta 2100
gcaacaaccc ttgggtaata cagagtgtat actggttcaa tgaatggttg ggctttgaaa 2160
aggaggggaa taaagtgttg gaatcagtgg atgaaataat ggatgaataa aaggaaatgg 2220
tactcaattt ggtactattt tgttcattat gtatctaaac atccaataaa aagaaccaag 2280
aatcaaaaat gcacgtgttt ctact 2305

<210> SEQ ID NO 72
<211> LENGTH: 2369
<212> TYPE: DNA
<213> ORGANISM: Influenza B Virus

<400> SEQUENCE: 72
agcagaagcg gagcctttaa gatgaatata aatccttatt ttctcttcat agatgtgccc 60
gtacaggcag caatttcaac aacattccca tacactggtg ttcccccttta ttcccatgga 120 acaggaacag gctacacaat agacaccgtg atcagaacgc atgagtactc aaacaagggg 180
aaacagtaca tttctgatgt tacaggatgc acaatggtag atccaacaaa tggaccatta 240
cccgaagata atgagccgag tgcctatgcg caattagatt gcgttttaga ggctttggat 300
agaatggatg aagaacaccc aggtcttttt caagcagcct cacagaatgc tatggaggcc 360
ctaatggtca caactgtaga caaattaacc caggggagac agacttttga ttggacagta 420
tgcagaaacc aacctgctgc aacggcactg aacacaacaa taacctcttt taggttgaat 480
gatttaaatg gagccgacaa aggtggatta ataccttttt gccaggatat cattgattca 540
ttagaccgac ctgaaatgac tttcttctca gtaaagaata taaagaaaaa attgcctgcc 600
aaaaacagaa agggtttcct cataaagagg ataccaatga aggtaaaaga caaaataacc 660
aaagtggaat acatcaaaag agcattatca ttaaacacaa tgacaaaaga cgctgaaaga 720

-continued ggcaaactga aaagaagagc gattgccact gctggaatac aaatcagagg gtttgtatta 780
gtagttgaaa acttggctaa aaatatatgt gaaaatctag aacaaagtgg tttaccagta 840
ggtggaaacg agaagaaagc caaactgtca aacgcagtgg ccaaaatgct cagtaactgc 900
ccaccaggag ggattagcat gacagtaaca ggagacaata caaaatggaa tgaatgttta 960
aacccaagaa tctttttggc tatgactgaa agaataacca gagacagccc agtttggttc 1020
agggattttt gtagtatagc accggtcctg ttctccaata agatagcaag attggggaaa 1080
gggtttatga taacaagcaa aacaaaaaga ctgaaggctc aaataccttg tcctgatctg 1140
tttagtatac cgttagaaag atataatgaa gaaacaaggg caaaattgaa aaagctaaaa 1200
ccattcttca atgaagaagg aactgcatct ttgtcgcctg ggatgatgat gggaatgttt 1260
aatatgctat ctaccgtgtt gggagtagct gcactaggta tcaagaacat tggaaacaaa 1320
gaatacttat gggatggact gcaatcttct gatgattttg ctctgtttgt taatgcaaag 1380
gatgaagaaa catgtatgga aggaataaac gacttttacc gaacatgtaa attattggga 1440
gtaaacatga gcaaaaagaa aagttactgt aatgagactg gaatgtttga atttacaagc 1500
atgttctaca gagatggatt tgtatctaat tttgcaatgg aactcccttc gtttggggtt 1560
gctggagtaa atgaatcagc agatatggca ataggaatga caataataaa gaacaacatg 1620
atcaacaatg gaatgggtcc ggcaacagca caaacagcca tacagttatt catagctgat 1680
tatagataca cctacaaatg ccacagggga gattccaaag tagaaggaaa gagaatgaaa 1740
atcataaagg agttatggga aaacactaaa ggaagagatg gtctattagt agcagatggt 1800
gggcccaaca tttacaattt gagaaacctg catatcccag aaatagtatt aaagtataat 1860
ctaatggacc ctgaatacaa agggcggtta cttcatcctc aaaatccctt tgtgggacat 1920
ttgtctattg agggcatcaa agaggcagac ataaccccag cacatggtcc agtaaagaaa 1980
atggactacg atgcggtgtc tggaactcat agttggagaa ccaaaagaaa cagatctata 2040
ctaaacactg atcagaggaa catgattctt gaggaacaat gctacgctaa atgttgcaac 2100
ctatttgagg cctgttttaa cagtgcatca tacaggaagc cagtgggtca acatagcatg 2160
cttgaggcta tggcccacag attaagaatg gatgcacgat tagattatga atcagggaga 2220
atgtcaaagg atgattttga gaaagcaatg gctcaccttg gtgagattgg gtacatataa 2280
gcttcgaaga tgtttatggg gttattggtc atcattgaat acatgcgata cacaaatgat 2340
taaaatgaaa aaaggctcgt gtttctact 2369

<210> SEQ ID NO 73
<211> LENGTH: 2396
<212> TYPE: DNA
<213> ORGANISM: Influenza B Virus

<400> SEQUENCE: 73
agcagaagcg gagcgttttc aagatgacat tggccaaaat tgaattgtta aaacaactgc 60
taagggacaa tgaagccaaa acagttttga agcaaacaac ggtagaccaa tataacataa 120
taagaaaatt caatacatca aggattgaaa agaatccttc actaaggatg aagtgggcca 180
tgtgttctaa ttttcccttg gctctaacca agggcgatat ggcaaacaga atccccttgg 240
aatacaaagg gatacaactt aaaacaaatg ctgaagacat aggaaccaaa ggccaaatgt 300
gctcaatagc agcagttact tggtggaata catatggacc aataggagat actgaaggtt 360
tcgaaagggt ctacgaaagc ttttttctca gaaaaatgag acttgacaac gccacttggg 420

```
gccgaataac ttttggccca gttgaaagag tgagaaaaag ggtactgcta aaccctctca    480
ccaaggaaat gcctccggat gaggcgagca atgtgataat ggaaatattg ttccctaaag    540
aagcaggaat accaagagaa tccacttgga tacataggga actgataaaa gaaaaaagag    600
aaaaattgaa aggaacaatg ataactccaa tcgtactggc atacatgctt gaaagagaac    660
tggttgctcg aagaagattc ttgccagtgg caggagcaac atcagctgag ttcatagaaa    720
tgctacactg cttacaaggt gaaaattgga gacaaatata tcacccagga gggaataaat    780
taactgagtc caggtctcaa tcaatgatag tagcttgtag aaaaataatc agaagatcaa    840
tagtcgcttc aaacccactg gagctagctg tagaaattgc aaacaagact gtgatagata    900
ctgaaccttt aaagtcatgt ctggcagcca tagacggagg tgatgtagct tgtgacataa    960
taagagctgc attaggacta aagatcagac aaagacaaag atttggacgg cttgagctaa   1020
aaagaatatc aggaagagga ttcaaaaatg atgaagaaat attaataggg aacggaacaa   1080
tacagaagat tggaatatgg gacggggaag aggagttcca tgtaagatgt ggtgaatgca   1140
ggggaatatt aaaaaagagt aaaatgaaac tggaaaaact actgataaat tcagccaaaa   1200
aggaggatat gagagattta ataatcttat gcatggtatt ttctcaagac actaggatgt   1260
tccaaggagt gagaggagaa ataaattttc ttaatcgagc aggccaactt ttatctccaa   1320
tgtaccaact ccaacgatat tttttgaata gaagcaacga cctttttgat caatgggggt   1380
atgaggaatc acccaaagca agtgaactac atgggataaa tgaatcaatg aatgcatctg   1440
actatacatt gaaagggatt gtagtgacaa gaaatgtaat tgacgacttt agctctattg   1500
aaacagaaaa agtatccata acaaaaaatc ttagtttaat aaaaaggact ggggaagtca   1560
taatgggagc taatgacgtg agtgaattag aatcacaagc acagctgatg ataacatatg   1620
atacacctaa aatgtgggaa atgggaacaa ccaaagaact ggtgcaaaac acttatcaat   1680
gggtgctaaa aaacttggtg acactgaagg ctcagtttct tctaggaaaa gaggacatgt   1740
tccaatggga tgcatttgaa gcatttgaga gcataattcc tcagaagatg gctggtcagt   1800
acagtggatt tgcaagagca gtgctcaaac aaatgagaga ccaggaggtt atgaaaactg   1860
accagttcat aaagttgttg cctttttgtt tctcaccacc aaaattaagg agcaatgggg   1920
agccttatca attcttaaaa cttgtgttga aaggaggagg ggaaaatttc atcgaagtaa   1980
ggaaagggtc ccctctattt tcctataatc cacaaacaga agtcctaact atatgcggca   2040
gaatgatgtc attaaaaggg aaaattgaag atgaagaaag gaatagatca atgggtaatg   2100
cagtattagc aggctttctc gttagtggca agtatgaccc agatcttgga gatttcaaaa   2160
ctattgaaga acttgaaaag ctgaaaccgg gggaaaaggc aaacatctta ctttatcaag   2220
gaaaaccagt taaagtagtt aaaaggaaaa ggtatagtgc tttgtccaat gacatttcac   2280
aaggaattaa gagacaaaga atgacagttg agtctatggg gtgggccttg agctaatata   2340
aatttatcca ttaattcaat gaacgcaatt gagtgaaaaa tgctcgtgtt tctact       2396
```

<210> SEQ ID NO 74
<211> LENGTH: 1844
<212> TYPE: DNA
<213> ORGANISM: Influenza B Virus

<400> SEQUENCE: 74

```
agcagaagca cagcattttc ttgtgaactt caagcaccag taaaagaact gaaaatcaaa     60
atgtccaaca tggatattga cggtataaac actgggacaa ttgacaaaac accggaagaa    120
ataacttctg gaaccagtgg gacaaccaga ccaatcatta gaccagcaac ccttgcccca    180
```

ccaagcaaca aacgaacccg taacccatcc ccggaaagag caaccacaag cagtgaagat 240
gatgtcggaa ggaaaaccca aaagaaacag accccgacag agataaagaa gagcgtctac 300
aacatggtgg tgaaactggg cgaattctat aaccagatga tggtcaaagc tggactcaat 360
gatgacatgg agagaaatct aatccaaaat gcgcatgccg tggaaagaat tctattggct 420
gccactgatg acaagaaaac cgagttccag aagaaaaaga atgccagaga tgtcaaagaa 480
gggaaagaag aaatagatca caacaaaaca ggaggcacct tttacaagat ggtaagagat 540
gataaaacca tctacttcag ccctataaga attacctttt taaaagaaga ggtgaaaaca 600
atgtacaaaa ccaccatggg gagtgatggc ttcagtggac taaatcacat aatgattggg 660
cattcacaga tgaatgatgt ctgtttccaa agatcaaagg cactaaaaag agttggactt 720
gatccttcat taatcagtac ctttgcggga agcacagtcc ccagaagatc aggtgcgact 780
ggtgttgcaa tcaaaggagg tggaacctta gtggctgaag ccattcgatt tataggaaga 840
gcaatggcag acagagggct attgagagac atcaaagcca agactgccta tgaaaagatt 900
cttctgaatc taaaaaacaa atgctctgcg ccccaacaaa aggctctagt tgatcaagtg 960
atcggaagca gaaatccggg gattgcagac attgaagatc taaccctgct tgctcgtagt 1020
atggtcgttg ttaggccctc tgtggcaagc aaagtggtgc ttcccataag catttacgcc 1080
aaaatacctc aactagggtt caatgttgaa gagtactcta tggttgggta cgaagccatg 1140
gctctttaca atatggcaac acctgtgtcc atattaagaa tgggagatga tgcaaaagat 1200
aaatcgcaat tattcttcat gtcttgcttc ggagctgcct atgaagacct gagagttttg 1260
tctgcattaa caggcacaga attcaagcct agatcagcat taaaatgcaa gggtttccat 1320
gttccagcaa aggaacaggt agaaggaatg ggagcagctc tgatgtccat caagctccag 1380
ttttgggctc cgatgaccag atctgggggg aacgaagtag gtggagacgg agggtctggc 1440
caaataagct gcagcccagt gtttgcagtg gaaagaccta ttgctctaag caagcaagct 1500
gtaagaagaa tgctgtcaat gaatattgag ggacgtgatg cagatgtcaa aggaaatcta 1560
ctcaagatga tgaatgactc aatggctaag aaaaccagtg gaaatgcttt cattgggaag 1620
aaaatgtttc aaatatcaga caaaaacaaa accaatccca ttgaaattcc aattaagcag 1680
accatcccca atttcttctt tgggagggac acagcagagg attatgatga cctcgattat 1740
taaggcaaca aaatagacac tatgactgtg attgtttcaa tacgtttgga atgtgggtgt 1800
ttattcttat taaaataaat ataaaaaatg ctgttgtttc tact 1844

<210> SEQ ID NO 75
<211> LENGTH: 1189
<212> TYPE: DNA
<213> ORGANISM: Influenza B Virus

<400> SEQUENCE: 75
agcagaagca cgcactttct taaaatgtcg ctgtttggag acacaattgc ctacctgctt 60
tcattgacag aagatggaga aggcaaagca gaactagcag aaaaattaca ctgttggttt 120
ggtgggaaag aatttgacct agactctgcc ttggaatgga taaaaaacaa aagatgctta 180
actgatatac aaaaagcact aattggtgcc tctatatgct ttttaaaacc caaagaccag 240
gaaagaaaaa gaagattcat cacagagccc ttatcaggaa tgggaacaac agcaacaaaa 300
aagaaaggcc tgattctggc tgagagaaaa atgagaagat gtgtgagctt tcatgaagca 360
tttgaaatag cagaaggcca tgaaagctca gcgctactat actgtctcat ggtcatgtac 420
ctgaatcctg gaaattattc aatgcaagta aaactaggaa cgctctgtgc tttatgcgag 480
aaacaagcat cacattcaca cagggctcat agcagagcag cgagatcttc agtgcctgga 540
gtgagacgag aaatgcagat ggtctcagct atgaacacag caaaaacaat gaatggaatg 600
ggaaaaggag aagacgtcca aaagctggca gaagagttgc aaagcaacat tggagtgctg 660
agatctcttg gggcaagcca aaagaatggg gaagggattg caaaggatgt aatggaagtg 720
ctaaagcaga gctccatggg aaattcagct cttgtgaaga aatatctata atgctcgaac 780
catttcagat tcttacaatt tgttctttta tcttatcagc tctccatttc atggcttgga 840
caatagggca tttgaatcaa ataaaaagag gaataaacat gaaaatacga ataaaaggtc 900
caaacaaaga gacaataaac agagaggtat caattttgag acacagttac caaaaagaaa 960
tccaggccaa agaaacaatg aaggaagtac tctctgacaa catggaggta ttgaatgacc 1020
acataataat tgaggggctt tctgccgaag agataataaa aatgggtgaa acagttttgg 1080
agatagaaga attgcattaa attcaatttt actgtatttc ttactatgca tttaagcaaa 1140
ttgtaatcaa tgtcagcaaa taaactggaa aaagtgcgtt gtttctact 1189

<210> SEQ ID NO 76
<211> LENGTH: 1101
<212> TYPE: DNA
<213> ORGANISM: Influenza B Virus

<400> SEQUENCE: 76
agcagaagca gaggatttgt ttagtcactg gcaaacaggg aaaaatggcg aacaacaaca 60
tgaccacaac acaaattgag gtgggtccgg gagcaaccaa tgccaccata aactttgaag 120
caggaattct agagtgctat gaaaggcttt catggcaaag agcccttgac taccctggtc 180
aagaccgcct aaacagacta aagagaaaat tagagtcaag aataaagact cacaacaaaa 240
gtgagcctga aagtaaaagg atgtcccttg aagagagaaa agcaattgga gtaaaaatga 300
tgaaagtact cctatttatg aatccgtctg ctggaattga agggtttgag ccatactgta 360
tgaaaagttc ctcaaatagc aactgtacga aatacaattg gactgattac ccttcaacac 420
cagagaggtg ccttgatgac atagaggaag aaccagagga tgttgatggc ccaactgaaa 480
tagtattaag ggacatgaac aacaaagatg caaggcaaaa gataaaggag gaagtaaaca 540
ctcagaaaga agggaagttc cgtttgacaa taaaaaggga tatgcgtaat gtattgtcct 600
tgagagtgtt ggtaaacgga acattcctca aacaccccaa tggacacaag tccttatcaa 660
ctctgcatag attgaatgca tatgaccaga gtggaaggct tgttgctaaa cttgttgcca 720
ctgatgatct tacagtggag gatgaagaag atggccatcg gatcctcaac tcactcttcg 780
agcgtcttaa tgaaggacat tcaaagccaa ttcgagcagc tgaaactgcg gtgggagtct 840
tatcccaatt tggtcaagag caccgattat caccagaaga gggagacaat tagactggtc 900
acggaagaac tttatctttt aagtaaaaga attgatgata acatactatt ccacaaaaca 960
gtaatagcta acagctccat aatagctgac atggttgtat cattatcatt attagaaaca 1020
ttgtatgaaa tgaaggatgt ggttgaagtg tacagcaggc agtgcttgtg aatttaaaat 1080
aaaaatcctc ttgttactac t 1101

<210> SEQ ID NO 77
<211> LENGTH: 2305
<212> TYPE: DNA
<213> ORGANISM: Influenza B Virus

<400> SEQUENCE: 77

-continued

```
agcagaagcg gtgcgtttga tttgccataa tggatacttt tattacaaga aacttccaga     60
ctacaataat acaaaaggcc aaaaacacaa tggcagaatt tagtgaagat cctgaattac    120
aaccagcaat gctattcaac atctgcgtcc atctagaggt ttgctatgta ataagtgaca    180
tgaattttct tgacgaagaa ggaaaatcat atacagcatt agaaggacaa ggaaaagaac    240
aaaacttgag accacaatat gaagtaattg agggaatgcc aagaaccata gcatggatgg    300
tccaaagatc cttagctcaa gagcatggaa tagagactcc aaagtatctg gctgatttgt    360
ttgattataa aaccaagaga tttatagaag ttggaataac aaaaggattg gctgatgatt    420
acttttggaa aaagaaagaa aagctgggaa atagcatgga actgatgata ttcagctaca    480
atcaagacta ttcgttaagt aatgaatcct cattggatga ggaagggaaa gggagagtgc    540
taagcagact cacagaactt caggctgaat taagtctgaa aaacctatgg caagttctca    600
taggagaaga agatgttgaa aagggaattg actttaaact tggacaaaca atatctagac    660
taagggatat atctgttcca gctggtttct ccaattttga aggaatgagg agctacatag    720
acaatataga tcctaaagga gcaatagaaa gaaatctagc aaggatgtct cccttagtat    780
cagccacacc taaaaagttg aaatgggagg acctaagacc aatagggcct cacatttaca    840
accatgagtt accagaagtt ccatataatg cctttcttct aatgtctgat gaattggggc    900
tggccaatat gactgaggga aagtccaaaa aaccgaagac attagccaaa gaatgtctag    960
aaaagtactc aacactacgg gatcaaactg acccaatatt aataatgaaa agcgaaaaag   1020
ctaacgaaaa tttcctatgg aagctgtgga gggactgtgt aaatacaata agtaatgagg   1080
aaatgagtaa cgagttacag aaaaccaatt atgccaagtg ggccacagga gatggattaa   1140
cataccagaa aataatgaaa gaagtagcaa tagatgacga aacaatgtgc caagaagagc   1200
ctaaaatccc taacaaatgt agagtggctg cttgggttca aacagagatg aatttattga   1260
gcactctgac aagtaaaaga gctctggacc taccagaaat agggccagac gtagcacccg   1320
tggagcatgt agggagtgaa agaaggaaat actttgttaa tgaaatcaac tgctgtaagg   1380
cctctacagt tatgatgaag tatgtgcttt ttcacacttc attattgaat gaaagcaatg   1440
ccagcatggg aaaatataaa gtaataccaa taaccaatag agtagtaaat gaaaaaggag   1500
aaagtttcga catgctttat ggtctggcgg ttaaaggaca atctcatctg aggggagata   1560
ctgatgttgt aacagttgtg actttcgaat ttagtggtac agatcccaga gtggactcag   1620
gaaagtggcc aaaatatact gtgtttagga ttggctccct atttgtgagt gggagggaaa   1680
aatctgtgta cctatattgc cgagtgaatg gcacaaataa gatccaaatg aaatggggaa   1740
tggaagctag aagatgtctg cttcaatcaa tgcaacaaat ggaagcaatt gttgaacaag   1800
aatcatcgat acaaggatat gacatgacca aagcttgttt caagggagac agagtaaata   1860
gccccaaaac ttttagtatt gggactcaag aaggaaaact agtaaaagga tcctttggga   1920
aagcactaag agtaatattt accaaatgtt tgatgcacta tgtatttgga aatgcccaat   1980
tggaggggtt tagtgccgag tctaggagac ttctactgtt aattcaagca ctaaaggaca   2040
gaaagggccc ttgggtgttc gacttagagg gaatgtattc tggaatagaa gaatgtatta   2100
gtaacaaccc ttgggtaata cagagtgcat actggttcaa tgaatggttg ggctttgaaa   2160
aggaggggag taaagtatta gaatcagtag atgaaataat gaatgaatga aaaaacatag   2220
tactcaattt ggtactattt tgttcattat gtatctaaac atccaataaa aagaatcgag   2280
aatcaaaaat gcacgtgttt ctact                                         2305
```

<210> SEQ ID NO 78
<211> LENGTH: 2369
<212> TYPE: DNA
<213> ORGANISM: Influenza B Virus

<400> SEQUENCE: 78
agcagaagcg gagcctttaa gatgaatata aatccttatt ttctcttcat agatgtaccc 60
atacaggcag caatttcaac aacattccca tacaccggtg ttcccccttta ctcccatgga 120 acgggaacag gccacacaat agacaccgtg atcagaacac atgagtactc gaacaaggga 180
aaacagtatg tttctgacat cacaggatgt acaatggtag atccaacaaa tgggccatta 240
cccgaagaca atgagccgag tgcctatgca caattagatt gcgttctgga ggctttggat 300
agaatggatg aagaacatcc aggtttgttt caagcagcct cacagaatgc catggaggca 360
ctaatggtca caactgtaga caaattaacc caggggagac agacttttga ttggacagta 420
tgcagaaacc agcctgctgc aacggcacta aacacaacaa taacctcctt taggttgaat 480
gatttgaatg gagctgacaa gggtggattg gtacccttt gccaagatat cattgattca 540
ttggacaaac ctgaaatgac tttcttctca gtaaagaata taaagaaaaa attgcctgct 600
aaaaacagaa agggtttcct cataaagaga ataccaatga aagtaaaaga caggataacc 660
agagtggaat acatcaaaag agcattatca ttaaacacaa tgacaaaaga tgctgaaagg 720
ggcaaactaa aaagaagagc gattgcaacc gctggaatac aaatcagagg gtttgtatta 780
gtagttgaaa acttggctaa aaatatctgt gaaaatctag aacaaagtgg tttgcccgta 840
ggtggaaatg aaaagaaggc caaactgtca aatgcagtgg ccaaaatgct cagtaactgc 900
ccaccaggag ggatcagcat gacagtaaca ggagacaata ctaaatggaa tgaatgctta 960
aatccaagaa tctttttggc tatgactgaa aggataacaa gagacagccc aatttggttc 1020
cgggattttt gtagtatagc accggtcttg ttctccaata aaatagccag attgggaaaa 1080
ggatttatga taacaagcaa aacaaaaaga ctgaaggctc aaataccttg tccagatctg 1140
tttagcatac cattagaaag atataatgaa gaaacaaggg caaaattaaa aaagctgaaa 1200
ccattcttca atgaagaagg aacggcatct ttgtcgcctg ggatgatgat gggaatgttt 1260
aatatgctat ctaccgtgtt gggagtagcc gcactaggta tcaaaaacat tggaaacaaa 1320
gaatatttat gggatggact gcaatcttct gatgattttg ctctgtttgt taatgcaaaa 1380
gatgaagaga catgtatgga aggaataaac gacttttacc gaacatgtaa attattggga 1440
ataaacatga gcaaaaagaa aagttactgt aatgaaactg gaatgtttga atttacaagc 1500
atgttctata gagatggatt tgtatctaat tttgcaatgg aaattccttc atttggagtt 1560
gctggagtaa atgaatcagc agatatggca ataggaatga caataataaa gaacaatatg 1620
atcaacaatg ggatgggtcc agcaacagca caaacagcca tacaattatt catagctgat 1680
tataggtaca cctacaaatg ccacagggga gattccaaag tggaaggaaa aagaatgaaa 1740
attataaagg agctatggga aaacactaaa ggaagagatg gtctgttagt ggcagatggt 1800
gggcccaaca tttacaattt gagaaactta catatcccag aaatagtatt gaagtacaac 1860
ctaatggacc ctgaatacaa agggcggtta cttcatcctc aaaatccatt tgtaggacat 1920
ttatctattg agggcatcaa agaagcagat ataaccccag cacatggtcc cgtaaagaaa 1980
atggattatg atgcagtatc tggaactcat agttggagaa ccaaaaggaa cagatctata 2040
ctaaatactg accagaggaa catgattctt gaggaacaat gctacgctaa gtgttgcaac 2100
ctttttgagg cctgttttaa tagtgcatca tacaggaaac cagtaggtca gcacagcatg 2160
cttgaggcta tggcccacag attaagagtg gatgcacgac tagattatga atcaggaaga 2220
atgtcaaagg atgattttga gaaagcaatg gctcaccttg gtgagattgg gtacatataa 2280
gctccgaaga tgtctatggg gttattggtc atcattgaat acatgtgata aacaaatgat 2340
taaaatgaaa aaaggctcgt gtttctact 2369

<210> SEQ ID NO 79
<211> LENGTH: 2396
<212> TYPE: DNA
<213> ORGANISM: Influenza B Virus

<400> SEQUENCE: 79
agcagaagcg gagcgttttc aagatgacat tggctaaaat tgaattgtta aaacaactgt 60
taagggacaa tgaagccaaa acagtattga aacaaacaac ggtagaccaa tataacataa 120
taagaaaatt caatacatca agaattgaaa agaacccttc attgaggatg aagtgggcaa 180
tgtgttctaa ttttcccttg gctctgacca agggtgatat ggcaaacaga atccccttgg 240
aatacaaggg aatacaactt aaaacaaatg ctgaagacat aggaactaaa ggccaaatgt 300
gctcaatagc agcagttacc tggtggaata catatggacc aataggagat actgaaggtt 360
tcgaaaaggt ctacgaaagc ttttttctca gaaagatgag acttgacaat gccacttggg 420
gccgaataac ttttggccca gttgaaagag taagaaaaag ggtactgcta aaccctctca 480
ccaaggaaat gcctccagat gaagcaagta atgtgataat ggaaatattg ttccctaagg 540
aagcaggaat accaagagaa tctacttgga tacataggga actgataaaa gaaaaaagag 600
aaaaattgaa aggaacaatg ataactccca ttgtactggc atacatgctt gagagagaat 660
tggttgccag aagaaggttc ctgccggtgg caggagcaac atcagctgag ttcatagaaa 720
tgctacactg cttacaaggt gaaaattgga gacaaatata tcacccagga ggaaataaac 780
taactgaatc taggtctcaa tcgatgattg tagcttgtag aaagataatc agaagatcaa 840
tagtcgcatc aaacccatta gagctagctg tagaaattgc aaacaagact gtgatagata 900
ctgaaccttt aaaatcatgt ctgacagcca tagacggagg tgatgtagcc tgtgacataa 960
taagagctgc attaggacta aagatcagac aaagacaaag atttggacga cttgaactaa 1020
agagaatatc aggaagagga ttcaaaaatg atgaagaaat attaatcggg aacggaacaa 1080
tacagaagat tggaatatgg gacggagaag aggagttcca tgtaagatgt ggtgaatgca 1140
ggggaatatt aaaaaagagc aaaatgagaa tggaaaaact actaataaat tcagctaaaa 1200
aggaagacat gaaagattta ataatcttgt gcatggtatt ttctcaagac actaggatgt 1260
tccaaggagt gagaggagaa ataaattttc ttaatagagc aggccaactt ttatctccaa 1320
tgtaccaact ccaaagatat tttttgaata gaagcaacga tctctttgat caatgggggt 1380
atgaggaatc acccaaagca agtgagctac atggaataaa tgaattaatg aatgcatctg 1440
actacacttt gaaaggggtt gtagtaacaa aaaatgtaat tgatgatttt agttctactg 1500
aaacagaaaa agtatctata acaaaaaatc ttagtttaat aaaaaggact ggggaagtca 1560
taatgggggc taatgacgta agtgaattag aatcacaagc tcagctaatg ataacatatg 1620
atacacctaa gatgtgggag atgggaacaa ccaaagaact ggtgcaaaac acctaccaat 1680
gggtgctgaa aaatttggta acactgaagg ctcagtttct tctaggaaaa gaagacatgt 1740
tccaatggga tgcatttgaa gcatttgaaa gcataatccc ccagaagatg gctggccagt 1800
acagtggatt tgcaagagca gtgctcaaac aaatgagaga ccaagaggtt atgaaaactg 1860
accagttcat aaagttgttg cccttttgtt tctcaccacc aaaattaagg agaaatgggg 1920
agccttatca gttcttgagg cttgtattga agggaggagg agaaaatttc atcgaagtaa 1980
ggaaagggtc ccctctattc tcttacaatc cacaaacaga agtcctaact atatgcggca 2040
gaatgatgtc attaaaaggg aaaattgaag atgaagaaag gaatagatca atggggaatg 2100
cagtattagc gggctttctc gttagtggca agtatgaccc agatcttgga gatttcaaaa 2160
ctattgaaga acttgaaaag ctgaaaccgg gggagaaagc aaacatctta ctttatcaag 2220
gaaagcccgt taaagtagtt aaaaggaaaa gatatagtgc tttatccaat gacatttcac 2280
aaggaattaa gagacaaaga atgacagttg agtccatggg gtgggccttg agctaatata 2340
aatttatcca ttaattcaat aaacacaatt gagtgaaaaa tgctcgtgtt tctact 2396

<210> SEQ ID NO 80
<211> LENGTH: 1844
<212> TYPE: DNA
<213> ORGANISM: Influenza B Virus

<400> SEQUENCE: 80
agcagaagca cagcattttc ttattaactt caagtaccaa caaaagaact gaaaatcaaa 60
atgtccaaca tggatattga cggtatcaac actgggacaa ttgacaaaac accggaagaa 120
ataacttctg gaaccagtgg gacaaccaga ccaatcatca gaccagcaac ccttgcccca 180
ccaagcaaca aacgaacccg gaacccatcc ccggaaagag caaccacaag cagtgaagct 240
gatgtcggaa ggaaaaccca aaagaaacag accccgacag agataaagaa gagcgtctac 300
aatatggtag tgaaactggg tgaattctat aaccagatga tggtcaaagc tggactcaac 360
gatgacatgg agagaaacct aatccaaaat gcgcatgctg tggaaagaat tctattggct 420
gccactgatg acaagaaaac tgaattccag aggaaaaaga atgccagaga tgtcaaagaa 480
ggaaaagaag aaatagacca caacaaaaca ggaggcacct tttacaagat ggtaagagat 540
gataaaacca tctacttcag ccctataaga attacctttt taaaagaaga ggtgaaaaca 600
atgtacaaaa ccaccatggg gagtgatggc ttcagtggac taaatcacat aatgattggg 660
cattcacaga tgaatgatgt ctgtttccaa agatcaaagg ccctaaaaag agttggactt 720
gacccttcat taatcagtac ctttgcagga agcacactcc ccagaagatc aggtgcaact 780
ggtgttgcaa tcaaaggagg tggaacttta gtggctgaag ccattcgatt tataggaaga 840
gcaatggcag acagagggct attgagagac atcaaagcca agactgccta tgaaaagatt 900
cttctgaatc taaaaaacaa atgctctgcg ccccaacaaa aggctctagt tgatcaagtg 960
atcggaagta gaaatccagg gattgcagac attgaagacc taaccctgct tgctcgtagt 1020
atggtcgttg ttaggccctc tgtggcgagc aaagtagtgc ttcccataag catttatgct 1080
aaaatacctc aactagggtt caatgttgaa gaatactcta tggttgggta tgaagccatg 1140
gctctctaca atatggcaac acctgtttcc atattaagaa tgggagatga tgcaaaagat 1200
aaatcgcaat tattcttcat gtcttgcttc ggagctgcct atgaagacct gagagttttg 1260
tctgcattaa caggcataga attcaagcct agatcagcat taaaatgcaa gggtttccat 1320
gttccagcaa aggaacaggt ggaaggaatg gggcagctc tgatgtccat caagctccag 1380
ttttgggctc caatgaccag atctggaggg aacgaagtag gtggagacgg agggtctggc 1440
caaataagtt gcagcccagt gtttgcagta gaaagaccta ttgctctaag caagcaagct 1500
gtaagaagaa tgctttcaat gaatattgag ggacgtgatg cagatgtcaa aggaaatcta 1560
ctcaagatga tgaatgactc aatggctaag aaaaccaatg gaaatgcttt cattgggaag 1620
aaaatgtttc aaatatcaga caaaaacaaa accaatcccg ttgaaattcc aattaagcag 1680
accatcccca atttcttctt tgggagggac acagcagagg attatgatga cctcgattat 1740
taaagcaaca aaatagacac tatgactgtg attgtttcaa tacgtttgga atgtgggtgt 1800
ttactcttat tgaaataaat ataaaaaatg ctgttgtttc tact 1844

<210> SEQ ID NO 81
<211> LENGTH: 1190
<212> TYPE: DNA
<213> ORGANISM: Influenza B Virus

<400> SEQUENCE: 81
agcagaagca cgcactttct taaaatgtcg ctgtttggag acacaattgc ctacctgctt 60
tcattgacag aagatggaga aggcaaagca gaactagcag aaaaattaca ctgttggttc 120
ggtgggaaag aatttgacct agactctgcc ttggaatgga taaaaaacaa aagatgctta 180
actgatatac agaaagcact aattggtgcc tctatctgct tttaaaacc aaaagaccaa 240 gaaagaaaaa gaagattcat cacagagccc ctatcaggaa tgggaacaac agcaacaaaa 300
aagaagggcc tgattctagc tgagagaaaa atgagaagat gtgtgagttt tcatgaagca 360
tttgaaatag cagaaggcca tgaaagctca gcgctactat attgtctcat ggtcatgtac 420
ctgaaccctg gaaattattc aatgcaagta aaactaggaa cgctctgtgc tttgtgcgag 480
aaacaagcat cacattcaca cagggctcat agcagagcag caagatcttc agtgcctgga 540
gtgaggcgag aaatgcagat ggtctcagct atgaacacag caaaaacaat gaatggaatg 600
ggaaagggag aagacgtcca aaaactggca gaagagctgc aaagcaacat tggagtattg 660
agatctcttg ggcaagtcaa aaagaatggg gaaggaattg caaaggatgt gatggaagtg 720
ctaaagcaga gctctatggg aaattcagct cttgtgaaga aatacctata atgctcgaac 780
catttcagat tctttcaatt tgttctttca tcttatcagc tctccatttc atggcttgga 840
caatagggca tttgaatcaa ataaaaagag gagtaaacat gaaaatacga ataaaaaatc 900
caaataaaga gacaataaac agagaggtat caattttgag acacagttac caaaaagaaa 960
tccaggccaa agaaacaatg aaggaagtac tctctgacaa catggaggta ttgagtgacc 1020
acatagtaat tgaggggctt tctgctgaag agataataaa aatgggtgaa acagttttgg 1080
aggtagaaga attgcattaa attcaatttt tactgtattt cttgctatgc atttaagcaa 1140
attgtaatca atgtcagcaa ataaactgga aaaagtgcgt tgtttctact 1190

<210> SEQ ID NO 82
<211> LENGTH: 1096
<212> TYPE: DNA
<213> ORGANISM: Influenza B Virus

<400> SEQUENCE: 82
agcagaagca gaggatttgt ttagtcactg gcaaacgaaa aaatggcgga caacatgacc 60
acaacacaaa ttgaggtggg tccgggagca accaatgcca ccataaactt tgaagcagga 120
attttggagt gctatgaaag gctttcatgg caaagagccc ttgactaccc tggtcaagac 180
cgcctaaaca aactaaagag aaaattggaa tcaagaataa agactcacaa caaaagtgag 240
ccagaaagta aaaggatgtc tcttgaagag agaaaagcta ttggggtaaa aatgatgaaa 300
gtgctcctat ttatgaaccc atctgctgga gttgaagggt ttgagccata ttgtatgaaa 360
aatccctcca atagcaactg tccagactgc aattgggctg attaccctcc aacaccagga 420

-continued

```
aagtaccttg atggcataga agaagaaccg gagaatgttg gtgactcaac tgaaatagta    480

ttaagggaca tgaacaacaa agatgcaagg caaaagataa aagaggaagt aaacactcag    540

aaagaaggga aattccgttt gacaataaaa agggatatac gtaatgtgtt gtccttgaga    600

gtgttggtaa acggaacatt catcaagcac cctaatggat acaagtcctt atcaactctg    660

catagattga atgcatatga ccagagtgga agacttgttg ctaaacttgt tgctactgat    720

gatcttacag tggaggatga agaagatggc catcggatcc tcaactcact cttcgagcgt    780

cttaatgaag gacattcaaa gccaattcga gcagctgaaa ctgcggtggg agtcttatcc    840

caatttggtc aagagcaccg attatcacca gaagagagag acaattagac tggttacgga    900

agaactttat cttttaagta aaagaattga tgataacata ttgttccaca aaacagtaat    960

agccaacagc tccataatag ctgacatgat tgtatcatta tcattattgg aaacattgta   1020

tgaaatgaag gatgtggttg aagtgtacag caggcagtgc ttgtgaattt aaaataaaaa   1080

tcctcttgtt actact                                                   1096
```

<210> SEQ ID NO 83
<211> LENGTH: 726
<212> TYPE: PRT
<213> ORGANISM: Influenza B Virus

<400> SEQUENCE: 83

```
Met Asp Thr Phe Ile Thr Arg Asn Phe Gln Thr Thr Ile Ile Gln Lys
1               5                   10                  15

Ala Lys Asn Thr Met Ala Glu Phe Ser Glu Asp Pro Glu Leu Gln Pro
            20                  25                  30

Ala Met Leu Phe Asn Ile Cys Val His Leu Glu Val Cys Tyr Val Ile
        35                  40                  45

Ser Asp Met Asn Phe Leu Asp Glu Glu Gly Lys Ala Tyr Thr Ala Leu
    50                  55                  60

Glu Gly Gln Gly Lys Glu Gln Asn Leu Arg Pro Gln Tyr Glu Val Ile
65                  70                  75                  80

Glu Gly Met Pro Arg Thr Ile Ala Trp Met Val Gln Arg Ser Leu Ala
                85                  90                  95

Gln Glu His Gly Ile Glu Thr Pro Lys Tyr Leu Ala Asp Leu Phe Asp
            100                 105                 110

Tyr Lys Thr Lys Arg Phe Ile Glu Val Gly Ile Thr Lys Gly Leu Ala
        115                 120                 125

Asp Asp Tyr Phe Trp Lys Lys Lys Glu Lys Leu Gly Asn Ser Met Glu
    130                 135                 140

Leu Met Ile Phe Ser Tyr Asn Gln Asp Tyr Ser Leu Ser Asn Glu Ser
145                 150                 155                 160

Ser Leu Asp Glu Glu Gly Lys Gly Arg Val Leu Ser Arg Leu Thr Glu
                165                 170                 175

Leu Gln Ala Glu Leu Ser Leu Lys Asn Leu Trp Gln Val Leu Ile Gly
            180                 185                 190

Glu Glu Asp Val Glu Lys Gly Ile Asp Phe Lys Leu Gly Gln Thr Ile
        195                 200                 205

Ser Arg Leu Arg Asp Ile Ser Val Pro Ala Gly Phe Ser Asn Phe Glu
    210                 215                 220

Gly Met Arg Ser Tyr Ile Asp Asn Ile Asp Pro Lys Gly Ala Ile Glu
225                 230                 235                 240

Arg Asn Leu Ala Arg Met Ser Pro Leu Val Ser Val Thr Pro Lys Lys
                245                 250                 255
```

```
Leu Thr Trp Glu Asp Leu Arg Pro Ile Gly Pro His Ile Tyr Asp His
            260                 265                 270

Glu Leu Pro Glu Val Pro Tyr Asn Ala Phe Leu Leu Met Ser Asp Glu
        275                 280                 285

Leu Gly Leu Ala Asn Met Thr Glu Gly Lys Ser Lys Lys Pro Lys Thr
    290                 295                 300

Leu Ala Lys Glu Cys Leu Glu Lys Tyr Ser Thr Leu Arg Asp Gln Thr
305                 310                 315                 320

Asp Pro Ile Leu Ile Met Lys Ser Glu Lys Ala Asn Glu Asn Phe Leu
                325                 330                 335

Trp Lys Leu Trp Arg Asp Cys Val Asn Thr Ile Ser Asn Glu Glu Thr
            340                 345                 350

Ser Asn Glu Leu Gln Lys Thr Asn Tyr Ala Lys Trp Ala Thr Gly Asp
        355                 360                 365

Gly Leu Thr Tyr Gln Lys Ile Met Lys Glu Val Ala Ile Asp Asp Glu
    370                 375                 380

Thr Met Cys Gln Glu Glu Pro Lys Ile Pro Asn Lys Cys Arg Val Ala
385                 390                 395                 400

Ala Trp Val Gln Thr Glu Met Asn Leu Leu Ser Thr Leu Thr Ser Lys
                405                 410                 415

Arg Ala Leu Asp Leu Pro Glu Ile Gly Pro Asp Ile Ala Pro Val Glu
            420                 425                 430

His Val Gly Ser Glu Arg Arg Lys Tyr Phe Val Asn Glu Ile Asn Tyr
        435                 440                 445

Cys Lys Ala Ser Thr Val Met Met Lys Tyr Val Leu Phe His Thr Ser
    450                 455                 460

Leu Leu Asn Glu Ser Asn Ala Ser Met Gly Lys Tyr Lys Val Ile Pro
465                 470                 475                 480

Ile Thr Asn Arg Val Val Asn Glu Lys Gly Glu Ser Phe Asp Met Leu
                485                 490                 495

Tyr Gly Leu Ala Val Lys Gly Gln Ser His Leu Arg Gly Asp Thr Asp
            500                 505                 510

Val Val Thr Val Val Thr Phe Glu Phe Ser Ser Thr Asp Pro Arg Val
        515                 520                 525

Asp Ser Gly Lys Trp Pro Lys Tyr Thr Val Phe Arg Ile Gly Ser Leu
    530                 535                 540

Phe Val Ser Gly Arg Glu Lys Ser Val Tyr Leu Tyr Cys Arg Val Asn
545                 550                 555                 560

Gly Thr Asn Lys Ile Gln Met Lys Trp Gly Met Glu Ala Arg Arg Cys
                565                 570                 575

Leu Leu Gln Ser Met Gln Gln Met Glu Ala Ile Val Glu Gln Glu Ser
            580                 585                 590

Ser Ile Gln Gly Tyr Asp Met Thr Lys Ala Cys Phe Lys Gly Asp Arg
        595                 600                 605

Val Asn Ser Pro Lys Thr Phe Ser Ile Gly Thr Gln Glu Gly Lys Leu
    610                 615                 620

Val Lys Gly Ser Phe Gly Lys Ala Leu Arg Val Ile Phe Thr Lys Cys
625                 630                 635                 640

Leu Met His Tyr Val Phe Gly Asn Ala Gln Leu Glu Gly Phe Ser Ala
                645                 650                 655

Glu Ser Arg Arg Leu Leu Leu Leu Ile Gln Ala Leu Lys Asp Arg Lys
            660                 665                 670
```

Gly Pro Trp Val Phe Asp Leu Glu Gly Met Tyr Ser Gly Ile Glu Glu
675 680 685

Cys Ile Ser Asn Asn Pro Trp Val Ile Gln Ser Val Tyr Trp Phe Asn
690 695 700

Glu Trp Leu Gly Phe Glu Lys Glu Gly Asn Lys Val Leu Glu Ser Val
705 710 715 720

Asp Glu Ile Met Asp Glu
725

<210> SEQ ID NO 84
<211> LENGTH: 752
<212> TYPE: PRT
<213> ORGANISM: Influenza B Virus

<400> SEQUENCE: 84

Met Asn Ile Asn Pro Tyr Phe Leu Phe Ile Asp Val Pro Val Gln Ala
1 5 10 15

Ala Ile Ser Thr Thr Phe Pro Tyr Thr Gly Val Pro Pro Tyr Ser His
20 25 30

Gly Thr Gly Thr Gly Tyr Thr Ile Asp Thr Val Ile Arg Thr His Glu
35 40 45

Tyr Ser Asn Lys Gly Lys Gln Tyr Ile Ser Asp Val Thr Gly Cys Thr
50 55 60

Met Val Asp Pro Thr Asn Gly Pro Leu Pro Glu Asp Asn Glu Pro Ser
65 70 75 80

Ala Tyr Ala Gln Leu Asp Cys Val Leu Glu Ala Leu Asp Arg Met Asp
85 90 95

Glu Glu His Pro Gly Leu Phe Gln Ala Ala Ser Gln Asn Ala Met Glu
100 105 110

Ala Leu Met Val Thr Thr Val Asp Lys Leu Thr Gln Gly Arg Gln Thr
115 120 125

Phe Asp Trp Thr Val Cys Arg Asn Gln Pro Ala Ala Thr Ala Leu Asn
130 135 140

Thr Thr Ile Thr Ser Phe Arg Leu Asn Asp Leu Asn Gly Ala Asp Lys
145 150 155 160

Gly Gly Leu Ile Pro Phe Cys Gln Asp Ile Ile Asp Ser Leu Asp Arg
165 170 175

Pro Glu Met Thr Phe Phe Ser Val Lys Asn Ile Lys Lys Lys Leu Pro
180 185 190

Ala Lys Asn Arg Lys Gly Phe Leu Ile Lys Arg Ile Pro Met Lys Val
195 200 205

Lys Asp Lys Ile Thr Lys Val Glu Tyr Ile Lys Arg Ala Leu Ser Leu
210 215 220

Asn Thr Met Thr Lys Asp Ala Glu Arg Gly Lys Leu Lys Arg Arg Ala
225 230 235 240

Ile Ala Thr Ala Gly Ile Gln Ile Arg Gly Phe Val Leu Val Val Glu
245 250 255

Asn Leu Ala Lys Asn Ile Cys Glu Asn Leu Glu Gln Ser Gly Leu Pro
260 265 270

Val Gly Gly Asn Glu Lys Lys Ala Lys Leu Ser Asn Ala Val Ala Lys
275 280 285

Met Leu Ser Asn Cys Pro Pro Gly Gly Ile Ser Met Thr Val Thr Gly
290 295 300

Asp Asn Thr Lys Trp Asn Glu Cys Leu Asn Pro Arg Ile Phe Leu Ala
305 310 315 320

-continued

```
Met Thr Glu Arg Ile Thr Arg Asp Ser Pro Val Trp Phe Arg Asp Phe
                325                 330                 335

Cys Ser Ile Ala Pro Val Leu Phe Ser Asn Lys Ile Ala Arg Leu Gly
            340                 345                 350

Lys Gly Phe Met Ile Thr Ser Lys Thr Lys Arg Leu Lys Ala Gln Ile
        355                 360                 365

Pro Cys Pro Asp Leu Phe Ser Ile Pro Leu Glu Arg Tyr Asn Glu Glu
    370                 375                 380

Thr Arg Ala Lys Leu Lys Lys Leu Lys Pro Phe Phe Asn Glu Glu Gly
385                 390                 395                 400

Thr Ala Ser Leu Ser Pro Gly Met Met Met Gly Met Phe Asn Met Leu
                405                 410                 415

Ser Thr Val Leu Gly Val Ala Ala Leu Gly Ile Lys Asn Ile Gly Asn
            420                 425                 430

Lys Glu Tyr Leu Trp Asp Gly Leu Gln Ser Ser Asp Asp Phe Ala Leu
        435                 440                 445

Phe Val Asn Ala Lys Asp Glu Glu Thr Cys Met Glu Gly Ile Asn Asp
    450                 455                 460

Phe Tyr Arg Thr Cys Lys Leu Leu Gly Val Asn Met Ser Lys Lys Lys
465                 470                 475                 480

Ser Tyr Cys Asn Glu Thr Gly Met Phe Glu Phe Thr Ser Met Phe Tyr
                485                 490                 495

Arg Asp Gly Phe Val Ser Asn Phe Ala Met Glu Leu Pro Ser Phe Gly
            500                 505                 510

Val Ala Gly Val Asn Glu Ser Ala Asp Met Ala Ile Gly Met Thr Ile
        515                 520                 525

Ile Lys Asn Asn Met Ile Asn Asn Gly Met Gly Pro Ala Thr Ala Gln
    530                 535                 540

Thr Ala Ile Gln Leu Phe Ile Ala Asp Tyr Arg Tyr Thr Tyr Lys Cys
545                 550                 555                 560

His Arg Gly Asp Ser Lys Val Glu Gly Lys Arg Met Lys Ile Ile Lys
                565                 570                 575

Glu Leu Trp Glu Asn Thr Lys Gly Arg Asp Gly Leu Leu Val Ala Asp
            580                 585                 590

Gly Gly Pro Asn Ile Tyr Asn Leu Arg Asn Leu His Ile Pro Glu Ile
        595                 600                 605

Val Leu Lys Tyr Asn Leu Met Asp Pro Glu Tyr Lys Gly Arg Leu Leu
    610                 615                 620

His Pro Gln Asn Pro Phe Val Gly His Leu Ser Ile Glu Gly Ile Lys
625                 630                 635                 640

Glu Ala Asp Ile Thr Pro Ala His Gly Pro Val Lys Lys Met Asp Tyr
                645                 650                 655

Asp Ala Val Ser Gly Thr His Ser Trp Arg Thr Lys Arg Asn Arg Ser
            660                 665                 670

Ile Leu Asn Thr Asp Gln Arg Asn Met Ile Leu Glu Glu Gln Cys Tyr
        675                 680                 685

Ala Lys Cys Cys Asn Leu Phe Glu Ala Cys Phe Asn Ser Ala Ser Tyr
    690                 695                 700

Arg Lys Pro Val Gly Gln His Ser Met Leu Glu Ala Met Ala His Arg
705                 710                 715                 720

Leu Arg Met Asp Ala Arg Leu Asp Tyr Glu Ser Gly Arg Met Ser Lys
                725                 730                 735
```

Asp Asp Phe Glu Lys Ala Met Ala His Leu Gly Glu Ile Gly Tyr Ile
740 745 750

<210> SEQ ID NO 85
<211> LENGTH: 770
<212> TYPE: PRT
<213> ORGANISM: Influenza B Virus

<400> SEQUENCE: 85

Met Thr Leu Ala Lys Ile Glu Leu Leu Lys Gln Leu Leu Arg Asp Asn
1 5 10 15

Glu Ala Lys Thr Val Leu Lys Gln Thr Thr Val Asp Gln Tyr Asn Ile
20 25 30

Ile Arg Lys Phe Asn Thr Ser Arg Ile Glu Lys Asn Pro Ser Leu Arg
35 40 45

Met Lys Trp Ala Met Cys Ser Asn Phe Pro Leu Ala Leu Thr Lys Gly
50 55 60

Asp Met Ala Asn Arg Ile Pro Leu Glu Tyr Lys Gly Ile Gln Leu Lys
65 70 75 80

Thr Asn Ala Glu Asp Ile Gly Thr Lys Gly Gln Met Cys Ser Ile Ala
85 90 95

Ala Val Thr Trp Trp Asn Thr Tyr Gly Pro Ile Gly Asp Thr Glu Gly
100 105 110

Phe Glu Arg Val Tyr Glu Ser Phe Phe Leu Arg Lys Met Arg Leu Asp
115 120 125

Asn Ala Thr Trp Gly Arg Ile Thr Phe Gly Pro Val Glu Arg Val Arg
130 135 140

Lys Arg Val Leu Leu Asn Pro Leu Thr Lys Glu Met Pro Pro Asp Glu
145 150 155 160

Ala Ser Asn Val Ile Met Glu Ile Leu Phe Pro Lys Glu Ala Gly Ile
165 170 175

Pro Arg Glu Ser Thr Trp Ile His Arg Glu Leu Ile Lys Glu Lys Arg
180 185 190

Glu Lys Leu Lys Gly Thr Met Ile Thr Pro Ile Val Leu Ala Tyr Met
195 200 205

Leu Glu Arg Glu Leu Val Ala Arg Arg Arg Phe Leu Pro Val Ala Gly
210 215 220

Ala Thr Ser Ala Glu Phe Ile Glu Met Leu His Cys Leu Gln Gly Glu
225 230 235 240

Asn Trp Arg Gln Ile Tyr His Pro Gly Gly Asn Lys Leu Thr Glu Ser
245 250 255

Arg Ser Gln Ser Met Ile Val Ala Cys Arg Lys Ile Ile Arg Arg Ser
260 265 270

Ile Val Ala Ser Asn Pro Leu Glu Leu Ala Val Glu Ile Ala Asn Lys
275 280 285

Thr Val Ile Asp Thr Glu Pro Leu Lys Ser Cys Leu Ala Ala Ile Asp
290 295 300

Gly Gly Asp Val Ala Cys Asp Ile Ile Arg Ala Ala Leu Gly Leu Lys
305 310 315 320

Ile Arg Gln Arg Gln Arg Phe Gly Arg Leu Glu Leu Lys Arg Ile Ser
325 330 335

Gly Arg Gly Phe Lys Asn Asp Glu Glu Ile Leu Ile Gly Asn Gly Thr
340 345 350

Ile Gln Lys Ile Gly Ile Trp Asp Gly Glu Glu Glu Phe His Val Arg
355 360 365

-continued

```
Cys Gly Glu Cys Arg Gly Ile Leu Lys Lys Ser Lys Met Lys Leu Glu
    370                 375                 380

Lys Leu Leu Ile Asn Ser Ala Lys Lys Glu Asp Met Arg Asp Leu Ile
385                 390                 395                 400

Ile Leu Cys Met Val Phe Ser Gln Asp Thr Arg Met Phe Gln Gly Val
                405                 410                 415

Arg Gly Glu Ile Asn Phe Leu Asn Arg Ala Gly Gln Leu Leu Ser Pro
            420                 425                 430

Met Tyr Gln Leu Gln Arg Tyr Phe Leu Asn Arg Ser Asn Asp Leu Phe
        435                 440                 445

Asp Gln Trp Gly Tyr Glu Glu Ser Pro Lys Ala Ser Glu Leu His Gly
    450                 455                 460

Ile Asn Glu Ser Met Asn Ala Ser Asp Tyr Thr Leu Lys Gly Ile Val
465                 470                 475                 480

Val Thr Arg Asn Val Ile Asp Asp Phe Ser Ser Ile Glu Thr Glu Lys
                485                 490                 495

Val Ser Ile Thr Lys Asn Leu Ser Leu Ile Lys Arg Thr Gly Glu Val
            500                 505                 510

Ile Met Gly Ala Asn Asp Val Ser Glu Leu Glu Ser Gln Ala Gln Leu
        515                 520                 525

Met Ile Thr Tyr Asp Thr Pro Lys Met Trp Glu Met Gly Thr Thr Lys
    530                 535                 540

Glu Leu Val Gln Asn Thr Tyr Gln Trp Val Leu Lys Asn Leu Val Thr
545                 550                 555                 560

Leu Lys Ala Gln Phe Leu Leu Gly Lys Glu Asp Met Phe Gln Trp Asp
                565                 570                 575

Ala Phe Glu Ala Phe Glu Ser Ile Ile Pro Gln Lys Met Ala Gly Gln
            580                 585                 590

Tyr Ser Gly Phe Ala Arg Ala Val Leu Lys Gln Met Arg Asp Gln Glu
        595                 600                 605

Val Met Lys Thr Asp Gln Phe Ile Lys Leu Leu Pro Phe Cys Phe Ser
    610                 615                 620

Pro Pro Lys Leu Arg Ser Asn Gly Glu Pro Tyr Gln Phe Leu Lys Leu
625                 630                 635                 640

Val Leu Lys Gly Gly Gly Glu Asn Phe Ile Glu Val Arg Lys Gly Ser
                645                 650                 655

Pro Leu Phe Ser Tyr Asn Pro Gln Thr Glu Val Leu Thr Ile Cys Gly
            660                 665                 670

Arg Met Met Ser Leu Lys Gly Lys Ile Glu Asp Glu Glu Arg Asn Arg
        675                 680                 685

Ser Met Gly Asn Ala Val Leu Ala Gly Phe Leu Val Ser Gly Lys Tyr
    690                 695                 700

Asp Pro Asp Leu Gly Asp Phe Lys Thr Ile Glu Glu Leu Glu Lys Leu
705                 710                 715                 720

Lys Pro Gly Glu Lys Ala Asn Ile Leu Leu Tyr Gln Gly Lys Pro Val
                725                 730                 735

Lys Val Val Lys Arg Lys Arg Tyr Ser Ala Leu Ser Asn Asp Ile Ser
            740                 745                 750

Gln Gly Ile Lys Arg Gln Arg Met Thr Val Glu Ser Met Gly Trp Ala
        755                 760                 765

Leu Ser
    770
```

<210> SEQ ID NO 86
<211> LENGTH: 560
<212> TYPE: PRT
<213> ORGANISM: Influenza B Virus

<400> SEQUENCE: 86

Met Ser Asn Met Asp Ile Asp Gly Ile Asn Thr Gly Thr Ile Asp Lys
1               5                   10                  15

Thr Pro Glu Glu Ile Thr Ser Gly Thr Ser Gly Thr Thr Arg Pro Ile
            20                  25                  30

Ile Arg Pro Ala Thr Leu Ala Pro Pro Ser Asn Lys Arg Thr Arg Asn
        35                  40                  45

Pro Ser Pro Glu Arg Ala Thr Thr Ser Ser Glu Asp Asp Val Gly Arg
    50                  55                  60

Lys Thr Gln Lys Lys Gln Thr Pro Thr Glu Ile Lys Lys Ser Val Tyr
65                  70                  75                  80

Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala His
            100                 105                 110

Ala Val Glu Arg Ile Leu Leu Ala Ala Thr Asp Asp Lys Lys Thr Glu
        115                 120                 125

Phe Gln Lys Lys Lys Asn Ala Arg Asp Val Lys Glu Gly Lys Glu Glu
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Ala Leu Lys Arg Val Gly Leu Asp Pro Ser Leu
    210                 215                 220

Ile Ser Thr Phe Ala Gly Ser Thr Val Pro Arg Arg Ser Gly Ala Thr
225                 230                 235                 240

Gly Val Ala Ile Lys Gly Gly Gly Thr Leu Val Ala Glu Ala Ile Arg
                245                 250                 255

Phe Ile Gly Arg Ala Met Ala Asp Arg Gly Leu Leu Arg Asp Ile Lys
            260                 265                 270

Ala Lys Thr Ala Tyr Glu Lys Ile Leu Leu Asn Leu Lys Asn Lys Cys
        275                 280                 285

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
                325                 330                 335

Ser Ile Tyr Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
        355                 360                 365

Val Ser Ile Leu Arg Met Gly Asp Asp Ala Lys Asp Lys Ser Gln Leu
    370                 375                 380

```
Phe Phe Met Ser Cys Phe Gly Ala Ala Tyr Glu Asp Leu Arg Val Leu
385                 390                 395                 400

Ser Ala Leu Thr Gly Thr Glu Phe Lys Pro Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Val Gly Gly Asp Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495

Lys Gly Asn Leu Leu Lys Met Met Asn Asp Ser Met Ala Lys Lys Thr
            500                 505                 510

Ser Gly Asn Ala Phe Ile Gly Lys Lys Met Phe Gln Ile Ser Asp Lys
        515                 520                 525

Asn Lys Thr Asn Pro Ile Glu Ile Pro Ile Lys Gln Thr Ile Pro Asn
    530                 535                 540

Phe Phe Phe Gly Arg Asp Thr Ala Glu Asp Tyr Asp Asp Leu Asp Tyr
545                 550                 555                 560


<210> SEQ ID NO 87
<211> LENGTH: 248
<212> TYPE: PRT
<213> ORGANISM: Influenza B Virus

<400> SEQUENCE: 87

Met Ser Leu Phe Gly Asp Thr Ile Ala Tyr Leu Leu Ser Leu Thr Glu
1               5                   10                  15

Asp Gly Glu Gly Lys Ala Glu Leu Ala Glu Lys Leu His Cys Trp Phe
            20                  25                  30

Gly Gly Lys Glu Phe Asp Leu Asp Ser Ala Leu Glu Trp Ile Lys Asn
        35                  40                  45

Lys Arg Cys Leu Thr Asp Ile Gln Lys Ala Leu Ile Gly Ala Ser Ile
    50                  55                  60

Cys Phe Leu Lys Pro Lys Asp Gln Glu Arg Lys Arg Arg Phe Ile Thr
65                  70                  75                  80

Glu Pro Leu Ser Gly Met Gly Thr Thr Ala Thr Lys Lys Lys Gly Leu
                85                  90                  95

Ile Leu Ala Glu Arg Lys Met Arg Arg Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Gly Asn Tyr Ser Met Gln Val Lys Leu
    130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Ser Asn
```

```
        195                 200                 205

Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245


<210> SEQ ID NO 88
<211> LENGTH: 109
<212> TYPE: PRT
<213> ORGANISM: Influenza B Virus

<400> SEQUENCE: 88

Met Leu Glu Pro Phe Gln Ile Leu Thr Ile Cys Ser Phe Ile Leu Ser
1               5                   10                  15

Ala Leu His Phe Met Ala Trp Thr Ile Gly His Leu Asn Gln Ile Lys
            20                  25                  30

Arg Gly Ile Asn Met Lys Ile Arg Ile Lys Gly Pro Asn Lys Glu Thr
        35                  40                  45

Ile Asn Arg Glu Val Ser Ile Leu Arg His Ser Tyr Gln Lys Glu Ile
    50                  55                  60

Gln Ala Lys Glu Thr Met Lys Glu Val Leu Ser Asp Asn Met Glu Val
65                  70                  75                  80

Leu Asn Asp His Ile Ile Ile Glu Gly Leu Ser Ala Glu Glu Ile Ile
                85                  90                  95

Lys Met Gly Glu Thr Val Leu Glu Ile Glu Glu Leu His
            100                 105


<210> SEQ ID NO 89
<211> LENGTH: 282
<212> TYPE: PRT
<213> ORGANISM: Influenza B Virus

<400> SEQUENCE: 89

Met Ala Asn Asn Asn Met Thr Thr Thr Gln Ile Glu Val Gly Pro Gly
1               5                   10                  15

Ala Thr Asn Ala Thr Ile Asn Phe Glu Ala Gly Ile Leu Glu Cys Tyr
            20                  25                  30

Glu Arg Leu Ser Trp Gln Arg Ala Leu Asp Tyr Pro Gly Gln Asp Arg
        35                  40                  45

Leu Asn Arg Leu Lys Arg Lys Leu Glu Ser Arg Ile Lys Thr His Asn
    50                  55                  60

Lys Ser Glu Pro Glu Ser Lys Arg Met Ser Leu Glu Glu Arg Lys Ala
65                  70                  75                  80

Ile Gly Val Lys Met Met Lys Val Leu Leu Phe Met Asn Pro Ser Ala
                85                  90                  95

Gly Ile Glu Gly Phe Glu Pro Tyr Cys Met Lys Ser Ser Ser Asn Ser
            100                 105                 110

Asn Cys Thr Lys Tyr Asn Trp Thr Asp Tyr Pro Ser Thr Pro Glu Arg
        115                 120                 125

Cys Leu Asp Asp Ile Glu Glu Glu Pro Glu Asp Val Asp Gly Pro Thr
    130                 135                 140

Glu Ile Val Leu Arg Asp Met Asn Asn Lys Asp Ala Arg Gln Lys Ile
145                 150                 155                 160

Lys Glu Glu Val Asn Thr Gln Lys Glu Gly Lys Phe Arg Leu Thr Ile
```

```
                165                 170                 175

Lys Arg Asp Met Arg Asn Val Leu Ser Leu Arg Val Leu Val Asn Gly
            180                 185                 190

Thr Phe Leu Lys His Pro Asn Gly His Lys Ser Leu Ser Thr Leu His
        195                 200                 205

Arg Leu Asn Ala Tyr Asp Gln Ser Gly Arg Leu Val Ala Lys Leu Val
    210                 215                 220

Ala Thr Asp Asp Leu Thr Val Glu Asp Glu Glu Asp Gly His Arg Ile
225                 230                 235                 240

Leu Asn Ser Leu Phe Glu Arg Leu Asn Glu Gly His Ser Lys Pro Ile
                245                 250                 255

Arg Ala Ala Glu Thr Ala Val Gly Val Leu Ser Gln Phe Gly Gln Glu
            260                 265                 270

His Arg Leu Ser Pro Glu Glu Gly Asp Asn
        275                 280


<210> SEQ ID NO 90
<211> LENGTH: 123
<212> TYPE: PRT
<213> ORGANISM: Influenza B Virus

<400> SEQUENCE: 90

Met Ala Asn Asn Asn Met Thr Thr Thr Gln Ile Glu Trp Arg Met Lys
1               5                   10                  15

Lys Met Ala Ile Gly Ser Ser Thr His Ser Ser Ser Val Leu Met Lys
            20                  25                  30

Asp Ile Gln Ser Gln Phe Glu Gln Leu Lys Leu Arg Trp Glu Ser Tyr
        35                  40                  45

Pro Asn Leu Val Lys Ser Thr Asp Tyr His Gln Lys Arg Glu Thr Ile
    50                  55                  60

Arg Leu Val Thr Glu Glu Leu Tyr Leu Leu Ser Lys Arg Ile Asp Asp
65                  70                  75                  80

Asn Ile Leu Phe His Lys Thr Val Ile Ala Asn Ser Ser Ile Ile Ala
                85                  90                  95

Asp Met Val Val Ser Leu Ser Leu Leu Glu Thr Leu Tyr Glu Met Lys
            100                 105                 110

Asp Val Val Glu Val Tyr Ser Arg Gln Cys Leu
        115                 120


<210> SEQ ID NO 91
<211> LENGTH: 726
<212> TYPE: PRT
<213> ORGANISM: Influenza B Virus

<400> SEQUENCE: 91

Met Asp Thr Phe Ile Thr Arg Asn Phe Gln Thr Thr Ile Ile Gln Lys
1               5                   10                  15

Ala Lys Asn Thr Met Ala Glu Phe Ser Glu Asp Pro Glu Leu Gln Pro
            20                  25                  30

Ala Met Leu Phe Asn Ile Cys Val His Leu Glu Val Cys Tyr Val Ile
        35                  40                  45

Ser Asp Met Asn Phe Leu Asp Glu Glu Gly Lys Ser Tyr Thr Ala Leu
    50                  55                  60

Glu Gly Gln Gly Lys Glu Gln Asn Leu Arg Pro Gln Tyr Glu Val Ile
65                  70                  75                  80

Glu Gly Met Pro Arg Thr Ile Ala Trp Met Val Gln Arg Ser Leu Ala
```

```
                85                  90                  95

Gln Glu His Gly Ile Glu Thr Pro Lys Tyr Leu Ala Asp Leu Phe Asp
            100                 105                 110

Tyr Lys Thr Lys Arg Phe Ile Glu Val Gly Ile Thr Lys Gly Leu Ala
        115                 120                 125

Asp Asp Tyr Phe Trp Lys Lys Lys Glu Lys Leu Gly Asn Ser Met Glu
    130                 135                 140

Leu Met Ile Phe Ser Tyr Asn Gln Asp Tyr Ser Leu Ser Asn Glu Ser
145                 150                 155                 160

Ser Leu Asp Glu Glu Gly Lys Gly Arg Val Leu Ser Arg Leu Thr Glu
                165                 170                 175

Leu Gln Ala Glu Leu Ser Leu Lys Asn Leu Trp Gln Val Leu Ile Gly
            180                 185                 190

Glu Glu Asp Val Glu Lys Gly Ile Asp Phe Lys Leu Gly Gln Thr Ile
        195                 200                 205

Ser Arg Leu Arg Asp Ile Ser Val Pro Ala Gly Phe Ser Asn Phe Glu
    210                 215                 220

Gly Met Arg Ser Tyr Ile Asp Asn Ile Asp Pro Lys Gly Ala Ile Glu
225                 230                 235                 240

Arg Asn Leu Ala Arg Met Ser Pro Leu Val Ser Ala Thr Pro Lys Lys
                245                 250                 255

Leu Lys Trp Glu Asp Leu Arg Pro Ile Gly Pro His Ile Tyr Asn His
            260                 265                 270

Glu Leu Pro Glu Val Pro Tyr Asn Ala Phe Leu Leu Met Ser Asp Glu
        275                 280                 285

Leu Gly Leu Ala Asn Met Thr Glu Gly Lys Ser Lys Lys Pro Lys Thr
    290                 295                 300

Leu Ala Lys Glu Cys Leu Glu Lys Tyr Ser Thr Leu Arg Asp Gln Thr
305                 310                 315                 320

Asp Pro Ile Leu Ile Met Lys Ser Glu Lys Ala Asn Glu Asn Phe Leu
                325                 330                 335

Trp Lys Leu Trp Arg Asp Cys Val Asn Thr Ile Ser Asn Glu Glu Met
            340                 345                 350

Ser Asn Glu Leu Gln Lys Thr Asn Tyr Ala Lys Trp Ala Thr Gly Asp
        355                 360                 365

Gly Leu Thr Tyr Gln Lys Ile Met Lys Glu Val Ala Ile Asp Asp Glu
    370                 375                 380

Thr Met Cys Gln Glu Glu Pro Lys Ile Pro Asn Lys Cys Arg Val Ala
385                 390                 395                 400

Ala Trp Val Gln Thr Glu Met Asn Leu Leu Ser Thr Leu Thr Ser Lys
                405                 410                 415

Arg Ala Leu Asp Leu Pro Glu Ile Gly Pro Asp Val Ala Pro Val Glu
            420                 425                 430

His Val Gly Ser Glu Arg Arg Lys Tyr Phe Val Asn Glu Ile Asn Cys
        435                 440                 445

Cys Lys Ala Ser Thr Val Met Met Lys Tyr Val Leu Phe His Thr Ser
    450                 455                 460

Leu Leu Asn Glu Ser Asn Ala Ser Met Gly Lys Tyr Lys Val Ile Pro
465                 470                 475                 480

Ile Thr Asn Arg Val Val Asn Glu Lys Gly Glu Ser Phe Asp Met Leu
                485                 490                 495

Tyr Gly Leu Ala Val Lys Gly Gln Ser His Leu Arg Gly Asp Thr Asp
            500                 505                 510
```

```
Val Val Thr Val Val Thr Phe Glu Phe Ser Gly Thr Asp Pro Arg Val
        515                 520                 525

Asp Ser Gly Lys Trp Pro Lys Tyr Thr Val Phe Arg Ile Gly Ser Leu
    530                 535                 540

Phe Val Ser Gly Arg Glu Lys Ser Val Tyr Leu Tyr Cys Arg Val Asn
545                 550                 555                 560

Gly Thr Asn Lys Ile Gln Met Lys Trp Gly Met Glu Ala Arg Arg Cys
                565                 570                 575

Leu Leu Gln Ser Met Gln Gln Met Glu Ala Ile Val Glu Gln Glu Ser
            580                 585                 590

Ser Ile Gln Gly Tyr Asp Met Thr Lys Ala Cys Phe Lys Gly Asp Arg
        595                 600                 605

Val Asn Ser Pro Lys Thr Phe Ser Ile Gly Thr Gln Glu Gly Lys Leu
    610                 615                 620

Val Lys Gly Ser Phe Gly Lys Ala Leu Arg Val Ile Phe Thr Lys Cys
625                 630                 635                 640

Leu Met His Tyr Val Phe Gly Asn Ala Gln Leu Glu Gly Phe Ser Ala
                645                 650                 655

Glu Ser Arg Arg Leu Leu Leu Leu Ile Gln Ala Leu Lys Asp Arg Lys
            660                 665                 670

Gly Pro Trp Val Phe Asp Leu Glu Gly Met Tyr Ser Gly Ile Glu Glu
        675                 680                 685

Cys Ile Ser Asn Asn Pro Trp Val Ile Gln Ser Ala Tyr Trp Phe Asn
    690                 695                 700

Glu Trp Leu Gly Phe Glu Lys Glu Gly Ser Lys Val Leu Glu Ser Val
705                 710                 715                 720

Asp Glu Ile Met Asn Glu
                725


<210> SEQ ID NO 92
<211> LENGTH: 752
<212> TYPE: PRT
<213> ORGANISM: Influenza B Virus

<400> SEQUENCE: 92

Met Asn Ile Asn Pro Tyr Phe Leu Phe Ile Asp Val Pro Ile Gln Ala
1               5                   10                  15

Ala Ile Ser Thr Thr Phe Pro Tyr Thr Gly Val Pro Pro Tyr Ser His
            20                  25                  30

Gly Thr Gly Thr Gly His Thr Ile Asp Thr Val Ile Arg Thr His Glu
        35                  40                  45

Tyr Ser Asn Lys Gly Lys Gln Tyr Val Ser Asp Ile Thr Gly Cys Thr
    50                  55                  60

Met Val Asp Pro Thr Asn Gly Pro Leu Pro Glu Asp Asn Glu Pro Ser
65                  70                  75                  80

Ala Tyr Ala Gln Leu Asp Cys Val Leu Glu Ala Leu Asp Arg Met Asp
                85                  90                  95

Glu Glu His Pro Gly Leu Phe Gln Ala Ala Ser Gln Asn Ala Met Glu
            100                 105                 110

Ala Leu Met Val Thr Thr Val Asp Lys Leu Thr Gln Gly Arg Gln Thr
        115                 120                 125

Phe Asp Trp Thr Val Cys Arg Asn Gln Pro Ala Ala Thr Ala Leu Asn
    130                 135                 140

Thr Thr Ile Thr Ser Phe Arg Leu Asn Asp Leu Asn Gly Ala Asp Lys
```

-continued

```
145                 150                 155                 160

Gly Gly Leu Val Pro Phe Cys Gln Asp Ile Ile Asp Ser Leu Asp Lys
                165                 170                 175

Pro Glu Met Thr Phe Phe Ser Val Lys Asn Ile Lys Lys Lys Leu Pro
            180                 185                 190

Ala Lys Asn Arg Lys Gly Phe Leu Ile Lys Arg Ile Pro Met Lys Val
        195                 200                 205

Lys Asp Arg Ile Thr Arg Val Glu Tyr Ile Lys Arg Ala Leu Ser Leu
    210                 215                 220

Asn Thr Met Thr Lys Asp Ala Glu Arg Gly Lys Leu Lys Arg Arg Ala
225                 230                 235                 240

Ile Ala Thr Ala Gly Ile Gln Ile Arg Gly Phe Val Leu Val Val Glu
                245                 250                 255

Asn Leu Ala Lys Asn Ile Cys Glu Asn Leu Glu Gln Ser Gly Leu Pro
            260                 265                 270

Val Gly Gly Asn Glu Lys Lys Ala Lys Leu Ser Asn Ala Val Ala Lys
        275                 280                 285

Met Leu Ser Asn Cys Pro Pro Gly Gly Ile Ser Met Thr Val Thr Gly
    290                 295                 300

Asp Asn Thr Lys Trp Asn Glu Cys Leu Asn Pro Arg Ile Phe Leu Ala
305                 310                 315                 320

Met Thr Glu Arg Ile Thr Arg Asp Ser Pro Ile Trp Phe Arg Asp Phe
                325                 330                 335

Cys Ser Ile Ala Pro Val Leu Phe Ser Asn Lys Ile Ala Arg Leu Gly
            340                 345                 350

Lys Gly Phe Met Ile Thr Ser Lys Thr Lys Arg Leu Lys Ala Gln Ile
        355                 360                 365

Pro Cys Pro Asp Leu Phe Ser Ile Pro Leu Glu Arg Tyr Asn Glu Glu
    370                 375                 380

Thr Arg Ala Lys Leu Lys Lys Leu Lys Pro Phe Phe Asn Glu Glu Gly
385                 390                 395                 400

Thr Ala Ser Leu Ser Pro Gly Met Met Met Gly Met Phe Asn Met Leu
                405                 410                 415

Ser Thr Val Leu Gly Val Ala Ala Leu Gly Ile Lys Asn Ile Gly Asn
            420                 425                 430

Lys Glu Tyr Leu Trp Asp Gly Leu Gln Ser Ser Asp Asp Phe Ala Leu
        435                 440                 445

Phe Val Asn Ala Lys Asp Glu Glu Thr Cys Met Glu Gly Ile Asn Asp
    450                 455                 460

Phe Tyr Arg Thr Cys Lys Leu Leu Gly Ile Asn Met Ser Lys Lys Lys
465                 470                 475                 480

Ser Tyr Cys Asn Glu Thr Gly Met Phe Glu Phe Thr Ser Met Phe Tyr
                485                 490                 495

Arg Asp Gly Phe Val Ser Asn Phe Ala Met Glu Ile Pro Ser Phe Gly
            500                 505                 510

Val Ala Gly Val Asn Glu Ser Ala Asp Met Ala Ile Gly Met Thr Ile
        515                 520                 525

Ile Lys Asn Asn Met Ile Asn Asn Gly Met Gly Pro Ala Thr Ala Gln
    530                 535                 540

Thr Ala Ile Gln Leu Phe Ile Ala Asp Tyr Arg Tyr Thr Tyr Lys Cys
545                 550                 555                 560

His Arg Gly Asp Ser Lys Val Glu Gly Lys Arg Met Lys Ile Ile Lys
                565                 570                 575
```

```
Glu Leu Trp Glu Asn Thr Lys Gly Arg Asp Gly Leu Leu Val Ala Asp
            580                 585                 590

Gly Gly Pro Asn Ile Tyr Asn Leu Arg Asn Leu His Ile Pro Glu Ile
        595                 600                 605

Val Leu Lys Tyr Asn Leu Met Asp Pro Glu Tyr Lys Gly Arg Leu Leu
    610                 615                 620

His Pro Gln Asn Pro Phe Val Gly His Leu Ser Ile Glu Gly Ile Lys
625                 630                 635                 640

Glu Ala Asp Ile Thr Pro Ala His Gly Pro Val Lys Lys Met Asp Tyr
                645                 650                 655

Asp Ala Val Ser Gly Thr His Ser Trp Arg Thr Lys Arg Asn Arg Ser
            660                 665                 670

Ile Leu Asn Thr Asp Gln Arg Asn Met Ile Leu Glu Glu Gln Cys Tyr
        675                 680                 685

Ala Lys Cys Cys Asn Leu Phe Glu Ala Cys Phe Asn Ser Ala Ser Tyr
    690                 695                 700

Arg Lys Pro Val Gly Gln His Ser Met Leu Glu Ala Met Ala His Arg
705                 710                 715                 720

Leu Arg Val Asp Ala Arg Leu Asp Tyr Glu Ser Gly Arg Met Ser Lys
                725                 730                 735

Asp Asp Phe Glu Lys Ala Met Ala His Leu Gly Glu Ile Gly Tyr Ile
            740                 745                 750


<210> SEQ ID NO 93
<211> LENGTH: 770
<212> TYPE: PRT
<213> ORGANISM: Influenza B Virus

<400> SEQUENCE: 93

Met Thr Leu Ala Lys Ile Glu Leu Leu Lys Gln Leu Leu Arg Asp Asn
1               5                   10                  15

Glu Ala Lys Thr Val Leu Lys Gln Thr Thr Val Asp Gln Tyr Asn Ile
            20                  25                  30

Ile Arg Lys Phe Asn Thr Ser Arg Ile Glu Lys Asn Pro Ser Leu Arg
        35                  40                  45

Met Lys Trp Ala Met Cys Ser Asn Phe Pro Leu Ala Leu Thr Lys Gly
    50                  55                  60

Asp Met Ala Asn Arg Ile Pro Leu Glu Tyr Lys Gly Ile Gln Leu Lys
65                  70                  75                  80

Thr Asn Ala Glu Asp Ile Gly Thr Lys Gly Gln Met Cys Ser Ile Ala
                85                  90                  95

Ala Val Thr Trp Trp Asn Thr Tyr Gly Pro Ile Gly Asp Thr Glu Gly
            100                 105                 110

Phe Glu Lys Val Tyr Glu Ser Phe Phe Leu Arg Lys Met Arg Leu Asp
        115                 120                 125

Asn Ala Thr Trp Gly Arg Ile Thr Phe Gly Pro Val Glu Arg Val Arg
    130                 135                 140

Lys Arg Val Leu Leu Asn Pro Leu Thr Lys Glu Met Pro Pro Asp Glu
145                 150                 155                 160

Ala Ser Asn Val Ile Met Glu Ile Leu Phe Pro Lys Glu Ala Gly Ile
                165                 170                 175

Pro Arg Glu Ser Thr Trp Ile His Arg Glu Leu Ile Lys Glu Lys Arg
            180                 185                 190

Glu Lys Leu Lys Gly Thr Met Ile Thr Pro Ile Val Leu Ala Tyr Met
```

-continued

```
        195                 200                 205

Leu Glu Arg Glu Leu Val Ala Arg Arg Arg Phe Leu Pro Val Ala Gly
    210                 215                 220

Ala Thr Ser Ala Glu Phe Ile Glu Met Leu His Cys Leu Gln Gly Glu
225                 230                 235                 240

Asn Trp Arg Gln Ile Tyr His Pro Gly Gly Asn Lys Leu Thr Glu Ser
                245                 250                 255

Arg Ser Gln Ser Met Ile Val Ala Cys Arg Lys Ile Ile Arg Arg Ser
            260                 265                 270

Ile Val Ala Ser Asn Pro Leu Glu Leu Ala Val Glu Ile Ala Asn Lys
        275                 280                 285

Thr Val Ile Asp Thr Glu Pro Leu Lys Ser Cys Leu Thr Ala Ile Asp
    290                 295                 300

Gly Gly Asp Val Ala Cys Asp Ile Ile Arg Ala Ala Leu Gly Leu Lys
305                 310                 315                 320

Ile Arg Gln Arg Gln Arg Phe Gly Arg Leu Glu Leu Lys Arg Ile Ser
                325                 330                 335

Gly Arg Gly Phe Lys Asn Asp Glu Glu Ile Leu Ile Gly Asn Gly Thr
            340                 345                 350

Ile Gln Lys Ile Gly Ile Trp Asp Gly Glu Glu Glu Phe His Val Arg
        355                 360                 365

Cys Gly Glu Cys Arg Gly Ile Leu Lys Lys Ser Lys Met Arg Met Glu
    370                 375                 380

Lys Leu Leu Ile Asn Ser Ala Lys Lys Glu Asp Met Lys Asp Leu Ile
385                 390                 395                 400

Ile Leu Cys Met Val Phe Ser Gln Asp Thr Arg Met Phe Gln Gly Val
                405                 410                 415

Arg Gly Glu Ile Asn Phe Leu Asn Arg Ala Gly Gln Leu Leu Ser Pro
            420                 425                 430

Met Tyr Gln Leu Gln Arg Tyr Phe Leu Asn Arg Ser Asn Asp Leu Phe
        435                 440                 445

Asp Gln Trp Gly Tyr Glu Glu Ser Pro Lys Ala Ser Glu Leu His Gly
    450                 455                 460

Ile Asn Glu Leu Met Asn Ala Ser Asp Tyr Thr Leu Lys Gly Val Val
465                 470                 475                 480

Val Thr Lys Asn Val Ile Asp Asp Phe Ser Ser Thr Glu Thr Glu Lys
                485                 490                 495

Val Ser Ile Thr Lys Asn Leu Ser Leu Ile Lys Arg Thr Gly Glu Val
            500                 505                 510

Ile Met Gly Ala Asn Asp Val Ser Glu Leu Glu Ser Gln Ala Gln Leu
        515                 520                 525

Met Ile Thr Tyr Asp Thr Pro Lys Met Trp Glu Met Gly Thr Thr Lys
    530                 535                 540

Glu Leu Val Gln Asn Thr Tyr Gln Trp Val Leu Lys Asn Leu Val Thr
545                 550                 555                 560

Leu Lys Ala Gln Phe Leu Leu Gly Lys Glu Asp Met Phe Gln Trp Asp
                565                 570                 575

Ala Phe Glu Ala Phe Glu Ser Ile Ile Pro Gln Lys Met Ala Gly Gln
            580                 585                 590

Tyr Ser Gly Phe Ala Arg Ala Val Leu Lys Gln Met Arg Asp Gln Glu
        595                 600                 605

Val Met Lys Thr Asp Gln Phe Ile Lys Leu Leu Pro Phe Cys Phe Ser
    610                 615                 620
```

Pro Pro Lys Leu Arg Arg Asn Gly Glu Pro Tyr Gln Phe Leu Arg Leu
625 630 635 640

Val Leu Lys Gly Gly Gly Glu Asn Phe Ile Glu Val Arg Lys Gly Ser
645 650 655

Pro Leu Phe Ser Tyr Asn Pro Gln Thr Glu Val Leu Thr Ile Cys Gly
660 665 670

Arg Met Met Ser Leu Lys Gly Lys Ile Glu Asp Glu Glu Arg Asn Arg
675 680 685

Ser Met Gly Asn Ala Val Leu Ala Gly Phe Leu Val Ser Gly Lys Tyr
690 695 700

Asp Pro Asp Leu Gly Asp Phe Lys Thr Ile Glu Glu Leu Glu Lys Leu
705 710 715 720

Lys Pro Gly Glu Lys Ala Asn Ile Leu Leu Tyr Gln Gly Lys Pro Val
725 730 735

Lys Val Val Lys Arg Lys Arg Tyr Ser Ala Leu Ser Asn Asp Ile Ser
740 745 750

Gln Gly Ile Lys Arg Gln Arg Met Thr Val Glu Ser Met Gly Trp Ala
755 760 765

Leu Ser
770

<210> SEQ ID NO 94
<211> LENGTH: 560
<212> TYPE: PRT
<213> ORGANISM: Influenza B Virus

<400> SEQUENCE: 94

Met Ser Asn Met Asp Ile Asp Gly Ile Asn Thr Gly Thr Ile Asp Lys
1 5 10 15

Thr Pro Glu Glu Ile Thr Ser Gly Thr Ser Gly Thr Thr Arg Pro Ile
20 25 30

Ile Arg Pro Ala Thr Leu Ala Pro Pro Ser Asn Lys Arg Thr Arg Asn
35 40 45

Pro Ser Pro Glu Arg Ala Thr Thr Ser Ser Glu Ala Asp Val Gly Arg
50 55 60

Lys Thr Gln Lys Lys Gln Thr Pro Thr Glu Ile Lys Lys Ser Val Tyr
65 70 75 80

Asn Met Val Val Lys Leu Gly Glu Phe Tyr Asn Gln Met Met Val Lys
85 90 95

Ala Gly Leu Asn Asp Asp Met Glu Arg Asn Leu Ile Gln Asn Ala His
100 105 110

Ala Val Glu Arg Ile Leu Leu Ala Ala Thr Asp Asp Lys Lys Thr Glu
115 120 125

Phe Gln Arg Lys Lys Asn Ala Arg Asp Val Lys Glu Gly Lys Glu Glu
130 135 140

Ile Asp His Asn Lys Thr Gly Gly Thr Phe Tyr Lys Met Val Arg Asp
145 150 155 160

Asp Lys Thr Ile Tyr Phe Ser Pro Ile Arg Ile Thr Phe Leu Lys Glu
165 170 175

Glu Val Lys Thr Met Tyr Lys Thr Thr Met Gly Ser Asp Gly Phe Ser
180 185 190

Gly Leu Asn His Ile Met Ile Gly His Ser Gln Met Asn Asp Val Cys
195 200 205

Phe Gln Arg Ser Lys Ala Leu Lys Arg Val Gly Leu Asp Pro Ser Leu

-continued

```
    210                 215                 220

Ile Ser Thr Phe Ala Gly Ser Thr Leu Pro Arg Arg Ser Gly Ala Thr
225                 230                 235                 240

Gly Val Ala Ile Lys Gly Gly Gly Thr Leu Val Ala Glu Ala Ile Arg
                245                 250                 255

Phe Ile Gly Arg Ala Met Ala Asp Arg Gly Leu Leu Arg Asp Ile Lys
            260                 265                 270

Ala Lys Thr Ala Tyr Glu Lys Ile Leu Leu Asn Leu Lys Asn Lys Cys
        275                 280                 285

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
                325                 330                 335

Ser Ile Tyr Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
        355                 360                 365

Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Leu Arg Val Leu
385                 390                 395                 400

Ser Ala Leu Thr Gly Ile Glu Phe Lys Pro Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Val Gly Gly Asp Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495

Lys Gly Asn Leu Leu Lys Met Met Asn Asp Ser Met Ala Lys Lys Thr
            500                 505                 510

Asn Gly Asn Ala Phe Ile Gly Lys Lys Met Phe Gln Ile Ser Asp Lys
        515                 520                 525

Asn Lys Thr Asn Pro Val Glu Ile Pro Ile Lys Gln Thr Ile Pro Asn
    530                 535                 540

Phe Phe Phe Gly Arg Asp Thr Ala Glu Asp Tyr Asp Asp Leu Asp Tyr
545                 550                 555                 560


<210> SEQ ID NO 95
<211> LENGTH: 248
<212> TYPE: PRT
<213> ORGANISM: Influenza B Virus

<400> SEQUENCE: 95

Met Ser Leu Phe Gly Asp Thr Ile Ala Tyr Leu Leu Ser Leu Thr Glu
1               5                   10                  15

Asp Gly Glu Gly Lys Ala Glu Leu Ala Glu Lys Leu His Cys Trp Phe
            20                  25                  30
```

```
Gly Gly Lys Glu Phe Asp Leu Asp Ser Ala Leu Glu Trp Ile Lys Asn
        35                  40                  45

Lys Arg Cys Leu Thr Asp Ile Gln Lys Ala Leu Ile Gly Ala Ser Ile
    50                  55                  60

Cys Phe Leu Lys Pro Lys Asp Gln Glu Arg Lys Arg Arg Phe Ile Thr
65                  70                  75                  80

Glu Pro Leu Ser Gly Met Gly Thr Thr Ala Thr Lys Lys Lys Gly Leu
                85                  90                  95

Ile Leu Ala Glu Arg Lys Met Arg Arg Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Gly Asn Tyr Ser Met Gln Val Lys Leu
    130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Ser Asn
        195                 200                 205

Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245


<210> SEQ ID NO 96
<211> LENGTH: 109
<212> TYPE: PRT
<213> ORGANISM: Influenza B Virus

<400> SEQUENCE: 96

Met Leu Glu Pro Phe Gln Ile Leu Ser Ile Cys Ser Phe Ile Leu Ser
1               5                   10                  15

Ala Leu His Phe Met Ala Trp Thr Ile Gly His Leu Asn Gln Ile Lys
            20                  25                  30

Arg Gly Val Asn Met Lys Ile Arg Ile Lys Asn Pro Asn Lys Glu Thr
        35                  40                  45

Ile Asn Arg Glu Val Ser Ile Leu Arg His Ser Tyr Gln Lys Glu Ile
    50                  55                  60

Gln Ala Lys Glu Thr Met Lys Glu Val Leu Ser Asp Asn Met Glu Val
65                  70                  75                  80

Leu Ser Asp His Ile Val Ile Glu Gly Leu Ser Ala Glu Glu Ile Ile
                85                  90                  95

Lys Met Gly Glu Thr Val Leu Glu Val Glu Glu Leu His
            100                 105


<210> SEQ ID NO 97
<211> LENGTH: 281
<212> TYPE: PRT
<213> ORGANISM: Influenza B Virus

<400> SEQUENCE: 97
```

-continued

Met Ala Asp Asn Met Thr Thr Thr Gln Ile Glu Val Gly Pro Gly Ala
1 5 10 15

Thr Asn Ala Thr Ile Asn Phe Glu Ala Gly Ile Leu Glu Cys Tyr Glu
20 25 30

Arg Leu Ser Trp Gln Arg Ala Leu Asp Tyr Pro Gly Gln Asp Arg Leu
35 40 45

Asn Lys Leu Lys Arg Lys Leu Glu Ser Arg Ile Lys Thr His Asn Lys
50 55 60

Ser Glu Pro Glu Ser Lys Arg Met Ser Leu Glu Glu Arg Lys Ala Ile
65 70 75 80

Gly Val Lys Met Met Lys Val Leu Leu Phe Met Asn Pro Ser Ala Gly
85 90 95

Val Glu Gly Phe Glu Pro Tyr Cys Met Lys Asn Pro Ser Asn Ser Asn
100 105 110

Cys Pro Asp Cys Asn Trp Ala Asp Tyr Pro Pro Thr Pro Gly Lys Tyr
115 120 125

Leu Asp Gly Ile Glu Glu Glu Pro Glu Asn Val Gly Asp Ser Thr Glu
130 135 140

Ile Val Leu Arg Asp Met Asn Asn Lys Asp Ala Arg Gln Lys Ile Lys
145 150 155 160

Glu Glu Val Asn Thr Gln Lys Glu Gly Lys Phe Arg Leu Thr Ile Lys
165 170 175

Arg Asp Ile Arg Asn Val Leu Ser Leu Arg Val Leu Val Asn Gly Thr
180 185 190

Phe Ile Lys His Pro Asn Gly Tyr Lys Ser Leu Ser Thr Leu His Arg
195 200 205

Leu Asn Ala Tyr Asp Gln Ser Gly Arg Leu Val Ala Lys Leu Val Ala
210 215 220

Thr Asp Asp Leu Thr Val Glu Asp Glu Glu Asp Gly His Arg Ile Leu
225 230 235 240

Asn Ser Leu Phe Glu Arg Leu Asn Glu Gly His Ser Lys Pro Ile Arg
245 250 255

Ala Ala Glu Thr Ala Val Gly Val Leu Ser Gln Phe Gly Gln Glu His
260 265 270

Arg Leu Ser Pro Glu Glu Arg Asp Asn
275 280

<210> SEQ ID NO 98
<211> LENGTH: 122
<212> TYPE: PRT
<213> ORGANISM: Influenza B Virus

<400> SEQUENCE: 98

Met Ala Asp Asn Met Thr Thr Thr Gln Ile Glu Trp Arg Met Lys Lys
1 5 10 15

Met Ala Ile Gly Ser Ser Thr His Ser Ser Ser Val Leu Met Lys Asp
20 25 30

Ile Gln Ser Gln Phe Glu Gln Leu Lys Leu Arg Trp Glu Ser Tyr Pro
35 40 45

Asn Leu Val Lys Ser Thr Asp Tyr His Gln Lys Arg Glu Thr Ile Arg
50 55 60

Leu Val Thr Glu Glu Leu Tyr Leu Leu Ser Lys Arg Ile Asp Asp Asn
65 70 75 80

Ile Leu Phe His Lys Thr Val Ile Ala Asn Ser Ser Ile Ile Ala Asp
85 90 95

```
Met Ile Val Ser Leu Ser Leu Leu Glu Thr Leu Tyr Glu Met Lys Asp
            100                 105                 110

Val Val Glu Val Tyr Ser Arg Gln Cys Leu
        115                 120


<210> SEQ ID NO 99
<211> LENGTH: 469
<212> TYPE: PRT
<213> ORGANISM: Influenza A Virus

<400> SEQUENCE: 99

Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
```

-continued

```
            340                 345                 350

Tyr Gly Asn Gly Val Trp Ile Gly Arg Thr Lys Ser Ile Ser Ser Arg
        355                 360                 365

Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465


<210> SEQ ID NO 100
<211> LENGTH: 1812
<212> TYPE: DNA
<213> ORGANISM: Influenza B Virus

<400> SEQUENCE: 100

agcattttct tgtgagcttc gagcactaat aaaactgaaa atcaaaatgt ccaacatgga      60

tattgacagt ataaataccg gaacaatcga taaaaaacca gaagaactga ctcccggaac     120

cagtggggca accagaccaa tcatcaagcc agcaaccctt gctccgccaa gcaacaaacg     180

aacccgaaat ccatccccag aaaggacaac cacaagcagt gaaaccgata tcggaaggaa     240

aatccaaaag aaacaaaccc caacagagat aaagaagagc gtctacaaca tggtggtaaa     300

gctgggtgaa ttctacaacc agatgatggt caaagctgga cttaatgatg acatggaaag     360

gaatctaatc caaaatgcac aagctgtgga gagaatccta ttggctgcaa ctgatgacaa     420

gaaaactgaa taccaaaaga aaaggaatgc cagagatgtc aaagaaggga aggaagaaat     480

agaccacaac aagacaggag gcacctttta taagatggta agagatgata aaaccatcta     540

cttcagccct ataaaaatta cctttttaaa agaagaggtg aaaacaatgt acaagaccac     600

catggggagt gatggtttca gtggactaaa tcacattatg attggacatt cacagatgaa     660

cgatgtctgt ttccaaagat caaaggcact gaaaagggtt ggacttgacc cttcattaat     720

cagtactttt gccggaagca cactacccag aagatcaggt acaactggtg ttgcaatcaa     780

aggaggtgga actttagtgg cagaagccat tcgatttata ggaagagcaa tggcagacag     840

agggctactg agagacatca aggccaagac agcctatgaa aagattcttc tgaatctgaa     900

aaacaagtgc tctgcgcccc aacaaaaggc tctagttgat caagtgatcg gaagtaggaa     960

cccagggatt gcagacatag aagacctaac tctgcttgcc agaagcatga tagttgtcag    1020

accctctgta gcgagcaaag tggtgcttcc cataagcatt tatgctaaaa tacctcaact    1080

aggattcaat atcgaagaat actctatggt tgggtatgaa gccatggctc tttataatat    1140

ggcaacacct gtttccatat taagaatggg agatgacgca aaagataaat ctcaactatt    1200

cttcatgtcg tgcttcggag ctgcctatga agatctaaga gtgttatctg cactaacggg    1260

caccgaattt aagcctagat cagcactaaa atgcaagggt ttccatgtcc cggctaagga    1320

gcaagtagaa ggaatggggg cagctctgat gtccatcaag cttcagttct gggccccaat    1380
```

gaccagatct ggagggaatg aagtaagtgg agaaggaggg tctggtcaaa taagttgcag 1440
ccctgtgttt gcagtagaaa gacctattgc tctaagcaag caagctgtaa gaagaatgct 1500
gtcaatgaac gttgaaggac gtgatgcaga tgtcaaagga aatctactca aaatgatgaa 1560
tgattcgatg gcaaagaaaa ccagtggaaa tgctttcatt gggaagaaaa tgtttcaaat 1620
atcagacaaa aacaaagtca atcccattga gattccaatt aagcagacca tccccagttt 1680
cttctttggg agggacacag cagaggatta tgatgacctc gattattaaa gcaataaaat 1740
agacactatg gctgtgactg tttcagtacg tttgggatgt gggtgtttac tcttattgaa 1800
ataaatgtaa aa 1812

<210> SEQ ID NO 101
<211> LENGTH: 560
<212> TYPE: PRT
<213> ORGANISM: Influenza B Virus

<400> SEQUENCE: 101

Met Ser Asn Met Asp Ile Asp Gly Ile Asn Thr Gly Thr Ile Asp Lys
1 5 10 15

Thr Pro Glu Glu Ile Thr Ser Gly Thr Ser Gly Ala Thr Arg Pro Ile
20 25 30

Ile Lys Pro Ala Thr Leu Ala Pro Pro Ser Asn Lys Arg Thr Arg Asn
35 40 45

Pro Ser Pro Glu Arg Ala Thr Thr Ser Ser Glu Ala Ile Val Gly Arg
50 55 60

Arg Thr Gln Lys Lys Gln Thr Pro Thr Glu Ile Lys Lys Ser Val Tyr
65 70 75 80

Asn Met Val Val Lys Leu Gly Glu Phe Tyr Asn Gln Met Met Val Lys
85 90 95

Ala Gly Leu Asn Asp Asp Met Glu Arg Asn Leu Ile Gln Asn Ala His
100 105 110

Ala Val Glu Arg Ile Leu Leu Ala Ala Thr Asp Asp Lys Lys Thr Glu
115 120 125

Tyr Gln Lys Lys Lys Asn Ala Arg Asp Val Lys Glu Gly Lys Glu Glu
130 135 140

Ile Asp His Asn Lys Thr Gly Gly Thr Phe Tyr Lys Met Val Arg Asp
145 150 155 160

Asp Lys Thr Ile Tyr Phe Ser Pro Ile Arg Ile Thr Phe Leu Lys Glu
165 170 175

Glu Val Lys Thr Met Tyr Lys Thr Thr Met Gly Ser Asp Gly Phe Ser
180 185 190

Gly Leu Asn His Ile Met Ile Gly His Ser Gln Met Asn Asp Val Cys
195 200 205

Phe Gln Arg Ser Lys Ala Leu Lys Arg Val Gly Leu Asp Pro Ser Leu
210 215 220

Ile Ser Thr Phe Ala Gly Ser Thr Leu Pro Arg Arg Ser Gly Ala Thr
225 230 235 240

Gly Val Ala Ile Lys Gly Gly Gly Thr Leu Val Ala Glu Ala Ile Arg
245 250 255

Phe Ile Gly Arg Ala Met Ala Asp Arg Gly Leu Leu Arg Asp Ile Arg
260 265 270

Ala Lys Thr Ala Tyr Glu Lys Ile Leu Leu Asn Leu Lys Asn Lys Cys
275 280 285

```
Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
                325                 330                 335

Ser Ile Asn Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
        355                 360                 365

Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Gln Arg Val Leu
385                 390                 395                 400

Ser Ala Leu Thr Gly Thr Glu Phe Lys Pro Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Val Gly Gly Asp Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495

Lys Gly Asn Leu Leu Lys Met Met Asn Asp Ser Met Ala Lys Lys Thr
            500                 505                 510

Asn Gly Asn Ala Phe Ile Gly Lys Lys Met Phe Gln Ile Ser Asp Lys
        515                 520                 525

Asn Lys Ile Asn Pro Val Asp Ile Pro Ile Lys Gln Thr Ile Pro Asn
    530                 535                 540

Phe Phe Phe Gly Arg Asp Thr Ala Glu Asp Tyr Asp Asp Leu Asp Tyr
545                 550                 555                 560
```

<210> SEQ ID NO 102
<211> LENGTH: 560
<212> TYPE: PRT
<213> ORGANISM: Influenza B Virus

<400> SEQUENCE: 102

```
Met Ser Asn Met Asp Ile Asp Gly Ile Asn Thr Gly Thr Ile Asp Lys
1               5                   10                  15

Thr Pro Glu Glu Ile Thr Ser Gly Thr Ser Gly Ala Thr Arg Pro Ile
            20                  25                  30

Ile Lys Pro Ala Thr Leu Ala Pro Pro Ser Asn Lys Arg Thr Arg Asn
        35                  40                  45

Pro Ser Pro Glu Arg Ala Ala Thr Ser Ser Glu Ala Asp Val Gly Arg
    50                  55                  60

Arg Thr Gln Lys Lys Gln Thr Pro Thr Glu Ile Lys Lys Ser Val Tyr
65                  70                  75                  80

Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala His
            100                 105                 110
```

-continued

```
Ala Ala Glu Arg Ile Leu Leu Ala Ala Thr Asp Asp Lys Lys Thr Glu
        115                 120                 125

Phe Gln Lys Lys Lys Asn Ala Arg Asp Val Lys Glu Gly Lys Glu Glu
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Ala Leu Lys Arg Val Gly Leu Asp Pro Ser Leu
    210                 215                 220

Ile Ser Thr Phe Ala Gly Ser Thr Leu Pro Arg Arg Ser Gly Ala Thr
225                 230                 235                 240

Gly Val Ala Ile Lys Gly Gly Gly Thr Leu Val Ala Glu Ala Ile Arg
                245                 250                 255

Phe Ile Gly Arg Ala Met Ala Asp Arg Gly Leu Leu Arg Asp Ile Arg
            260                 265                 270

Ala Lys Thr Ala Tyr Glu Lys Ile Leu Leu Asn Leu Lys Asn Lys Cys
        275                 280                 285

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
                325                 330                 335

Ser Ile Asn Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
        355                 360                 365

Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Gln Arg Val Leu
385                 390                 395                 400

Ser Ala Leu Thr Gly Thr Glu Phe Lys His Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Val Gly Gly Asp Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495

Lys Gly Asn Leu Leu Lys Met Met Asn Asp Ser Met Thr Lys Lys Thr
            500                 505                 510

Asn Gly Asn Ala Phe Ile Gly Lys Lys Met Phe Gln Ile Ser Asp Lys
        515                 520                 525
```

```
Asn Lys Thr Asn Pro Ile Glu Ile Pro Ile Lys Gln Thr Ile Pro Asn
    530                 535                 540

Phe Phe Phe Gly Arg Asp Thr Ala Glu Asp Tyr Asp Asp Leu Asp Tyr
545                 550                 555                 560


<210> SEQ ID NO 103
<211> LENGTH: 1842
<212> TYPE: DNA
<213> ORGANISM: Influenza B Virus

<400> SEQUENCE: 103

agcagaagca cagcattttc ttgtgaactt caagtaccaa caaaaactga aaatcaaaat      60

gtccaacatg gatattgacg gcatcaacac tggaacaatt gacaaaacac cagaagaaat     120

aacttccgga accagtgggg caaccagacc aatcatcaag ccagcaaccc ttgccccacc     180

aagcaataaa cgaacccgaa acccatcccc agaaagggca accacaagca gcgaagcgat     240

tgtcggaagg agaacccaaa agaaacaaac cccgacagag ataaagaaga gcgtctacaa     300

tatggtagtg aaactgggtg aattctacaa ccagatgatg gtcaaagctg gactcaacga     360

tgacatggag agaaacctaa tccaaaatgc acatgctgtg gaaagaattc tattggctgc     420

tactgatgac aagaaaactg aataccaaaa gaaaaagaat gccagagatg tcaaagaagg     480

gaaagaagaa atagaccaca acaaaacagg aggcaccttt tataagatgg taagagatga     540

taaaaccatc tacttcagcc ctataagaat taccttttta aaagaagagg tgaaaacaat     600

gtacaagacc accatgggga gtgatggttt cagtggacta aatcacatca tgattgggca     660

ttcacagatg aacgatgtct gtttccaaag atcaaaggca ctaaaaagag ttggacttga     720

cccttcatta atcagtactt ttgcaggaag cacactcccc agaagatcag gtgcaactgg     780

tgttgcgatc aaaggaggtg gaactttagt ggcagaagcc attcgattta taggaagagc     840

aatggcagac agagggctat tgagagacat cagagccaag acggcctatg aaaagattct     900

tctgaatctg aaaaacaagt gctctgcgcc ccaacaaaag gctctagttg atcaagtgat     960

cggaagtaga aacccaggga ttgcagacat agaagaccta accctgcttg cccgaagcat    1020

ggtcgttgtc aggccctctg tagcgagcaa agtggtgctt cccataagca ttaatgctaa    1080

aatacctcaa ctagggttca atgttgaaga atactctatg gttgggtatg aagccatggc    1140

tctttataat atggcaacac ctgtttccat attaagaatg ggagacgatg caaaagataa    1200

atcacaatta ttcttcatgt cttgctttgg agctgcctat gaagaccaaa gagttttgtc    1260

tgcactaacc ggcacagaat tcaagcctag gtcagcatta aagtgcaagg gtttccacgt    1320

tccagcaaag gagcaagtgg aaggaatggg ggcagctctg atgtccatca agctccagtt    1380

ttgggcccca atgaccagat ctgggggaa cgaagtaggt ggagacggag ggtctggtca    1440

aataagttgc agccccgtgt ttgcagtaga gagacctatt gctctaagca agcaagctgt    1500

aagaagaatg ctgtcaatga atattgaggg acgtgatgca gatgtcaaag gaaatctact    1560

caagatgatg aatgattcaa tggctaagaa aaccaatgga aatgctttca ttgggaagaa    1620

aatgtttcaa atatcagaca aaaacaaaat caatcccgtt gatattccaa ttaagcagac    1680

catccccaat ttcttctttg ggagggacac agcagaggat tatgatgacc tcgattatta    1740

aagcaacaaa atagacacta tggctgtgac tgtttcagta cgtttggaat gtgggtgttt    1800

actcttattg aaataaatgt aaaaaatgct gttgtttcta ct                       1842


<210> SEQ ID NO 104
<211> LENGTH: 1842
```

<212> TYPE: DNA
<213> ORGANISM: Influenza B Virus

<400> SEQUENCE: 104
agcagaagca cagcattttc ttgtgaactt caagtaccaa caaaaactga aaatcaaaat 60
gtccaacatg gatattgacg gcatcaacac tggaacaatt gacaaaacac cagaagaaat 120
aacttccgga accagtgggg caaccagacc aatcatcaaa ccagcaaccc ttgccccacc 180
aagcaacaaa cgaacccgaa acccatcccc ggaaagggca gccacaagca gtgaagctga 240
tgtcggaagg agaacccaaa agaaacaaac cccgacagag ataaagaaga gcgtctacaa 300
tatggtagtg aaactgggtg aattctacaa ccagatgatg gtcaaagctg gactcaacga 360
tgacatggag agaaacctaa tccaaaatgc acatgctgcg gaaagaattc tattggctgc 420
tactgatgac aagaaaactg aattccaaaa gaaaaagaat gccagagatg tcaaagaagg 480
gaaagaagaa atagaccaca acaaaacagg aggcaccttt tacaagatgg taagagatga 540
taaaaccatc tacttcagcc ctataagaat taccttttta aaagaagagg tgaaaacaat 600
gtacaaaacc accatgggga gtgatggttt cagtggacta aatcacatca tgattgggca 660
ttcacagatg aacgatgtct gtttccaaag atcaaaggca ctaaaaagag ttggacttga 720
cccttcatta atcagtactt ttgcaggaag cacactcccc agaagatcag gtgcaactgg 780
tgttgcgatc aaaggaggtg gaactttagt ggcagaagcc attcgattta taggaagagc 840
aatggcagac agagggctat tgagagacat cagagccaag acggcctatg aaaagattct 900
tctgaatctg aaaaacaagt gctctgcgcc ccaacaaaag gctctagttg atcaagtgat 960
cggaagtaga aatccaggga ttgcagacat agaagaccta accctgcttg cccgaagcat 1020
ggtcgttgtc aggccctctg tagcgagcaa agtggtgctt cccataagca ttaatgccaa 1080
aatacctcaa ctagggttca atgttgaaga atactctatg gttgggtatg aagccatggc 1140
tctttataat atggcaacac ctgtttccat attaagaatg ggagacgatg caaaagataa 1200
atcacaatta ttcttcatgt cttgcttcgg agctgcctat gaagaccaaa gagttttgtc 1260
tgcactaaca ggcacagaat tcaagcatag gtcagcatta aagtgcaagg gtttccacgt 1320
tccagcaaag gagcaagtgg aaggaatggg ggcagctctg atgtccatca agctccagtt 1380
ttgggctcca atgaccagat ctgggggggaa tgaagtaggt ggagacggag ggtctggtca 1440
aataagttgc agccccgtgt ttgcagtaga aagacctatt gctctaagca agcaagctgt 1500
aagaagaatg ctgtcaatga atattgaggg acgtgatgca gatgtcaaag gaaatctact 1560
caagatgatg aatgattcaa tgactaagaa aaccaatgga aatgctttca ttgggaagaa 1620
aatgtttcaa atatcagaca aaaacaaaac caatcccatt gagattccaa ttaagcagac 1680
catccccaat ttcttctttg ggagggacac agcagaggat tatgatgacc tcgattatta 1740
aagcaacaaa atagacacta tggctgtgac tgtttcagta cgtttggaat gtgggtgttt 1800
acttttattg aaataaatgt aaaaaatgct gttgtttcta ct 1842

<210> SEQ ID NO 105
<211> LENGTH: 32
<212> TYPE: DNA
<213> ORGANISM: Influenza A Virus

<400> SEQUENCE: 105
agcaaaagca ggggaaaata aaagcaacca aa 32

<210> SEQ ID NO 106

<211> LENGTH: 51
<212> TYPE: DNA
<213> ORGANISM: Influenza A Virus

<400> SEQUENCE: 106
atgaaagtaa aactactggt tctgttatgt acatttacag ctacatatgc a 51

<210> SEQ ID NO 107
<211> LENGTH: 77
<212> TYPE: DNA
<213> ORGANISM: Influenza A Virus

<400> SEQUENCE: 107
agattctggc gatctactca acagtcgcca gttccctggt tcttttggtc tccctggggg 60
caatcagctt ctggatg 77

<210> SEQ ID NO 108
<211> LENGTH: 39
<212> TYPE: DNA
<213> ORGANISM: Influenza A Virus

<400> SEQUENCE: 108
tgttccaatg ggtctttgca gtgtagaata tgcatctaa 39

<210> SEQ ID NO 109
<211> LENGTH: 45
<212> TYPE: DNA
<213> ORGANISM: Influenza A Virus

<400> SEQUENCE: 109
gaccagaatt tcagaaatat aaggaaaaac acccttgttt ctact 45

<210> SEQ ID NO 110
<211> LENGTH: 20
<212> TYPE: DNA
<213> ORGANISM: Influenza A Virus

<400> SEQUENCE: 110
agcaaaagca ggagtttaaa 20

<210> SEQ ID NO 111
<211> LENGTH: 18
<212> TYPE: DNA
<213> ORGANISM: Influenza A Virus

<400> SEQUENCE: 111
atgaatccaa atcaaaaa 18

<210> SEQ ID NO 112
<211> LENGTH: 87
<212> TYPE: DNA
<213> ORGANISM: Influenza A Virus

<400> SEQUENCE: 112
ataataacca ttggatcaat cagtatagca atcggaataa ttagtctaat gttgcaaata 60
ggaaatatta tttcaatatg ggctagt 87

<210> SEQ ID NO 113
<211> LENGTH: 29
<212> TYPE: DNA
<213> ORGANISM: Influenza A Virus

<400> SEQUENCE: 113
ctcgttgaaa aaaactcctt gtttctact 29

<210> SEQ ID NO 114
<211> LENGTH: 32
<212> TYPE: DNA
<213> ORGANISM: Influenza A Virus

<400> SEQUENCE: 114
agcaaaagca ggggaaaata aaaacaacca aa 32

<210> SEQ ID NO 115
<211> LENGTH: 51
<212> TYPE: DNA
<213> ORGANISM: Influenza A Virus

<400> SEQUENCE: 115
atgaaggcaa acctactggt cctgttatgt gcacttgcag ctgcagatgc a 51

<210> SEQ ID NO 116
<211> LENGTH: 78
<212> TYPE: DNA
<213> ORGANISM: Influenza A Virus

<400> SEQUENCE: 116
cagattctgg cgatctactc aactgtcgcc agttcactgg tgcttttggt ctccctgggg 60
gcaatcagtt tctggatg 78

<210> SEQ ID NO 117
<211> LENGTH: 39
<212> TYPE: DNA
<213> ORGANISM: Influenza A Virus

<400> SEQUENCE: 117
tgttctaatg gatctttgca gtgcagaata tgcatctga 39

<210> SEQ ID NO 118
<211> LENGTH: 45
<212> TYPE: DNA
<213> ORGANISM: Influenza A Virus

<400> SEQUENCE: 118
gattagaatt tcagagatat gaggaaaaac acccttgttt ctact 45

<210> SEQ ID NO 119
<211> LENGTH: 20
<212> TYPE: DNA
<213> ORGANISM: Influenza A Virus

<400> SEQUENCE: 119
agcaaaagca ggggtttaaa 20

<210> SEQ ID NO 120
<211> LENGTH: 18
<212> TYPE: DNA
<213> ORGANISM: Influenza A Virus

<400> SEQUENCE: 120
atgaatccaa atcagaaa 18

<210> SEQ ID NO 121
<211> LENGTH: 87
<212> TYPE: DNA

<213> ORGANISM: Influenza A Virus

<400> SEQUENCE: 121
ataataacca ttggatcaat ctgtctggta gtcggactaa ttagcctaat attgcaaata 60
gggaatataa tctcaatatg gattagc 87

<210> SEQ ID NO 122
<211> LENGTH: 28
<212> TYPE: DNA
<213> ORGANISM: Influenza A Virus

<400> SEQUENCE: 122
tctgttcaaa aaactccttg tttctact 28

<210> SEQ ID NO 123
<211> LENGTH: 83
<212> TYPE: DNA
<213> ORGANISM: Influenza A Virus

<400> SEQUENCE: 123
agcaaaagca ggggaaaaca aaagcaacaa aaatgaaggc aatactagta gttctgctat 60
atacatttgc aaccgcaaat gca 83

<210> SEQ ID NO 124
<211> LENGTH: 83
<212> TYPE: DNA
<213> ORGANISM: Influenza A Virus

<400> SEQUENCE: 124
agcaaaagca ggggaaaata aaaacaacca aaatgaaggc aaacctactg gctcttctag 60
agacatttgc agctgcagat gca 83

<210> SEQ ID NO 125
<211> LENGTH: 83
<212> TYPE: DNA
<213> ORGANISM: Influenza A Virus

<400> SEQUENCE: 125
agcaaaagca ggggaaaata aaagcaacca aaatgaaagt aaaactactg gttctgttat 60
gtacatttac agctacatat gca 83

<210> SEQ ID NO 126
<211> LENGTH: 161
<212> TYPE: DNA
<213> ORGANISM: Influenza A Virus

<400> SEQUENCE: 126
cagattttgg cgatctattc aactgtcgcc agttcattgg tactggtagt ctccctgggg 60
gcaatcagtt tctggatgtg ctctaatggg tctctacagt gtagaatatg tatttaacat 120
taggatttca gaagcatgag aaaaacaccc ttgtttctac t 161

<210> SEQ ID NO 127
<211> LENGTH: 162
<212> TYPE: DNA
<213> ORGANISM: Influenza A Virus

<400> SEQUENCE: 127
cagattctgg cgatctactc aactgtcgcc agttcactgg tgcttttggt ctccctgggg 60
gcaatcagtt tctggatgtg ttctaatgga tctttgcagt gcagaatatg catctgagat 120
tagaatttca gagatatgag gaaaaacacc cttgtttcta ct 162

<210> SEQ ID NO 128
<211> LENGTH: 162
<212> TYPE: DNA
<213> ORGANISM: Influenza A Virus

<400> SEQUENCE: 128
cagattctgg cgatctactc aacagtcgcc agttccctgg ttcttttggt ctccctgggg 60
gcaatcagtt tctggatgtg ttctaatggg tctttgcagt gtagaatatg catctaagac 120
cagaatttca gaaatataag gaaaaacacc cttgtttcta ct 162

<210> SEQ ID NO 129
<211> LENGTH: 17
<212> TYPE: PRT
<213> ORGANISM: Influenza A Virus

<400> SEQUENCE: 129

Met Lys Ala Ile Leu Val Val Leu Leu Tyr Thr Phe Ala Thr Ala Asn
1 5 10 15

Ala

<210> SEQ ID NO 130
<211> LENGTH: 17
<212> TYPE: PRT
<213> ORGANISM: Influenza A Virus

<400> SEQUENCE: 130

Met Lys Ala Asn Leu Leu Val Leu Leu Cys Ala Leu Ala Ala Ala Asp
1 5 10 15

Ala

<210> SEQ ID NO 131
<211> LENGTH: 17
<212> TYPE: PRT
<213> ORGANISM: Influenza A Virus

<400> SEQUENCE: 131

Met Lys Val Lys Leu Leu Val Leu Leu Cys Thr Phe Thr Ala Thr Tyr
1 5 10 15

Ala

<210> SEQ ID NO 132
<211> LENGTH: 38
<212> TYPE: PRT
<213> ORGANISM: Influenza A Virus

<400> SEQUENCE: 132

Gln Ile Leu Ala Ile Tyr Ser Thr Val Ala Ser Ser Leu Val Leu Val
1 5 10 15

Val Ser Leu Gly Ala Ile Ser Phe Trp Met Cys Ser Asn Gly Ser Leu
20 25 30

Gln Cys Arg Ile Cys Ile
35

<210> SEQ ID NO 133
<211> LENGTH: 38
<212> TYPE: PRT
<213> ORGANISM: Influenza A Virus

<400> SEQUENCE: 133

Gln Ile Leu Ala Ile Tyr Ser Thr Val Ala Ser Ser Leu Val Leu Leu
1 5 10 15

Val Ser Leu Gly Ala Ile Ser Phe Trp Met Cys Ser Asn Gly Ser Leu
20 25 30

Gln Cys Arg Ile Cys Ile
35

<210> SEQ ID NO 134
<211> LENGTH: 38
<212> TYPE: PRT
<213> ORGANISM: Influenza A Virus

<400> SEQUENCE: 134

Gln Ile Leu Ala Ile Tyr Ser Thr Val Ala Ser Ser Leu Val Leu Leu
1 5 10 15

Val Ser Leu Gly Ala Ile Ser Phe Trp Met Cys Ser Asn Gly Ser Leu
20 25 30

Gln Cys Arg Ile Cys Ile
35

<210> SEQ ID NO 135
<211> LENGTH: 125
<212> TYPE: DNA
<213> ORGANISM: Influenza A Virus

<400> SEQUENCE: 135
agcaaaagca ggggtttaaa atgaatccaa accaaaagat aataaccatt ggttcggtct 60
gtataacaat tggaatggct aacttaatat tacaaattgg aaacataatc tcaatatgga 120
ttagc 125

<210> SEQ ID NO 136
<211> LENGTH: 125
<212> TYPE: DNA
<213> ORGANISM: Influenza A Virus

<400> SEQUENCE: 136
agcaaaagca ggggtttaaa atgaatccaa atcagaaaat aataaccatt ggatcaatct 60
gtctggtagt cggactaatt agcctaatat tgcaaatagg gaatataatc tcaatatgga 120
ttagc 125

<210> SEQ ID NO 137
<211> LENGTH: 125
<212> TYPE: DNA
<213> ORGANISM: Influenza A Virus

<400> SEQUENCE: 137
agcaaaagca ggagtttaaa atgaatccaa atcaaaaaat aataaccatt ggatcaatca 60
gtatagcaat cggaataatt agtctaatgt tgcaaatagg aaatattatt tcaatatggg 120
ctagt 125

<210> SEQ ID NO 138
<211> LENGTH: 32
<212> TYPE: DNA
<213> ORGANISM: Influenza A Virus

<400> SEQUENCE: 138
taatttgttc aaaaaaactc cttgtttcta ct 32

-continued

```
<210> SEQ ID NO 139
<211> LENGTH: 32
<212> TYPE: DNA
<213> ORGANISM: Influenza A Virus

<400> SEQUENCE: 139

taatctgttc aaaaaaactc cttgtttcta ct                                    32


<210> SEQ ID NO 140
<211> LENGTH: 32
<212> TYPE: DNA
<213> ORGANISM: Influenza A Virus

<400> SEQUENCE: 140

taactcgttg aaaaaaactc cttgtttcta ct                                    32


<210> SEQ ID NO 141
<211> LENGTH: 35
<212> TYPE: PRT
<213> ORGANISM: Influenza A Virus

<400> SEQUENCE: 141

Met Asn Pro Asn Gln Lys Ile Ile Thr Ile Gly Ser Ile Ser Ile Ala
1               5                   10                  15

Ile Gly Ile Ile Ser Leu Ile Leu Gln Ile Gly Asn Ile Ile Ser Ile
            20                  25                  30

Trp Ala Ser
        35


<210> SEQ ID NO 142
<211> LENGTH: 35
<212> TYPE: PRT
<213> ORGANISM: Influenza A Virus

<400> SEQUENCE: 142

Met Asn Pro Asn Gln Lys Ile Ile Thr Ile Gly Ser Ile Cys Leu Val
1               5                   10                  15

Val Gly Leu Ile Ser Leu Ile Leu Gln Ile Gly Asn Ile Ile Ser Ile
            20                  25                  30

Trp Ile Ser
        35


<210> SEQ ID NO 143
<211> LENGTH: 35
<212> TYPE: PRT
<213> ORGANISM: Influenza A Virus

<400> SEQUENCE: 143

Met Asn Pro Asn Gln Lys Ile Ile Thr Ile Gly Ser Ile Ser Ile Ala
1               5                   10                  15

Ile Gly Ile Ile Ser Leu Met Leu Gln Ile Gly Asn Ile Ile Ser Ile
            20                  25                  30

Trp Ala Ser
        35
```